US011634714B2

(12) United States Patent
van Deutekom et al.

(10) Patent No.: US 11,634,714 B2
(45) Date of Patent: Apr. 25, 2023

(54) OLIGONUCLEOTIDE COMPRISING AN INOSINE FOR TREATING DMD

(71) Applicant: BioMarin Technologies B.V., Leiden (NL)

(72) Inventors: Judith Christina Theodora van Deutekom, Dordrecht (NL); Josephus Johannes de Kimpe, Utrecht (NL); Gerard Johannes Platenburg, Voorschoten (NL)

(*) Notice: Subject to any disclaimer, the term of this patent is extended or adjusted under 35 U.S.C. 154(b) by 156 days.

(21) Appl. No.: 17/302,500

(22) Filed: May 4, 2021

(65) Prior Publication Data

US 2021/0254071 A1    Aug. 19, 2021

Related U.S. Application Data

(63) Continuation of application No. 16/694,980, filed on Nov. 25, 2019, now Pat. No. 11,034,956, which is a continuation of application No. 15/468,239, filed on Mar. 24, 2017, now Pat. No. 10,533,171, which is a continuation of application No. 15/168,662, filed on May 31, 2016, now abandoned, which is a continuation of application No. 14/678,517, filed on Apr. 3, 2015, now abandoned, which is a continuation of application No. 13/266,110, filed as application No. PCT/NL2010/050230 on Apr. 26, 2010, now abandoned.

(60) Provisional application No. 61/172,506, filed on Apr. 24, 2009.

(30) Foreign Application Priority Data

Apr. 24, 2009    (EP) .................................... 09158731

(51) Int. Cl.
| | | |
|---|---|---|
| C07H 21/04 | (2006.01) | |
| C12N 15/113 | (2010.01) | |
| C12N 15/11 | (2006.01) | |
| A61K 48/00 | (2006.01) | |

(52) U.S. Cl.
CPC ............ *C12N 15/113* (2013.01); *A61K 48/00* (2013.01); *C12N 15/111* (2013.01); *C12N 2310/11* (2013.01); *C12N 2310/315* (2013.01); *C12N 2310/3181* (2013.01); *C12N 2310/321* (2013.01); *C12N 2310/3231* (2013.01); *C12N 2310/331* (2013.01); *C12N 2310/333* (2013.01); *C12N 2310/336* (2013.01); *C12N 2320/33* (2013.01)

(58) Field of Classification Search
None
See application file for complete search history.

(56) References Cited

U.S. PATENT DOCUMENTS

| | | | |
|---|---|---|---|
| 5,034,506 | A | 7/1991 | Summerton et al. |
| 5,418,139 | A | 5/1995 | Campbell |
| 5,541,308 | A | 7/1996 | Hogan et al. |
| 5,593,974 | A | 1/1997 | Rosenberg et al. |
| 5,608,046 | A | 3/1997 | Cook et al. |
| 5,627,263 | A | 5/1997 | Ruoslahti et al. |
| 5,658,764 | A | 8/1997 | Pergolizzi et al. |
| 5,741,645 | A | 4/1998 | Orr et al. |
| 5,766,847 | A | 6/1998 | Jäckle et al. |
| 5,853,995 | A | 12/1998 | Lee |
| 5,869,252 | A | 2/1999 | Bouma et al. |
| 5,916,808 | A | 6/1999 | Kole et al. |
| 5,962,332 | A | 10/1999 | Singer et al. |
| 5,968,909 | A | 10/1999 | Agrawal et al. |
| 5,976,879 | A | 11/1999 | Kole et al. |
| 6,124,100 | A | 9/2000 | Jin |
| 6,130,207 | A | 10/2000 | Dean et al. |
| 6,133,031 | A | 10/2000 | Monia et al. |
| 6,172,208 | B1 | 1/2001 | Cook |
| 6,172,216 | B1 | 1/2001 | Bennett et al. |
| 6,210,892 | B1 | 4/2001 | Bennett et al. |
| 6,251,589 | B1 | 6/2001 | Tsuji et al. |
| 6,280,938 | B1 | 8/2001 | Ranum et al. |
| 6,300,060 | B1 | 10/2001 | Kantoff et al. |
| 6,322,978 | B1 | 11/2001 | Kahn et al. |
| 6,329,501 | B1 | 12/2001 | Smith et al. |
| 6,355,481 | B1 | 3/2002 | Li et al. |
| 6,355,690 | B1 | 3/2002 | Tsuji |

(Continued)

FOREIGN PATENT DOCUMENTS

| | | |
|---|---|---|
| CA | 2 319 149 A1 | 10/2001 |
| CA | 2 526 893 A1 | 11/2004 |

(Continued)

OTHER PUBLICATIONS

Anthony et al., "Dystrophin quantification and clinical corelations in Becker muscular dystrophy: implications for clinical trials 2011," Brain 134(1 2):3547-3559 (2011).
Bernasconi et al., "Cortisol increases transfection efficiency of cells." FEBS Lett. 419(1):103-106 (1997).
BioMarin Press Release. "BioMarin Announces Withdrawal of Market Authorization Application for Kyndrisa™ (drisapersen) in Europe," May 31, 2016.

(Continued)

*Primary Examiner* — Kimberly Chong
(74) *Attorney, Agent, or Firm* — Rimon, P.C.; Dale L. Rieger

(57) ABSTRACT

The invention provides an oligonucleotide comprising an inosine, and/or a nucleotide containing a base able to form a wobble base pair or a functional equivalent thereof, wherein the oligonucleotide, or a functional equivalent thereof, comprises a sequence which is complementary to at least part of a dystrophin pre-m RNA exon or at least part of a non-exon region of a dystrophin pre-m RNA said part being a contiguous stretch comprising at least 8 nucleotides. The invention further provides the use of said oligonucleotide for preventing or treating DMD or BMD.

9 Claims, 2 Drawing Sheets

Specification includes a Sequence Listing.

(56) References Cited

U.S. PATENT DOCUMENTS

| | | |
|---|---|---|
| 6,369,038 B1 | 4/2002 | Blumenfeld et al. |
| 6,379,698 B1 | 4/2002 | Leamon |
| 6,399,575 B1 | 6/2002 | Smith et al. |
| 6,514,755 B1 | 2/2003 | Ranum et al. |
| 6,623,927 B1 | 9/2003 | Brahmachari et al. |
| 6,653,466 B2 | 11/2003 | Matsuo |
| 6,653,467 B1 | 11/2003 | Matsuo et al. |
| 6,670,461 B1 | 12/2003 | Wengel et al. |
| 6,727,355 B2 | 4/2004 | Matsuo et al. |
| 6,794,192 B2 | 9/2004 | Parums et al. |
| 6,902,896 B2 | 6/2005 | Ranum et al. |
| 6,982,150 B2 | 1/2006 | Sheetz et al. |
| 7,001,994 B2 | 2/2006 | Zhu |
| 7,118,893 B2 | 10/2006 | Ranum et al. |
| 7,189,530 B2 | 3/2007 | Botstein et al. |
| 7,202,210 B2 | 4/2007 | Wolfman et al. |
| 7,250,404 B2 | 7/2007 | Felgner et al. |
| 7,355,018 B2 | 4/2008 | Glass |
| 7,405,193 B2 | 7/2008 | Lodish et al. |
| 7,442,782 B2 | 10/2008 | Ranum et al. |
| 7,514,551 B2 | 4/2009 | Rabbani et al. |
| 7,534,879 B2 | 5/2009 | van Deutekom |
| 7,589,189 B2 | 9/2009 | Ichiro et al. |
| 7,655,785 B1 | 2/2010 | Bentwich |
| 7,771,727 B2 | 8/2010 | Fuselier et al. |
| 7,807,816 B2 | 10/2010 | Wilton et al. |
| 7,902,160 B2 | 3/2011 | Matsuo et al. |
| 7,960,541 B2 | 6/2011 | Wilton et al. |
| 8,084,601 B2 | 12/2011 | Popplewell et al. |
| 8,232,384 B2 | 7/2012 | Wilton |
| 8,324,371 B2 | 12/2012 | Popplewell et al. |
| 9,528,109 B2 | 12/2016 | de Kimpe et al. |
| 10,533,171 B2 | 1/2020 | van Deutekom et al. |
| 11,034,956 B2 | 6/2021 | van Deutekom et al. |
| 2001/0056077 A1 | 12/2001 | Matsuo |
| 2002/0049173 A1 | 4/2002 | Bennett |
| 2002/0055481 A1 | 5/2002 | Matsuo et al. |
| 2002/0115824 A1 | 8/2002 | Engler et al. |
| 2002/0165150 A1 | 11/2002 | Ben-Sasson |
| 2003/0045488 A1 | 3/2003 | Brown et al. |
| 2003/0073215 A1 | 4/2003 | Baker et al. |
| 2003/0082763 A1 | 5/2003 | Baker et al. |
| 2003/0082766 A1 | 5/2003 | Baker et al. |
| 2003/0109476 A1 | 6/2003 | Ktniec et al. |
| 2003/0124523 A1 | 7/2003 | Asselbergs et al. |
| 2003/0130224 A1 | 7/2003 | Monahan et al. |
| 2003/0134790 A1 | 7/2003 | Langenfeld |
| 2003/0235845 A1 | 12/2003 | Van Ommen et al. |
| 2003/0236214 A1 | 12/2003 | Wolff et al. |
| 2004/0101852 A1 | 5/2004 | Bennett et al. |
| 2004/0132684 A1 | 7/2004 | Sanpath et al. |
| 2004/0226056 A1 | 11/2004 | Roch et al. |
| 2005/0096284 A1 | 5/2005 | McSwiggen |
| 2005/0222009 A1 | 10/2005 | Lamensdorf et al. |
| 2005/0246794 A1 | 11/2005 | Khvorova et al. |
| 2005/0277133 A1 | 12/2005 | McSwiggen |
| 2005/0288246 A1 | 12/2005 | Iversen et al. |
| 2006/0074034 A1 | 4/2006 | Collins et al. |
| 2006/0148740 A1 | 7/2006 | Platenburg |
| 2007/0082861 A1 | 4/2007 | Matsuo et al. |
| 2007/0141628 A1 | 6/2007 | Cummingham et al. |
| 2007/0275914 A1 | 11/2007 | Manoharan et al. |
| 2007/0292408 A1 | 12/2007 | Singh et al. |
| 2008/0015158 A1 | 1/2008 | Ichiro et al. |
| 2008/0039418 A1 | 2/2008 | Freier |
| 2008/0113351 A1 | 5/2008 | Naito et al. |
| 2008/0200409 A1 | 8/2008 | Wilson et al. |
| 2008/0207538 A1 | 8/2008 | Lawrence et al. |
| 2008/0249294 A1 | 10/2008 | Haeberli et al. |
| 2010/0081627 A1 | 4/2010 | Sampath et al. |
| 2010/0099750 A1 | 4/2010 | McSwiggen et al. |
| 2010/0130591 A1 | 5/2010 | Sazani et al. |
| 2010/0168212 A1 | 7/2010 | Popplewell et al. |
| 2010/0248239 A1 | 9/2010 | Highsmith, Jr. et al. |
| 2011/0015258 A1 | 1/2011 | Wilton et al. |
| 2011/0263682 A1 | 10/2011 | de Kimpe et al. |
| 2011/0294753 A1 | 12/2011 | DeKimpe et al. |
| 2012/0029057 A1 | 2/2012 | Wilton et al. |
| 2012/0029058 A1 | 2/2012 | Wilton et al. |
| 2012/0041050 A1 | 2/2012 | Wilton et al. |
| 2012/0108652 A1 | 5/2012 | Popplewell et al. |

FOREIGN PATENT DOCUMENTS

| | | |
|---|---|---|
| EP | 438512 A1 | 7/1991 |
| EP | 0 558 697 A1 | 1/1993 |
| EP | 558697 A1 | 9/1993 |
| EP | 0 614 977 B1 | 9/1994 |
| EP | 850300 A1 | 7/1998 |
| EP | 0 850 300 B1 | 10/1999 |
| EP | 1 015 628 A1 | 7/2000 |
| EP | 1 054 058 A1 | 11/2000 |
| EP | 1 133 993 A1 | 9/2001 |
| EP | 1 160 318 A2 | 12/2001 |
| EP | 1 191 097 A1 | 3/2002 |
| EP | 1 191 098 A2 | 3/2002 |
| EP | 1 380 644 A1 | 1/2004 |
| EP | 1 487 493 B1 | 12/2004 |
| EP | 1 501 931 A2 | 2/2005 |
| EP | 1 544 297 A2 | 6/2005 |
| EP | 438512 B2 | 7/2005 |
| EP | 1 567 667 A1 | 8/2005 |
| EP | 1 568 769 A1 | 8/2005 |
| EP | 1 495 769 A1 | 11/2005 |
| EP | 1 619 249 A1 | 1/2006 |
| EP | 1 015 628 B1 | 4/2006 |
| EP | 1 857 548 A1 | 11/2007 |
| EP | 1 567 667 B1 | 10/2008 |
| EP | 1 501 931 B1 | 11/2009 |
| JP | 2002-325582 A | 11/2002 |
| KR | 2003-0035047 A | 5/2003 |
| WO | WO 90/04040 A1 | 4/1990 |
| WO | WO 93/001286 A2 | 1/1993 |
| WO | WO 95/16718 A1 | 6/1995 |
| WO | WO 95/21184 A1 | 8/1995 |
| WO | WO 95/30774 A1 | 11/1995 |
| WO | WO 97/12899 A1 | 4/1997 |
| WO | WO 97/30067 A1 | 8/1997 |
| WO | WO 98/18920 A1 | 5/1998 |
| WO | WO 98/43993 A2 | 10/1998 |
| WO | WO 98/49345 A1 | 11/1998 |
| WO | WO 98/53804 A1 | 12/1998 |
| WO | WO 99/16871 A2 | 4/1999 |
| WO | WO 99/55857 A2 | 11/1999 |
| WO | WO 01/16312 A2 | 3/2001 |
| WO | WO 01/59102 A2 | 8/2001 |
| WO | WO 01/79283 A1 | 10/2001 |
| WO | WO 01/083503 A2 | 11/2001 |
| WO | WO 01/083695 A2 | 11/2001 |
| WO | WO 02/24906 A1 | 3/2002 |
| WO | WO 02/26812 A1 | 4/2002 |
| WO | WO 02/29006 A2 | 4/2002 |
| WO | WO 02/029056 A2 | 4/2002 |
| WO | WO 03/002739 A1 | 1/2003 |
| WO | WO 03/013437 A2 | 2/2003 |
| WO | WO 03/014145 A2 | 2/2003 |
| WO | WO 03/019476 A1 | 3/2003 |
| WO | WO 03/037172 A2 | 5/2003 |
| WO | WO 03/062258 A1 | 7/2003 |
| WO | WO 03/095647 A2 | 11/2003 |
| WO | WO 2004/011060 A2 | 2/2004 |
| WO | WO 2004/015106 A1 | 2/2004 |
| WO | WO 2004/016787 A1 | 2/2004 |
| WO | WO 2004/037854 A1 | 5/2004 |
| WO | WO 2004/047741 A2 | 6/2004 |
| WO | WO 2004/083432 A1 | 9/2004 |
| WO | WO 2004/083446 A2 | 9/2004 |
| WO | WO 2004/101787 A1 | 11/2004 |
| WO | WO 2004/108157 A1 | 12/2004 |
| WO | WO 2005/019453 A2 | 3/2005 |
| WO | WO 2005/023836 A2 | 3/2005 |
| WO | WO 2005/035550 A2 | 4/2005 |
| WO | WO 2005/085476 A1 | 9/2005 |
| WO | WO 2005/086768 A2 | 9/2005 |

(56) References Cited

FOREIGN PATENT DOCUMENTS

| | | |
|---|---|---|
| WO | WO 2005/105995 A2 | 11/2005 |
| WO | WO 2005/115439 A2 | 12/2005 |
| WO | WO 2005/116204 A1 | 12/2005 |
| WO | WO 2006/000057 A1 | 1/2006 |
| WO | WO 2006/007910 A1 | 1/2006 |
| WO | WO 2006/017522 A2 | 2/2006 |
| WO | WO 2006/031267 A2 | 3/2006 |
| WO | WO 2006/054262 A2 | 5/2006 |
| WO | WO 2006/083800 A2 | 8/2006 |
| WO | WO 2006/108052 A2 | 10/2006 |
| WO | WO 2006/112705 A2 | 10/2006 |
| WO | WO 2006/121960 A2 | 11/2006 |
| WO | WO 2007/002904 A2 | 1/2007 |
| WO | WO 2007/044362 A2 | 4/2007 |
| WO | WO 2007/089584 A2 | 8/2007 |
| WO | WO 2007/089611 A2 | 8/2007 |
| WO | WO 2007/117438 A2 | 10/2007 |
| WO | WO 2007/123402 A2 | 11/2007 |
| WO | WO 2007/135105 A1 | 11/2007 |
| WO | WO 2008/011170 A2 | 1/2008 |
| WO | WO 2008/018795 A1 | 2/2008 |
| WO | WO 2008/021136 A2 | 2/2008 |
| WO | WO 2008/039418 A2 | 4/2008 |
| WO | WO 2008/043561 A2 | 4/2008 |
| WO | WO 2008/103060 A1 | 8/2008 |
| WO | WO 2009/005793 A2 | 1/2009 |
| WO | WO 2009/008727 A2 | 1/2009 |
| WO | WO 2009/015384 A1 | 1/2009 |
| WO | WO 2009/054725 A2 | 4/2009 |
| WO | WO 2010/048586 A1 | 4/2010 |

OTHER PUBLICATIONS

Braun et al., "In vitro and in vivo effects of glucocorticoids on gene transfer to skeletal muscle." FEBS Lett. 454(3):277-282 (1999).
Bushby et al., "145th ENMC International Workshop: planning for an International Trial of Steroid Dosage Regimes in DMD (FOR DMD), Oct. 22-24, 2006, Naarden, The Netherlands," Neuromuscul. Disord. 17(5):423-428 (2007) (Epub Apr. 11, 2007).
Bushby et al., "Report on the 124th ENMC International Workshop. Treatment of Duchenne muscular dystrophy; defining the gold standards of management in the use of corticosteroids. Apr. 2-4, 2004, Naarden, The Netherlands," Neuromuscul. Disord. 14(8-9):526-534 (2004).
Chan et al. "Antisense oligonucleotides: from design to therapeutic application." Clin. Exp. Phannacol. Physiol. 33(5-6):533-540 (2006).
Cirak et al., "Exon skipping and dystrophin restoration in patients with Duchenne muscular dystrophy after systemic phosphoradiamidate morpholino oligomer treatment: an open-label, phase 2, dose-escalation study, " Lancet 378(9791):595-605 (2011).
EXONDYS 51™ prescribing information highlights (eteplirsen label) (dated Sep. 2016).
FDA News Release, "FDA grants accelerated approval to first drug for Duchenne muscular dystrophy." Sep. 19, 2016.
Goemans et al., "Systemic administration of PRO051 in Duchenne's muscular dystrophy," N. Engl. J. Med. 364(16):1513-1522 (2011) (Epub Mar. 23, 2011).
Goemans et al., "Comparison of ambulatory capacity and disease progression of Duchenne muscular dystrophy subjects enrolled in the drisapersen DMD114673 study with a matched natural history cohort of subjects on daily corticosteroids," Neuromuscul. Disord. 27(3):203-213 (2017) (Epub Nov. 25, 2016).
Hardiman et al. "Methylprednisolone selectively affects dystrophin expression in human muscle cultures," Neurology 43(2):342-345 (1993).
Hussein et al., "The effects of glucocorticoid therapy on the inflammatory and dendritic cells in muscular dystrophies," Int. J. Exp. Pathol. 87(6):451-461 (2006).
Khan, "Corticosteroid therapy in Duchenne muscular dystrophy," J. Neurol. Sci. 120(1):8-14 (1993).
Manning et al., "What has the mdx mouse model of Duchenne muscular dystrophy contributed to our understanding of this disease?" J. Muscle Res. Cell Motil. 36(2):155-167 (2015) (Epub Feb. 11, 2015).
Manzur et al., "Glucocorticoid corticosteroids for Duchenne muscular dystrophy (Review)," Cochrane Database of Systematic Reviews 1:1-74 (2008).
Merlini & Sabatelli. "Improving clinical trial design for Duchenne." BMC Neurology 15:153 (2015).
Moxley et al., "Practice parameter: corticosteroid treatment of Duchenne dystrophy: report of the Quality Standards Subcommittee of the American Academy of Neurology and the Practice Committee of the Child Neurology Society," Neurology 64(1):13-20 (2005).
Muntoni et al., "Steroids in Duchenne muscular dystrophy: from clinical trials to genomic research," Neuromuscul. Disord. 12 Suppl 1:S162-S165 (2002).
Muntoni et al., "128th ENMC International Workshop on 'Preclinical optimization and Phase I/II Clinical Trials Using Antisense Oligonucleotides in Duchenne Muscular Dystrophy' Oct. 22-24, 2004, Naarden. The Netherlands," Neuromuscul. Disord. 15(6):450-457 (2005).
Priorty document EP 07119351.0, filed Oct. 26, 2007.
Priority document U.S. Appl. No. 61/000,670, filed Oct. 26, 2007.
U.S. Food and Drug Administration (FDA) Briefing Document to the Peripheral and Central Nervous System Drugs Advisory Committee Meeting. Nov. 24, 2015, NDA 206031, Drisapersen.
USAN Council Statement for Drisapersen.
Wehling-Henricks et al., "Prednisolone decreases cellular adhesion molecules required for inflammatory cell infiltration in dystrophin-deficient skeletal muscle," Neuromuscul. Disord. 14:483-490 (2004).
Welch et al., "PTC 124 targets genetic disioders caused by nonsense mutations," 447(7140):87-91 (2007) (Epub Apr. 22, 2007).
Wuebbles et al., "Levels of α7 integrin and laminin-α2 are increased following prednisone treatment in the mdx mouse and GRMD dog models of Duchenne muscular dystrophy," Dis. Model Mech. 6(5):1175-1184 (2013).
Aartsma-Rus et al., "Antisense-induced exon skipping for duplications in Duchenne muscular dystrophy," BMC Med. Genet. 8:43 (2007).
Aartsma-Rus et al., "Antisense-induced multiexon skipping for Duchenne muscular dystrophy makes more sense," Am. J. Hum. Genet. 74(1):83-92 (2004) (Epub Dec. 16, 2003).
Aartsma-Rus et al., "Antisense-mediated exon skipping: a versatile tool with therapeutic and research applications," RNA 13(10):1609-1624 (2007) (Epub Aug. 7, 2007).
Aartsma-Rus et al., "Comparative analysis of antisense oligonucleotide analogs fortargeted DMD exon 46 skipping in muscle cells," Gene Ther. 11(18):1391-1398 (2004).
Aartsma-Rus et al., "Exploring the frontiers of therapeutic exon skipping for Duchenne muscular dystrophy by double targeting within one or multiple exons," Mol. Ther. 14(3):401-407 (2006) (Epub Jun. 6, 2006).
Aartsma-Rus et al., "Functional analysis of 114 exon-internal AONs for targeted DMD exon skipping: indication for steric hindrance of SR protein binding sites," Oligonucleotides 15(4):284-297 (2005).
Aartsma-Rus et al., "Guidelines for antisense oligonucleotide design and insight into splicemodulating mechanisms," Mol. Ther. Mar. 2009;17(3):548-553 (2009) (Epub Sep. 23, 2008).
Aartsma-Rus et al., "Targeted exon skipping as a potential gene correction therapy for Duchenne muscular dystrophy," Neuromuscul. Disord. 12 Suppl 1;S71-S77 (2002).
Aartsma-Rus et al., "Theoretic applicability of antisense-mediated exon skipping for Duchenne muscular dystrophy mutations," Hum. Mutat. 30(3):293-299 (2009).
Aartsma-Rus et al., "Therapeutic antisense-induced exon skipping in cultured muscle cells from six different DMD patients," Hum. Mol. Genet. 12(8):907-914 (2003).
Aartsma-Rus et al., "Therapeutic modulation of DMD splicing by blocking exonic splicing enhancer sites with antisense oligonucleotides," Ann. N.Y. Acad. Sci. 1082:74-76 (2006).

(56) References Cited

OTHER PUBLICATIONS

Abbs et al., "A convenient multiplex PCR system for the detection of dystrophin gene deletions: a comparative analysis with cDNA hybridisation shows mistypings by both methods," J. Med. Genet. 28(5):304-311 (1991).
Agrawal and Kandimalla, "Antisense therapeutics: is it as simple as complementary base recognition?" Mol. Med. Today 6(2):72-81 (2000).
Alter, "Systemic delivery of morpholino oligonucleotide restores dystrophin expression bodywide and improves dystrophic pathology," Nat. Med. 12(2):175-177 (2006) (Epub Jan. 29, 2006).
Anderson and Vargas, "Correlated NOS-Imu and myf5 expression by satellite cells in mdx mouse muscle regeneration during NOS manipulation and deflazacort treatment," Neuromuscul. Disord. 13(5):388-396 (2003).
Arap et al., "Steps toward mapping the human vasculature by phage display," Nat. Med. 8(2):121-127 (2002).
Arechavala-Gomeza et al., "Comparative analysis of antisense oligonucleotide sequences for targeted skipping of exon 51 during dystrophin pre-mRNA splicing in human muscle," Hum. Gene Ther. 18(9):798-810 (2007).
Arruda, "The role of immunosuppression in gene- and cell-based treatments for duchenne muscular dystrophy," Mol. Ther. 15(6):1040-1041 (2007).
Arzumanov et al., "Inhibition of HIV-1 Tat-dependent trans activation by steric block chimeric 2'-O-methyl/LNA oligoribonucleotides," Biochemistry 40(48):14645-14654 (2001).
Austin et al., "Cloning and characterization of alternatively spliced isoforms of Dp71," Hum. Mol. Genet 4(9):1475-1483 (1995).
Austin et al., "Expression and synthesis of alternatively spliced variants of Dp71 in adult human brain," Neuromuscul. Disord. 10(3):187-193 (2000).
Barabino et al., "Antisense probes targeted to an internal domain in U2 snRNP specifically inhibit the second step of pre-mRNA splicing," Nucleic Acids Res. 20(17):4457-4464 (1992).
Barany, "The ligase chain reaction in a PCR world," PCR Methods Appl. 1(1):5-16 (1991).
Bijvoet et al., "Recombinant human acid alpha-glucosidase: high level production in mouse milk, biochemical characteristics, correction of enzyme deficiency in GSDII KO mice," Hum. Mol. Genet. 7(11):1815-1824 (1998).
Bionity.COM News, Leiden University Medical Center and Prosensa B.V. Announce First Successful Clinical Study with RNA-based Therapeutic PR0051, dated Jan. 3, 2008, <http://www.bionity.com/news/e/76185>.
Biopharmiaceutiques, Merging Pharma & Biotech, Edition 48, Jan. 10, 2008. <http://www.biogharmaceutigues.com/ en/num>, visted Jan. 11, 2008.
Bremmer-Bout et al., "Targeted exon skipping in transgenic hDMD mice: A model for direct preclinical screening of human-specific antisense oligonucleotides," Mol. Ther. 10(2):232-240 (2004).
Brett et al., "EST comparison indicates 38% of human mRNAs contain possible alternative splice forms," FEBS Lett. 474(1):83-86 (2000).
Brown et al., "Gene delivery with synthetic (non viral) carriers," Int J Phann. 229(1-2):1-21 (2001). (Abstract).
Brown et al., "Structure and mutation of the dystrophin gene," Dystrophin: Gene, Protein and Cell Biology, Brown and Lucy, eds., Cambridge University Press, pp. 1-16 (1997).
Buck et al., "Design strategies and performance of custom DNA sequencing primers," BioTechniques 27(3):528-536 (1999).
Burnett et al., "DNA sequence-specific poly amides alleviate transcription inhibition associated with long GAA.TIC repeats in Friedreich's ataxia." Proc. Natl. Acad. Sci. U.S.A. 103(31):11497-11502 (2006) (Epub Jul. 20, 2006).
Caplen et al., "Rescue of polyglutamine-mediated cytotoxicity by double-stranded RNA-mediated RNA interference," Hum. Mol. Genet. 11(2):175-184 (2002).

Cartegni et al.. "Listening to silence and understanding nonsense, exonic mutations that affect splicing," Nat. Rev. Genet. 3(4):285-298 (2002).
Chaubourt et al., "Muscular nitric oxide synthase (muNOS) and utrophin," J. Physiol. Paris 96(1-2):43-52 (2002).
Coulter et al., "Identification of a new class of exonic splicing enhancers by in vivo selection," Mol. Cell. Biol. 17(4):2143-2150 (1997).
Crooke, In Basic Principles of Antisense Therapeutics, Handbook of Experimental Phamacology, vol. 131, Chapter 1, Springer-Verlag eds., New York, pp. 1-50 (1998).
Dahlqvist et al., "Functional Notch signaling is required for BMP4-induced inhibition of myogenic differentiation," Development 130(24):6089-6099 (2003).
De Angelis et al., "Chimeric snRNA molecules canying antisense sequences against the splice junctions of exon 51 of the dystrophin pre-mRNA induce exon skipping and restoration of a dystrophin synthesis in Delta 48-50 DMD cells," Proc. Natl. Acad. Sci. U.S.A. 99(14):9456-9461 (2002) (Epub Jun. 20, 2002).
Denny et al., "Oligo-riboprobes. Tools for in situ hybridization." Histochemistry 89(5):481-483 (1988).
Dickson et al., "Screening for antisense modulation of dystrophin pre-mRNA splicing," Neuromuscul. Disord. 12 Suppl 1:S67-S70 (2002).
Dirksen et al., "Mapping the SF2/ASF binding sites in the bovine growth hormone exonic splicing enhancer," J. Biol. Chem. 275(37):29170-29177 (2000).
Duboc et al., "Effect of perindopril on the onset and progression of left ventricular dysfunction in Duchenne muscular dystrophy," J. Am. Coll. Cardiol. 45(6):855-857 (2005).
Dunckley et al., "Modification of splicing in the dystrophin gene in cultured Mdx muscle cells by antisense oligoribonucleotides," Hum. Mol. Genet 7(7):1083-1090 (1998).
Dunckley et al., "Modulation of Splicing in the DMD Gene by Antisense Oligoribonucleotides," Nucleosides & Nucleotides 16(7-9):1665-1668 (1997).
El-Andaloussi et al., "Induction of splice correction by cell-penetrating peptide nucleic acids," J. Gene Med. 8(10):1262-1273 (2006).
Erba et al., "Structure, chromosome location, and expression of the human gamma-actin gene: differential evolution, location, and expression of the cytoskeletal beta- and gamma-actin genes," Mol. Cell. Biol. 8(4):1775-1789 (1988).
Errington et al., "Target selection for antisense oligonucleotide induced exon skipping in the dystrophin gene," J. Gene Med. 5(6):518-527 (2003).
European Office Action for Application No. EP 05076770.6, dated Jan. 29, 2007, 5 pages.
European Patent Office, Communication pursuant to Article 94(3) EPC, Application No. 10177969.2-1404, dated Aug. 22, 2013, 5 pages.
European Patent Office, Communication pursuant to Article 94(3) EPC, Application No. 10718717.1-1401, dated Dec. 19, 2013, 5 pages.
European Patent Office, Decision to refuse a European Patent application, Application No. 01979073.2-1402, dated Jan. 7, 2015, 10 pages.
European Search Report Annex for EP 03077205 dated Dec. 10, 2003, 1 page.
European Search Report Annex for EP 03077205 dated Oct. 12, 2003.
Extended European Search Report, Application No. 10177969.2-2401, dated Dec. 16, 2010, 5 pages.
Feener et al., "Alternative splicing of human dystrophin mRNA generates isoforms at the carboxy terminus," Nature 338(6215):509-511 (1989).
Fluiter, "In vivo tumor growth inhibition and biodistribution studies of locked nucleic acid (LNA) antisense oligonucleotides," Nucleic Acids Res. 31(3):953-962 (2003).
Fu et al., "An unstable triplet repeat in a gene related to myotonic muscular dystrophy," Science 255(5049):1256-1258 (1992).

(56) References Cited

OTHER PUBLICATIONS

Furling et al., "Viral vector producing antisense RNA restores myotonic dystrophy myoblast functions," Gene Ther. 10(9):795-802 (2003).
Galderisi et al., "Myotonic dystrophy: antisense oligonucleotide inhibition of DMPK gene expression in vito," Biochem. Biophys. Res. Commun. 221(3):750-754 (1996).
Garcia-Blanco et al., "Alternative splicing in disease and therapy," Nat. Biotechnol. 22(5):535-546 (2004).
GenBank accession No. AZ993191.1, 2M0278E12F mouse 10kb plasmid UUGC2M library Mus muscu genomic clone UUGC2M0278E12F, genomic survey sequence, entry created and last updated on Apr. 27, 2001.
GenBank accession No. EW162121.1, ifat0126_k17.yl fat Sus sciofa cDNA5-, mRNA sequence, entry created on Aug. 13, 2007, last updated on Mar. 3, 2011.
Ghosh et al., "Mannose 6-phosphate receptors: new twists in the tale," Nat. Rev. Mol. Cell Biol. 4(3):202-212 (2003).
Ginjaar et al., "Dystrophin nonsense mutation induces different levels of exon 29 skipping and leads to variable phenotypes within one BMD family," Eur. J. Hum. Genet. 8(10):793-796 (2000).
Gollins et al., "High-efficiency plasmid gene transfer into dystrophic muscle," Gene Ther. 10(6):504-512 (2003).
Grady, Early drug test shows promise in treating muscular dystrophy, International Herald Tribune, Jan. 3, 2008, Health & Science, p. 9.
Grady, Promising Dystrophy Drug Clears Early Test, The New York Times, Dec. 27, 2007.
Granchelli et al., "Pre-clinical screening of drugs using the mdx mouse," Neuromuscul. Disord. 10(4-5):235-239 (2000).
Grayaznov, "Oligonucleotide N3'-->P5' phosphoramidates as potential therapeutic agents," Biochim. Biophys. Acta 1489(1):131-140 (1999).
Hagiwara et al., "A novel point mutation (G-1 to T) in a 5' splice donor site of intron 13 of the dystrophin gene results in exon skipping and is responsible for Becker muscular dystrophy," Am. J. Hum. Genet 54(1):53-61 (1994).
Handa et al., "The AUUCU repeats responsible for spinocerebellar ataxia type 10 form unusual RNA hairpins," J. Biol. Chem. 280(32):29340-29345 (2005) (Epub Jun. 20, 2005).
Hansen, Product Development—Addition by subtraction, BioCentury, The Bernstein Report on BioBusiness, Jan. 7, 2008, p. A28 of 38.
Hasholt et al., "Antisense downregulation of mutant huntingtin in a cell model," J. Gene Med. 5(6):528-538 (2003).
Hassan, "Keys to the hidden treasures of the mannose 6-phosphate/insulin-like growth factor 2 receptor," Am. J. Pathol. 162(1):3-6 (2003).
Heemskerk et al., "In vivo comparison of 2'-O-methyl phosphorothioate and morpholino antisense oligonucleotides for Duchenne muscular dystrophy exon skipping." J. Gene Med. 11(3):257-266 (2009).
Highfield, Science: Boffin log, The Daily Telegraph, http://www.telegragh.co.uk/science/science-news/3320286/Science-Boffin-log.html, (Hope for Muscular Dystrophy Drug) Jan. 1, 2008.
Hoffman et al., "Somatic reversion/suppression of the mouse mdx phenotype in vivo," J. Neurol. Sci. 99(1):9-25 (1990).
Hoffman, "Skipping toward personalized molecular medicine," N. Engl. J. Med. 357(26):2719-2722 (2007).
Hussey et al., "Analysis of five Duchenne muscular dystrophy exons and gender determination using conventional duplex polymerase chain reaction on single cells," Mol. Hum. Reprod. 5(11):1089-1094 (1999).
Iezzi et al., "Deacetylase inhibitors increase muscle cell size by promoting myoblast recruitment and fusion through induction of follistatin," Dev. Cell 6(5):673-684 (2004).
Ikezawa et al., "Dystrophin gene analysis on 130 patients with Duchenne muscular dystrophy with a special reference to muscle mRNA analysis," Brain Dev. 20(3):165-168 (1998).
International Preliminary Examination Report, International Application No. PCT/NL01/00697, dated Aug. 1, 2002, 2 pages.
International Search Report for International Application No. PCT/NL2008/050673 dated Feb. 9, 2009.
International Search Report for International ApplicationNo. PCT/NL2006/000209, dated Oct. 5, 2006.
International Search Report for International Application No. PCT/EP2007/054842, dated Aug. 21, 2007, 3 pages.
International Search Report for International Application No. PCT/NL2010/050230 dated Jun. 24, 2010.
International Search Report, International ApplicationNo. PCT/NL2004/000196, dated Oct. 28, 2004, 8 pages.
International Search Report, International Application No. PCT/NL01/00697, dated Dec. 21, 2001, 2 pages.
Ito et al., "Purine-rich exon sequences are not necessarily splicing enhancer sequence in the dystrophin gene," Kobe J. Med. Sci. 47(5):193-202 (2001).
Karras et al., "Deletion of individual exons and induction of soluble murine interleukin-5 receptor-alpha chain expression through antisense oligonucleotide-mediated redirection of pre-mRNA splicing," Mol. Pharmacol. 58(2):380-387 (2000).
Kerr et al., "Bmp Regulates Skeletal Myogenesis at Two Steps," Molecular Cellular Proteomics, vol. 2, No. 9 (2003). (Abstract).
Kinali et al., "Local restoration of dystrophin expression with the morpholino oligomer AVI-4658 in Duchenne muscular dystrophy: a single-blind, placebo-controlled, dose-escalation, proof-of-concept study," Lancet Neurol. 8(10):918-928 (2009) (Epub Aug. 25, 2009).
Kurrek et al., "Design of antisense oligonucleotides stabilized by locked nucleic acids," Nucleic Acids Res. 30(9):1911-1918 (2002).
Langlois et al., "Hammerhead ribozyme-mediated destruction of nuclear foci in myotonic dystrophy myoblasts," Mol. Ther. 7(5 Pt 1):670-680 (2003).
Laptev et al., "Specific inhibition of expression of a human collagen gene (COLI A1) with modified antisense oligonucleotides. The most effective target sites are clustered in double-stranded regions of the predicted secondary structur for the mRNA," Biochemistry 33(36):11033-11039 (1994).
Lee et al., "Receptor mediated uptake of peptides that bind the human transferrin receptor," Eur. J. Biochem. 268(7):2004-2012 (2001).
Leiden University' Medical Center and ProSensa B.V. Announce New England Journal of Medicine Publication of First Successful Clinical Study with RNA-based Therapeutic PR0051 in Duchenne Muscular Dystrophy, Dec. 27, 2007.
Letter from Katholieke Universiteit Leuven to Dr. N. Goemans, Child Neurology, UZ dated Jan. 22, 2008, regarding a Phase I/II, open label, escalating dose, pilot study to assess the effect, safety, tolerability and pharmacokinetics of multiple subcutaneous of PR 051 in patients with Duchenne muscular dystrophy. PROOS 1-02 (translation provided).
Letter from Prosensa Therapeutics B.V to Federal Agency for Medicines and Health Products dated Jan. 9, 2008, regarding A Phase I/II, open label, escalating dose, pilot study to assess the effect, safety, tolerability and pharmacokinetics of multiple SC Doses of Drisapersen in Patients With Duchenne Muscular Dystrophy and to Assess the Potential for IV Dosing as an Alternative Route of Administration.
Lewin, "Genes VII," Nuclear Splicing, Chapert 22, pp. 704-705 (Jan. 2000).
Liu et al., "A mechanism for exon skipping caused by nonsense or missense mutations in BRCA 1 and other genes," Nat. Genet. 27(1):55-58 (2001).
Liu et al., "Identification of functional exonic splicing enhancer motifs recognized by individual SR proteins," Genes Dev. 12(13):1998-2012 (1998).
Liu et al., "Specific inhibition of Huntington's disease gene expression by siRNAs in cultured cells," Proc. Japan Acad., vol. 79B, Series B, No. 10, pp. 293-298 (2003).
Lu et al., "Functional amounts of dystrophin produced by skipping the mutated exon in the mdx dystrophic mouse," Nat. Med. 9(8):1009-1014 (2003) (Epub Jul. 6, 2003).
Lu et al., "Massive idiosyncratic exon skipping corrects the nonsense mutation in dystrophic mouse muscle and produces functional revertant fibersbv clonal expansion," J. Cell Biol. 148(5):985-996 (2000).

(56) References Cited

OTHER PUBLICATIONS

Lu et al., "Non-viral gene delivery in skeletal muscle: a protein factory," Gene Ther. 10(2):131-142 (2003).
Lu et al. "Systemic delivery of antisense oligoribonucleotide restores dystrophin expression in body-wide skeletal muscles," Proc. Natl. Acad. Sci. U.S.A. 102(1):198-203 (2005) (Epub Dec. 17, 2004).
LUMC and Prosensa report positive results of DMD study, Pharmaceutical Business Review Onlin, dated Dec. 28, 2007, http://www.pharmaceutical-business-review.com/article_news_print.asp?guid=8462FD44-F35D-4EOB-BC.
Mann et al., "Antisense-induced exon skipping and synthesis of dystrophin in the mdx mouse," Proc. Natl. Acad. Sci. U.S.A. 98(1):42-47 (2001).
Mann et al., "Improved antisense oligonucleotide induced exon skipping in the mdx mouse model of muscular dystrophy," J. Gene Med. 4(6):644-654 (2002).
Martiniuk et al., "Correction of glycogen storage disease type II by enzyme replacement with a recombinant human acid maltase produced by over-expression in a CHO-DHFR(neg) cell line," Biochem. Biophys. Res. Commun. 276(3):917-923 (2000).
Matsuo et al., "Duchenne/Becker muscular dystrophy: from molecular diagnosis to gene therapy," Brain Dev. 18(3):167-172 (1996).
Matsuo et al., "Exon skipping during splicing of dystrophin mRNA precursor due to an intraexon deletion in the dystrophin gene of Duchenne muscular dystrophy kobe," J. Clin. Invest. 87(6):2127-2131 (1991).
Matsuo et al.. "Partial deletion of a dystrophin gene leads to exon skipping and to loss of an intraexon hairpin structure from the predicted mRNA precursor," Biochem. Biophys. Res. Commun, 182(2):495-500 (1992).
McClorey et al., "Induced dystrophin exon skipping in human muscle explants," Neuromuscul. Disord. 16(9-10):583-590 (2006) (Epub Aug. 21, 2006).
Miller er al., "Antisense oligonucleotides: strategies for delivery," PSTT 1(9):377-386 (1998).
Monaco et al., "An explanation for the phenotypic differences between patients bearing partial deletions of the DMD locus," Genomics 2(1):90-95 (1988).
Moon et al., "Target site search and effective inhibition of leukaemic cell growth by a covalently closed multiple anti-sense oligonucleotide to c-myb," Biochem J. 346 Pt 2:295-303 (2000).
Munroe, "Antisense RNA inhibits splicing of pre-mRNA in vitro," EMBO J. 7(8):2523-2532 (1988).
Muntoni et al., "A mutation in the dystrophin gene selectively affecting dystrophin expression in the heart," J. Clin. Invest. 96(2):693-699 (1995).
Muntoni et al., 149th ENMC International Workshop and 1st TREAT-NMD Workshop on: "Planning Phase I/II Clinical trials using Systemically Delivered Antisense Oligonucleotides in Duchenne Muscular Dystrophy," Neuromuscular Disorders, 2008, pp. 268-275, vol. 18.
New Clinical Trial Results Show How Personalized Medicine Will Alter Treatment of Genetic Disorders, Medical News Today, Dec. 29, 2007, http://www.medicalnewstoday.com/article/92777.php.
Nishio et al., "Identification of a novel first exon in the human dystrophin gene and of a new promoter located more than 500 kb upstream of the nearest known promoter," J. Clin. Invest. 94(3):1037-1042 (1994).
O'Shaughnessy et al., "Superior survival with capecitabine plus docetaxel combination therapy in anthracycline-pretreated patients with advanced breast cancer: phase III trial results," J. Clin. Oncol. 20(12):2812-2823 (2002).
Opalinska et al., "Nucleic-acid therapeutics: basic principles and recent applications," Nat. Rev. Drug Discov. 1(7):503-514 (2002).
Oxford Dictionary of English, 2nd Edition, Revised, Oxford University Press, p. 158 (2005).
Partial European Search Report-Application No. EP 03077205, dated Dec. 10, 2003, 5 pages.
Patel and Amthor, "The fuction of Myostatin and strategies of Myostatin blockade-new hope for therapies aimed at promoting growth of skeletal muscle," Neuromuscul. Disord. 15(2):117-126 (2005) (Epub Jan. 11, 2005).
Patent Trial and Appeal Board, *University of Western Australia* (U.S. Pat. No. 8,455,636) v. *Academisch Ziekenhuis Leiden* (U.S. Appl. No. 11/233,495), Decision—Motions—37 C.F.R. § 41.125(a), 53 pages, entered Apr. 29, 2016 [Patent Interference No. 106,007 (RES)].
Patent Trial and Appeal Board, *University of Western Australia* (U.S. Pat. No. 8,455,636) v. *Academisch Ziekenhuis Leiden* (U.S. Appl. No. 11/233,495), Decision—Motions—37 C.F.R. § 41.125(a) (Substitute), 53 pages, entered May 12, 2016 [Patent Interference No. 106,007 (RES)].
Patent Trial and Appeal Board, *University of Western Australia* (U.S. Pat. No. 8,455,636) v. *Academisch Ziekenhuis Leiden* (U.S. Appl. No. 11/233,495), Judgment—Motions—37 C.F R. § 41.127, 3 pages, entered Apr. 29, 2016 [Patent Interference No. 106,007 (RES)].
Patent Trial and Appeal Board, *University of Western Australia* (U.S. Pat. No. 8,455,636) v. *Academisch Ziekenhuis Leiden* (U.S. Appl. No. 11/233,495), Redeclaration—37 C.F.R. § 41.203(c), 2 pages, entered Apr. 29, 2016 [Patent Interference No. 106,007 (RES)].
Patent Trial and Appeal Board, *University of Western Australia* (U.S. Pat. No. 8,455,636) v. *Academisch Ziekenhuis Leiden* (U.S. Appl. No. 11/233,495); *University of Western Australia* (U.S. Pat. Nos. 7,960,541 and 7,807,816) v. *Academisch Ziekenhuis Leiden* (U.S. Appl. No. 13/550,210), Order-Oral Argument—37 C.F.R. § 41.124, 2 pages, entered Mar. 29, 2016 [Patent Interference Nos. 106,007 (RES) and 106,008 (RES)].
Patent Trial and Appeal Board, *University of Western Australia* (U.S. Pat. No. 8,455,636) v. *Academisch Ziekenhuis Leiden* (U.S. Appl. No. 11/233,495), Withdrawal and Reissue of Decision on Motions, 2 pages, entered May 12, 2016 [Patent Interference No. 106,007 (RES)].
Politano et al., "Gentamicin administration in Duchenne patients with premature stop codon. Preliminary results," Acta Myol. 22(1):15-21 (2003).
Popplewell et al., "Design of phosphorodiamidate morpholino oligomers (PMOs) for the induction of exon skipping of the human DMD gene," Mol. Ther. 17(3):554-561 (2009) (Epub Jan. 13, 2009).
Pramano et al., "Induction of exon skipping of the dystrophin transcript in lymphoblastoid cells by transfecting an antisense oligodeoxynucleotide complementary to an exon recognition sequence," Biochem. Biophys. Res. Commun. 226(2):445-449 (1996).
Prosensa Technologies, B.V, Response to Communication pursuant to Rule 161(2) and Rule 162 EPC, European Patent Application No. 10718717.1, dated Jun. 4, 2012, 3 pages.
Prosensa Technologies, B.V, Response to Communication pursuant to Article 94(3) EPC, European Patent Application No. 10718717.1, dated Apr. 14, 2014, 3 pages.
Radley et al., "Duchenne muscular dystrophy: focus on pharmaceutical and nutritional interventions," Int. J. Biochem. Cell Biol. 39(3):469-477 (2007) (Epub Oct. 10, 2006).
Rando, "Oligonucleotide mediated gene therapy for muscular dystrophies," Neuromuscul. Disord. 12 Suppl 1:S55-S60 (2002).
Reuter, "Deflazacort vs. prednisone in Duchenne muscular dystrophy: trends of an ongoing study," Brain Dev. 17 Suppl:39-43 (1995).
Request for an Opinion under Section 74(A) in relation to Patent No. EP (UK) 1619249B in the name of Academisch Ziekenhuis Leden, dated Jun. 4, 2009.
Request for UK IPO Opinion (Section 74A & Rule 93)—EP (UK) 1619249 dated Mar. 9, 2009.
Reuser et al., "Uptake and stability of human and bovine acid alpha-glucosidase in cultured fibroblasts and skeletal muscle cells from glycogenosis type II patients," Exp Cell Res. (1):178-189 (1984).
Roberts et al., "Direct detection of dystrophin gene rearrangements by analysis of dystrophin mRNA in peripheral blood lymphocytes," Am. J. Hum. Genet. 49(2):298-310 (1991).

(56) References Cited

OTHER PUBLICATIONS

Roberts et al., "Direct diagnosis of carriers of Duchenne and Becker muscular dystrophy by amplification of lymphocyte RNA," Lancet 336(8730):1523-1526 (1990).
Roberts et al., "Exon structure of the human dystrophin gene," Genomics 16(2):536-538 (1993).
Roberts et al., "Searching for the 1 in 2,400,000: a review of dystrophin gene point mutations," Hum. Mutat. 4(1):1-11 (1994).
Rolland et al. "Overactivity of exercise-sensitive cation channels and their impaired modulation by IGF-1 in mdx native muscle fibers: beneficial effect of pentoxifylline," Neurobiol. Dis. 24(3):466-474 (2006) (Epub Sep. 28, 2006).
Rosen et al., "Combination chemotherapy and radiation therapy in the treatment of metastatic osteogenic sarcoma," Cancer 35(3):622-630 (1975).
Samoylova et al., "Elucidation of muscle-binding peptides by phage display screening," Muscle Nerve. 22(4):460-466 (1999).
Sarepta Therapeutics, Inc., Third party observations pursuant to Article 115 EPC and Rule 114 EPC against European patent application EP 10718717.1, dated Oct. 16, 2015, 19 pages.
Scanlon, "Anti-genes: siRNA, ribozymes and antisense," Curr. Pharm. Biotechnol. 5(5):415-420 (2004).
Ségalat et al., "CAPON expression in skeletal muscle is regulated by position, repair, Nos. activity, and dystrophy," Exp. Cell Res. 302(2):170-179 (2005).
Sertić et al., "Deletion screening of the Duchenne/Becker muscular dystrophy gene in Croatian population," Coll. Antropol. 21(1):151-156 (1997).
Shapiro et al., "RNA splice junctions of different classes of eukaryotes: sequence statistics and functional implications in gene expression," Nucleic Acids Res. 15(17):7155-7174 (1987).
Sherrat et al., "Exon skipping and translation in patients with frameshift deletions in the dystrophin gene," Am. J. Hum. Genet. 53(5):1007-1015 (1993).
Shiga et al., "Disruption of the splicing enhancer sequence within exon 27 of the dystrophin gene by a nonsense mutation induces partial skipping of the exon and is responsible for Becker muscular dystrophy," J. Clin. Invest. 100(9):2204-2210 (1997).
Simões-Wüst et al.. "Bcl-xl antisense treatment induces apoptosis in breast carcinoma cells," Int. J. Cancer 87(4):582-590 (2000).
Sironi et al., "The dystrophin gene is alternatively spliced throughout its coding sequence," FEBS Lett. 517(1-3):163-166 (2002).
Smith et al., "Muscle-specific peptide #5" (Mar. 23, 1999) http://www.ebi.ac.uk/cgi-bin/epo/epofetch?AAW89659 (downloaded Jul. 16, 2007, XP 002442550).
Spitali et al., "Exon skipping-mediated dystrophin reading frame restoration for small mutations," Hum. Mutat. 30(11):1527-1534 (2009).
Sterrenburg et al., "Gene expression profiling highlights defective myogenesis in DMD patients and a possible role for bone morphogenetic protein 4," Neurobiol. Dis. 23(1):228-236 (2006) (Epub May 6, 2006).
Surono et al., "Chimeric RNA/ethylene-bridged nucleic acids promote dystrophin expression in myocytes of duchenne muscular dystrophy by inducing skipping of the nonsense mutation-encoding exon," Hum. Gene Ther. 15(8):749-757 (2004).
Surono et al., "Six novel transcripts that remove a huge intron ranging from 250 to 800 kb are produced by alternative splicing of the 5' region of the dystrophin gene in human skeletal muscle," Biochem Biophys Res Commun. 239(3):895-899 (1997).
Suter et al., "Double-target antisense U 7 snRNAs promote efficient skipping of an abenant exon in three human beta-thalassemic mutations," Hum. Mol. Genet. 8(13):2415-2423 (1999).
Suwanmanee et al., "Restoration of human beta-globin gene expression in murine and human IVS2-654 thalassemic erythroid cells by free uptake of antisense oligonucleotides," Mol. Pharmacol. 62(3):545-553 (2002).
Takeshima et al., "Intravenous Infusion of an Antisense Oligonucleotide Results in Exon Skipping in Muscle Dystrophin mRNA of Duchenne Muscular Dystrophy," Pediatric Res. 59(5):690-694 (2006).

Takeshima et al., "Modulation of in vitro splicing of the upstream intron by modifying an intraexon sequence which is deleted from the dystrophin gene in dystrophin Kobe," J. Clin Invest. 95(2):515-520 (1995).
Takeshima et al., "Oligonucleotides against a splicing enhancer sequence led to dystrophin production in muscle cells from a Duchenne muscular dystrophy patient," Brain Dev. 23(8):788-790 (2001).
Tanaka et al., "Polypurine sequences within a downstream exon function as a splicing enhancer," Mol. Cell. Biol. 14(2):1347-1354 (1994).
Tennyson et al., "The human dystrophin gene requires 16 hours to be transcribed and is cotranscriptionally spliced," Nat. Genet. 9(2):184-190 (1995).
Thanh et al., "Characterization of revertant muscle fibers in Duchenne muscular dystrophy, using exon-specific monoclonal antibodies against dystrophin," Am. J. Hum. Genet. 56(3):725-731 (1995).
Tian and Kole, "Selection of novel exon recognition elements from a pool of random sequences," Mol. Cell. Biol. 15(11):6291-6298 (1995).
TREAT-NMD Neuromuscular Network, Newsletter 24, Jan. 11, 2008, 6 pages.
Tsuchida, "The role of myostatin and bone morphogenetic proteins in muscular disorders," Expert Opin. Biol. Ther. 6(2):147-154 (2006).
University of Western Australia, *University of Western Australia v. Academisch Ziekenhuis Leiden*, Motion of Appellant University of Western Australia to Stay Appeal Pending Appeals in Two Related Interferences, Document 4-1, 7 pages, entered May 6, 2016 [Patent Interference No. 106,013] [Civil Action No. 2016-1937].
USPTO Office Action for U.S. Appl. No. 11/233,507, dated Jun. 15, 2007.
USPTO Office Action for U.S. Appl. No. 11/233,507, dated Mar. 19, 2008.
USPTO Office Action for U.S. Appl. No. 10/395,031, dated Apr. 2, 2009.
USPTO Office Action for U.S. Appl. No. 10/395,031, dated Aug. 23, 2007.
USPTO Office Action for U.S. Appl. No. 10/395,031, dated Feb. 6, 2006.
USPTO Office Action for U.S. Appl. No. 10/395,031, dated Jul. 8, 2005.
USPTO Office Action for U.S. Appl. No. 10/395,031, dated May 30, 2008.
USPTO Office Action for U.S. Appl. No. 10/395,031, dated Nov. 30, 2006.
USPTO Office Action for U.S. Appl. No. 11/233,495, dated Dec. 1, 2008.
USPTO Office Action for U.S. Appl. No. 11/233,507, dated Nov. 12, 2008.
Van Deutekom et al., "Advances in Duchenne muscular dystrophy gene therapy," Nat. Rev. Genet. 4(10):774-783 (2003).
Van Deutekom et al., "Antisense-induced exon skipping restores dystrophin expression in DMD patient derived muscle cells," Hum. Mol. Genet. 10(15):1547-1554 (2001).
Van Deutekom et al., "Local dystrophin restoration with antisense oligonucleotide PRO051," N. Engl. J. Med. 357(26):2677-2686 (2007).
Van Ommen et al., "The therapeutic potential of antisense-mediated exon skipping," Curr. Opin. Mol. Ther. 10(2):140-149 (2008).
Van Vliet et al., "Assessment of the feasibility of exon 45-55 multiexon skipping for Duchenne muscular dystrophy," BMC Med. Genet. 9:105 (2008).
Varani et al., "The G x U wobble base pair. A fundamental building block of RNA structure crucial to RNA function in diverse biological systems," EMBO Rep. 1(1):18-23 (2000).
Verreault et al., "Gene silencing in the development of personalized cancer treatment: the targets, the agents and the delivery systems," Curr. Gene Ther. 6(4):505-533 (2006).
Vickers et al., "Efficient reduction of target RNAs by small interfering RNA and RNase H-dependent antisense agents. A comparative analysis," J. Biol. Chem. 278(9):7108-7118 (2003) (Epub Dec. 23, 2002).

(56) References Cited

OTHER PUBLICATIONS

Wang et al., "Adeno-associated virus vector canying human minidystrophin genes effectively ameliorates muscular dystrophy in mdx mouse model," Proc. Natl. Acad. Sci. U.S.A. 97(25):13714-13719 (2000).
Watakabe et al., "The role of exon sequences in splice site selection," Genes Dev. 7(3):407-418 (1993).
Weisbart et al., "Cell type specific targeted intracellular delivery into muscle of a monoclonal antibody that binds myosin IIb," Mol. Immunol. 39(13):783-789 (2003). (Abstract).
Wells et al., "Enhanced in vivo delivery of antisense oligonucleotides to restore dystrophin expression in adult mdx mouse muscle," FEBS Lett. 552(2-3):145-149 (2003).
Wenk et al., "Quantitation of Mr 46000 and Mr 300000 mannose 6-phosphate receptors in human cells and tissues," Biochem. Int. 23(4):723-731 (1991).
Wheway et al., "The dystrophin lymphocyte promoter revisited: 4.5-megabase intron, or artifact?" Neuromuscul. Disord. 13(1):17-20 (2003).
Wilton et al., "Antisense oligonucleotide-induced exon skipping across the human dystrophin gene transcript," Mol. Ther. 15(7):1288-1296 (2007) (Epub Feb. 6, 2007).
Wilton et al., "Antisense oligonucleotides, exon skipping and the dystrophin gene transcript," Acta Myol. 24(3):222-229 (2005).
Wilton et al., "Specific removal of the nonsense mutation from the mdx dystrophin mRNA using antisense oligonucleotides," Neuromuscul. Disord. 9(5):330-338 (1999).
Yen et al., "Sequence-specific cleavage of Huntingtin mRNA by catalytic DNA," Ann. Neurol. 46(3):366-373 (1999).
Yin et al., "Effective exon skipping and restoration of dystrophin expression by peptide nucleic acid antisense oligonucleotides in mix mice," Mol. Ther. 16(1):38-45 (2008) (Epub Oct. 30, 2007).
Yokota et al., "Efficacy of systemic morpholino exon-skipping in Duchenne dystrophy dogs," Ann. Neurol. 65(6):667-676 (2009).
Zhang et al., "Efficient expression of naked dna delivered intraarterially to limb muscles of nonhuman primates," Hum. Gene Ther. 12(4):427-438 (2001).
Zhou et al., "Current understanding of dystrophin-related muscular dystrophy and therapeutic challenges ahead," Chin. Med. J. (Engl). 119(16):1381-1391 (2006).
Chaires et al. eds , Methods in Enzymology: Drug-Nucleic Acid Interactions, Academic Press. San Diego, CA, 340:488-493 (2001).
Reich et al., "Sequence-dependence effects on DNA stability resulting from guanosine replacements by inosine." Nucleic Acids Research 22(11): 2089-2093 (1994).

SEQUENCE LISTING

<160> NUMBER OF SEQ ID NOS: 577

<210> SEQ ID NO 1
<211> LENGTH: 3685
<212> TYPE: PRT
<213> ORGANISM: Homo sapiens

<400> SEQUENCE: 1

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

```
Asn Ile Ile Leu His Trp Gln Val Lys Asn Val Met Lys Asn Ile Met
            115                 120                 125
Ala Gly Leu Gln Gln Thr Asn Ser Glu Lys Ile Leu Leu Ser Trp Val
130                 135                 140
Arg Gln Ser Thr Arg Asn Tyr Pro Gln Val Asn Val Ile Asn Phe Thr
145                 150                 155                 160
Thr Ser Trp Ser Asp Gly Leu Ala Leu Asn Ala Leu Ile His Ser His
                165                 170                 175
Arg Pro Asp Leu Phe Asp Trp Asn Ser Val Val Cys Gln Gln Ser Ala
                180                 185                 190
Thr Gln Arg Leu Glu His Ala Phe Asn Ile Ala Arg Tyr Gln Leu Gly
                195                 200                 205
Ile Glu Lys Leu Leu Asp Pro Glu Asp Val Asp Thr Thr Tyr Pro Asp
210                 215                 220
Lys Lys Ser Ile Leu Met Tyr Ile Thr Ser Leu Phe Gln Val Leu Pro
225                 230                 235                 240
Gln Gln Val Ser Ile Glu Ala Ile Gln Glu Val Glu Met Leu Pro Arg
                245                 250                 255
Pro Pro Lys Val Thr Lys Glu Glu His Phe Gln Leu His His Gln Met
            260                 265                 270
His Tyr Ser Gln Gln Ile Thr Val Ser Leu Ala Gln Gly Tyr Glu Arg
        275                 280                 285
Thr Ser Ser Pro Lys Pro Arg Phe Lys Ser Tyr Ala Tyr Thr Gln Ala
        290                 295                 300
Ala Tyr Val Thr Thr Ser Asp Pro Thr Arg Ser Pro Phe Pro Ser Gln
305                 310                 315                 320
His Leu Glu Ala Pro Glu Asp Lys Ser Phe Gly Ser Ser Leu Met Glu
                325                 330                 335
Ser Glu Val Asn Leu Asp Arg Tyr Gln Thr Ala Leu Glu Glu Val Leu
                340                 345                 350
Ser Trp Leu Leu Ser Ala Glu Asp Thr Leu Gln Ala Gln Gly Glu Ile
            355                 360                 365
Ser Asn Asp Val Glu Val Val Lys Asp Gln Phe His Thr His Glu Gly
        370                 375                 380
Tyr Met Met Asp Leu Thr Ala His Gln Gly Arg Val Gly Asn Ile Leu
385                 390                 395                 400
Gln Leu Gly Ser Lys Leu Ile Gly Thr Gly Lys Leu Ser Glu Asp Glu
                405                 410                 415
Glu Thr Glu Val Gln Glu Gln Met Asn Leu Leu Asn Ser Arg Trp Glu
            420                 425                 430
Cys Leu Arg Val Ala Ser Met Glu Lys Gln Ser Asn Leu His Arg Val
        435                 440                 445
Leu Met Asp Leu Gln Asn Gln Lys Leu Lys Glu Leu Asn Asp Trp Leu
        450                 455                 460
Thr Lys Thr Glu Glu Arg Thr Arg Lys Met Glu Glu Pro Leu Gly
465                 470                 475                 480
Pro Asp Leu Glu Asp Leu Lys Arg Gln Val Gln Gln His Lys Val Leu
                485                 490                 495
Gln Glu Asp Leu Glu Gln Glu Gln Val Arg Val Asn Ser Leu Thr His
            500                 505                 510
Met Val Val Val Asp Glu Ser Ser Gly Asp His Ala Thr Ala Ala
        515                 520                 525
```

```
Leu Glu Glu Gln Leu Lys Val Leu Gly Asp Arg Trp Ala Asn Ile Cys
        530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
                565                 570                 575

Glu Lys Glu Asp Ala Val Asn Lys Ile His Thr Thr Gly Phe Lys Asp
                580                 585                 590

Gln Asn Glu Met Leu Ser Ser Leu Gln Lys Leu Ala Val Leu Lys Ala
        595                 600                 605

Asp Leu Glu Lys Lys Gln Ser Met Gly Lys Leu Tyr Ser Leu Lys
610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                645                 650                 655

Lys Leu Glu Lys Ser Thr Ala Gln Ile Ser Gln Ala Val Thr Thr Thr
                660                 665                 670

Gln Pro Ser Leu Thr Gln Thr Thr Val Met Glu Thr Val Thr Thr Val
        675                 680                 685

Thr Thr Arg Glu Gln Ile Leu Val Lys His Ala Gln Glu Glu Leu Pro
        690                 695                 700

Pro Pro Pro Pro Gln Lys Lys Arg Gln Ile Thr Val Asp Ser Glu Ile
705                 710                 715                 720

Arg Lys Arg Leu Asp Val Asp Ile Thr Glu Leu His Ser Trp Ile Thr
                725                 730                 735

Arg Ser Glu Ala Val Leu Gln Ser Pro Glu Phe Ala Ile Phe Arg Lys
                740                 745                 750

Glu Gly Asn Phe Ser Asp Leu Lys Glu Lys Val Asn Ala Ile Glu Arg
        755                 760                 765

Glu Lys Ala Glu Lys Phe Arg Lys Leu Gln Asp Ala Ser Arg Ser Ala
770                 775                 780

Gln Ala Leu Val Glu Gln Met Val Asn Glu Gly Val Asn Ala Asp Ser
785                 790                 795                 800

Ile Lys Gln Ala Ser Glu Gln Leu Asn Ser Arg Trp Ile Glu Phe Cys
                805                 810                 815

Gln Leu Leu Ser Glu Arg Leu Asn Trp Leu Glu Tyr Gln Asn Asn Ile
                820                 825                 830

Ile Ala Phe Tyr Asn Gln Leu Gln Gln Leu Glu Gln Met Thr Thr Thr
        835                 840                 845

Ala Glu Asn Trp Leu Lys Ile Gln Pro Thr Thr Pro Ser Glu Pro Thr
850                 855                 860

Ala Ile Lys Ser Gln Leu Lys Ile Cys Lys Asp Glu Val Asn Arg Leu
865                 870                 875                 880

Ser Gly Leu Gln Pro Gln Ile Glu Arg Leu Lys Ile Gln Ser Ile Ala
                885                 890                 895

Leu Lys Glu Lys Gly Gln Gly Pro Met Phe Leu Asp Ala Asp Phe Val
        900                 905                 910

Ala Phe Thr Asn His Phe Lys Gln Val Phe Ser Asp Val Gln Ala Arg
        915                 920                 925

Glu Lys Glu Leu Gln Thr Ile Phe Asp Thr Leu Pro Pro Met Arg Tyr
930                 935                 940
```

```
Gln Glu Thr Met Ser Ala Ile Arg Thr Trp Val Gln Gln Ser Glu Thr
945                 950                 955                 960

Lys Leu Ser Ile Pro Gln Leu Ser Val Thr Asp Tyr Glu Ile Met Glu
            965                 970                 975

Gln Arg Leu Gly Glu Leu Gln Ala Leu Gln Ser Ser Leu Gln Glu Gln
        980                 985                 990

Gln Ser Gly Leu Tyr Tyr Leu Ser Thr Thr Val Lys Glu Met Ser Lys
        995                 1000                1005

Lys Ala Pro Ser Glu Ile Ser Arg Lys Tyr Gln Ser Glu Phe Glu
    1010                1015                1020

Glu Ile Glu Gly Arg Trp Lys Lys Leu Ser Ser Gln Leu Val Glu
    1025                1030                1035

His Cys Gln Lys Leu Glu Glu Gln Met Asn Lys Leu Arg Lys Ile
    1040                1045                1050

Gln Asn His Ile Gln Thr Leu Lys Lys Trp Met Ala Glu Val Asp
    1055                1060                1065

Val Phe Leu Lys Glu Glu Trp Pro Ala Leu Gly Asp Ser Glu Ile
    1070                1075                1080

Leu Lys Lys Gln Leu Lys Gln Cys Arg Leu Leu Val Ser Asp Ile
    1085                1090                1095

Gln Thr Ile Gln Pro Ser Leu Asn Ser Val Asn Glu Gly Gly Gln
    1100                1105                1110

Lys Ile Lys Asn Glu Ala Glu Pro Glu Phe Ala Ser Arg Leu Glu
    1115                1120                1125

Thr Glu Leu Lys Glu Leu Asn Thr Gln Trp Asp His Met Cys Gln
    1130                1135                1140

Gln Val Tyr Ala Arg Lys Glu Ala Leu Lys Gly Gly Leu Glu Lys
    1145                1150                1155

Thr Val Ser Leu Gln Lys Asp Leu Ser Glu Met His Glu Trp Met
    1160                1165                1170

Thr Gln Ala Glu Glu Glu Tyr Leu Glu Arg Asp Phe Glu Tyr Lys
    1175                1180                1185

Thr Pro Asp Glu Leu Gln Lys Ala Val Glu Glu Met Lys Arg Ala
    1190                1195                1200

Lys Glu Glu Ala Gln Gln Lys Glu Ala Lys Val Lys Leu Leu Thr
    1205                1210                1215

Glu Ser Val Asn Ser Val Ile Ala Gln Ala Pro Pro Val Ala Gln
    1220                1225                1230

Glu Ala Leu Lys Lys Glu Leu Glu Thr Leu Thr Thr Asn Tyr Gln
    1235                1240                1245

Trp Leu Cys Thr Arg Leu Asn Gly Lys Cys Lys Thr Leu Glu Glu
    1250                1255                1260

Val Trp Ala Cys Trp His Glu Leu Leu Ser Tyr Leu Glu Lys Ala
    1265                1270                1275

Asn Lys Trp Leu Asn Glu Val Glu Phe Lys Leu Lys Thr Thr Glu
    1280                1285                1290

Asn Ile Pro Gly Gly Ala Glu Glu Ile Ser Glu Val Leu Asp Ser
    1295                1300                1305

Leu Glu Asn Leu Met Arg His Ser Glu Asp Asn Pro Asn Gln Ile
    1310                1315                1320

Arg Ile Leu Ala Gln Thr Leu Thr Asp Gly Gly Val Met Asp Glu
    1325                1330                1335
```

```
Leu Ile Asn Glu Glu Leu Glu Thr Phe Asn Ser Arg Trp Arg Glu
1340                1345                1350

Leu His Glu Glu Ala Val Arg Arg Gln Lys Leu Leu Glu Gln Ser
1355                1360                1365

Ile Gln Ser Ala Gln Glu Thr Glu Lys Ser Leu His Leu Ile Gln
1370                1375                1380

Glu Ser Leu Thr Phe Ile Asp Lys Gln Leu Ala Ala Tyr Ile Ala
1385                1390                1395

Asp Lys Val Asp Ala Ala Gln Met Pro Gln Glu Ala Gln Lys Ile
1400                1405                1410

Gln Ser Asp Leu Thr Ser His Glu Ile Ser Leu Glu Glu Met Lys
1415                1420                1425

Lys His Asn Gln Gly Lys Glu Ala Ala Gln Arg Val Leu Ser Gln
1430                1435                1440

Ile Asp Val Ala Gln Lys Lys Leu Gln Asp Val Ser Met Lys Phe
1445                1450                1455

Arg Leu Phe Gln Lys Pro Ala Asn Phe Glu Gln Arg Leu Gln Glu
1460                1465                1470

Ser Lys Met Ile Leu Asp Glu Val Lys Met His Leu Pro Ala Leu
1475                1480                1485

Glu Thr Lys Ser Val Glu Gln Glu Val Val Gln Ser Gln Leu Asn
1490                1495                1500

His Cys Val Asn Leu Tyr Lys Ser Leu Ser Glu Val Lys Ser Glu
1505                1510                1515

Val Glu Met Val Ile Lys Thr Gly Arg Gln Ile Val Gln Lys Lys
1520                1525                1530

Gln Thr Glu Asn Pro Lys Glu Leu Asp Glu Arg Val Thr Ala Leu
1535                1540                1545

Lys Leu His Tyr Asn Glu Leu Gly Ala Lys Val Thr Glu Arg Lys
1550                1555                1560

Gln Gln Leu Glu Lys Cys Leu Lys Leu Ser Arg Lys Met Arg Lys
1565                1570                1575

Glu Met Asn Val Leu Thr Glu Trp Leu Ala Ala Thr Asp Met Glu
1580                1585                1590

Leu Thr Lys Arg Ser Ala Val Glu Gly Met Pro Ser Asn Leu Asp
1595                1600                1605

Ser Glu Val Ala Trp Gly Lys Ala Thr Gln Lys Glu Ile Glu Lys
1610                1615                1620

Gln Lys Val His Leu Lys Ser Ile Thr Glu Val Gly Glu Ala Leu
1625                1630                1635

Lys Thr Val Leu Gly Lys Lys Glu Thr Leu Val Glu Asp Lys Leu
1640                1645                1650

Ser Leu Leu Asn Ser Asn Trp Ile Ala Val Thr Ser Arg Ala Glu
1655                1660                1665

Glu Trp Leu Asn Leu Leu Leu Glu Tyr Gln Lys His Met Glu Thr
1670                1675                1680

Phe Asp Gln Asn Val Asp His Ile Thr Lys Trp Ile Ile Gln Ala
1685                1690                1695

Asp Thr Leu Leu Asp Glu Ser Glu Lys Lys Lys Pro Gln Gln Lys
1700                1705                1710

Glu Asp Val Leu Lys Arg Leu Lys Ala Glu Leu Asn Asp Ile Arg
1715                1720                1725
```

```
Pro Lys Val Asp Ser Thr Arg Asp Gln Ala Ala Asn Leu Met Ala
    1730            1735            1740

Asn Arg Gly Asp His Cys Arg Lys Leu Val Glu Pro Gln Ile Ser
    1745            1750            1755

Glu Leu Asn His Arg Phe Ala Ala Ile Ser His Arg Ile Lys Thr
    1760            1765            1770

Gly Lys Ala Ser Ile Pro Leu Lys Glu Leu Glu Gln Phe Asn Ser
    1775            1780            1785

Asp Ile Gln Lys Leu Leu Glu Pro Leu Glu Ala Glu Ile Gln Gln
    1790            1795            1800

Gly Val Asn Leu Lys Glu Glu Asp Phe Asn Lys Asp Met Asn Glu
    1805            1810            1815

Asp Asn Glu Gly Thr Val Lys Glu Leu Leu Gln Arg Gly Asp Asn
    1820            1825            1830

Leu Gln Gln Arg Ile Thr Asp Glu Arg Lys Arg Glu Glu Ile Lys
    1835            1840            1845

Ile Lys Gln Gln Leu Leu Gln Thr Lys His Asn Ala Leu Lys Asp
    1850            1855            1860

Leu Arg Ser Gln Arg Arg Lys Lys Ala Leu Glu Ile Ser His Gln
    1865            1870            1875

Trp Tyr Gln Tyr Lys Arg Gln Ala Asp Asp Leu Leu Lys Cys Leu
    1880            1885            1890

Asp Asp Ile Glu Lys Lys Leu Ala Ser Leu Pro Glu Pro Arg Asp
    1895            1900            1905

Glu Arg Lys Ile Lys Glu Ile Asp Arg Glu Leu Gln Lys Lys Lys
    1910            1915            1920

Glu Glu Leu Asn Ala Val Arg Arg Gln Ala Glu Gly Leu Ser Glu
    1925            1930            1935

Asp Gly Ala Ala Met Ala Val Glu Pro Thr Gln Ile Gln Leu Ser
    1940            1945            1950

Lys Arg Trp Arg Glu Ile Glu Ser Lys Phe Ala Gln Phe Arg Arg
    1955            1960            1965

Leu Asn Phe Ala Gln Ile His Thr Val Arg Glu Glu Thr Met Met
    1970            1975            1980

Val Met Thr Glu Asp Met Pro Leu Glu Ile Ser Tyr Val Pro Ser
    1985            1990            1995

Thr Tyr Leu Thr Glu Ile Thr His Val Ser Gln Ala Leu Leu Glu
    2000            2005            2010

Val Glu Gln Leu Leu Asn Ala Pro Asp Leu Cys Ala Lys Asp Phe
    2015            2020            2025

Glu Asp Leu Phe Lys Gln Glu Glu Ser Leu Lys Asn Ile Lys Asp
    2030            2035            2040

Ser Leu Gln Gln Ser Ser Gly Arg Ile Asp Ile Ile His Ser Lys
    2045            2050            2055

Lys Thr Ala Ala Leu Gln Ser Ala Thr Pro Val Glu Arg Val Lys
    2060            2065            2070

Leu Gln Glu Ala Leu Ser Gln Leu Asp Phe Gln Trp Glu Lys Val
    2075            2080            2085

Asn Lys Met Tyr Lys Asp Arg Gln Gly Arg Phe Asp Arg Ser Val
    2090            2095            2100

Glu Lys Trp Arg Arg Phe His Tyr Asp Ile Lys Ile Phe Asn Gln
    2105            2110            2115
```

-continued

Trp Leu Thr Glu Ala Glu Gln Phe Leu Arg Lys Thr Gln Ile Pro
2120             2125                 2130

Glu Asn Trp Glu His Ala Lys Tyr Lys Trp Tyr Leu Lys Glu Leu
2135             2140                 2145

Gln Asp Gly Ile Gly Gln Arg Gln Thr Val Val Arg Thr Leu Asn
2150             2155                 2160

Ala Thr Gly Glu Glu Ile Ile Gln Gln Ser Ser Lys Thr Asp Ala
2165             2170                 2175

Ser Ile Leu Gln Glu Lys Leu Gly Ser Leu Asn Leu Arg Trp Gln
2180             2185                 2190

Glu Val Cys Lys Gln Leu Ser Asp Arg Lys Lys Arg Leu Glu Glu
2195             2200                 2205

Gln Lys Asn Ile Leu Ser Glu Phe Gln Arg Asp Leu Asn Glu Phe
2210             2215                 2220

Val Leu Trp Leu Glu Glu Ala Asp Asn Ile Ala Ser Ile Pro Leu
2225             2230                 2235

Glu Pro Gly Lys Glu Gln Gln Leu Lys Glu Lys Leu Glu Gln Val
2240             2245                 2250

Lys Leu Leu Val Glu Glu Leu Pro Leu Arg Gln Gly Ile Leu Lys
2255             2260                 2265

Gln Leu Asn Glu Thr Gly Gly Pro Val Leu Val Ser Ala Pro Ile
2270             2275                 2280

Ser Pro Glu Glu Gln Asp Lys Leu Glu Asn Lys Leu Lys Gln Thr
2285             2290                 2295

Asn Leu Gln Trp Ile Lys Val Ser Arg Ala Leu Pro Glu Lys Gln
2300             2305                 2310

Gly Glu Ile Glu Ala Gln Ile Lys Asp Leu Gly Gln Leu Glu Lys
2315             2320                 2325

Lys Leu Glu Asp Leu Glu Glu Gln Leu Asn His Leu Leu Leu Trp
2330             2335                 2340

Leu Ser Pro Ile Arg Asn Gln Leu Glu Ile Tyr Asn Gln Pro Asn
2345             2350                 2355

Gln Glu Gly Pro Phe Asp Val Gln Glu Thr Glu Ile Ala Val Gln
2360             2365                 2370

Ala Lys Gln Pro Asp Val Glu Glu Ile Leu Ser Lys Gly Gln His
2375             2380                 2385

Leu Tyr Lys Glu Lys Pro Ala Thr Gln Pro Val Lys Arg Lys Leu
2390             2395                 2400

Glu Asp Leu Ser Ser Glu Trp Lys Ala Val Asn Arg Leu Leu Gln
2405             2410                 2415

Glu Leu Arg Ala Lys Gln Pro Asp Leu Ala Pro Gly Leu Thr Thr
2420             2425                 2430

Ile Gly Ala Ser Pro Thr Gln Thr Val Thr Leu Val Thr Gln Pro
2435             2440                 2445

Val Val Thr Lys Glu Thr Ala Ile Ser Lys Leu Glu Met Pro Ser
2450             2455                 2460

Ser Leu Met Leu Glu Val Pro Ala Leu Ala Asp Phe Asn Arg Ala
2465             2470                 2475

Trp Thr Glu Leu Thr Asp Trp Leu Ser Leu Leu Asp Gln Val Ile
2480             2485                 2490

Lys Ser Gln Arg Val Met Val Gly Asp Leu Glu Asp Ile Asn Glu
2495             2500                 2505

```
Met Ile Ile Lys Gln Lys Ala Thr Met Gln Asp Leu Glu Gln Arg
2510                2515                2520

Arg Pro Gln Leu Glu Glu Leu Ile Thr Ala Ala Gln Asn Leu Lys
2525                2530                2535

Asn Lys Thr Ser Asn Gln Glu Ala Arg Thr Ile Ile Thr Asp Arg
2540                2545                2550

Ile Glu Arg Ile Gln Asn Gln Trp Asp Glu Val Gln Glu His Leu
2555                2560                2565

Gln Asn Arg Arg Gln Gln Leu Asn Glu Met Leu Lys Asp Ser Thr
2570                2575                2580

Gln Trp Leu Glu Ala Lys Glu Glu Ala Glu Gln Val Leu Gly Gln
2585                2590                2595

Ala Arg Ala Lys Leu Glu Ser Trp Lys Glu Gly Pro Tyr Thr Val
2600                2605                2610

Asp Ala Ile Gln Lys Lys Ile Thr Glu Thr Lys Gln Leu Ala Lys
2615                2620                2625

Asp Leu Arg Gln Trp Gln Thr Asn Val Asp Val Ala Asn Asp Leu
2630                2635                2640

Ala Leu Lys Leu Leu Arg Asp Tyr Ser Ala Asp Asp Thr Arg Lys
2645                2650                2655

Val His Met Ile Thr Glu Asn Ile Asn Ala Ser Trp Arg Ser Ile
2660                2665                2670

His Lys Arg Val Ser Glu Arg Glu Ala Ala Leu Glu Glu Thr His
2675                2680                2685

Arg Leu Leu Gln Gln Phe Pro Leu Asp Leu Glu Lys Phe Leu Ala
2690                2695                2700

Trp Leu Thr Glu Ala Glu Thr Thr Ala Asn Val Leu Gln Asp Ala
2705                2710                2715

Thr Arg Lys Glu Arg Leu Leu Glu Asp Ser Lys Gly Val Lys Glu
2720                2725                2730

Leu Met Lys Gln Trp Gln Asp Leu Gln Gly Glu Ile Glu Ala His
2735                2740                2745

Thr Asp Val Tyr His Asn Leu Asp Glu Asn Ser Gln Lys Ile Leu
2750                2755                2760

Arg Ser Leu Glu Gly Ser Asp Asp Ala Val Leu Leu Gln Arg Arg
2765                2770                2775

Leu Asp Asn Met Asn Phe Lys Trp Ser Glu Leu Arg Lys Lys Ser
2780                2785                2790

Leu Asn Ile Arg Ser His Leu Glu Ala Ser Ser Asp Gln Trp Lys
2795                2800                2805

Arg Leu His Leu Ser Leu Gln Glu Leu Leu Val Trp Leu Gln Leu
2810                2815                2820

Lys Asp Asp Glu Leu Ser Arg Gln Ala Pro Ile Gly Gly Asp Phe
2825                2830                2835

Pro Ala Val Gln Lys Gln Asn Asp Val His Arg Ala Phe Lys Arg
2840                2845                2850

Glu Leu Lys Thr Lys Glu Pro Val Ile Met Ser Thr Leu Glu Thr
2855                2860                2865

Val Arg Ile Phe Leu Thr Glu Gln Pro Leu Glu Gly Leu Glu Lys
2870                2875                2880

Leu Tyr Gln Glu Pro Arg Glu Leu Pro Pro Glu Glu Arg Ala Gln
2885                2890                2895
```

```
Asn Val Thr Arg Leu Leu Arg Lys Gln Ala Glu Glu Val Asn Thr
    2900                2905                2910

Glu Trp Glu Lys Leu Asn Leu His Ser Ala Asp Trp Gln Arg Lys
    2915                2920                2925

Ile Asp Glu Thr Leu Glu Arg Leu Gln Glu Leu Gln Glu Ala Thr
    2930                2935                2940

Asp Glu Leu Asp Leu Lys Leu Arg Gln Ala Glu Val Ile Lys Gly
    2945                2950                2955

Ser Trp Gln Pro Val Gly Asp Leu Leu Ile Asp Ser Leu Gln Asp
    2960                2965                2970

His Leu Glu Lys Val Lys Ala Leu Arg Gly Glu Ile Ala Pro Leu
    2975                2980                2985

Lys Glu Asn Val Ser His Val Asn Asp Leu Ala Arg Gln Leu Thr
    2990                2995                3000

Thr Leu Gly Ile Gln Leu Ser Pro Tyr Asn Leu Ser Thr Leu Glu
    3005                3010                3015

Asp Leu Asn Thr Arg Trp Lys Leu Leu Gln Val Ala Val Glu Asp
    3020                3025                3030

Arg Val Arg Gln Leu His Glu Ala His Arg Asp Phe Gly Pro Ala
    3035                3040                3045

Ser Gln His Phe Leu Ser Thr Ser Val Gln Gly Pro Trp Glu Arg
    3050                3055                3060

Ala Ile Ser Pro Asn Lys Val Pro Tyr Tyr Ile Asn His Glu Thr
    3065                3070                3075

Gln Thr Thr Cys Trp Asp His Pro Lys Met Thr Glu Leu Tyr Gln
    3080                3085                3090

Ser Leu Ala Asp Leu Asn Asn Val Arg Phe Ser Ala Tyr Arg Thr
    3095                3100                3105

Ala Met Lys Leu Arg Arg Leu Gln Lys Ala Leu Cys Leu Asp Leu
    3110                3115                3120

Leu Ser Leu Ser Ala Ala Cys Asp Ala Leu Asp Gln His Asn Leu
    3125                3130                3135

Lys Gln Asn Asp Gln Pro Met Asp Ile Leu Gln Ile Ile Asn Cys
    3140                3145                3150

Leu Thr Thr Ile Tyr Asp Arg Leu Glu Gln Glu His Asn Asn Leu
    3155                3160                3165

Val Asn Val Pro Leu Cys Val Asp Met Cys Leu Asn Trp Leu Leu
    3170                3175                3180

Asn Val Tyr Asp Thr Gly Arg Thr Gly Arg Ile Arg Val Leu Ser
    3185                3190                3195

Phe Lys Thr Gly Ile Ile Ser Leu Cys Lys Ala His Leu Glu Asp
    3200                3205                3210

Lys Tyr Arg Tyr Leu Phe Lys Gln Val Ala Ser Ser Thr Gly Phe
    3215                3220                3225

Cys Asp Gln Arg Arg Leu Gly Leu Leu Leu His Asp Ser Ile Gln
    3230                3235                3240

Ile Pro Arg Gln Leu Gly Glu Val Ala Ser Phe Gly Gly Ser Asn
    3245                3250                3255

Ile Glu Pro Ser Val Arg Ser Cys Phe Gln Phe Ala Asn Asn Lys
    3260                3265                3270

Pro Glu Ile Glu Ala Ala Leu Phe Leu Asp Trp Met Arg Leu Glu
    3275                3280                3285
```

-continued

```
Pro Gln Ser Met Val Trp Leu Pro Val Leu His Arg Val Ala Ala
    3290                3295                3300

Ala Glu Thr Ala Lys His Gln Ala Lys Cys Asn Ile Cys Lys Glu
    3305                3310                3315

Cys Pro Ile Ile Gly Phe Arg Tyr Arg Ser Leu Lys His Phe Asn
    3320                3325                3330

Tyr Asp Ile Cys Gln Ser Cys Phe Phe Ser Gly Arg Val Ala Lys
    3335                3340                3345

Gly His Lys Met His Tyr Pro Met Val Glu Tyr Cys Thr Pro Thr
    3350                3355                3360

Thr Ser Gly Glu Asp Val Arg Asp Phe Ala Lys Val Leu Lys Asn
    3365                3370                3375

Lys Phe Arg Thr Lys Arg Tyr Phe Ala Lys His Pro Arg Met Gly
    3380                3385                3390

Tyr Leu Pro Val Gln Thr Val Leu Glu Gly Asp Asn Met Glu Thr
    3395                3400                3405

Pro Val Thr Leu Ile Asn Phe Trp Pro Val Asp Ser Ala Pro Ala
    3410                3415                3420

Ser Ser Pro Gln Leu Ser His Asp Asp Thr His Ser Arg Ile Glu
    3425                3430                3435

His Tyr Ala Ser Arg Leu Ala Glu Met Glu Asn Ser Asn Gly Ser
    3440                3445                3450

Tyr Leu Asn Asp Ser Ile Ser Pro Asn Glu Ser Ile Asp Asp Glu
    3455                3460                3465

His Leu Leu Ile Gln His Tyr Cys Gln Ser Leu Asn Gln Asp Ser
    3470                3475                3480

Pro Leu Ser Gln Pro Arg Ser Pro Ala Gln Ile Leu Ile Ser Leu
    3485                3490                3495

Glu Ser Glu Glu Arg Gly Glu Leu Glu Arg Ile Leu Ala Asp Leu
    3500                3505                3510

Glu Glu Glu Asn Arg Asn Leu Gln Ala Glu Tyr Asp Arg Leu Lys
    3515                3520                3525

Gln Gln His Glu His Lys Gly Leu Ser Pro Leu Pro Ser Pro Pro
    3530                3535                3540

Glu Met Met Pro Thr Ser Pro Gln Ser Pro Arg Asp Ala Glu Leu
    3545                3550                3555

Ile Ala Glu Ala Lys Leu Leu Arg Gln His Lys Gly Arg Leu Glu
    3560                3565                3570

Ala Arg Met Gln Ile Leu Glu Asp His Asn Lys Gln Leu Glu Ser
    3575                3580                3585

Gln Leu His Arg Leu Arg Gln Leu Leu Glu Gln Pro Gln Ala Glu
    3590                3595                3600

Ala Lys Val Asn Gly Thr Thr Val Ser Ser Pro Ser Thr Ser Leu
    3605                3610                3615

Gln Arg Ser Asp Ser Ser Gln Pro Met Leu Leu Arg Val Val Gly
    3620                3625                3630

Ser Gln Thr Ser Asp Ser Met Gly Glu Glu Asp Leu Leu Ser Pro
    3635                3640                3645

Pro Gln Asp Thr Ser Thr Gly Leu Glu Glu Val Met Glu Gln Leu
    3650                3655                3660
```

```
Asn Asn Ser Phe Pro Ser Ser Arg Gly Arg Asn Thr Pro Gly Lys
3665                3670                3675

Pro Met Arg Glu Asp Thr Met
    3680                3685
```

<210> SEQ ID NO 2
<211> LENGTH: 25
<212> TYPE: RNA
<213> ORGANISM: Artificial
<220> FEATURE:
<223> OTHER INFORMATION: oligonucleotide

<400> SEQUENCE: 2
guaccuccaa caucaaggaa gaugg                                  25

<210> SEQ ID NO 3
<211> LENGTH: 25
<212> TYPE: RNA
<213> ORGANISM: Artificial
<220> FEATURE:
<223> OTHER INFORMATION: oligonucleotide

<400> SEQUENCE: 3
uaccuccaac aucaaggaag auggc                                  25

<210> SEQ ID NO 4
<211> LENGTH: 25
<212> TYPE: RNA
<213> ORGANISM: Artificial
<220> FEATURE:
<223> OTHER INFORMATION: oligonucleotide

<400> SEQUENCE: 4
accuccaaca ucaaggaaga uggca                                  25

<210> SEQ ID NO 5
<211> LENGTH: 25
<212> TYPE: RNA
<213> ORGANISM: Artificial
<220> FEATURE:
<223> OTHER INFORMATION: oligonucleotide

<400> SEQUENCE: 5
ccuccaacau caaggaagau ggcau                                  25

<210> SEQ ID NO 6
<211> LENGTH: 25
<212> TYPE: RNA
<213> ORGANISM: Artificial
<220> FEATURE:
<223> OTHER INFORMATION: oligonucleotide

<400> SEQUENCE: 6
cuccaacauc aaggaagaug gcauu                                  25

<210> SEQ ID NO 7
<211> LENGTH: 25
<212> TYPE: RNA
<213> ORGANISM: Artificial
<220> FEATURE:
<223> OTHER INFORMATION: oligonucleotide

<400> SEQUENCE: 7
uccaacauca aggaagaugg cauuu                                  25

```
<210> SEQ ID NO 8
<211> LENGTH: 25
<212> TYPE: RNA
<213> ORGANISM: Artificial
<220> FEATURE:
<223> OTHER INFORMATION: oligonucleotide

<400> SEQUENCE: 8
ccaacaucaa ggaagauggc auuuc                                              25

<210> SEQ ID NO 9
<211> LENGTH: 25
<212> TYPE: RNA
<213> ORGANISM: Artificial
<220> FEATURE:
<223> OTHER INFORMATION: oligonucleotide

<400> SEQUENCE: 9
caacaucaag gaagauggca uuucu                                              25

<210> SEQ ID NO 10
<211> LENGTH: 25
<212> TYPE: RNA
<213> ORGANISM: Artificial
<220> FEATURE:
<223> OTHER INFORMATION: oligonucleotide

<400> SEQUENCE: 10
aacaucaagg aagauggcau uucua                                              25

<210> SEQ ID NO 11
<211> LENGTH: 25
<212> TYPE: RNA
<213> ORGANISM: Artificial
<220> FEATURE:
<223> OTHER INFORMATION: oligonucleotide

<400> SEQUENCE: 11
acaucaagga agauggcauu ucuag                                              25

<210> SEQ ID NO 12
<211> LENGTH: 25
<212> TYPE: RNA
<213> ORGANISM: Artificial
<220> FEATURE:
<223> OTHER INFORMATION: oligonucleotide

<400> SEQUENCE: 12
caucaaggaa gauggcauuu cuagu                                              25

<210> SEQ ID NO 13
<211> LENGTH: 25
<212> TYPE: RNA
<213> ORGANISM: Artificial
<220> FEATURE:
<223> OTHER INFORMATION: oligonucleotide

<400> SEQUENCE: 13
aucaaggaag auggcauuuc uaguu                                              25

<210> SEQ ID NO 14
<211> LENGTH: 25
<212> TYPE: RNA
<213> ORGANISM: Artificial
<220> FEATURE:
<223> OTHER INFORMATION: oligonucleotide
```

```
<400> SEQUENCE: 14
ucaaggaaga uggcauuucu aguuu                                    25

<210> SEQ ID NO 15
<211> LENGTH: 25
<212> TYPE: RNA
<213> ORGANISM: Artificial
<220> FEATURE:
<223> OTHER INFORMATION: oligonucleotide

<400> SEQUENCE: 15
caaggaagau ggcauuucua guuug                                    25

<210> SEQ ID NO 16
<211> LENGTH: 25
<212> TYPE: RNA
<213> ORGANISM: Artificial
<220> FEATURE:
<223> OTHER INFORMATION: oligonucleotide

<400> SEQUENCE: 16
aaggaagaug gcauuucuag uuugg                                    25

<210> SEQ ID NO 17
<211> LENGTH: 25
<212> TYPE: RNA
<213> ORGANISM: Artificial
<220> FEATURE:
<223> OTHER INFORMATION: oligonucleotide

<400> SEQUENCE: 17
aggaagaugg cauuucuagu uugga                                    25

<210> SEQ ID NO 18
<211> LENGTH: 25
<212> TYPE: RNA
<213> ORGANISM: Artificial
<220> FEATURE:
<223> OTHER INFORMATION: oligonucleotide

<400> SEQUENCE: 18
ggaagauggc auuucuaguu uggag                                    25

<210> SEQ ID NO 19
<211> LENGTH: 25
<212> TYPE: RNA
<213> ORGANISM: Artificial
<220> FEATURE:
<223> OTHER INFORMATION: oligonucleotide

<400> SEQUENCE: 19
gaagauggca uuucuaguuu ggaga                                    25

<210> SEQ ID NO 20
<211> LENGTH: 25
<212> TYPE: RNA
<213> ORGANISM: Artificial
<220> FEATURE:
<223> OTHER INFORMATION: oligonucleotide

<400> SEQUENCE: 20
aagauggcau uucuaguuug gagau                                    25

<210> SEQ ID NO 21
```

```
<211> LENGTH: 25
<212> TYPE: RNA
<213> ORGANISM: Artificial
<220> FEATURE:
<223> OTHER INFORMATION: oligonucleotide

<400> SEQUENCE: 21
agauggcauu ucuaguuugg agaug                                           25

<210> SEQ ID NO 22
<211> LENGTH: 25
<212> TYPE: RNA
<213> ORGANISM: Artificial
<220> FEATURE:
<223> OTHER INFORMATION: oligonucleotide

<400> SEQUENCE: 22
gauggcauuu cuaguuugga gaugg                                           25

<210> SEQ ID NO 23
<211> LENGTH: 25
<212> TYPE: RNA
<213> ORGANISM: Artificial
<220> FEATURE:
<223> OTHER INFORMATION: oligonucleotide

<400> SEQUENCE: 23
auggcauuuc uaguuggag auggc                                            25

<210> SEQ ID NO 24
<211> LENGTH: 25
<212> TYPE: RNA
<213> ORGANISM: Artificial
<220> FEATURE:
<223> OTHER INFORMATION: oligonucleotide

<400> SEQUENCE: 24
uggcauuucu aguuuggaga uggca                                           25

<210> SEQ ID NO 25
<211> LENGTH: 25
<212> TYPE: RNA
<213> ORGANISM: Artificial
<220> FEATURE:
<223> OTHER INFORMATION: oligonucleotide

<400> SEQUENCE: 25
ggcauuucua guuuggagau ggcag                                           25

<210> SEQ ID NO 26
<211> LENGTH: 25
<212> TYPE: RNA
<213> ORGANISM: Artificial
<220> FEATURE:
<223> OTHER INFORMATION: oligonucleotide

<400> SEQUENCE: 26
gcauuucuag uuuggagaug gcagu                                           25

<210> SEQ ID NO 27
<211> LENGTH: 25
<212> TYPE: RNA
<213> ORGANISM: Artificial
<220> FEATURE:
<223> OTHER INFORMATION: oligonucleotide
```

<400> SEQUENCE: 27
cauuucuagu uuggagaugg caguu                               25

<210> SEQ ID NO 28
<211> LENGTH: 25
<212> TYPE: RNA
<213> ORGANISM: Artificial
<220> FEATURE:
<223> OTHER INFORMATION: oligonucleotide

<400> SEQUENCE: 28
auuucuaguu uggagauggc aguuu                               25

<210> SEQ ID NO 29
<211> LENGTH: 25
<212> TYPE: RNA
<213> ORGANISM: Artificial
<220> FEATURE:
<223> OTHER INFORMATION: oligonucleotide

<400> SEQUENCE: 29
uuucuaguuu ggagauggca guuuc                               25

<210> SEQ ID NO 30
<211> LENGTH: 25
<212> TYPE: RNA
<213> ORGANISM: Artificial
<220> FEATURE:
<223> OTHER INFORMATION: oligonucleotide

<400> SEQUENCE: 30
uucuaguuug gagauggcag uuucc                               25

<210> SEQ ID NO 31
<211> LENGTH: 25
<212> TYPE: RNA
<213> ORGANISM: Artificial
<220> FEATURE:
<223> OTHER INFORMATION: oligonucleotide

<400> SEQUENCE: 31
ucuaguuugg agauggcagu uuccu                               25

<210> SEQ ID NO 32
<211> LENGTH: 25
<212> TYPE: RNA
<213> ORGANISM: Artificial
<220> FEATURE:
<223> OTHER INFORMATION: oligonucleotide

<400> SEQUENCE: 32
cuaguuugga gauggcaguu uccuu                               25

<210> SEQ ID NO 33
<211> LENGTH: 25
<212> TYPE: RNA
<213> ORGANISM: Artificial
<220> FEATURE:
<223> OTHER INFORMATION: oligonucleotide

<400> SEQUENCE: 33
uaguuuggag auggcaguuu ccuua                               25

<210> SEQ ID NO 34

<211> LENGTH: 25
<212> TYPE: RNA
<213> ORGANISM: Artificial
<220> FEATURE:
<223> OTHER INFORMATION: oligonucleotide

<400> SEQUENCE: 34
aguuuggaga uggcaguuuc cuuag                               25

<210> SEQ ID NO 35
<211> LENGTH: 25
<212> TYPE: RNA
<213> ORGANISM: Artificial
<220> FEATURE:
<223> OTHER INFORMATION: oligonucleotide

<400> SEQUENCE: 35
guuuggagau ggcaguuucc uuagu                               25

<210> SEQ ID NO 36
<211> LENGTH: 25
<212> TYPE: RNA
<213> ORGANISM: Artificial
<220> FEATURE:
<223> OTHER INFORMATION: oligonucleotide

<400> SEQUENCE: 36
uuuggagaug gcaguuuccu uagua                               25

<210> SEQ ID NO 37
<211> LENGTH: 25
<212> TYPE: RNA
<213> ORGANISM: Artificial
<220> FEATURE:
<223> OTHER INFORMATION: oligonucleotide

<400> SEQUENCE: 37
uuggagaugg caguuuccuu aguaa                               25

<210> SEQ ID NO 38
<211> LENGTH: 25
<212> TYPE: RNA
<213> ORGANISM: Artificial
<220> FEATURE:
<223> OTHER INFORMATION: oligonucleotide

<400> SEQUENCE: 38
uggagauggc aguuuccuua guaac                               25

<210> SEQ ID NO 39
<211> LENGTH: 25
<212> TYPE: RNA
<213> ORGANISM: Artificial
<220> FEATURE:
<223> OTHER INFORMATION: oligonucleotide

<400> SEQUENCE: 39
gagauggcag uuuccuuagu aacca                               25

<210> SEQ ID NO 40
<211> LENGTH: 25
<212> TYPE: RNA
<213> ORGANISM: Artificial
<220> FEATURE:
<223> OTHER INFORMATION: oligonucleotide -continued

```
<400> SEQUENCE: 40
agauggcagu uccuuaguag accac                                              25

<210> SEQ ID NO 41
<211> LENGTH: 25
<212> TYPE: RNA
<213> ORGANISM: Artificial
<220> FEATURE:
<223> OTHER INFORMATION: oligonucleotide

<400> SEQUENCE: 41
gauggcaguu uccuuaguaa ccaca                                              25

<210> SEQ ID NO 42
<211> LENGTH: 25
<212> TYPE: RNA
<213> ORGANISM: Artificial
<220> FEATURE:
<223> OTHER INFORMATION: oligonucleotide

<400> SEQUENCE: 42
auggcaguuu ccuuaguaac cacag                                              25

<210> SEQ ID NO 43
<211> LENGTH: 25
<212> TYPE: RNA
<213> ORGANISM: Artificial
<220> FEATURE:
<223> OTHER INFORMATION: oligonucleotide

<400> SEQUENCE: 43
uggcaguuuc cuuaguaacc acagg                                              25

<210> SEQ ID NO 44
<211> LENGTH: 25
<212> TYPE: RNA
<213> ORGANISM: Artificial
<220> FEATURE:
<223> OTHER INFORMATION: oligonucleotide

<400> SEQUENCE: 44
ggcaguuucc uuaguaacca caggu                                              25

<210> SEQ ID NO 45
<211> LENGTH: 25
<212> TYPE: RNA
<213> ORGANISM: Artificial
<220> FEATURE:
<223> OTHER INFORMATION: oligonucleotide

<400> SEQUENCE: 45
gcaguuuccu uaguaaccac agguu                                              25

<210> SEQ ID NO 46
<211> LENGTH: 25
<212> TYPE: RNA
<213> ORGANISM: Artificial
<220> FEATURE:
<223> OTHER INFORMATION: oligonucleotide

<400> SEQUENCE: 46
caguuuccuu aguaaccaca gguug                                              25

<210> SEQ ID NO 47
```

<211> LENGTH: 25
<212> TYPE: RNA
<213> ORGANISM: Artificial
<220> FEATURE:
<223> OTHER INFORMATION: oligonucleotide

<400> SEQUENCE: 47 aguuccuua guaaccacag guugu                                              25

<210> SEQ ID NO 48
<211> LENGTH: 25
<212> TYPE: RNA
<213> ORGANISM: Artificial
<220> FEATURE:
<223> OTHER INFORMATION: oligonucleotide

<400> SEQUENCE: 48 guuccuuag uaaccacagg uugug                                              25

<210> SEQ ID NO 49
<211> LENGTH: 25
<212> TYPE: RNA
<213> ORGANISM: Artificial
<220> FEATURE:
<223> OTHER INFORMATION: oligonucleotide

<400> SEQUENCE: 49 uuccuuagu aaccacaggu ugugu                                              25

<210> SEQ ID NO 50
<211> LENGTH: 25
<212> TYPE: RNA
<213> ORGANISM: Artificial
<220> FEATURE:
<223> OTHER INFORMATION: oligonucleotide

<400> SEQUENCE: 50
uuccuuagua accacagguu guguc                                             25

<210> SEQ ID NO 51
<211> LENGTH: 25
<212> TYPE: RNA
<213> ORGANISM: Artificial
<220> FEATURE:
<223> OTHER INFORMATION: oligonucleotide

<400> SEQUENCE: 51
uccuuaguaa ccacagguug uguca                                             25

<210> SEQ ID NO 52
<211> LENGTH: 25
<212> TYPE: RNA
<213> ORGANISM: Artificial
<220> FEATURE:
<223> OTHER INFORMATION: oligonucleotide

<400> SEQUENCE: 52
ccuuaguaac cacagguugu gucac                                             25

<210> SEQ ID NO 53
<211> LENGTH: 25
<212> TYPE: RNA
<213> ORGANISM: Artificial
<220> FEATURE:
<223> OTHER INFORMATION: oligonucleotide

<400> SEQUENCE: 53
cuuaguaacc acagguugug ucacc                                    25

<210> SEQ ID NO 54
<211> LENGTH: 25
<212> TYPE: RNA
<213> ORGANISM: Artificial
<220> FEATURE:
<223> OTHER INFORMATION: oligonucleotide

<400> SEQUENCE: 54
uuaguaacca cagguugugu cacca                                    25

<210> SEQ ID NO 55
<211> LENGTH: 25
<212> TYPE: RNA
<213> ORGANISM: Artificial
<220> FEATURE:
<223> OTHER INFORMATION: oligonucleotide

<400> SEQUENCE: 55
uaguaaccac agguuguguc accag                                    25

<210> SEQ ID NO 56
<211> LENGTH: 25
<212> TYPE: RNA
<213> ORGANISM: Artificial
<220> FEATURE:
<223> OTHER INFORMATION: oligonucleotide

<400> SEQUENCE: 56
aguaaccaca gguuguguca ccaga                                    25

<210> SEQ ID NO 57
<211> LENGTH: 25
<212> TYPE: RNA
<213> ORGANISM: Artificial
<220> FEATURE:
<223> OTHER INFORMATION: oligonucleotide

<400> SEQUENCE: 57
guaaccacag guugugucac cagag                                    25

<210> SEQ ID NO 58
<211> LENGTH: 25
<212> TYPE: RNA
<213> ORGANISM: Artificial
<220> FEATURE:
<223> OTHER INFORMATION: oligonucleotide

<400> SEQUENCE: 58
uaaccacagg uugugucacc agagu                                    25

<210> SEQ ID NO 59
<211> LENGTH: 25
<212> TYPE: RNA
<213> ORGANISM: Artificial
<220> FEATURE:
<223> OTHER INFORMATION: oligonucleotide

<400> SEQUENCE: 59
aaccacaggu ugugucacca gagua                                    25

<210> SEQ ID NO 60

```
<211> LENGTH: 25
<212> TYPE: RNA
<213> ORGANISM: Artificial
<220> FEATURE:
<223> OTHER INFORMATION: oligonucleotide

<400> SEQUENCE: 60
accacagguu gugucaccag aguaa                                              25

<210> SEQ ID NO 61
<211> LENGTH: 25
<212> TYPE: RNA
<213> ORGANISM: Artificial
<220> FEATURE:
<223> OTHER INFORMATION: oligonucleotide

<400> SEQUENCE: 61
ccacagguug ugucaccaga guaac                                              25

<210> SEQ ID NO 62
<211> LENGTH: 25
<212> TYPE: RNA
<213> ORGANISM: Artificial
<220> FEATURE:
<223> OTHER INFORMATION: oligonucleotide

<400> SEQUENCE: 62
cacagguugu gucaccagag uaaca                                              25

<210> SEQ ID NO 63
<211> LENGTH: 25
<212> TYPE: RNA
<213> ORGANISM: Artificial
<220> FEATURE:
<223> OTHER INFORMATION: oligonucleotide

<400> SEQUENCE: 63
acagguugug ucaccagagu aacag                                              25

<210> SEQ ID NO 64
<211> LENGTH: 25
<212> TYPE: RNA
<213> ORGANISM: Artificial
<220> FEATURE:
<223> OTHER INFORMATION: oligonucleotide

<400> SEQUENCE: 64
cagguugugu caccagagua acagu                                              25

<210> SEQ ID NO 65
<211> LENGTH: 25
<212> TYPE: RNA
<213> ORGANISM: Artificial
<220> FEATURE:
<223> OTHER INFORMATION: oligonucleotide

<400> SEQUENCE: 65
agguuguguc accagaguaa caguc                                              25

<210> SEQ ID NO 66
<211> LENGTH: 25
<212> TYPE: RNA
<213> ORGANISM: Artificial
<220> FEATURE:
<223> OTHER INFORMATION: oligonucleotide
```

```
<400> SEQUENCE: 66
gguuguguca ccagaguaac agucu                                              25

<210> SEQ ID NO 67
<211> LENGTH: 25
<212> TYPE: RNA
<213> ORGANISM: Artificial
<220> FEATURE:
<223> OTHER INFORMATION: oligonucleotide

<400> SEQUENCE: 67
guugugucac cagaguaaca gucug                                              25

<210> SEQ ID NO 68
<211> LENGTH: 25
<212> TYPE: RNA
<213> ORGANISM: Artificial
<220> FEATURE:
<223> OTHER INFORMATION: oligonucleotide

<400> SEQUENCE: 68
uugugucacc agaguaacag ucuga                                              25

<210> SEQ ID NO 69
<211> LENGTH: 25
<212> TYPE: RNA
<213> ORGANISM: Artificial
<220> FEATURE:
<223> OTHER INFORMATION: oligonucleotide

<400> SEQUENCE: 69
ugugucacca gaguaacagu cugag                                              25

<210> SEQ ID NO 70
<211> LENGTH: 25
<212> TYPE: RNA
<213> ORGANISM: Artificial
<220> FEATURE:
<223> OTHER INFORMATION: oligonucleotide

<400> SEQUENCE: 70
gugucaccag aguaacaguc ugagu                                              25

<210> SEQ ID NO 71
<211> LENGTH: 25
<212> TYPE: RNA
<213> ORGANISM: Artificial
<220> FEATURE:
<223> OTHER INFORMATION: oligonucleotide

<400> SEQUENCE: 71
ugucaccaga guaacagucu gagua                                              25

<210> SEQ ID NO 72
<211> LENGTH: 25
<212> TYPE: RNA
<213> ORGANISM: Artificial
<220> FEATURE:
<223> OTHER INFORMATION: oligonucleotide

<400> SEQUENCE: 72
gucaccagag uaacagucug aguag                                              25

<210> SEQ ID NO 73
```

```
<211> LENGTH: 25
<212> TYPE: RNA
<213> ORGANISM: Artificial
<220> FEATURE:
<223> OTHER INFORMATION: oligonucleotide

<400> SEQUENCE: 73
ucaccagagu aacagucuga guagg                                              25

<210> SEQ ID NO 74
<211> LENGTH: 25
<212> TYPE: RNA
<213> ORGANISM: Artificial
<220> FEATURE:
<223> OTHER INFORMATION: oligonucleotide

<400> SEQUENCE: 74
caccagagua acagucugag uagga                                              25

<210> SEQ ID NO 75
<211> LENGTH: 25
<212> TYPE: RNA
<213> ORGANISM: Artificial
<220> FEATURE:
<223> OTHER INFORMATION: oligonucleotide

<400> SEQUENCE: 75
accagaguaa cagucugagu aggag                                              25

<210> SEQ ID NO 76
<211> LENGTH: 25
<212> TYPE: RNA
<213> ORGANISM: Artificial
<220> FEATURE:
<223> OTHER INFORMATION: oligonucleotide

<400> SEQUENCE: 76
uuugccgcug cccaaugcca uccug                                              25

<210> SEQ ID NO 77
<211> LENGTH: 25
<212> TYPE: RNA
<213> ORGANISM: Artificial
<220> FEATURE:
<223> OTHER INFORMATION: oligonucleotide

<400> SEQUENCE: 77
auucaauguu cugacaacag uuugc                                              25

<210> SEQ ID NO 78
<211> LENGTH: 25
<212> TYPE: RNA
<213> ORGANISM: Artificial
<220> FEATURE:
<223> OTHER INFORMATION: oligonucleotide

<400> SEQUENCE: 78
ccaguugcau ucaauguucu gacaa                                              25

<210> SEQ ID NO 79
<211> LENGTH: 22
<212> TYPE: RNA
<213> ORGANISM: Artificial
<220> FEATURE:
<223> OTHER INFORMATION: oligonucleotide
```

```
<400> SEQUENCE: 79
caguugcauu caauguucug ac                                              22

<210> SEQ ID NO 80
<211> LENGTH: 20
<212> TYPE: RNA
<213> ORGANISM: Artificial
<220> FEATURE:
<223> OTHER INFORMATION: oligonucleotide

<400> SEQUENCE: 80
aguugcauuc aauguucuga                                                 20

<210> SEQ ID NO 81
<211> LENGTH: 21
<212> TYPE: RNA
<213> ORGANISM: Artificial
<220> FEATURE:
<223> OTHER INFORMATION: oligonucleotide

<400> SEQUENCE: 81
gauugcugaa uuauuucuuc c                                               21

<210> SEQ ID NO 82
<211> LENGTH: 25
<212> TYPE: RNA
<213> ORGANISM: Artificial
<220> FEATURE:
<223> OTHER INFORMATION: oligonucleotide

<400> SEQUENCE: 82
gauugcugaa uuauuucuuc cccag                                           25

<210> SEQ ID NO 83
<211> LENGTH: 25
<212> TYPE: RNA
<213> ORGANISM: Artificial
<220> FEATURE:
<223> OTHER INFORMATION: oligonucleotide

<400> SEQUENCE: 83
auugcugaau uauuucuucc ccagu                                           25

<210> SEQ ID NO 84
<211> LENGTH: 25
<212> TYPE: RNA
<213> ORGANISM: Artificial
<220> FEATURE:
<223> OTHER INFORMATION: oligonucleotide

<400> SEQUENCE: 84
uugcugaauu auuucuuccc caguu                                           25

<210> SEQ ID NO 85
<211> LENGTH: 25
<212> TYPE: RNA
<213> ORGANISM: Artificial
<220> FEATURE:
<223> OTHER INFORMATION: oligonucleotide

<400> SEQUENCE: 85
ugcugaauua uuucuucccc aguug                                           25

<210> SEQ ID NO 86
```

```
<211> LENGTH: 25
<212> TYPE: RNA
<213> ORGANISM: Artificial
<220> FEATURE:
<223> OTHER INFORMATION: oligonucleotide

<400> SEQUENCE: 86
gcugaauuau ucuucccca guugc                                          25

<210> SEQ ID NO 87
<211> LENGTH: 25
<212> TYPE: RNA
<213> ORGANISM: Artificial
<220> FEATURE:
<223> OTHER INFORMATION: oligonucleotide

<400> SEQUENCE: 87
cugaauuauu ucuucccag uugca                                          25

<210> SEQ ID NO 88
<211> LENGTH: 25
<212> TYPE: RNA
<213> ORGANISM: Artificial
<220> FEATURE:
<223> OTHER INFORMATION: oligonucleotide

<400> SEQUENCE: 88
ugaauuauuu cuucccagu ugcau                                          25

<210> SEQ ID NO 89
<211> LENGTH: 25
<212> TYPE: RNA
<213> ORGANISM: Artificial
<220> FEATURE:
<223> OTHER INFORMATION: oligonucleotide

<400> SEQUENCE: 89
gaauuauuuc uucccaguu gcauu                                          25

<210> SEQ ID NO 90
<211> LENGTH: 25
<212> TYPE: RNA
<213> ORGANISM: Artificial
<220> FEATURE:
<223> OTHER INFORMATION: oligonucleotide

<400> SEQUENCE: 90
aauuauuucu uccccaguug cauuc                                         25

<210> SEQ ID NO 91
<211> LENGTH: 25
<212> TYPE: RNA
<213> ORGANISM: Artificial
<220> FEATURE:
<223> OTHER INFORMATION: oligonucleotide

<400> SEQUENCE: 91
auuauuucuu ccccaguugc auuca                                         25

<210> SEQ ID NO 92
<211> LENGTH: 25
<212> TYPE: RNA
<213> ORGANISM: Artificial
<220> FEATURE:
<223> OTHER INFORMATION: oligonucleotide
```

-continued

```
<400> SEQUENCE: 92
uuauuucuuc cccaguugca uucaa                                          25

<210> SEQ ID NO 93
<211> LENGTH: 25
<212> TYPE: RNA
<213> ORGANISM: Artificial
<220> FEATURE:
<223> OTHER INFORMATION: oligonucleotide

<400> SEQUENCE: 93
uauuucuucc ccaguugcau ucaau                                          25

<210> SEQ ID NO 94
<211> LENGTH: 25
<212> TYPE: RNA
<213> ORGANISM: Artificial
<220> FEATURE:
<223> OTHER INFORMATION: oligonucleotide

<400> SEQUENCE: 94
auuucuuccc caguugcauu caaug                                          25

<210> SEQ ID NO 95
<211> LENGTH: 25
<212> TYPE: RNA
<213> ORGANISM: Artificial
<220> FEATURE:
<223> OTHER INFORMATION: oligonucleotide

<400> SEQUENCE: 95
uuucuucccc aguugcauuc aaugu                                          25

<210> SEQ ID NO 96
<211> LENGTH: 25
<212> TYPE: RNA
<213> ORGANISM: Artificial
<220> FEATURE:
<223> OTHER INFORMATION: oligonucleotide

<400> SEQUENCE: 96
uucuuccccA guugcauuca auguu                                          25

<210> SEQ ID NO 97
<211> LENGTH: 25
<212> TYPE: RNA
<213> ORGANISM: Artificial
<220> FEATURE:
<223> OTHER INFORMATION: oligonucleotide

<400> SEQUENCE: 97
ucuuccccag uugcauucaa uguuc                                          25

<210> SEQ ID NO 98
<211> LENGTH: 25
<212> TYPE: RNA
<213> ORGANISM: Artificial
<220> FEATURE:
<223> OTHER INFORMATION: oligonucleotide

<400> SEQUENCE: 98
cuuccccagu ugcauucaau guucu                                          25

<210> SEQ ID NO 99
```

```
<211> LENGTH: 25
<212> TYPE: RNA
<213> ORGANISM: Artificial
<220> FEATURE:
<223> OTHER INFORMATION: oligonucleotide

<400> SEQUENCE: 99
uuccccaguu gcauucaaug uucug                                          25

<210> SEQ ID NO 100
<211> LENGTH: 25
<212> TYPE: RNA
<213> ORGANISM: Artificial
<220> FEATURE:
<223> OTHER INFORMATION: oligonucleotide

<400> SEQUENCE: 100
uccccaguug cauucaaugu ucuga                                          25

<210> SEQ ID NO 101
<211> LENGTH: 25
<212> TYPE: RNA
<213> ORGANISM: Artificial
<220> FEATURE:
<223> OTHER INFORMATION: oligonucleotide

<400> SEQUENCE: 101
ccccaguugc auucaauguu cugac                                          25

<210> SEQ ID NO 102
<211> LENGTH: 25
<212> TYPE: RNA
<213> ORGANISM: Artificial
<220> FEATURE:
<223> OTHER INFORMATION: oligonucleotide

<400> SEQUENCE: 102
cccaguugca uucaauguuc ugaca                                          25

<210> SEQ ID NO 103
<211> LENGTH: 25
<212> TYPE: RNA
<213> ORGANISM: Artificial
<220> FEATURE:
<223> OTHER INFORMATION: oligonucleotide

<400> SEQUENCE: 103
ccaguugcau ucaauguucu gacaa                                          25

<210> SEQ ID NO 104
<211> LENGTH: 25
<212> TYPE: RNA
<213> ORGANISM: Artificial
<220> FEATURE:
<223> OTHER INFORMATION: oligonucleotide

<400> SEQUENCE: 104
caguugcauu caauguucug acaac                                          25

<210> SEQ ID NO 105
<211> LENGTH: 25
<212> TYPE: RNA
<213> ORGANISM: Artificial
<220> FEATURE:
<223> OTHER INFORMATION: oligonucleotide
```

```
<400> SEQUENCE: 105
aguugcauuc aauguucuga caaca                                    25

<210> SEQ ID NO 106
<211> LENGTH: 20
<212> TYPE: RNA
<213> ORGANISM: Artificial
<220> FEATURE:
<223> OTHER INFORMATION: oligonucleotide

<400> SEQUENCE: 106
uccuguagaa uacuggcauc                                          20

<210> SEQ ID NO 107
<211> LENGTH: 27
<212> TYPE: RNA
<213> ORGANISM: Artificial
<220> FEATURE:
<223> OTHER INFORMATION: oligonucleotide

<400> SEQUENCE: 107
ugcagaccuc cugccaccgc agauuca                                  27

<210> SEQ ID NO 108
<211> LENGTH: 34
<212> TYPE: RNA
<213> ORGANISM: Artificial
<220> FEATURE:
<223> OTHER INFORMATION: oligonucleotide

<400> SEQUENCE: 108
uugcagaccu ccugccaccg cagauucagg cuuc                          34

<210> SEQ ID NO 109
<211> LENGTH: 25
<212> TYPE: RNA
<213> ORGANISM: Artificial
<220> FEATURE:
<223> OTHER INFORMATION: oligonucleotide

<400> SEQUENCE: 109
guugcauuca auguucugac aacag                                    25

<210> SEQ ID NO 110
<211> LENGTH: 25
<212> TYPE: RNA
<213> ORGANISM: Artificial
<220> FEATURE:
<223> OTHER INFORMATION: oligonucleotide

<400> SEQUENCE: 110
uugcauucaa uguucugaca acagu                                    25

<210> SEQ ID NO 111
<211> LENGTH: 25
<212> TYPE: RNA
<213> ORGANISM: Artificial
<220> FEATURE:
<223> OTHER INFORMATION: oligonucleotide

<400> SEQUENCE: 111
ugcauucaau guucugacaa caguu                                    25

<210> SEQ ID NO 112
```

```
<211> LENGTH: 25
<212> TYPE: RNA
<213> ORGANISM: Artificial
<220> FEATURE:
<223> OTHER INFORMATION: oligonucleotide

<400> SEQUENCE: 112
gcauucaaug uucugacaac aguuu                                              25

<210> SEQ ID NO 113
<211> LENGTH: 25
<212> TYPE: RNA
<213> ORGANISM: Artificial
<220> FEATURE:
<223> OTHER INFORMATION: oligonucleotide

<400> SEQUENCE: 113
cauucaaugu ucugacaaca guuug                                              25

<210> SEQ ID NO 114
<211> LENGTH: 25
<212> TYPE: RNA
<213> ORGANISM: Artificial
<220> FEATURE:
<223> OTHER INFORMATION: oligonucleotide

<400> SEQUENCE: 114
auucaauguu cugacaacag uuugc                                              25

<210> SEQ ID NO 115
<211> LENGTH: 25
<212> TYPE: RNA
<213> ORGANISM: Artificial
<220> FEATURE:
<223> OTHER INFORMATION: oligonucleotide

<400> SEQUENCE: 115
ucaauguucu gacaacaguu ugccg                                              25

<210> SEQ ID NO 116
<211> LENGTH: 25
<212> TYPE: RNA
<213> ORGANISM: Artificial
<220> FEATURE:
<223> OTHER INFORMATION: oligonucleotide

<400> SEQUENCE: 116
caauguucug acaacaguuu gccgc                                              25

<210> SEQ ID NO 117
<211> LENGTH: 25
<212> TYPE: RNA
<213> ORGANISM: Artificial
<220> FEATURE:
<223> OTHER INFORMATION: oligonucleotide

<400> SEQUENCE: 117
aauguucuga caacaguuug ccgcu                                              25

<210> SEQ ID NO 118
<211> LENGTH: 25
<212> TYPE: RNA
<213> ORGANISM: Artificial
<220> FEATURE:
<223> OTHER INFORMATION: oligonucleotide
```

```
<400> SEQUENCE: 118
auguucugac aacaguuugc cgcug                                              25

<210> SEQ ID NO 119
<211> LENGTH: 25
<212> TYPE: RNA
<213> ORGANISM: Artificial
<220> FEATURE:
<223> OTHER INFORMATION: oligonucleotide

<400> SEQUENCE: 119
uguucugaca acaguuugcc gcugc                                              25

<210> SEQ ID NO 120
<211> LENGTH: 25
<212> TYPE: RNA
<213> ORGANISM: Artificial
<220> FEATURE:
<223> OTHER INFORMATION: oligonucleotide

<400> SEQUENCE: 120
guucugacaa caguuugccg cugcc                                              25

<210> SEQ ID NO 121
<211> LENGTH: 25
<212> TYPE: RNA
<213> ORGANISM: Artificial
<220> FEATURE:
<223> OTHER INFORMATION: oligonucleotide

<400> SEQUENCE: 121
uucugacaac aguuugccgc ugccc                                              25

<210> SEQ ID NO 122
<211> LENGTH: 25
<212> TYPE: RNA
<213> ORGANISM: Artificial
<220> FEATURE:
<223> OTHER INFORMATION: oligonucleotide

<400> SEQUENCE: 122
ucugacaaca guuugccgcu gccca                                              25

<210> SEQ ID NO 123
<211> LENGTH: 25
<212> TYPE: RNA
<213> ORGANISM: Artificial
<220> FEATURE:
<223> OTHER INFORMATION: oligonucleotide

<400> SEQUENCE: 123
cugacaacag uuugccgcug cccaa                                              25

<210> SEQ ID NO 124
<211> LENGTH: 25
<212> TYPE: RNA
<213> ORGANISM: Artificial
<220> FEATURE:
<223> OTHER INFORMATION: oligonucleotide

<400> SEQUENCE: 124
ugacaacagu uugccgcugc ccaau                                              25

<210> SEQ ID NO 125
```

```
<211> LENGTH: 25
<212> TYPE: RNA
<213> ORGANISM: Artificial
<220> FEATURE:
<223> OTHER INFORMATION: oligonucleotide

<400> SEQUENCE: 125
gacaacaguu ugccgcugcc caaug                                              25

<210> SEQ ID NO 126
<211> LENGTH: 25
<212> TYPE: RNA
<213> ORGANISM: Artificial
<220> FEATURE:
<223> OTHER INFORMATION: oligonucleotide

<400> SEQUENCE: 126
acaacaguuu gccgcugccc aaugc                                              25

<210> SEQ ID NO 127
<211> LENGTH: 25
<212> TYPE: RNA
<213> ORGANISM: Artificial
<220> FEATURE:
<223> OTHER INFORMATION: oligonucleotide

<400> SEQUENCE: 127
caacaguuug ccgcugccca augcc                                              25

<210> SEQ ID NO 128
<211> LENGTH: 25
<212> TYPE: RNA
<213> ORGANISM: Artificial
<220> FEATURE:
<223> OTHER INFORMATION: oligonucleotide

<400> SEQUENCE: 128
aacaguuugc cgcugcccaa ugcca                                              25

<210> SEQ ID NO 129
<211> LENGTH: 25
<212> TYPE: RNA
<213> ORGANISM: Artificial
<220> FEATURE:
<223> OTHER INFORMATION: oligonucleotide

<400> SEQUENCE: 129
acaguuugcc gcugcccaau gccau                                              25

<210> SEQ ID NO 130
<211> LENGTH: 25
<212> TYPE: RNA
<213> ORGANISM: Artificial
<220> FEATURE:
<223> OTHER INFORMATION: oligonucleotide

<400> SEQUENCE: 130
caguuugccg cugcccaaug ccauc                                              25

<210> SEQ ID NO 131
<211> LENGTH: 25
<212> TYPE: RNA
<213> ORGANISM: Artificial
<220> FEATURE:
<223> OTHER INFORMATION: oligonucleotide
```

<400> SEQUENCE: 131
aguuugccgc ugcccaaugc caucc                                              25

<210> SEQ ID NO 132
<211> LENGTH: 25
<212> TYPE: RNA
<213> ORGANISM: Artificial
<220> FEATURE:
<223> OTHER INFORMATION: oligonucleotide

<400> SEQUENCE: 132
guuugccgcu gcccaaugcc auccu                                              25

<210> SEQ ID NO 133
<211> LENGTH: 25
<212> TYPE: RNA
<213> ORGANISM: Artificial
<220> FEATURE:
<223> OTHER INFORMATION: oligonucleotide

<400> SEQUENCE: 133
uuugccgcug cccaaugcca uccug                                              25

<210> SEQ ID NO 134
<211> LENGTH: 25
<212> TYPE: RNA
<213> ORGANISM: Artificial
<220> FEATURE:
<223> OTHER INFORMATION: oligonucleotide

<400> SEQUENCE: 134
uugccgcugc ccaaugccau ccugg                                              25

<210> SEQ ID NO 135
<211> LENGTH: 25
<212> TYPE: RNA
<213> ORGANISM: Artificial
<220> FEATURE:
<223> OTHER INFORMATION: oligonucleotide

<400> SEQUENCE: 135
ugccgcugcc caaugccauc cugga                                              25

<210> SEQ ID NO 136
<211> LENGTH: 25
<212> TYPE: RNA
<213> ORGANISM: Artificial
<220> FEATURE:
<223> OTHER INFORMATION: oligonucleotide

<400> SEQUENCE: 136
gccgcugccc aaugccaucc uggag                                              25

<210> SEQ ID NO 137
<211> LENGTH: 25
<212> TYPE: RNA
<213> ORGANISM: Artificial
<220> FEATURE:
<223> OTHER INFORMATION: oligonucleotide

<400> SEQUENCE: 137
ccgcugccca augccauccu ggagu                                              25

<210> SEQ ID NO 138

```
<211> LENGTH: 25
<212> TYPE: RNA
<213> ORGANISM: Artificial
<220> FEATURE:
<223> OTHER INFORMATION: oligonucleotide

<400> SEQUENCE: 138
cgcugcccaa ugccauccug gaguu                                          25

<210> SEQ ID NO 139
<211> LENGTH: 20
<212> TYPE: RNA
<213> ORGANISM: Artificial
<220> FEATURE:
<223> OTHER INFORMATION: oligonucleotide

<400> SEQUENCE: 139
uguuuuugag gauugcugaa                                                20

<210> SEQ ID NO 140
<211> LENGTH: 40
<212> TYPE: RNA
<213> ORGANISM: Artificial
<220> FEATURE:
<223> OTHER INFORMATION: oligonucleotide

<400> SEQUENCE: 140
uguucugaca acaguuugcc gcugcccaau gccauccugg                          40

<210> SEQ ID NO 141
<211> LENGTH: 25
<212> TYPE: RNA
<213> ORGANISM: Artificial
<220> FEATURE:
<223> OTHER INFORMATION: oligonucleotide

<400> SEQUENCE: 141
cucuggccug uccuaagacc ugcuc                                          25

<210> SEQ ID NO 142
<211> LENGTH: 25
<212> TYPE: RNA
<213> ORGANISM: Artificial
<220> FEATURE:
<223> OTHER INFORMATION: oligonucleotide

<400> SEQUENCE: 142
ucuggccugu ccuaagaccu gcuca                                          25

<210> SEQ ID NO 143
<211> LENGTH: 25
<212> TYPE: RNA
<213> ORGANISM: Artificial
<220> FEATURE:
<223> OTHER INFORMATION: oligonucleotide

<400> SEQUENCE: 143
cuggccuguc cuaagaccug cucag                                          25

<210> SEQ ID NO 144
<211> LENGTH: 25
<212> TYPE: RNA
<213> ORGANISM: Artificial
<220> FEATURE:
<223> OTHER INFORMATION: oligonucleotide
```

-continued

<400> SEQUENCE: 144
uggccugucc uaagaccugc ucagc                                          25

<210> SEQ ID NO 145
<211> LENGTH: 25
<212> TYPE: RNA
<213> ORGANISM: Artificial
<220> FEATURE:
<223> OTHER INFORMATION: oligonucleotide

<400> SEQUENCE: 145
ggccuguccu aagaccugcu cagcu                                          25

<210> SEQ ID NO 146
<211> LENGTH: 25
<212> TYPE: RNA
<213> ORGANISM: Artificial
<220> FEATURE:
<223> OTHER INFORMATION: oligonucleotide

<400> SEQUENCE: 146
gccuguccua agaccugcuc agcuu                                          25

<210> SEQ ID NO 147
<211> LENGTH: 25
<212> TYPE: RNA
<213> ORGANISM: Artificial
<220> FEATURE:
<223> OTHER INFORMATION: oligonucleotide

<400> SEQUENCE: 147
ccuguccuaa gaccugcuca gcuuc                                          25

<210> SEQ ID NO 148
<211> LENGTH: 25
<212> TYPE: RNA
<213> ORGANISM: Artificial
<220> FEATURE:
<223> OTHER INFORMATION: oligonucleotide

<400> SEQUENCE: 148
cuguccuaag accugcucag cuucu                                          25

<210> SEQ ID NO 149
<211> LENGTH: 25
<212> TYPE: RNA
<213> ORGANISM: Artificial
<220> FEATURE:
<223> OTHER INFORMATION: oligonucleotide

<400> SEQUENCE: 149
uguccuaaga ccugcucagc uucuu                                          25

<210> SEQ ID NO 150
<211> LENGTH: 25
<212> TYPE: RNA
<213> ORGANISM: Artificial
<220> FEATURE:
<223> OTHER INFORMATION: oligonucleotide

<400> SEQUENCE: 150
guccuaagac cugcucagcu ucuuc                                          25

<210> SEQ ID NO 151

```
<211> LENGTH: 25
<212> TYPE: RNA
<213> ORGANISM: Artificial
<220> FEATURE:
<223> OTHER INFORMATION: oligonucleotide

<400> SEQUENCE: 151
uccuaagacc ugcucagcuu cuucc                                 25

<210> SEQ ID NO 152
<211> LENGTH: 25
<212> TYPE: RNA
<213> ORGANISM: Artificial
<220> FEATURE:
<223> OTHER INFORMATION: oligonucleotide

<400> SEQUENCE: 152
ccuaagaccu gcucagcuuc uuccu                                 25

<210> SEQ ID NO 153
<211> LENGTH: 25
<212> TYPE: RNA
<213> ORGANISM: Artificial
<220> FEATURE:
<223> OTHER INFORMATION: oligonucleotide

<400> SEQUENCE: 153
cuaagaccug cucagcuucu uccuu                                 25

<210> SEQ ID NO 154
<211> LENGTH: 25
<212> TYPE: RNA
<213> ORGANISM: Artificial
<220> FEATURE:
<223> OTHER INFORMATION: oligonucleotide

<400> SEQUENCE: 154
uaagaccugc ucagcuucuu ccuua                                 25

<210> SEQ ID NO 155
<211> LENGTH: 25
<212> TYPE: RNA
<213> ORGANISM: Artificial
<220> FEATURE:
<223> OTHER INFORMATION: oligonucleotide

<400> SEQUENCE: 155
aagaccugcu cagcuucuuc cuuag                                 25

<210> SEQ ID NO 156
<211> LENGTH: 25
<212> TYPE: RNA
<213> ORGANISM: Artificial
<220> FEATURE:
<223> OTHER INFORMATION: oligonucleotide

<400> SEQUENCE: 156
agaccugcuc agcuucuucc uuagc                                 25

<210> SEQ ID NO 157
<211> LENGTH: 25
<212> TYPE: RNA
<213> ORGANISM: Artificial
<220> FEATURE:
<223> OTHER INFORMATION: oligonucleotide
```

<400> SEQUENCE: 157
gaccugcuca gcuucuuccu uagcu                                              25

<210> SEQ ID NO 158
<211> LENGTH: 25
<212> TYPE: RNA
<213> ORGANISM: Artificial
<220> FEATURE:
<223> OTHER INFORMATION: oligonucleotide

<400> SEQUENCE: 158
accugcucag cuucuuccuu agcuu                                              25

<210> SEQ ID NO 159
<211> LENGTH: 25
<212> TYPE: RNA
<213> ORGANISM: Artificial
<220> FEATURE:
<223> OTHER INFORMATION: oligonucleotide

<400> SEQUENCE: 159
ccugcucagc uucuuccuua gcuuc                                              25

<210> SEQ ID NO 160
<211> LENGTH: 25
<212> TYPE: RNA
<213> ORGANISM: Artificial
<220> FEATURE:
<223> OTHER INFORMATION: oligonucleotide

<400> SEQUENCE: 160
cugcucagcu ucuuccuuag cuucc                                              25

<210> SEQ ID NO 161
<211> LENGTH: 25
<212> TYPE: RNA
<213> ORGANISM: Artificial
<220> FEATURE:
<223> OTHER INFORMATION: oligonucleotide

<400> SEQUENCE: 161
ugcucagcuu cuuccuuagc uucca                                              25

<210> SEQ ID NO 162
<211> LENGTH: 25
<212> TYPE: RNA
<213> ORGANISM: Artificial
<220> FEATURE:
<223> OTHER INFORMATION: oligonucleotide

<400> SEQUENCE: 162
gcucagcuuc uuccuuagcu uccag                                              25

<210> SEQ ID NO 163
<211> LENGTH: 25
<212> TYPE: RNA
<213> ORGANISM: Artificial
<220> FEATURE:
<223> OTHER INFORMATION: oligonucleotide

<400> SEQUENCE: 163
cucagcuucu uccuuagcuu ccagc                                              25

<210> SEQ ID NO 164

<210> SEQ ID NO 164
<211> LENGTH: 25
<212> TYPE: RNA
<213> ORGANISM: Artificial
<220> FEATURE:
<223> OTHER INFORMATION: oligonucleotide

<400> SEQUENCE: 164
ucagcuucuu ccuuagcuuc cagcc                                    25

<210> SEQ ID NO 165
<211> LENGTH: 25
<212> TYPE: RNA
<213> ORGANISM: Artificial
<220> FEATURE:
<223> OTHER INFORMATION: oligonucleotide

<400> SEQUENCE: 165
cagcuucuuc cuuagcuucc agcca                                    25

<210> SEQ ID NO 166
<211> LENGTH: 25
<212> TYPE: RNA
<213> ORGANISM: Artificial
<220> FEATURE:
<223> OTHER INFORMATION: oligonucleotide

<400> SEQUENCE: 166
agcuucuucc uuagcuucca gccau                                    25

<210> SEQ ID NO 167
<211> LENGTH: 25
<212> TYPE: RNA
<213> ORGANISM: Artificial
<220> FEATURE:
<223> OTHER INFORMATION: oligonucleotide

<400> SEQUENCE: 167
gcuucuuccu uagcuuccag ccauu                                    25

<210> SEQ ID NO 168
<211> LENGTH: 25
<212> TYPE: RNA
<213> ORGANISM: Artificial
<220> FEATURE:
<223> OTHER INFORMATION: oligonucleotide

<400> SEQUENCE: 168
cuucuuccuu agcuuccagc cauug                                    25

<210> SEQ ID NO 169
<211> LENGTH: 25
<212> TYPE: RNA
<213> ORGANISM: Artificial
<220> FEATURE:
<223> OTHER INFORMATION: oligonucleotide

<400> SEQUENCE: 169
uucuuccuua gcuuccagcc auugu                                    25

<210> SEQ ID NO 170
<211> LENGTH: 25
<212> TYPE: RNA
<213> ORGANISM: Artificial
<220> FEATURE:
<223> OTHER INFORMATION: oligonucleotide

<400> SEQUENCE: 170
ucuuccuuag cuuccagcca uugug                                           25

<210> SEQ ID NO 171
<211> LENGTH: 25
<212> TYPE: RNA
<213> ORGANISM: Artificial
<220> FEATURE:
<223> OTHER INFORMATION: oligonucleotide

<400> SEQUENCE: 171
cuuccuuagc uuccagccau ugugu                                           25

<210> SEQ ID NO 172
<211> LENGTH: 25
<212> TYPE: RNA
<213> ORGANISM: Artificial
<220> FEATURE:
<223> OTHER INFORMATION: oligonucleotide

<400> SEQUENCE: 172
uuccuuagcu uccagccauu guguu                                           25

<210> SEQ ID NO 173
<211> LENGTH: 25
<212> TYPE: RNA
<213> ORGANISM: Artificial
<220> FEATURE:
<223> OTHER INFORMATION: oligonucleotide

<400> SEQUENCE: 173
uccuuagcuu ccagccauug uguug                                           25

<210> SEQ ID NO 174
<211> LENGTH: 25
<212> TYPE: RNA
<213> ORGANISM: Artificial
<220> FEATURE:
<223> OTHER INFORMATION: oligonucleotide

<400> SEQUENCE: 174
ccuuagcuuc cagccaugug guuga                                           25

<210> SEQ ID NO 175
<211> LENGTH: 25
<212> TYPE: RNA
<213> ORGANISM: Artificial
<220> FEATURE:
<223> OTHER INFORMATION: oligonucleotide

<400> SEQUENCE: 175
cuuagcuucc agccauugug uugaa                                           25

<210> SEQ ID NO 176
<211> LENGTH: 25
<212> TYPE: RNA
<213> ORGANISM: Artificial
<220> FEATURE:
<223> OTHER INFORMATION: oligonucleotide

<400> SEQUENCE: 176
uuagcuucca gccauugugu ugaau                                           25

<210> SEQ ID NO 177

```
<211> LENGTH: 25
<212> TYPE: RNA
<213> ORGANISM: Artificial
<220> FEATURE:
<223> OTHER INFORMATION: oligonucleotide

<400> SEQUENCE: 177
uagcuuccag ccauuguguu gaauc                                 25

<210> SEQ ID NO 178
<211> LENGTH: 25
<212> TYPE: RNA
<213> ORGANISM: Artificial
<220> FEATURE:
<223> OTHER INFORMATION: oligonucleotide

<400> SEQUENCE: 178
agcuuccagc cauuguguug aaucc                                 25

<210> SEQ ID NO 179
<211> LENGTH: 25
<212> TYPE: RNA
<213> ORGANISM: Artificial
<220> FEATURE:
<223> OTHER INFORMATION: oligonucleotide

<400> SEQUENCE: 179
gcuuccagcc auuguuuga auccu                                  25

<210> SEQ ID NO 180
<211> LENGTH: 25
<212> TYPE: RNA
<213> ORGANISM: Artificial
<220> FEATURE:
<223> OTHER INFORMATION: oligonucleotide

<400> SEQUENCE: 180
cuuccagcca uuguguugaa uccuu                                 25

<210> SEQ ID NO 181
<211> LENGTH: 25
<212> TYPE: RNA
<213> ORGANISM: Artificial
<220> FEATURE:
<223> OTHER INFORMATION: oligonucleotide

<400> SEQUENCE: 181
uuccagccau uguguugaau ccuuu                                 25

<210> SEQ ID NO 182
<211> LENGTH: 25
<212> TYPE: RNA
<213> ORGANISM: Artificial
<220> FEATURE:
<223> OTHER INFORMATION: oligonucleotide

<400> SEQUENCE: 182
uccagccauu guguugaauc cuuua                                 25

<210> SEQ ID NO 183
<211> LENGTH: 25
<212> TYPE: RNA
<213> ORGANISM: Artificial
<220> FEATURE:
<223> OTHER INFORMATION: oligonucleotide
```

<400> SEQUENCE: 183
ccagccauug uguugaaucc uuuaa                                          25

<210> SEQ ID NO 184
<211> LENGTH: 25
<212> TYPE: RNA
<213> ORGANISM: Artificial
<220> FEATURE:
<223> OTHER INFORMATION: oligonucleotide

<400> SEQUENCE: 184
cagccauugu guugaauccu uuaac                                          25

<210> SEQ ID NO 185
<211> LENGTH: 25
<212> TYPE: RNA
<213> ORGANISM: Artificial
<220> FEATURE:
<223> OTHER INFORMATION: oligonucleotide

<400> SEQUENCE: 185
agccauugug uugaauccuu uaaca                                          25

<210> SEQ ID NO 186
<211> LENGTH: 25
<212> TYPE: RNA
<213> ORGANISM: Artificial
<220> FEATURE:
<223> OTHER INFORMATION: oligonucleotide

<400> SEQUENCE: 186
gccauugugu ugaauccuuu aacau                                          25

<210> SEQ ID NO 187
<211> LENGTH: 25
<212> TYPE: RNA
<213> ORGANISM: Artificial
<220> FEATURE:
<223> OTHER INFORMATION: oligonucleotide

<400> SEQUENCE: 187
ccauuguguu gaauccuuua acauu                                          25

<210> SEQ ID NO 188
<211> LENGTH: 25
<212> TYPE: RNA
<213> ORGANISM: Artificial
<220> FEATURE:
<223> OTHER INFORMATION: oligonucleotide

<400> SEQUENCE: 188
cauuguguug aauccuuuaa cauuu                                          25

<210> SEQ ID NO 189
<211> LENGTH: 20
<212> TYPE: RNA
<213> ORGANISM: Artificial
<220> FEATURE:
<223> OTHER INFORMATION: oligonucleotide

<400> SEQUENCE: 189
ucagcuucug uuagccacug                                                20

<210> SEQ ID NO 190

```
<211> LENGTH: 20
<212> TYPE: RNA
<213> ORGANISM: Artificial
<220> FEATURE:
<223> OTHER INFORMATION: oligonucleotide

<400> SEQUENCE: 190
uucagcuucu guuagccacu                                              20

<210> SEQ ID NO 191
<211> LENGTH: 21
<212> TYPE: RNA
<213> ORGANISM: Artificial
<220> FEATURE:
<223> OTHER INFORMATION: oligonucleotide

<400> SEQUENCE: 191
uucagcuucu guuagccacu g                                            21

<210> SEQ ID NO 192
<211> LENGTH: 21
<212> TYPE: RNA
<213> ORGANISM: Artificial
<220> FEATURE:
<223> OTHER INFORMATION: oligonucleotide

<400> SEQUENCE: 192
ucagcuucug uuagccacug a                                            21

<210> SEQ ID NO 193
<211> LENGTH: 22
<212> TYPE: RNA
<213> ORGANISM: Artificial
<220> FEATURE:
<223> OTHER INFORMATION: oligonucleotide

<400> SEQUENCE: 193
uucagcuucu guuagccacu ga                                           22

<210> SEQ ID NO 194
<211> LENGTH: 21
<212> TYPE: RNA
<213> ORGANISM: Artificial
<220> FEATURE:
<223> OTHER INFORMATION: oligonucleotide

<400> SEQUENCE: 194
ucagcuucug uuagccacug a                                            21

<210> SEQ ID NO 195
<211> LENGTH: 22
<212> TYPE: RNA
<213> ORGANISM: Artificial
<220> FEATURE:
<223> OTHER INFORMATION: oligonucleotide

<400> SEQUENCE: 195
uucagcuucu guuagccacu ga                                           22

<210> SEQ ID NO 196
<211> LENGTH: 22
<212> TYPE: RNA
<213> ORGANISM: Artificial
<220> FEATURE:
<223> OTHER INFORMATION: oligonucleotide
```

<400> SEQUENCE: 196
ucagcuucug uuagccacug au                                          22

<210> SEQ ID NO 197
<211> LENGTH: 23
<212> TYPE: RNA
<213> ORGANISM: Artificial
<220> FEATURE:
<223> OTHER INFORMATION: oligonucleotide

<400> SEQUENCE: 197
uucagcuucu guuagccacu gau                                         23

<210> SEQ ID NO 198
<211> LENGTH: 23
<212> TYPE: RNA
<213> ORGANISM: Artificial
<220> FEATURE:
<223> OTHER INFORMATION: oligonucleotide

<400> SEQUENCE: 198
ucagcuucug uuagccacug auu                                         23

<210> SEQ ID NO 199
<211> LENGTH: 24
<212> TYPE: RNA
<213> ORGANISM: Artificial
<220> FEATURE:
<223> OTHER INFORMATION: oligonucleotide

<400> SEQUENCE: 199
uucagcuucu guuagccacu gauu                                        24

<210> SEQ ID NO 200
<211> LENGTH: 24
<212> TYPE: RNA
<213> ORGANISM: Artificial
<220> FEATURE:
<223> OTHER INFORMATION: oligonucleotide

<400> SEQUENCE: 200
ucagcuucug uuagccacug auua                                        24

<210> SEQ ID NO 201
<211> LENGTH: 24
<212> TYPE: RNA
<213> ORGANISM: Artificial
<220> FEATURE:
<223> OTHER INFORMATION: oligonucleotide

<400> SEQUENCE: 201
uucagcuucu guuagccacu gaua                                        24

<210> SEQ ID NO 202
<211> LENGTH: 25
<212> TYPE: RNA
<213> ORGANISM: Artificial
<220> FEATURE:
<223> OTHER INFORMATION: oligonucleotide

<400> SEQUENCE: 202
ucagcuucug uuagccacug auuaa                                       25

<210> SEQ ID NO 203

```
<211> LENGTH: 26
<212> TYPE: RNA
<213> ORGANISM: Artificial
<220> FEATURE:
<223> OTHER INFORMATION: oligonucleotide

<400> SEQUENCE: 203
uucagcuucu guuagccacu gauuaa                                          26

<210> SEQ ID NO 204
<211> LENGTH: 26
<212> TYPE: RNA
<213> ORGANISM: Artificial
<220> FEATURE:
<223> OTHER INFORMATION: oligonucleotide

<400> SEQUENCE: 204
ucagcuucug uuagccacug auuaaa                                          26

<210> SEQ ID NO 205
<211> LENGTH: 27
<212> TYPE: RNA
<213> ORGANISM: Artificial
<220> FEATURE:
<223> OTHER INFORMATION: oligonucleotide

<400> SEQUENCE: 205
uucagcuucu guuagccacu gauuaaa                                         27

<210> SEQ ID NO 206
<211> LENGTH: 19
<212> TYPE: RNA
<213> ORGANISM: Artificial
<220> FEATURE:
<223> OTHER INFORMATION: oligonucleotide

<400> SEQUENCE: 206
cagcuucugu uagccacug                                                  19

<210> SEQ ID NO 207
<211> LENGTH: 21
<212> TYPE: RNA
<213> ORGANISM: Artificial
<220> FEATURE:
<223> OTHER INFORMATION: oligonucleotide

<400> SEQUENCE: 207
cagcuucugu uagccacuga u                                               21

<210> SEQ ID NO 208
<211> LENGTH: 21
<212> TYPE: RNA
<213> ORGANISM: Artificial
<220> FEATURE:
<223> OTHER INFORMATION: oligonucleotide

<400> SEQUENCE: 208
agcuucuguu agccacugau u                                               21

<210> SEQ ID NO 209
<211> LENGTH: 22
<212> TYPE: RNA
<213> ORGANISM: Artificial
<220> FEATURE:
<223> OTHER INFORMATION: oligonucleotide
```

<400> SEQUENCE: 209
cagcuucugu uagccacuga uu                                        22

<210> SEQ ID NO 210
<211> LENGTH: 22
<212> TYPE: RNA
<213> ORGANISM: Artificial
<220> FEATURE:
<223> OTHER INFORMATION: oligonucleotide

<400> SEQUENCE: 210
agcuucuguu agccacugau ua                                        22

<210> SEQ ID NO 211
<211> LENGTH: 23
<212> TYPE: RNA
<213> ORGANISM: Artificial
<220> FEATURE:
<223> OTHER INFORMATION: oligonucleotide

<400> SEQUENCE: 211
cagcuucugu uagccacuga uua                                       23

<210> SEQ ID NO 212
<211> LENGTH: 23
<212> TYPE: RNA
<213> ORGANISM: Artificial
<220> FEATURE:
<223> OTHER INFORMATION: oligonucleotide

<400> SEQUENCE: 212
agcuucuguu agccacugau uaa                                       23

<210> SEQ ID NO 213
<211> LENGTH: 24
<212> TYPE: RNA
<213> ORGANISM: Artificial
<220> FEATURE:
<223> OTHER INFORMATION: oligonucleotide

<400> SEQUENCE: 213
cagcuucugu uagccacuga uuaa                                      24

<210> SEQ ID NO 214
<211> LENGTH: 24
<212> TYPE: RNA
<213> ORGANISM: Artificial
<220> FEATURE:
<223> OTHER INFORMATION: oligonucleotide

<400> SEQUENCE: 214
agcuucuguu agccacugau uaaa                                      24

<210> SEQ ID NO 215
<211> LENGTH: 25
<212> TYPE: RNA
<213> ORGANISM: Artificial
<220> FEATURE:
<223> OTHER INFORMATION: oligonucleotide

<400> SEQUENCE: 215
cagcuucugu uagccacuga uuaaa                                     25

<210> SEQ ID NO 216

```
<211> LENGTH: 24
<212> TYPE: RNA
<213> ORGANISM: Artificial
<220> FEATURE:
<223> OTHER INFORMATION: oligonucleotide

<400> SEQUENCE: 216
agcuucuguu agccacugau uaaa                                              24

<210> SEQ ID NO 217
<211> LENGTH: 20
<212> TYPE: RNA
<213> ORGANISM: Artificial
<220> FEATURE:
<223> OTHER INFORMATION: oligonucleotide

<400> SEQUENCE: 217
agcuucuguu agccacugau                                                   20

<210> SEQ ID NO 218
<211> LENGTH: 20
<212> TYPE: RNA
<213> ORGANISM: Artificial
<220> FEATURE:
<223> OTHER INFORMATION: oligonucleotide

<400> SEQUENCE: 218
gcuucuguua gccacugauu                                                   20

<210> SEQ ID NO 219
<211> LENGTH: 21
<212> TYPE: RNA
<213> ORGANISM: Artificial
<220> FEATURE:
<223> OTHER INFORMATION: oligonucleotide

<400> SEQUENCE: 219
agcuucuguu agccacugau u                                                 21

<210> SEQ ID NO 220
<211> LENGTH: 21
<212> TYPE: RNA
<213> ORGANISM: Artificial
<220> FEATURE:
<223> OTHER INFORMATION: oligonucleotide

<400> SEQUENCE: 220
gcuucuguua gccacugauu a                                                 21

<210> SEQ ID NO 221
<211> LENGTH: 22
<212> TYPE: RNA
<213> ORGANISM: Artificial
<220> FEATURE:
<223> OTHER INFORMATION: oligonucleotide

<400> SEQUENCE: 221
agcuucuguu agccacugau ua                                                22

<210> SEQ ID NO 222
<211> LENGTH: 22
<212> TYPE: RNA
<213> ORGANISM: Artificial
<220> FEATURE:
<223> OTHER INFORMATION: oligonucleotide
```

-continued

<400> SEQUENCE: 222
gcuucuguua gccacugauu aa                                    22

<210> SEQ ID NO 223
<211> LENGTH: 23
<212> TYPE: RNA
<213> ORGANISM: Artificial
<220> FEATURE:
<223> OTHER INFORMATION: oligonucleotide

<400> SEQUENCE: 223
agcuucuguu agccacugau uaa                                   23

<210> SEQ ID NO 224
<211> LENGTH: 23
<212> TYPE: RNA
<213> ORGANISM: Artificial
<220> FEATURE:
<223> OTHER INFORMATION: oligonucleotide

<400> SEQUENCE: 224
gcuucuguua gccacugauu aaa                                   23

<210> SEQ ID NO 225
<211> LENGTH: 24
<212> TYPE: RNA
<213> ORGANISM: Artificial
<220> FEATURE:
<223> OTHER INFORMATION: oligonucleotide

<400> SEQUENCE: 225
agcuucuguu agccacugau uaaa                                  24

<210> SEQ ID NO 226
<211> LENGTH: 23
<212> TYPE: RNA
<213> ORGANISM: Artificial
<220> FEATURE:
<223> OTHER INFORMATION: oligonucleotide

<400> SEQUENCE: 226
gcuucuguua gccacugauu aaa                                   23

<210> SEQ ID NO 227
<211> LENGTH: 23
<212> TYPE: RNA
<213> ORGANISM: Artificial
<220> FEATURE:
<223> OTHER INFORMATION: oligonucleotide

<400> SEQUENCE: 227
ccauuuguau uuagcauguu ccc                                   23

<210> SEQ ID NO 228
<211> LENGTH: 20
<212> TYPE: RNA
<213> ORGANISM: Artificial
<220> FEATURE:
<223> OTHER INFORMATION: oligonucleotide

<400> SEQUENCE: 228
agauaccauu uguauuuagc                                       20

<210> SEQ ID NO 229

```
<211> LENGTH: 19
<212> TYPE: RNA
<213> ORGANISM: Artificial
<220> FEATURE:
<223> OTHER INFORMATION: oligonucleotide

<400> SEQUENCE: 229
gccauuucuc aacagaucu                                                    19

<210> SEQ ID NO 230
<211> LENGTH: 23
<212> TYPE: RNA
<213> ORGANISM: Artificial
<220> FEATURE:
<223> OTHER INFORMATION: oligonucleotide

<400> SEQUENCE: 230
gccauuucuc aacagaucug uca                                               23

<210> SEQ ID NO 231
<211> LENGTH: 23
<212> TYPE: RNA
<213> ORGANISM: Artificial
<220> FEATURE:
<223> OTHER INFORMATION: oligonucleotide

<400> SEQUENCE: 231
auucucagga auugugucu uuc                                                23

<210> SEQ ID NO 232
<211> LENGTH: 21
<212> TYPE: RNA
<213> ORGANISM: Artificial
<220> FEATURE:
<223> OTHER INFORMATION: oligonucleotide

<400> SEQUENCE: 232
ucucaggaau uugugucuuu c                                                 21

<210> SEQ ID NO 233
<211> LENGTH: 18
<212> TYPE: RNA
<213> ORGANISM: Artificial
<220> FEATURE:
<223> OTHER INFORMATION: oligonucleotide

<400> SEQUENCE: 233
guucagcuuc uguuagcc                                                     18

<210> SEQ ID NO 234
<211> LENGTH: 21
<212> TYPE: RNA
<213> ORGANISM: Artificial
<220> FEATURE:
<223> OTHER INFORMATION: oligonucleotide

<400> SEQUENCE: 234
cugauuaaau aucuuuauau c                                                 21

<210> SEQ ID NO 235
<211> LENGTH: 18
<212> TYPE: RNA
<213> ORGANISM: Artificial
<220> FEATURE:
<223> OTHER INFORMATION: oligonucleotide
```

<400> SEQUENCE: 235
gccgccauuu cucaacag                                          18

<210> SEQ ID NO 236
<211> LENGTH: 18
<212> TYPE: RNA
<213> ORGANISM: Artificial
<220> FEATURE:
<223> OTHER INFORMATION: oligonucleotide

<400> SEQUENCE: 236
guauuuagca uguccca                                           18

<210> SEQ ID NO 237
<211> LENGTH: 18
<212> TYPE: RNA
<213> ORGANISM: Artificial
<220> FEATURE:
<223> OTHER INFORMATION: oligonucleotide

<400> SEQUENCE: 237
caggaauuug ugucuuuc                                          18

<210> SEQ ID NO 238
<211> LENGTH: 25
<212> TYPE: RNA
<213> ORGANISM: Artificial
<220> FEATURE:
<223> OTHER INFORMATION: oligonucleotide

<400> SEQUENCE: 238
gcuuuucuuu uaguugcugc ucuuu                                  25

<210> SEQ ID NO 239
<211> LENGTH: 25
<212> TYPE: RNA
<213> ORGANISM: Artificial
<220> FEATURE:
<223> OTHER INFORMATION: oligonucleotide

<400> SEQUENCE: 239
cuuuucuuuu aguugcugcu cuuuu                                  25

<210> SEQ ID NO 240
<211> LENGTH: 25
<212> TYPE: RNA
<213> ORGANISM: Artificial
<220> FEATURE:
<223> OTHER INFORMATION: oligonucleotide

<400> SEQUENCE: 240
uuuucuuuua guugcugcuc uuuuc                                  25

<210> SEQ ID NO 241
<211> LENGTH: 25
<212> TYPE: RNA
<213> ORGANISM: Artificial
<220> FEATURE:
<223> OTHER INFORMATION: oligonucleotide

<400> SEQUENCE: 241
uuucuuuuag uugcugcucu uuucc                                  25

<210> SEQ ID NO 242

```
<211> LENGTH: 25
<212> TYPE: RNA
<213> ORGANISM: Artificial
<220> FEATURE:
<223> OTHER INFORMATION: oligonucleotide

<400> SEQUENCE: 242
uucuuuuagu ugcugcucuu uucca                                        25

<210> SEQ ID NO 243
<211> LENGTH: 25
<212> TYPE: RNA
<213> ORGANISM: Artificial
<220> FEATURE:
<223> OTHER INFORMATION: oligonucleotide

<400> SEQUENCE: 243
ucuuuuaguu gcugcucuuu uccag                                        25

<210> SEQ ID NO 244
<211> LENGTH: 25
<212> TYPE: RNA
<213> ORGANISM: Artificial
<220> FEATURE:
<223> OTHER INFORMATION: oligonucleotide

<400> SEQUENCE: 244 cuuuaguug cugcucuuuu ccagg                                         25

<210> SEQ ID NO 245
<211> LENGTH: 25
<212> TYPE: RNA
<213> ORGANISM: Artificial
<220> FEATURE:
<223> OTHER INFORMATION: oligonucleotide

<400> SEQUENCE: 245
uuuuaguugc ugcucuuuuc caggu                                        25

<210> SEQ ID NO 246
<211> LENGTH: 25
<212> TYPE: RNA
<213> ORGANISM: Artificial
<220> FEATURE:
<223> OTHER INFORMATION: oligonucleotide

<400> SEQUENCE: 246
uuuaguugcu gcucuuuucc agguu                                        25

<210> SEQ ID NO 247
<211> LENGTH: 25
<212> TYPE: RNA
<213> ORGANISM: Artificial
<220> FEATURE:
<223> OTHER INFORMATION: oligonucleotide

<400> SEQUENCE: 247
uuaguugcug cucuuuucca gguuc                                        25

<210> SEQ ID NO 248
<211> LENGTH: 25
<212> TYPE: RNA
<213> ORGANISM: Artificial
<220> FEATURE:
<223> OTHER INFORMATION: oligonucleotide
```

```
<400> SEQUENCE: 248
uaguugcugc ucuuuccag guuca                                              25

<210> SEQ ID NO 249
<211> LENGTH: 25
<212> TYPE: RNA
<213> ORGANISM: Artificial
<220> FEATURE:
<223> OTHER INFORMATION: oligonucleotide

<400> SEQUENCE: 249
aguugcugcu cuuuuccagg uucaa                                             25

<210> SEQ ID NO 250
<211> LENGTH: 25
<212> TYPE: RNA
<213> ORGANISM: Artificial
<220> FEATURE:
<223> OTHER INFORMATION: oligonucleotide

<400> SEQUENCE: 250
guugcugcuc uuuccaggu ucaag                                              25

<210> SEQ ID NO 251
<211> LENGTH: 25
<212> TYPE: RNA
<213> ORGANISM: Artificial
<220> FEATURE:
<223> OTHER INFORMATION: oligonucleotide

<400> SEQUENCE: 251
uugcugcucu uuccagguu caagu                                              25

<210> SEQ ID NO 252
<211> LENGTH: 25
<212> TYPE: RNA
<213> ORGANISM: Artificial
<220> FEATURE:
<223> OTHER INFORMATION: oligonucleotide

<400> SEQUENCE: 252
ugcugcucuu uuccagguuc aagug                                             25

<210> SEQ ID NO 253
<211> LENGTH: 25
<212> TYPE: RNA
<213> ORGANISM: Artificial
<220> FEATURE:
<223> OTHER INFORMATION: oligonucleotide

<400> SEQUENCE: 253
gcugcucuuu uccagguuca agugg                                             25

<210> SEQ ID NO 254
<211> LENGTH: 25
<212> TYPE: RNA
<213> ORGANISM: Artificial
<220> FEATURE:
<223> OTHER INFORMATION: oligonucleotide

<400> SEQUENCE: 254
cugcucuuuu ccagguucaa guggg                                             25

<210> SEQ ID NO 255
```

```
<211> LENGTH: 25
<212> TYPE: RNA
<213> ORGANISM: Artificial
<220> FEATURE:
<223> OTHER INFORMATION: oligonucleotide

<400> SEQUENCE: 255
ugcucuuuuc cagguucaag uggga                                              25

<210> SEQ ID NO 256
<211> LENGTH: 25
<212> TYPE: RNA
<213> ORGANISM: Artificial
<220> FEATURE:
<223> OTHER INFORMATION: oligonucleotide

<400> SEQUENCE: 256
gcucuuuucc agguucaagu gggac                                              25

<210> SEQ ID NO 257
<211> LENGTH: 25
<212> TYPE: RNA
<213> ORGANISM: Artificial
<220> FEATURE:
<223> OTHER INFORMATION: oligonucleotide

<400> SEQUENCE: 257
cucuuuucca gguucaagug ggaua                                              25

<210> SEQ ID NO 258
<211> LENGTH: 25
<212> TYPE: RNA
<213> ORGANISM: Artificial
<220> FEATURE:
<223> OTHER INFORMATION: oligonucleotide

<400> SEQUENCE: 258
ucuuuuccag guucaagugg gauac                                              25

<210> SEQ ID NO 259
<211> LENGTH: 20
<212> TYPE: RNA
<213> ORGANISM: Artificial
<220> FEATURE:
<223> OTHER INFORMATION: oligonucleotide

<400> SEQUENCE: 259
ucuuuuccag guucaagugg                                                    20

<210> SEQ ID NO 260
<211> LENGTH: 25
<212> TYPE: RNA
<213> ORGANISM: Artificial
<220> FEATURE:
<223> OTHER INFORMATION: oligonucleotide

<400> SEQUENCE: 260
cuuuuccagg uucaaguggg auacu                                              25

<210> SEQ ID NO 261
<211> LENGTH: 25
<212> TYPE: RNA
<213> ORGANISM: Artificial
<220> FEATURE:
<223> OTHER INFORMATION: oligonucleotide
```

```
<400> SEQUENCE: 261
uuuuccaggu ucaaguggga uacua                                      25

<210> SEQ ID NO 262
<211> LENGTH: 25
<212> TYPE: RNA
<213> ORGANISM: Artificial
<220> FEATURE:
<223> OTHER INFORMATION: oligonucleotide

<400> SEQUENCE: 262
uuuccagguu caagugggau acuag                                      25

<210> SEQ ID NO 263
<211> LENGTH: 25
<212> TYPE: RNA
<213> ORGANISM: Artificial
<220> FEATURE:
<223> OTHER INFORMATION: oligonucleotide

<400> SEQUENCE: 263
uuccagguuc aagugggaua cuagc                                      25

<210> SEQ ID NO 264
<211> LENGTH: 25
<212> TYPE: RNA
<213> ORGANISM: Artificial
<220> FEATURE:
<223> OTHER INFORMATION: oligonucleotide

<400> SEQUENCE: 264
uccagguuca agugggauac uagca                                      25

<210> SEQ ID NO 265
<211> LENGTH: 25
<212> TYPE: RNA
<213> ORGANISM: Artificial
<220> FEATURE:
<223> OTHER INFORMATION: oligonucleotide

<400> SEQUENCE: 265
ccagguucaa gugggauacu agcaa                                      25

<210> SEQ ID NO 266
<211> LENGTH: 25
<212> TYPE: RNA
<213> ORGANISM: Artificial
<220> FEATURE:
<223> OTHER INFORMATION: oligonucleotide

<400> SEQUENCE: 266
cagguucaag ugggauacua gcaau                                      25

<210> SEQ ID NO 267
<211> LENGTH: 25
<212> TYPE: RNA
<213> ORGANISM: Artificial
<220> FEATURE:
<223> OTHER INFORMATION: oligonucleotide

<400> SEQUENCE: 267
agguucaagu gggauacuag caaug                                      25

<210> SEQ ID NO 268
```

```
<211> LENGTH: 25
<212> TYPE: RNA
<213> ORGANISM: Artificial
<220> FEATURE:
<223> OTHER INFORMATION: oligonucleotide

<400> SEQUENCE: 268
gguucaagug ggauacuagc aaugu                                       25

<210> SEQ ID NO 269
<211> LENGTH: 25
<212> TYPE: RNA
<213> ORGANISM: Artificial
<220> FEATURE:
<223> OTHER INFORMATION: oligonucleotide

<400> SEQUENCE: 269
guucaagugg gauacuagca auguu                                       25

<210> SEQ ID NO 270
<211> LENGTH: 25
<212> TYPE: RNA
<213> ORGANISM: Artificial
<220> FEATURE:
<223> OTHER INFORMATION: oligonucleotide

<400> SEQUENCE: 270 uucaagugggg auacuagcaa uguua                                      25

<210> SEQ ID NO 271
<211> LENGTH: 25
<212> TYPE: RNA
<213> ORGANISM: Artificial
<220> FEATURE:
<223> OTHER INFORMATION: oligonucleotide

<400> SEQUENCE: 271
ucaaguggga uacuagcaau guuau                                       25

<210> SEQ ID NO 272
<211> LENGTH: 25
<212> TYPE: RNA
<213> ORGANISM: Artificial
<220> FEATURE:
<223> OTHER INFORMATION: oligonucleotide

<400> SEQUENCE: 272
caagugggau acuagcaaug uuauc                                       25

<210> SEQ ID NO 273
<211> LENGTH: 25
<212> TYPE: RNA
<213> ORGANISM: Artificial
<220> FEATURE:
<223> OTHER INFORMATION: oligonucleotide

<400> SEQUENCE: 273
aagugggaua cuagcaaugu uaucu                                       25

<210> SEQ ID NO 274
<211> LENGTH: 25
<212> TYPE: RNA
<213> ORGANISM: Artificial
<220> FEATURE:
<223> OTHER INFORMATION: oligonucleotide
```

```
<400> SEQUENCE: 274
agugggauac uagcaauguu aucug                                  25

<210> SEQ ID NO 275
<211> LENGTH: 25
<212> TYPE: RNA
<213> ORGANISM: Artificial
<220> FEATURE:
<223> OTHER INFORMATION: oligonucleotide

<400> SEQUENCE: 275
gugggauacu agcaauguua ucugc                                  25

<210> SEQ ID NO 276
<211> LENGTH: 25
<212> TYPE: RNA
<213> ORGANISM: Artificial
<220> FEATURE:
<223> OTHER INFORMATION: oligonucleotide

<400> SEQUENCE: 276
ugggauacua gcaauguuau cugcu                                  25

<210> SEQ ID NO 277
<211> LENGTH: 25
<212> TYPE: RNA
<213> ORGANISM: Artificial
<220> FEATURE:
<223> OTHER INFORMATION: oligonucleotide

<400> SEQUENCE: 277
gggauacuag caauguuauc ugcuu                                  25

<210> SEQ ID NO 278
<211> LENGTH: 25
<212> TYPE: RNA
<213> ORGANISM: Artificial
<220> FEATURE:
<223> OTHER INFORMATION: oligonucleotide

<400> SEQUENCE: 278
ggauacuagc aauguuaucu gcuuc                                  25

<210> SEQ ID NO 279
<211> LENGTH: 25
<212> TYPE: RNA
<213> ORGANISM: Artificial
<220> FEATURE:
<223> OTHER INFORMATION: oligonucleotide

<400> SEQUENCE: 279
gauacuagca auguuaucug cuucc                                  25

<210> SEQ ID NO 280
<211> LENGTH: 25
<212> TYPE: RNA
<213> ORGANISM: Artificial
<220> FEATURE:
<223> OTHER INFORMATION: oligonucleotide

<400> SEQUENCE: 280
auacuagcaa uguuaucugc uuccu                                  25

<210> SEQ ID NO 281
```

```
<211> LENGTH: 25
<212> TYPE: RNA
<213> ORGANISM: Artificial
<220> FEATURE:
<223> OTHER INFORMATION: oligonucleotide

<400> SEQUENCE: 281
uacuagcaau guuaucugcu uccuc                                           25

<210> SEQ ID NO 282
<211> LENGTH: 25
<212> TYPE: RNA
<213> ORGANISM: Artificial
<220> FEATURE:
<223> OTHER INFORMATION: oligonucleotide

<400> SEQUENCE: 282
acuagcaaug uuaucugcuu ccucc                                           25

<210> SEQ ID NO 283
<211> LENGTH: 25
<212> TYPE: RNA
<213> ORGANISM: Artificial
<220> FEATURE:
<223> OTHER INFORMATION: oligonucleotide

<400> SEQUENCE: 283
cuagcaaugu uaucugcuuc cucca                                           25

<210> SEQ ID NO 284
<211> LENGTH: 25
<212> TYPE: RNA
<213> ORGANISM: Artificial
<220> FEATURE:
<223> OTHER INFORMATION: oligonucleotide

<400> SEQUENCE: 284
uagcaauguu aucugcuucc uccaa                                           25

<210> SEQ ID NO 285
<211> LENGTH: 25
<212> TYPE: RNA
<213> ORGANISM: Artificial
<220> FEATURE:
<223> OTHER INFORMATION: oligonucleotide

<400> SEQUENCE: 285
agcaauguua ucugcuuccu ccaac                                           25

<210> SEQ ID NO 286
<211> LENGTH: 25
<212> TYPE: RNA
<213> ORGANISM: Artificial
<220> FEATURE:
<223> OTHER INFORMATION: oligonucleotide

<400> SEQUENCE: 286
gcaauguuau cugcuuccuc caacc                                           25

<210> SEQ ID NO 287
<211> LENGTH: 25
<212> TYPE: RNA
<213> ORGANISM: Artificial
<220> FEATURE:
<223> OTHER INFORMATION: oligonucleotide
```

```
<400> SEQUENCE: 287
caauguuauc ugcuuccucc aacca                                    25

<210> SEQ ID NO 288
<211> LENGTH: 25
<212> TYPE: RNA
<213> ORGANISM: Artificial
<220> FEATURE:
<223> OTHER INFORMATION: oligonucleotide

<400> SEQUENCE: 288
aauguuaucu gcuuccucca accau                                    25

<210> SEQ ID NO 289
<211> LENGTH: 25
<212> TYPE: RNA
<213> ORGANISM: Artificial
<220> FEATURE:
<223> OTHER INFORMATION: oligonucleotide

<400> SEQUENCE: 289
auguuaucug cuuccuccaa ccaua                                    25

<210> SEQ ID NO 290
<211> LENGTH: 25
<212> TYPE: RNA
<213> ORGANISM: Artificial
<220> FEATURE:
<223> OTHER INFORMATION: oligonucleotide

<400> SEQUENCE: 290
uguuaucugc uuccuccaac cauaa                                    25

<210> SEQ ID NO 291
<211> LENGTH: 25
<212> TYPE: RNA
<213> ORGANISM: Artificial
<220> FEATURE:
<223> OTHER INFORMATION: oligonucleotide

<400> SEQUENCE: 291
agccucuuga uugcuggucu uguuu                                    25

<210> SEQ ID NO 292
<211> LENGTH: 25
<212> TYPE: RNA
<213> ORGANISM: Artificial
<220> FEATURE:
<223> OTHER INFORMATION: oligonucleotide

<400> SEQUENCE: 292
gccucuugau ugcuggucuu guuuu                                    25

<210> SEQ ID NO 293
<211> LENGTH: 25
<212> TYPE: RNA
<213> ORGANISM: Artificial
<220> FEATURE:
<223> OTHER INFORMATION: oligonucleotide

<400> SEQUENCE: 293
ccucuugauu gcuggucuug uuuuu                                    25

<210> SEQ ID NO 294
```

```
<211> LENGTH: 20
<212> TYPE: RNA
<213> ORGANISM: Artificial
<220> FEATURE:
<223> OTHER INFORMATION: oligonucleotide

<400> SEQUENCE: 294
ccucuugauu gcggucuug                                              20

<210> SEQ ID NO 295
<211> LENGTH: 25
<212> TYPE: RNA
<213> ORGANISM: Artificial
<220> FEATURE:
<223> OTHER INFORMATION: oligonucleotide

<400> SEQUENCE: 295
cucuugauug cggucuugu uuuc                                         25

<210> SEQ ID NO 296
<211> LENGTH: 25
<212> TYPE: RNA
<213> ORGANISM: Artificial
<220> FEATURE:
<223> OTHER INFORMATION: oligonucleotide

<400> SEQUENCE: 296
ucuugauugc uggcuuguu uuca                                         25

<210> SEQ ID NO 297
<211> LENGTH: 25
<212> TYPE: RNA
<213> ORGANISM: Artificial
<220> FEATURE:
<223> OTHER INFORMATION: oligonucleotide

<400> SEQUENCE: 297
cuugauugcu ggucuuguuu ucaa                                        25

<210> SEQ ID NO 298
<211> LENGTH: 25
<212> TYPE: RNA
<213> ORGANISM: Artificial
<220> FEATURE:
<223> OTHER INFORMATION: oligonucleotide

<400> SEQUENCE: 298
uugauugcug gucuuguuuu ucaaa                                       25

<210> SEQ ID NO 299
<211> LENGTH: 25
<212> TYPE: RNA
<213> ORGANISM: Artificial
<220> FEATURE:
<223> OTHER INFORMATION: oligonucleotide

<400> SEQUENCE: 299
ugauugcugg ucuuguuuuu caaau                                       25

<210> SEQ ID NO 300
<211> LENGTH: 25
<212> TYPE: RNA
<213> ORGANISM: Artificial
<220> FEATURE:
<223> OTHER INFORMATION: oligonucleotide
```

```
<400> SEQUENCE: 300
gauugcuggu cuuguuuuc aaauu                                          25

<210> SEQ ID NO 301
<211> LENGTH: 20
<212> TYPE: RNA
<213> ORGANISM: Artificial
<220> FEATURE:
<223> OTHER INFORMATION: oligonucleotide

<400> SEQUENCE: 301
gauugcuggu cuuguuuuc                                                20

<210> SEQ ID NO 302
<211> LENGTH: 25
<212> TYPE: RNA
<213> ORGANISM: Artificial
<220> FEATURE:
<223> OTHER INFORMATION: oligonucleotide

<400> SEQUENCE: 302 auugcgguc uuguuuuca aauuu                                           25

<210> SEQ ID NO 303
<211> LENGTH: 25
<212> TYPE: RNA
<213> ORGANISM: Artificial
<220> FEATURE:
<223> OTHER INFORMATION: oligonucleotide

<400> SEQUENCE: 303
uugcuggucu uguuuucaa auuu                                           25

<210> SEQ ID NO 304
<211> LENGTH: 25
<212> TYPE: RNA
<213> ORGANISM: Artificial
<220> FEATURE:
<223> OTHER INFORMATION: oligonucleotide

<400> SEQUENCE: 304
ugcuggucuu guuuucaaa uuuug                                          25

<210> SEQ ID NO 305
<211> LENGTH: 25
<212> TYPE: RNA
<213> ORGANISM: Artificial
<220> FEATURE:
<223> OTHER INFORMATION: oligonucleotide

<400> SEQUENCE: 305
gcuggucuug uuuucaaau uuugg                                          25

<210> SEQ ID NO 306
<211> LENGTH: 25
<212> TYPE: RNA
<213> ORGANISM: Artificial
<220> FEATURE:
<223> OTHER INFORMATION: oligonucleotide

<400> SEQUENCE: 306
cuggucuugu uuucaaauu uuggg                                          25

<210> SEQ ID NO 307
```

```
<210> SEQ ID NO 307
<211> LENGTH: 25
<212> TYPE: RNA
<213> ORGANISM: Artificial
<220> FEATURE:
<223> OTHER INFORMATION: oligonucleotide

<400> SEQUENCE: 307
uggucuuguu uuucaaauuu ugggc                                       25

<210> SEQ ID NO 308
<211> LENGTH: 25
<212> TYPE: RNA
<213> ORGANISM: Artificial
<220> FEATURE:
<223> OTHER INFORMATION: oligonucleotide

<400> SEQUENCE: 308
ggucuuguuu uucaaauuuu gggca                                       25

<210> SEQ ID NO 309
<211> LENGTH: 25
<212> TYPE: RNA
<213> ORGANISM: Artificial
<220> FEATURE:
<223> OTHER INFORMATION: oligonucleotide

<400> SEQUENCE: 309
gucuuguuuu ucaaauuuug ggcag                                       25

<210> SEQ ID NO 310
<211> LENGTH: 25
<212> TYPE: RNA
<213> ORGANISM: Artificial
<220> FEATURE:
<223> OTHER INFORMATION: oligonucleotide

<400> SEQUENCE: 310
ucuuguuuuu caaauuuugg gcagc                                       25

<210> SEQ ID NO 311
<211> LENGTH: 25
<212> TYPE: RNA
<213> ORGANISM: Artificial
<220> FEATURE:
<223> OTHER INFORMATION: oligonucleotide

<400> SEQUENCE: 311
cuuguuuuuc aaauuugggg cagcg                                       25

<210> SEQ ID NO 312
<211> LENGTH: 25
<212> TYPE: RNA
<213> ORGANISM: Artificial
<220> FEATURE:
<223> OTHER INFORMATION: oligonucleotide

<400> SEQUENCE: 312
uuguuuuuca aauuugggc agcgg                                        25

<210> SEQ ID NO 313
<211> LENGTH: 25
<212> TYPE: RNA
<213> ORGANISM: Artificial
<220> FEATURE:
<223> OTHER INFORMATION: oligonucleotide
```

<400> SEQUENCE: 313
uguuuuucaa auuugggca gcggu                                              25

<210> SEQ ID NO 314
<211> LENGTH: 25
<212> TYPE: RNA
<213> ORGANISM: Artificial
<220> FEATURE:
<223> OTHER INFORMATION: oligonucleotide

<400> SEQUENCE: 314
guuuuucaaa uuugggcag cggua                                              25

<210> SEQ ID NO 315
<211> LENGTH: 25
<212> TYPE: RNA
<213> ORGANISM: Artificial
<220> FEATURE:
<223> OTHER INFORMATION: oligonucleotide

<400> SEQUENCE: 315
uuuuucaaau uugggcagc gguaa                                              25

<210> SEQ ID NO 316
<211> LENGTH: 25
<212> TYPE: RNA
<213> ORGANISM: Artificial
<220> FEATURE:
<223> OTHER INFORMATION: oligonucleotide

<400> SEQUENCE: 316
uuuucaaauu ugggcagcg guaau                                              25

<210> SEQ ID NO 317
<211> LENGTH: 25
<212> TYPE: RNA
<213> ORGANISM: Artificial
<220> FEATURE:
<223> OTHER INFORMATION: oligonucleotide

<400> SEQUENCE: 317
uuucaaauuu ugggcagcgg uaaug                                             25

<210> SEQ ID NO 318
<211> LENGTH: 25
<212> TYPE: RNA
<213> ORGANISM: Artificial
<220> FEATURE:
<223> OTHER INFORMATION: oligonucleotide

<400> SEQUENCE: 318
uucaaauuuu gggcagcggu aauga                                             25

<210> SEQ ID NO 319
<211> LENGTH: 25
<212> TYPE: RNA
<213> ORGANISM: Artificial
<220> FEATURE:
<223> OTHER INFORMATION: oligonucleotide

<400> SEQUENCE: 319
ucaaauuuug gcagcggua augag                                              25

<210> SEQ ID NO 320

```
<211> LENGTH: 25
<212> TYPE: RNA
<213> ORGANISM: Artificial
<220> FEATURE:
<223> OTHER INFORMATION: oligonucleotide

<400> SEQUENCE: 320
caaauuuugg gcagcgguaa ugagu                                      25

<210> SEQ ID NO 321
<211> LENGTH: 25
<212> TYPE: RNA
<213> ORGANISM: Artificial
<220> FEATURE:
<223> OTHER INFORMATION: oligonucleotide

<400> SEQUENCE: 321
aaauuuuggg cagcgguaau gaguu                                      25

<210> SEQ ID NO 322
<211> LENGTH: 25
<212> TYPE: RNA
<213> ORGANISM: Artificial
<220> FEATURE:
<223> OTHER INFORMATION: oligonucleotide

<400> SEQUENCE: 322
aauuuugggc agcgguaaug aguuc                                      25

<210> SEQ ID NO 323
<211> LENGTH: 25
<212> TYPE: RNA
<213> ORGANISM: Artificial
<220> FEATURE:
<223> OTHER INFORMATION: oligonucleotide

<400> SEQUENCE: 323 auuuuggca gcgguaauga guucu                                       25

<210> SEQ ID NO 324
<211> LENGTH: 25
<212> TYPE: RNA
<213> ORGANISM: Artificial
<220> FEATURE:
<223> OTHER INFORMATION: oligonucleotide

<400> SEQUENCE: 324
uuuugggcag cgguaaugag uucuu                                      25

<210> SEQ ID NO 325
<211> LENGTH: 25
<212> TYPE: RNA
<213> ORGANISM: Artificial
<220> FEATURE:
<223> OTHER INFORMATION: oligonucleotide

<400> SEQUENCE: 325
uuugggcagc gguaaugagu ucuuc                                      25

<210> SEQ ID NO 326
<211> LENGTH: 25
<212> TYPE: RNA
<213> ORGANISM: Artificial
<220> FEATURE:
<223> OTHER INFORMATION: oligonucleotide
```

<400> SEQUENCE: 326
uugggcagcg guaaugaguu cuucc                                         25

<210> SEQ ID NO 327
<211> LENGTH: 25
<212> TYPE: RNA
<213> ORGANISM: Artificial
<220> FEATURE:
<223> OTHER INFORMATION: oligonucleotide

<400> SEQUENCE: 327
ugggcagcgg uaaugaguuc uucca                                         25

<210> SEQ ID NO 328
<211> LENGTH: 25
<212> TYPE: RNA
<213> ORGANISM: Artificial
<220> FEATURE:
<223> OTHER INFORMATION: oligonucleotide

<400> SEQUENCE: 328
gggcagcggu aaugaguucu uccaa                                         25

<210> SEQ ID NO 329
<211> LENGTH: 25
<212> TYPE: RNA
<213> ORGANISM: Artificial
<220> FEATURE:
<223> OTHER INFORMATION: oligonucleotide

<400> SEQUENCE: 329
ggcagcggua augaguucuu ccaac                                         25

<210> SEQ ID NO 330
<211> LENGTH: 25
<212> TYPE: RNA
<213> ORGANISM: Artificial
<220> FEATURE:
<223> OTHER INFORMATION: oligonucleotide

<400> SEQUENCE: 330
gcagcgguaa ugaguucuuc caacu                                         25

<210> SEQ ID NO 331
<211> LENGTH: 25
<212> TYPE: RNA
<213> ORGANISM: Artificial
<220> FEATURE:
<223> OTHER INFORMATION: oligonucleotide

<400> SEQUENCE: 331
cagcgguaau gaguucuucc aacug                                         25

<210> SEQ ID NO 332
<211> LENGTH: 25
<212> TYPE: RNA
<213> ORGANISM: Artificial
<220> FEATURE:
<223> OTHER INFORMATION: oligonucleotide

<400> SEQUENCE: 332
agcgguaaug aguucuucca acugg                                         25

<210> SEQ ID NO 333

```
<211> LENGTH: 25
<212> TYPE: RNA
<213> ORGANISM: Artificial
<220> FEATURE:
<223> OTHER INFORMATION: oligonucleotide

<400> SEQUENCE: 333
gcgguaauga guucuuccaa cuggg                                          25

<210> SEQ ID NO 334
<211> LENGTH: 25
<212> TYPE: RNA
<213> ORGANISM: Artificial
<220> FEATURE:
<223> OTHER INFORMATION: oligonucleotide

<400> SEQUENCE: 334
cgguaaugag uucuuccaac ugggg                                          25

<210> SEQ ID NO 335
<211> LENGTH: 25
<212> TYPE: RNA
<213> ORGANISM: Artificial
<220> FEATURE:
<223> OTHER INFORMATION: oligonucleotide

<400> SEQUENCE: 335
gguaaugagu ucuuccaacu gggga                                          25

<210> SEQ ID NO 336
<211> LENGTH: 22
<212> TYPE: RNA
<213> ORGANISM: Artificial
<220> FEATURE:
<223> OTHER INFORMATION: oligonucleotide

<400> SEQUENCE: 336
gguaaugagu ucuuccaacu gg                                             22

<210> SEQ ID NO 337
<211> LENGTH: 25
<212> TYPE: RNA
<213> ORGANISM: Artificial
<220> FEATURE:
<223> OTHER INFORMATION: oligonucleotide

<400> SEQUENCE: 337
guaaugaguu cuuccaacug gggac                                          25

<210> SEQ ID NO 338
<211> LENGTH: 25
<212> TYPE: RNA
<213> ORGANISM: Artificial
<220> FEATURE:
<223> OTHER INFORMATION: oligonucleotide

<400> SEQUENCE: 338
uaaugaguuc uuccaacugg ggacg                                          25

<210> SEQ ID NO 339
<211> LENGTH: 25
<212> TYPE: RNA
<213> ORGANISM: Artificial
<220> FEATURE:
<223> OTHER INFORMATION: oligonucleotide
```

<400> SEQUENCE: 339
aaugaguucu uccaacuggg gacgc                                    25

<210> SEQ ID NO 340
<211> LENGTH: 25
<212> TYPE: RNA
<213> ORGANISM: Artificial
<220> FEATURE:
<223> OTHER INFORMATION: oligonucleotide

<400> SEQUENCE: 340
augaguucuu ccaacugggg acgcc                                    25

<210> SEQ ID NO 341
<211> LENGTH: 25
<212> TYPE: RNA
<213> ORGANISM: Artificial
<220> FEATURE:
<223> OTHER INFORMATION: oligonucleotide

<400> SEQUENCE: 341
ugaguucuuc caacugggga cgccu                                    25

<210> SEQ ID NO 342
<211> LENGTH: 25
<212> TYPE: RNA
<213> ORGANISM: Artificial
<220> FEATURE:
<223> OTHER INFORMATION: oligonucleotide

<400> SEQUENCE: 342
gaguucuucc aacugggdac gccuc                                    25

<210> SEQ ID NO 343
<211> LENGTH: 25
<212> TYPE: RNA
<213> ORGANISM: Artificial
<220> FEATURE:
<223> OTHER INFORMATION: oligonucleotide

<400> SEQUENCE: 343
aguucuucca acuggggacg ccucu                                    25

<210> SEQ ID NO 344
<211> LENGTH: 25
<212> TYPE: RNA
<213> ORGANISM: Artificial
<220> FEATURE:
<223> OTHER INFORMATION: oligonucleotide

<400> SEQUENCE: 344
guucuuccaa cugggggacgc cucug                                   25

<210> SEQ ID NO 345
<211> LENGTH: 25
<212> TYPE: RNA
<213> ORGANISM: Artificial
<220> FEATURE:
<223> OTHER INFORMATION: oligonucleotide

<400> SEQUENCE: 345
uucuuccaac uggggacgcc ucugu                                    25

<210> SEQ ID NO 346

```
<211> LENGTH: 25
<212> TYPE: RNA
<213> ORGANISM: Artificial
<220> FEATURE:
<223> OTHER INFORMATION: oligonucleotide

<400> SEQUENCE: 346
ucuuccaacu ggggacgccu cuguu                                    25

<210> SEQ ID NO 347
<211> LENGTH: 25
<212> TYPE: RNA
<213> ORGANISM: Artificial
<220> FEATURE:
<223> OTHER INFORMATION: oligonucleotide

<400> SEQUENCE: 347
cuuccaacug gggacgccuc uguuc                                    25

<210> SEQ ID NO 348
<211> LENGTH: 25
<212> TYPE: RNA
<213> ORGANISM: Artificial
<220> FEATURE:
<223> OTHER INFORMATION: oligonucleotide

<400> SEQUENCE: 348
uuccaacugg ggacgccucu guucc                                    25

<210> SEQ ID NO 349
<211> LENGTH: 25
<212> TYPE: RNA
<213> ORGANISM: Artificial
<220> FEATURE:
<223> OTHER INFORMATION: oligonucleotide

<400> SEQUENCE: 349
uccaacuggg gacgccucug uucca                                    25

<210> SEQ ID NO 350
<211> LENGTH: 25
<212> TYPE: RNA
<213> ORGANISM: Artificial
<220> FEATURE:
<223> OTHER INFORMATION: oligonucleotide

<400> SEQUENCE: 350
ccaacugggg acgccucugu uccaa                                    25

<210> SEQ ID NO 351
<211> LENGTH: 25
<212> TYPE: RNA
<213> ORGANISM: Artificial
<220> FEATURE:
<223> OTHER INFORMATION: oligonucleotide

<400> SEQUENCE: 351
caacugggga cgccucuguu ccaaa                                    25

<210> SEQ ID NO 352
<211> LENGTH: 25
<212> TYPE: RNA
<213> ORGANISM: Artificial
<220> FEATURE:
<223> OTHER INFORMATION: oligonucleotide
```

<400> SEQUENCE: 352 aacugggac gccucuguuc caaau                                          25

<210> SEQ ID NO 353
<211> LENGTH: 25
<212> TYPE: RNA
<213> ORGANISM: Artificial
<220> FEATURE:
<223> OTHER INFORMATION: oligonucleotide

<400> SEQUENCE: 353 acugggacg ccucuguucc aaauc                                          25

<210> SEQ ID NO 354
<211> LENGTH: 25
<212> TYPE: RNA
<213> ORGANISM: Artificial
<220> FEATURE:
<223> OTHER INFORMATION: oligonucleotide

<400> SEQUENCE: 354
cuggggacgc cucuguucca aaucc                                         25

<210> SEQ ID NO 355
<211> LENGTH: 25
<212> TYPE: RNA
<213> ORGANISM: Artificial
<220> FEATURE:
<223> OTHER INFORMATION: oligonucleotide

<400> SEQUENCE: 355 ugggacgcc ucuguuccaa auccu                                          25

<210> SEQ ID NO 356
<211> LENGTH: 25
<212> TYPE: RNA
<213> ORGANISM: Artificial
<220> FEATURE:
<223> OTHER INFORMATION: oligonucleotide

<400> SEQUENCE: 356 gggacgccu cuguuccaaa uccug                                          25

<210> SEQ ID NO 357
<211> LENGTH: 25
<212> TYPE: RNA
<213> ORGANISM: Artificial
<220> FEATURE:
<223> OTHER INFORMATION: oligonucleotide

<400> SEQUENCE: 357
gggacgccuc uguuccaaau ccugc                                         25

<210> SEQ ID NO 358
<211> LENGTH: 25
<212> TYPE: RNA
<213> ORGANISM: Artificial
<220> FEATURE:
<223> OTHER INFORMATION: oligonucleotide

<400> SEQUENCE: 358
ggacgccucu guuccaaauc cugca                                         25

<210> SEQ ID NO 359

```
<211> LENGTH: 25
<212> TYPE: RNA
<213> ORGANISM: Artificial
<220> FEATURE:
<223> OTHER INFORMATION: oligonucleotide

<400> SEQUENCE: 359
gacgccucug uuccaaaucc ugcau                                    25

<210> SEQ ID NO 360
<211> LENGTH: 25
<212> TYPE: RNA
<213> ORGANISM: Artificial
<220> FEATURE:
<223> OTHER INFORMATION: oligonucleotide

<400> SEQUENCE: 360
ccaauagugg ucaguccagg agcua                                    25

<210> SEQ ID NO 361
<211> LENGTH: 25
<212> TYPE: RNA
<213> ORGANISM: Artificial
<220> FEATURE:
<223> OTHER INFORMATION: oligonucleotide

<400> SEQUENCE: 361
caauaguggu caguccagga gcuag                                    25

<210> SEQ ID NO 362
<211> LENGTH: 25
<212> TYPE: RNA
<213> ORGANISM: Artificial
<220> FEATURE:
<223> OTHER INFORMATION: oligonucleotide

<400> SEQUENCE: 362
aauagugguc aguccaggag cuagg                                    25

<210> SEQ ID NO 363
<211> LENGTH: 25
<212> TYPE: RNA
<213> ORGANISM: Artificial
<220> FEATURE:
<223> OTHER INFORMATION: oligonucleotide

<400> SEQUENCE: 363 auaggguca guccaggagc uaggu                                     25

<210> SEQ ID NO 364
<211> LENGTH: 21
<212> TYPE: RNA
<213> ORGANISM: Artificial
<220> FEATURE:
<223> OTHER INFORMATION: oligonucleotide

<400> SEQUENCE: 364
auagugguca guccaggagc u                                        21

<210> SEQ ID NO 365
<211> LENGTH: 25
<212> TYPE: RNA
<213> ORGANISM: Artificial
<220> FEATURE:
<223> OTHER INFORMATION: oligonucleotide
```

```
<400> SEQUENCE: 365
uaguggucag uccaggagcu agguc                                        25

<210> SEQ ID NO 366
<211> LENGTH: 25
<212> TYPE: RNA
<213> ORGANISM: Artificial
<220> FEATURE:
<223> OTHER INFORMATION: oligonucleotide

<400> SEQUENCE: 366
aguggucagu ccaggagcua gguca                                        25

<210> SEQ ID NO 367
<211> LENGTH: 25
<212> TYPE: RNA
<213> ORGANISM: Artificial
<220> FEATURE:
<223> OTHER INFORMATION: oligonucleotide

<400> SEQUENCE: 367
guggucaguc caggagcuag gucag                                        25

<210> SEQ ID NO 368
<211> LENGTH: 25
<212> TYPE: RNA
<213> ORGANISM: Artificial
<220> FEATURE:
<223> OTHER INFORMATION: oligonucleotide

<400> SEQUENCE: 368
uggucagucc aggagcuagg ucagg                                        25

<210> SEQ ID NO 369
<211> LENGTH: 25
<212> TYPE: RNA
<213> ORGANISM: Artificial
<220> FEATURE:
<223> OTHER INFORMATION: oligonucleotide

<400> SEQUENCE: 369
ggucagucca ggagcuaggu caggc                                        25

<210> SEQ ID NO 370
<211> LENGTH: 25
<212> TYPE: RNA
<213> ORGANISM: Artificial
<220> FEATURE:
<223> OTHER INFORMATION: oligonucleotide

<400> SEQUENCE: 370
gucaguccag gagcuagguc aggcu                                        25

<210> SEQ ID NO 371
<211> LENGTH: 25
<212> TYPE: RNA
<213> ORGANISM: Artificial
<220> FEATURE:
<223> OTHER INFORMATION: oligonucleotide

<400> SEQUENCE: 371
ucaguccagg agcuagguca ggcug                                        25

<210> SEQ ID NO 372
```

```
<211> LENGTH: 25
<212> TYPE: RNA
<213> ORGANISM: Artificial
<220> FEATURE:
<223> OTHER INFORMATION: oligonucleotide

<400> SEQUENCE: 372
caguccagga gcuaggucag gcugc                                              25

<210> SEQ ID NO 373
<211> LENGTH: 25
<212> TYPE: RNA
<213> ORGANISM: Artificial
<220> FEATURE:
<223> OTHER INFORMATION: oligonucleotide

<400> SEQUENCE: 373
aguccaggag cuaggucagg cugcu                                              25

<210> SEQ ID NO 374
<211> LENGTH: 25
<212> TYPE: RNA
<213> ORGANISM: Artificial
<220> FEATURE:
<223> OTHER INFORMATION: oligonucleotide

<400> SEQUENCE: 374
guccaggagc uaggucaggc ugcuu                                              25

<210> SEQ ID NO 375
<211> LENGTH: 25
<212> TYPE: RNA
<213> ORGANISM: Artificial
<220> FEATURE:
<223> OTHER INFORMATION: oligonucleotide

<400> SEQUENCE: 375
uccaggagcu aggucaggcu gcuuu                                              25

<210> SEQ ID NO 376
<211> LENGTH: 25
<212> TYPE: RNA
<213> ORGANISM: Artificial
<220> FEATURE:
<223> OTHER INFORMATION: oligonucleotide

<400> SEQUENCE: 376
ccaggagcua ggucaggcug cuuug                                              25

<210> SEQ ID NO 377
<211> LENGTH: 25
<212> TYPE: RNA
<213> ORGANISM: Artificial
<220> FEATURE:
<223> OTHER INFORMATION: oligonucleotide

<400> SEQUENCE: 377
caggagcuag gucaggcugc uuugc                                              25

<210> SEQ ID NO 378
<211> LENGTH: 25
<212> TYPE: RNA
<213> ORGANISM: Artificial
<220> FEATURE:
<223> OTHER INFORMATION: oligonucleotide
```

```
<400> SEQUENCE: 378
aggagcuagg ucaggcugcu uugcc                                              25

<210> SEQ ID NO 379
<211> LENGTH: 25
<212> TYPE: RNA
<213> ORGANISM: Artificial
<220> FEATURE:
<223> OTHER INFORMATION: oligonucleotide

<400> SEQUENCE: 379
ggagcuaggu caggcugcuu ugccc                                              25

<210> SEQ ID NO 380
<211> LENGTH: 25
<212> TYPE: RNA
<213> ORGANISM: Artificial
<220> FEATURE:
<223> OTHER INFORMATION: oligonucleotide

<400> SEQUENCE: 380
gagcuagguc aggcugcuuu gcccu                                              25

<210> SEQ ID NO 381
<211> LENGTH: 25
<212> TYPE: RNA
<213> ORGANISM: Artificial
<220> FEATURE:
<223> OTHER INFORMATION: oligonucleotide

<400> SEQUENCE: 381
agcuagguca ggcugcuuug cccuc                                              25

<210> SEQ ID NO 382
<211> LENGTH: 25
<212> TYPE: RNA
<213> ORGANISM: Artificial
<220> FEATURE:
<223> OTHER INFORMATION: oligonucleotide

<400> SEQUENCE: 382
gcuaggucag gcugcuuugc ccuca                                              25

<210> SEQ ID NO 383
<211> LENGTH: 25
<212> TYPE: RNA
<213> ORGANISM: Artificial
<220> FEATURE:
<223> OTHER INFORMATION: oligonucleotide

<400> SEQUENCE: 383
cucagcucuu gaaguaaacg guuua                                              25

<210> SEQ ID NO 384
<211> LENGTH: 25
<212> TYPE: RNA
<213> ORGANISM: Artificial
<220> FEATURE:
<223> OTHER INFORMATION: oligonucleotide

<400> SEQUENCE: 384
cagcucuuga aguaaacggu uuacc                                              25

<210> SEQ ID NO 385
```

```
<211> LENGTH: 25
<212> TYPE: RNA
<213> ORGANISM: Artificial
<220> FEATURE:
<223> OTHER INFORMATION: oligonucleotide

<400> SEQUENCE: 385
gcucuugaag uaaacgguuu accgc                                      25

<210> SEQ ID NO 386
<211> LENGTH: 25
<212> TYPE: RNA
<213> ORGANISM: Artificial
<220> FEATURE:
<223> OTHER INFORMATION: oligonucleotide

<400> SEQUENCE: 386
cuaggucagg cugcuuugcc cucag                                      25

<210> SEQ ID NO 387
<211> LENGTH: 25
<212> TYPE: RNA
<213> ORGANISM: Artificial
<220> FEATURE:
<223> OTHER INFORMATION: oligonucleotide

<400> SEQUENCE: 387
uaggucaggc ugcuuugccc ucagc                                      25

<210> SEQ ID NO 388
<211> LENGTH: 25
<212> TYPE: RNA
<213> ORGANISM: Artificial
<220> FEATURE:
<223> OTHER INFORMATION: oligonucleotide

<400> SEQUENCE: 388
aggucaggcu gcuuugcccu cagcu                                      25

<210> SEQ ID NO 389
<211> LENGTH: 25
<212> TYPE: RNA
<213> ORGANISM: Artificial
<220> FEATURE:
<223> OTHER INFORMATION: oligonucleotide

<400> SEQUENCE: 389
ggucaggcug cuuugcccuc agcuc                                      25

<210> SEQ ID NO 390
<211> LENGTH: 25
<212> TYPE: RNA
<213> ORGANISM: Artificial
<220> FEATURE:
<223> OTHER INFORMATION: oligonucleotide

<400> SEQUENCE: 390
gucaggcugc uuugcccuca gcucu                                      25

<210> SEQ ID NO 391
<211> LENGTH: 25
<212> TYPE: RNA
<213> ORGANISM: Artificial
<220> FEATURE:
<223> OTHER INFORMATION: oligonucleotide
```

```
<400> SEQUENCE: 391
ucaggcugcu ugcccucag cucuu                                         25

<210> SEQ ID NO 392
<211> LENGTH: 25
<212> TYPE: RNA
<213> ORGANISM: Artificial
<220> FEATURE:
<223> OTHER INFORMATION: oligonucleotide

<400> SEQUENCE: 392
caggcugcuu ugcccucagc ucuug                                        25

<210> SEQ ID NO 393
<211> LENGTH: 25
<212> TYPE: RNA
<213> ORGANISM: Artificial
<220> FEATURE:
<223> OTHER INFORMATION: oligonucleotide

<400> SEQUENCE: 393
aggcugcuuu gcccucagcu cuuga                                        25

<210> SEQ ID NO 394
<211> LENGTH: 25
<212> TYPE: RNA
<213> ORGANISM: Artificial
<220> FEATURE:
<223> OTHER INFORMATION: oligonucleotide

<400> SEQUENCE: 394
ggcugcuuug cccucagcuc uugaa                                        25

<210> SEQ ID NO 395
<211> LENGTH: 25
<212> TYPE: RNA
<213> ORGANISM: Artificial
<220> FEATURE:
<223> OTHER INFORMATION: oligonucleotide

<400> SEQUENCE: 395
gcugcuuugc ccucagcucu ugaag                                        25

<210> SEQ ID NO 396
<211> LENGTH: 25
<212> TYPE: RNA
<213> ORGANISM: Artificial
<220> FEATURE:
<223> OTHER INFORMATION: oligonucleotide

<400> SEQUENCE: 396
cugcuuugcc cucagcucuu gaagu                                        25

<210> SEQ ID NO 397
<211> LENGTH: 25
<212> TYPE: RNA
<213> ORGANISM: Artificial
<220> FEATURE:
<223> OTHER INFORMATION: oligonucleotide

<400> SEQUENCE: 397
ugcuuugccc ucagcucuug aagua                                        25

<210> SEQ ID NO 398
```

```
<211> LENGTH: 25
<212> TYPE: RNA
<213> ORGANISM: Artificial
<220> FEATURE:
<223> OTHER INFORMATION: oligonucleotide

<400> SEQUENCE: 398 gcuugcccu cagcucuuga aguaa                                          25

<210> SEQ ID NO 399
<211> LENGTH: 25
<212> TYPE: RNA
<213> ORGANISM: Artificial
<220> FEATURE:
<223> OTHER INFORMATION: oligonucleotide

<400> SEQUENCE: 399 cuugcccuc agcucuugaa guaaa                                          25

<210> SEQ ID NO 400
<211> LENGTH: 25
<212> TYPE: RNA
<213> ORGANISM: Artificial
<220> FEATURE:
<223> OTHER INFORMATION: oligonucleotide

<400> SEQUENCE: 400 uugcccuca gcucuugaag uaaac                                          25

<210> SEQ ID NO 401
<211> LENGTH: 25
<212> TYPE: RNA
<213> ORGANISM: Artificial
<220> FEATURE:
<223> OTHER INFORMATION: oligonucleotide

<400> SEQUENCE: 401
uugcccucag cucuugaagu aaacg                                         25

<210> SEQ ID NO 402
<211> LENGTH: 25
<212> TYPE: RNA
<213> ORGANISM: Artificial
<220> FEATURE:
<223> OTHER INFORMATION: oligonucleotide

<400> SEQUENCE: 402
ugcccucagc ucuugaagua aacgg                                         25

<210> SEQ ID NO 403
<211> LENGTH: 25
<212> TYPE: RNA
<213> ORGANISM: Artificial
<220> FEATURE:
<223> OTHER INFORMATION: oligonucleotide

<400> SEQUENCE: 403
gcccucagcu cuugaaguaa acggu                                         25

<210> SEQ ID NO 404
<211> LENGTH: 25
<212> TYPE: RNA
<213> ORGANISM: Artificial
<220> FEATURE:
<223> OTHER INFORMATION: oligonucleotide
```

<400> SEQUENCE: 404
cccucagcuc uugaaguaaa cgguu                               25

<210> SEQ ID NO 405
<211> LENGTH: 20
<212> TYPE: RNA
<213> ORGANISM: Artificial
<220> FEATURE:
<223> OTHER INFORMATION: oligonucleotide

<400> SEQUENCE: 405
ccucagcucu ugaaguaaac                                     20

<210> SEQ ID NO 406
<211> LENGTH: 21
<212> TYPE: RNA
<213> ORGANISM: Artificial
<220> FEATURE:
<223> OTHER INFORMATION: oligonucleotide

<400> SEQUENCE: 406
ccucagcucu ugaaguaaac g                                   21

<210> SEQ ID NO 407
<211> LENGTH: 20
<212> TYPE: RNA
<213> ORGANISM: Artificial
<220> FEATURE:
<223> OTHER INFORMATION: oligonucleotide

<400> SEQUENCE: 407
cucagcucuu gaaguaaacg                                     20

<210> SEQ ID NO 408
<211> LENGTH: 25
<212> TYPE: RNA
<213> ORGANISM: Artificial
<220> FEATURE:
<223> OTHER INFORMATION: oligonucleotide

<400> SEQUENCE: 408
ccucagcucu ugaaguaaac gguuu                               25

<210> SEQ ID NO 409
<211> LENGTH: 25
<212> TYPE: RNA
<213> ORGANISM: Artificial
<220> FEATURE:
<223> OTHER INFORMATION: oligonucleotide

<400> SEQUENCE: 409
ucagcucuug aaguaaacgg uuuac                               25

<210> SEQ ID NO 410
<211> LENGTH: 25
<212> TYPE: RNA
<213> ORGANISM: Artificial
<220> FEATURE:
<223> OTHER INFORMATION: oligonucleotide

<400> SEQUENCE: 410
agcucuugaa guaaacgguu uaccg                               25

<210> SEQ ID NO 411

```
<211> LENGTH: 25
<212> TYPE: RNA
<213> ORGANISM: Artificial
<220> FEATURE:
<223> OTHER INFORMATION: oligonucleotide

<400> SEQUENCE: 411
cucuugaagu aaacgguuua ccgcc                                     25

<210> SEQ ID NO 412
<211> LENGTH: 25
<212> TYPE: RNA
<213> ORGANISM: Artificial
<220> FEATURE:
<223> OTHER INFORMATION: oligonucleotide

<400> SEQUENCE: 412
ccacaggcgu ugcacuuugc aaugc                                     25

<210> SEQ ID NO 413
<211> LENGTH: 25
<212> TYPE: RNA
<213> ORGANISM: Artificial
<220> FEATURE:
<223> OTHER INFORMATION: oligonucleotide

<400> SEQUENCE: 413
cacaggcguu gcacuuugca augcu                                     25

<210> SEQ ID NO 414
<211> LENGTH: 25
<212> TYPE: RNA
<213> ORGANISM: Artificial
<220> FEATURE:
<223> OTHER INFORMATION: oligonucleotide

<400> SEQUENCE: 414
acaggcguug cacuuugcaa ugcug                                     25

<210> SEQ ID NO 415
<211> LENGTH: 25
<212> TYPE: RNA
<213> ORGANISM: Artificial
<220> FEATURE:
<223> OTHER INFORMATION: oligonucleotide

<400> SEQUENCE: 415
caggcguugc acuuugcaau gcugc                                     25

<210> SEQ ID NO 416
<211> LENGTH: 25
<212> TYPE: RNA
<213> ORGANISM: Artificial
<220> FEATURE:
<223> OTHER INFORMATION: oligonucleotide

<400> SEQUENCE: 416
aggcguugca cuuugcaaug cugcu                                     25

<210> SEQ ID NO 417
<211> LENGTH: 25
<212> TYPE: RNA
<213> ORGANISM: Artificial
<220> FEATURE:
<223> OTHER INFORMATION: oligonucleotide
```

```
<400> SEQUENCE: 417
ggcguugcac uuugcaaugc ugcug                                    25

<210> SEQ ID NO 418
<211> LENGTH: 25
<212> TYPE: RNA
<213> ORGANISM: Artificial
<220> FEATURE:
<223> OTHER INFORMATION: oligonucleotide

<400> SEQUENCE: 418
gcguugcacu uugcaaugcu gcugu                                    25

<210> SEQ ID NO 419
<211> LENGTH: 25
<212> TYPE: RNA
<213> ORGANISM: Artificial
<220> FEATURE:
<223> OTHER INFORMATION: oligonucleotide

<400> SEQUENCE: 419
cguugcacuu ugcaaugcug cuguc                                    25

<210> SEQ ID NO 420
<211> LENGTH: 23
<212> TYPE: RNA
<213> ORGANISM: Artificial
<220> FEATURE:
<223> OTHER INFORMATION: oligonucleotide

<400> SEQUENCE: 420
cguugcacuu ugcaaugcug cug                                      23

<210> SEQ ID NO 421
<211> LENGTH: 25
<212> TYPE: RNA
<213> ORGANISM: Artificial
<220> FEATURE:
<223> OTHER INFORMATION: oligonucleotide

<400> SEQUENCE: 421
guugcacuuu gcaaugcugc ugucu                                    25

<210> SEQ ID NO 422
<211> LENGTH: 25
<212> TYPE: RNA
<213> ORGANISM: Artificial
<220> FEATURE:
<223> OTHER INFORMATION: oligonucleotide

<400> SEQUENCE: 422
uugcacuuug caaugcugcu gucuu                                    25

<210> SEQ ID NO 423
<211> LENGTH: 25
<212> TYPE: RNA
<213> ORGANISM: Artificial
<220> FEATURE:
<223> OTHER INFORMATION: oligonucleotide

<400> SEQUENCE: 423
ugcacuuugc aaugcugcug ucuuc                                    25

<210> SEQ ID NO 424
```

```
<211> LENGTH: 25
<212> TYPE: RNA
<213> ORGANISM: Artificial
<220> FEATURE:
<223> OTHER INFORMATION: oligonucleotide

<400> SEQUENCE: 424
gcacuuugca augcugcugu cuucu                                25

<210> SEQ ID NO 425
<211> LENGTH: 25
<212> TYPE: RNA
<213> ORGANISM: Artificial
<220> FEATURE:
<223> OTHER INFORMATION: oligonucleotide

<400> SEQUENCE: 425
cacuuugcaa ugcugcuguc uucuu                                25

<210> SEQ ID NO 426
<211> LENGTH: 25
<212> TYPE: RNA
<213> ORGANISM: Artificial
<220> FEATURE:
<223> OTHER INFORMATION: oligonucleotide

<400> SEQUENCE: 426
acuuugcaau gcugcugucu cuug                                 25

<210> SEQ ID NO 427
<211> LENGTH: 25
<212> TYPE: RNA
<213> ORGANISM: Artificial
<220> FEATURE:
<223> OTHER INFORMATION: oligonucleotide

<400> SEQUENCE: 427
cuuugcaaug cugcugucuu cuugc                                25

<210> SEQ ID NO 428
<211> LENGTH: 25
<212> TYPE: RNA
<213> ORGANISM: Artificial
<220> FEATURE:
<223> OTHER INFORMATION: oligonucleotide

<400> SEQUENCE: 428
uuugcaaugc ugcugucuuc uugcu                                25

<210> SEQ ID NO 429
<211> LENGTH: 25
<212> TYPE: RNA
<213> ORGANISM: Artificial
<220> FEATURE:
<223> OTHER INFORMATION: oligonucleotide

<400> SEQUENCE: 429
uugcaaugcu gcugucuucu ugcua                                25

<210> SEQ ID NO 430
<211> LENGTH: 25
<212> TYPE: RNA
<213> ORGANISM: Artificial
<220> FEATURE:
<223> OTHER INFORMATION: oligonucleotide
```

```
<400> SEQUENCE: 430
ugcaaugcug cugucuucuu gcuau                                    25

<210> SEQ ID NO 431
<211> LENGTH: 25
<212> TYPE: RNA
<213> ORGANISM: Artificial
<220> FEATURE:
<223> OTHER INFORMATION: oligonucleotide

<400> SEQUENCE: 431
gcaaugcugc ugucuucuug cuaug                                    25

<210> SEQ ID NO 432
<211> LENGTH: 25
<212> TYPE: RNA
<213> ORGANISM: Artificial
<220> FEATURE:
<223> OTHER INFORMATION: oligonucleotide

<400> SEQUENCE: 432
caaugcugcu gucuucuugc uauga                                    25

<210> SEQ ID NO 433
<211> LENGTH: 25
<212> TYPE: RNA
<213> ORGANISM: Artificial
<220> FEATURE:
<223> OTHER INFORMATION: oligonucleotide

<400> SEQUENCE: 433
aaugcugcug ucuucuugcu augaa                                    25

<210> SEQ ID NO 434
<211> LENGTH: 25
<212> TYPE: RNA
<213> ORGANISM: Artificial
<220> FEATURE:
<223> OTHER INFORMATION: oligonucleotide

<400> SEQUENCE: 434
augcugcugu cuucuugcua ugaau                                    25

<210> SEQ ID NO 435
<211> LENGTH: 25
<212> TYPE: RNA
<213> ORGANISM: Artificial
<220> FEATURE:
<223> OTHER INFORMATION: oligonucleotide

<400> SEQUENCE: 435
ugcugcuguc uucuugcuau gaaua                                    25

<210> SEQ ID NO 436
<211> LENGTH: 25
<212> TYPE: RNA
<213> ORGANISM: Artificial
<220> FEATURE:
<223> OTHER INFORMATION: oligonucleotide

<400> SEQUENCE: 436
gcugcugucu cuugcuaug aauaa                                     25

<210> SEQ ID NO 437
```

```
<211> LENGTH: 25
<212> TYPE: RNA
<213> ORGANISM: Artificial
<220> FEATURE:
<223> OTHER INFORMATION: oligonucleotide

<400> SEQUENCE: 437
cugcugucuu cuugcuauga auaau                                          25

<210> SEQ ID NO 438
<211> LENGTH: 25
<212> TYPE: RNA
<213> ORGANISM: Artificial
<220> FEATURE:
<223> OTHER INFORMATION: oligonucleotide

<400> SEQUENCE: 438
ugcugucuuc uugcuaugaa uaaug                                          25

<210> SEQ ID NO 439
<211> LENGTH: 25
<212> TYPE: RNA
<213> ORGANISM: Artificial
<220> FEATURE:
<223> OTHER INFORMATION: oligonucleotide

<400> SEQUENCE: 439
gcugucuucu ugcuaugaau aaugu                                          25

<210> SEQ ID NO 440
<211> LENGTH: 25
<212> TYPE: RNA
<213> ORGANISM: Artificial
<220> FEATURE:
<223> OTHER INFORMATION: oligonucleotide

<400> SEQUENCE: 440
cugucuucuu gcuaugaaua auguc                                          25

<210> SEQ ID NO 441
<211> LENGTH: 25
<212> TYPE: RNA
<213> ORGANISM: Artificial
<220> FEATURE:
<223> OTHER INFORMATION: oligonucleotide

<400> SEQUENCE: 441
ugucuucuug cuaugaauaa uguca                                          25

<210> SEQ ID NO 442
<211> LENGTH: 25
<212> TYPE: RNA
<213> ORGANISM: Artificial
<220> FEATURE:
<223> OTHER INFORMATION: oligonucleotide

<400> SEQUENCE: 442
gucuucuugc uaugaauaau gucaa                                          25

<210> SEQ ID NO 443
<211> LENGTH: 25
<212> TYPE: RNA
<213> ORGANISM: Artificial
<220> FEATURE:
<223> OTHER INFORMATION: oligonucleotide
```

<400> SEQUENCE: 443
ucuucuugcu augaauaaug ucaau                                         25

<210> SEQ ID NO 444
<211> LENGTH: 25
<212> TYPE: RNA
<213> ORGANISM: Artificial
<220> FEATURE:
<223> OTHER INFORMATION: oligonucleotide

<400> SEQUENCE: 444
cuucuugcua ugaauaaugu caauc                                         25

<210> SEQ ID NO 445
<211> LENGTH: 25
<212> TYPE: RNA
<213> ORGANISM: Artificial
<220> FEATURE:
<223> OTHER INFORMATION: oligonucleotide

<400> SEQUENCE: 445
uucuugcuau gaauaauguc aaucc                                         25

<210> SEQ ID NO 446
<211> LENGTH: 25
<212> TYPE: RNA
<213> ORGANISM: Artificial
<220> FEATURE:
<223> OTHER INFORMATION: oligonucleotide

<400> SEQUENCE: 446
ucuugcuaug aauaaugcau auccg                                         25

<210> SEQ ID NO 447
<211> LENGTH: 25
<212> TYPE: RNA
<213> ORGANISM: Artificial
<220> FEATURE:
<223> OTHER INFORMATION: oligonucleotide

<400> SEQUENCE: 447
cuugcuauga auaaugucaa uccga                                         25

<210> SEQ ID NO 448
<211> LENGTH: 25
<212> TYPE: RNA
<213> ORGANISM: Artificial
<220> FEATURE:
<223> OTHER INFORMATION: oligonucleotide

<400> SEQUENCE: 448
uugcuaugaa uaaugucaau ccgac                                         25

<210> SEQ ID NO 449
<211> LENGTH: 25
<212> TYPE: RNA
<213> ORGANISM: Artificial
<220> FEATURE:
<223> OTHER INFORMATION: oligonucleotide

<400> SEQUENCE: 449
ugcuaugaau aaugucaauc cgacc                                         25

<210> SEQ ID NO 450

```
<211> LENGTH: 25
<212> TYPE: RNA
<213> ORGANISM: Artificial
<220> FEATURE:
<223> OTHER INFORMATION: oligonucleotide

<400> SEQUENCE: 450
gcuaugaaua augucaaucc gaccu                                        25

<210> SEQ ID NO 451
<211> LENGTH: 25
<212> TYPE: RNA
<213> ORGANISM: Artificial
<220> FEATURE:
<223> OTHER INFORMATION: oligonucleotide

<400> SEQUENCE: 451
cuaugaauaa ugucaauccg accug                                        25

<210> SEQ ID NO 452
<211> LENGTH: 25
<212> TYPE: RNA
<213> ORGANISM: Artificial
<220> FEATURE:
<223> OTHER INFORMATION: oligonucleotide

<400> SEQUENCE: 452
uaugaauaau gucaauccga ccuga                                        25

<210> SEQ ID NO 453
<211> LENGTH: 25
<212> TYPE: RNA
<213> ORGANISM: Artificial
<220> FEATURE:
<223> OTHER INFORMATION: oligonucleotide

<400> SEQUENCE: 453
augaauaaug ucaauccgac cugag                                        25

<210> SEQ ID NO 454
<211> LENGTH: 25
<212> TYPE: RNA
<213> ORGANISM: Artificial
<220> FEATURE:
<223> OTHER INFORMATION: oligonucleotide

<400> SEQUENCE: 454
ugaauaaugu caauccgacc ugagc                                        25

<210> SEQ ID NO 455
<211> LENGTH: 25
<212> TYPE: RNA
<213> ORGANISM: Artificial
<220> FEATURE:
<223> OTHER INFORMATION: oligonucleotide

<400> SEQUENCE: 455
gaauaauguc aauccgaccu gagcu                                        25

<210> SEQ ID NO 456
<211> LENGTH: 25
<212> TYPE: RNA
<213> ORGANISM: Artificial
<220> FEATURE:
<223> OTHER INFORMATION: oligonucleotide
```

-continued

<400> SEQUENCE: 456
aauaauguca auccgaccug agcuu                                          25

<210> SEQ ID NO 457
<211> LENGTH: 25
<212> TYPE: RNA
<213> ORGANISM: Artificial
<220> FEATURE:
<223> OTHER INFORMATION: oligonucleotide

<400> SEQUENCE: 457
auaaugucaa uccgaccuga gcuuu                                          25

<210> SEQ ID NO 458
<211> LENGTH: 25
<212> TYPE: RNA
<213> ORGANISM: Artificial
<220> FEATURE:
<223> OTHER INFORMATION: oligonucleotide

<400> SEQUENCE: 458
uaaugucaau ccgaccugag cuuug                                          25

<210> SEQ ID NO 459
<211> LENGTH: 25
<212> TYPE: RNA
<213> ORGANISM: Artificial
<220> FEATURE:
<223> OTHER INFORMATION: oligonucleotide

<400> SEQUENCE: 459
aaugucaauc cgaccugagc uuugu                                          25

<210> SEQ ID NO 460
<211> LENGTH: 25
<212> TYPE: RNA
<213> ORGANISM: Artificial
<220> FEATURE:
<223> OTHER INFORMATION: oligonucleotide

<400> SEQUENCE: 460
augucaaucc gaccugagcu uuguu                                          25

<210> SEQ ID NO 461
<211> LENGTH: 25
<212> TYPE: RNA
<213> ORGANISM: Artificial
<220> FEATURE:
<223> OTHER INFORMATION: oligonucleotide

<400> SEQUENCE: 461
ugucaauccg accugagcuu uguug                                          25

<210> SEQ ID NO 462
<211> LENGTH: 25
<212> TYPE: RNA
<213> ORGANISM: Artificial
<220> FEATURE:
<223> OTHER INFORMATION: oligonucleotide

<400> SEQUENCE: 462
gucaauccga ccugagcuuu guugu                                          25

<210> SEQ ID NO 463

```
<211> LENGTH: 25
<212> TYPE: RNA
<213> ORGANISM: Artificial
<220> FEATURE:
<223> OTHER INFORMATION: oligonucleotide

<400> SEQUENCE: 463
ucaauccgac cugagcuuug uugua                                         25

<210> SEQ ID NO 464
<211> LENGTH: 25
<212> TYPE: RNA
<213> ORGANISM: Artificial
<220> FEATURE:
<223> OTHER INFORMATION: oligonucleotide

<400> SEQUENCE: 464
caauccgacc ugagcuuugu uguag                                         25

<210> SEQ ID NO 465
<211> LENGTH: 25
<212> TYPE: RNA
<213> ORGANISM: Artificial
<220> FEATURE:
<223> OTHER INFORMATION: oligonucleotide

<400> SEQUENCE: 465
aauccgaccu gagcuuuguu guaga                                         25

<210> SEQ ID NO 466
<211> LENGTH: 25
<212> TYPE: RNA
<213> ORGANISM: Artificial
<220> FEATURE:
<223> OTHER INFORMATION: oligonucleotide

<400> SEQUENCE: 466
auccgaccug agcuuuguug uagac                                         25

<210> SEQ ID NO 467
<211> LENGTH: 25
<212> TYPE: RNA
<213> ORGANISM: Artificial
<220> FEATURE:
<223> OTHER INFORMATION: oligonucleotide

<400> SEQUENCE: 467
uccgaccuga gcuuuguugu agacu                                         25

<210> SEQ ID NO 468
<211> LENGTH: 25
<212> TYPE: RNA
<213> ORGANISM: Artificial
<220> FEATURE:
<223> OTHER INFORMATION: oligonucleotide

<400> SEQUENCE: 468
ccgaccugag cuuuguugua gacua                                         25

<210> SEQ ID NO 469
<211> LENGTH: 20
<212> TYPE: RNA
<213> ORGANISM: Artificial
<220> FEATURE:
<223> OTHER INFORMATION: oligonucleotide
```

<400> SEQUENCE: 469
cgaccugagc uuuguuguag    20

<210> SEQ ID NO 470
<211> LENGTH: 25
<212> TYPE: RNA
<213> ORGANISM: Artificial
<220> FEATURE:
<223> OTHER INFORMATION: oligonucleotide

<400> SEQUENCE: 470
cgaccugagc uuuguuguag acuau    25

<210> SEQ ID NO 471
<211> LENGTH: 25
<212> TYPE: RNA
<213> ORGANISM: Artificial
<220> FEATURE:
<223> OTHER INFORMATION: oligonucleotide

<400> SEQUENCE: 471
gaccugagcu uuguuguaga cuauc    25

<210> SEQ ID NO 472
<211> LENGTH: 25
<212> TYPE: RNA
<213> ORGANISM: Artificial
<220> FEATURE:
<223> OTHER INFORMATION: oligonucleotide

<400> SEQUENCE: 472
accugagcuu uguuguagac uauca    25

<210> SEQ ID NO 473
<211> LENGTH: 23
<212> TYPE: RNA
<213> ORGANISM: Artificial
<220> FEATURE:
<223> OTHER INFORMATION: oligonucleotide

<400> SEQUENCE: 473
ccugagcuuu guuguagacu auc    23

<210> SEQ ID NO 474
<211> LENGTH: 20
<212> TYPE: RNA
<213> ORGANISM: Artificial
<220> FEATURE:
<223> OTHER INFORMATION: oligonucleotide

<400> SEQUENCE: 474 cauuuugac cuacaugugg    20

<210> SEQ ID NO 475
<211> LENGTH: 20
<212> TYPE: RNA
<213> ORGANISM: Artificial
<220> FEATURE:
<223> OTHER INFORMATION: oligonucleotide

<400> SEQUENCE: 475
uuugaccuac auguggaaag    20

<210> SEQ ID NO 476

```
<211> LENGTH: 26
<212> TYPE: RNA
<213> ORGANISM: Artificial
<220> FEATURE:
<223> OTHER INFORMATION: oligonucleotide

<400> SEQUENCE: 476
uacauuuuug accuacaugu ggaaag                                        26

<210> SEQ ID NO 477
<211> LENGTH: 17
<212> TYPE: RNA
<213> ORGANISM: Artificial
<220> FEATURE:
<223> OTHER INFORMATION: oligonucleotide

<400> SEQUENCE: 477
ggucuccuua ccuauga                                                  17

<210> SEQ ID NO 478
<211> LENGTH: 24
<212> TYPE: RNA
<213> ORGANISM: Artificial
<220> FEATURE:
<223> OTHER INFORMATION: oligonucleotide

<400> SEQUENCE: 478
ucuuaccuau gacuauggau gaga                                          24

<210> SEQ ID NO 479
<211> LENGTH: 22
<212> TYPE: RNA
<213> ORGANISM: Artificial
<220> FEATURE:
<223> OTHER INFORMATION: oligonucleotide

<400> SEQUENCE: 479 auuuugacc uacagggaa ag                                              22

<210> SEQ ID NO 480
<211> LENGTH: 23
<212> TYPE: RNA
<213> ORGANISM: Artificial
<220> FEATURE:
<223> OTHER INFORMATION: oligonucleotide

<400> SEQUENCE: 480
uacgaguuga uugucggacc cag                                           23

<210> SEQ ID NO 481
<211> LENGTH: 25
<212> TYPE: RNA
<213> ORGANISM: Artificial
<220> FEATURE:
<223> OTHER INFORMATION: oligonucleotide

<400> SEQUENCE: 481
guggucuccu uaccuaugac ugugg                                         25

<210> SEQ ID NO 482
<211> LENGTH: 24
<212> TYPE: RNA
<213> ORGANISM: Artificial
<220> FEATURE:
<223> OTHER INFORMATION: oligonucleotide
```

-continued

```
<400> SEQUENCE: 482
ugucucagua aucuucuuac cuau                                              24

<210> SEQ ID NO 483
<211> LENGTH: 23
<212> TYPE: RNA
<213> ORGANISM: Artificial
<220> FEATURE:
<223> OTHER INFORMATION: oligonucleotide

<400> SEQUENCE: 483
ugcauguucc agucguugug ugg                                               23

<210> SEQ ID NO 484
<211> LENGTH: 25
<212> TYPE: RNA
<213> ORGANISM: Artificial
<220> FEATURE:
<223> OTHER INFORMATION: oligonucleotide

<400> SEQUENCE: 484
cacuauucca gucaaauagg ucugg                                             25

<210> SEQ ID NO 485
<211> LENGTH: 25
<212> TYPE: RNA
<213> ORGANISM: Artificial
<220> FEATURE:
<223> OTHER INFORMATION: oligonucleotide

<400> SEQUENCE: 485
auuuaccaac cuucaggauc gagua                                             25

<210> SEQ ID NO 486
<211> LENGTH: 21
<212> TYPE: RNA
<213> ORGANISM: Artificial
<220> FEATURE:
<223> OTHER INFORMATION: oligonucleotide

<400> SEQUENCE: 486
ggccuaaaac acauacacau a                                                 21

<210> SEQ ID NO 487
<211> LENGTH: 24
<212> TYPE: RNA
<213> ORGANISM: Artificial
<220> FEATURE:
<223> OTHER INFORMATION: oligonucleotide

<400> SEQUENCE: 487 gauaggugu aucaacaucu guaa                                               24

<210> SEQ ID NO 488
<211> LENGTH: 21
<212> TYPE: RNA
<213> ORGANISM: Artificial
<220> FEATURE:
<223> OTHER INFORMATION: oligonucleotide

<400> SEQUENCE: 488 gaugguggu aucaacaucu g                                                  21

<210> SEQ ID NO 489
```

```
<211> LENGTH: 19
<212> TYPE: RNA
<213> ORGANISM: Artificial
<220> FEATURE:
<223> OTHER INFORMATION: oligonucleotide

<400> SEQUENCE: 489
cuuccuggau ggcuugaau                                               19

<210> SEQ ID NO 490
<211> LENGTH: 20
<212> TYPE: RNA
<213> ORGANISM: Artificial
<220> FEATURE:
<223> OTHER INFORMATION: oligonucleotide

<400> SEQUENCE: 490
uguuguuguu uaugcucauu                                              20

<210> SEQ ID NO 491
<211> LENGTH: 19
<212> TYPE: RNA
<213> ORGANISM: Artificial
<220> FEATURE:
<223> OTHER INFORMATION: oligonucleotide

<400> SEQUENCE: 491
guacauuaag auggacuuc                                               19

<210> SEQ ID NO 492
<211> LENGTH: 20
<212> TYPE: RNA
<213> ORGANISM: Artificial
<220> FEATURE:
<223> OTHER INFORMATION: oligonucleotide

<400> SEQUENCE: 492
cuguugcagu aaucuaugag                                              20

<210> SEQ ID NO 493
<211> LENGTH: 20
<212> TYPE: RNA
<213> ORGANISM: Artificial
<220> FEATURE:
<223> OTHER INFORMATION: oligonucleotide

<400> SEQUENCE: 493
ugcaguaauc uaugaguuuc                                              20

<210> SEQ ID NO 494
<211> LENGTH: 18
<212> TYPE: RNA
<213> ORGANISM: Artificial
<220> FEATURE:
<223> OTHER INFORMATION: oligonucleotide

<400> SEQUENCE: 494
gagucuucua ggagccuu                                                18

<210> SEQ ID NO 495
<211> LENGTH: 23
<212> TYPE: RNA
<213> ORGANISM: Artificial
<220> FEATURE:
<223> OTHER INFORMATION: oligonucleotide
```

-continued

```
<400> SEQUENCE: 495
ugccauuguu ucaucagcuc uuu                                           23

<210> SEQ ID NO 496
<211> LENGTH: 20
<212> TYPE: RNA
<213> ORGANISM: Artificial
<220> FEATURE:
<223> OTHER INFORMATION: oligonucleotide

<400> SEQUENCE: 496
uccuguagga cauuggcagu                                               20

<210> SEQ ID NO 497
<211> LENGTH: 20
<212> TYPE: RNA
<213> ORGANISM: Artificial
<220> FEATURE:
<223> OTHER INFORMATION: oligonucleotide

<400> SEQUENCE: 497
cuuggagucu ucuaggagcc                                               20

<210> SEQ ID NO 498
<211> LENGTH: 30
<212> TYPE: RNA
<213> ORGANISM: Artificial
<220> FEATURE:
<223> OTHER INFORMATION: oligonucleotide

<400> SEQUENCE: 498
ccauuuugug aauguuuucu uuugaacauc                                    30

<210> SEQ ID NO 499
<211> LENGTH: 24
<212> TYPE: RNA
<213> ORGANISM: Artificial
<220> FEATURE:
<223> OTHER INFORMATION: oligonucleotide

<400> SEQUENCE: 499
cccauuuugu gaauguuuuc uuuu                                          24

<210> SEQ ID NO 500
<211> LENGTH: 24
<212> TYPE: RNA
<213> ORGANISM: Artificial
<220> FEATURE:
<223> OTHER INFORMATION: oligonucleotide

<400> SEQUENCE: 500
gaaaauugug cauuuaccca uuuu                                          24

<210> SEQ ID NO 501
<211> LENGTH: 22
<212> TYPE: RNA
<213> ORGANISM: Artificial
<220> FEATURE:
<223> OTHER INFORMATION: oligonucleotide

<400> SEQUENCE: 501
uugugcauuu acccauuuug ug                                            22

<210> SEQ ID NO 502
```

```
<211> LENGTH: 24
<212> TYPE: RNA
<213> ORGANISM: Artificial
<220> FEATURE:
<223> OTHER INFORMATION: oligonucleotide

<400> SEQUENCE: 502
cccugaggca uucccaucuu gaau                                          24

<210> SEQ ID NO 503
<211> LENGTH: 20
<212> TYPE: RNA
<213> ORGANISM: Artificial
<220> FEATURE:
<223> OTHER INFORMATION: oligonucleotide

<400> SEQUENCE: 503
aggacuuacu ugcuuuguuu                                               20

<210> SEQ ID NO 504
<211> LENGTH: 23
<212> TYPE: RNA
<213> ORGANISM: Artificial
<220> FEATURE:
<223> OTHER INFORMATION: oligonucleotide

<400> SEQUENCE: 504
cuugaauuua ggagauucau cug                                           23

<210> SEQ ID NO 505
<211> LENGTH: 23
<212> TYPE: RNA
<213> ORGANISM: Artificial
<220> FEATURE:
<223> OTHER INFORMATION: oligonucleotide

<400> SEQUENCE: 505
caucuucuga uaauuuuccu guu                                           23

<210> SEQ ID NO 506
<211> LENGTH: 20
<212> TYPE: RNA
<213> ORGANISM: Artificial
<220> FEATURE:
<223> OTHER INFORMATION: oligonucleotide

<400> SEQUENCE: 506
ccauuacagu ugucuguguu                                               20

<210> SEQ ID NO 507
<211> LENGTH: 23
<212> TYPE: RNA
<213> ORGANISM: Artificial
<220> FEATURE:
<223> OTHER INFORMATION: oligonucleotide

<400> SEQUENCE: 507
ugacagccug ugaaaucugu gag                                           23

<210> SEQ ID NO 508
<211> LENGTH: 20
<212> TYPE: RNA
<213> ORGANISM: Artificial
<220> FEATURE:
<223> OTHER INFORMATION: oligonucleotide
```

```
<400> SEQUENCE: 508
uaaucugccu cuucuuuugg                                            20

<210> SEQ ID NO 509
<211> LENGTH: 20
<212> TYPE: RNA
<213> ORGANISM: Artificial
<220> FEATURE:
<223> OTHER INFORMATION: oligonucleotide

<400> SEQUENCE: 509
cagcaguagu ugucaucugc                                            20

<210> SEQ ID NO 510
<211> LENGTH: 27
<212> TYPE: RNA
<213> ORGANISM: Artificial
<220> FEATURE:
<223> OTHER INFORMATION: oligonucleotide

<400> SEQUENCE: 510
gccugagcug aucugcuggc aucuugc                                    27

<210> SEQ ID NO 511
<211> LENGTH: 31
<212> TYPE: RNA
<213> ORGANISM: Artificial
<220> FEATURE:
<223> OTHER INFORMATION: oligonucleotide

<400> SEQUENCE: 511
gccugagcug aucugcuggc aucuugcagu u                               31

<210> SEQ ID NO 512
<211> LENGTH: 16
<212> TYPE: RNA
<213> ORGANISM: Artificial
<220> FEATURE:
<223> OTHER INFORMATION: oligonucleotide

<400> SEQUENCE: 512
ucugcuggca ucuugc                                                16

<210> SEQ ID NO 513
<211> LENGTH: 22
<212> TYPE: RNA
<213> ORGANISM: Artificial
<220> FEATURE:
<223> OTHER INFORMATION: oligonucleotide

<400> SEQUENCE: 513
gccgguugac uucauccugu gc                                         22

<210> SEQ ID NO 514
<211> LENGTH: 23
<212> TYPE: RNA
<213> ORGANISM: Artificial
<220> FEATURE:
<223> OTHER INFORMATION: oligonucleotide

<400> SEQUENCE: 514
gucugcaucc aggaacaugg guc                                        23

<210> SEQ ID NO 515
```

```
<211> LENGTH: 24
<212> TYPE: RNA
<213> ORGANISM: Artificial
<220> FEATURE:
<223> OTHER INFORMATION: oligonucleotide

<400> SEQUENCE: 515
uacuuacugu cguagcucu uucu                                              24

<210> SEQ ID NO 516
<211> LENGTH: 22
<212> TYPE: RNA
<213> ORGANISM: Artificial
<220> FEATURE:
<223> OTHER INFORMATION: oligonucleotide

<400> SEQUENCE: 516
cugcauccag gaacaugggu cc                                               22

<210> SEQ ID NO 517
<211> LENGTH: 24
<212> TYPE: RNA
<213> ORGANISM: Artificial
<220> FEATURE:
<223> OTHER INFORMATION: oligonucleotide

<400> SEQUENCE: 517
guugaagauc ugauagccgg uuga                                             24

<210> SEQ ID NO 518
<211> LENGTH: 17
<212> TYPE: RNA
<213> ORGANISM: Artificial
<220> FEATURE:
<223> OTHER INFORMATION: oligonucleotide

<400> SEQUENCE: 518
uaggugccug ccggcuu                                                     17

<210> SEQ ID NO 519
<211> LENGTH: 18
<212> TYPE: RNA
<213> ORGANISM: Artificial
<220> FEATURE:
<223> OTHER INFORMATION: oligonucleotide

<400> SEQUENCE: 519
uucagcugua gccacacc                                                    18

<210> SEQ ID NO 520
<211> LENGTH: 21
<212> TYPE: RNA
<213> ORGANISM: Artificial
<220> FEATURE:
<223> OTHER INFORMATION: oligonucleotide

<400> SEQUENCE: 520
cugaacugcu ggaaagucgc c                                                21

<210> SEQ ID NO 521
<211> LENGTH: 30
<212> TYPE: RNA
<213> ORGANISM: Artificial
<220> FEATURE:
<223> OTHER INFORMATION: oligonucleotide
```

```
<400> SEQUENCE: 521
cuggcuucca aaugggaccu gaaaaagaac                                30

<210> SEQ ID NO 522
<211> LENGTH: 21
<212> TYPE: RNA
<213> ORGANISM: Artificial
<220> FEATURE:
<223> OTHER INFORMATION: oligonucleotide

<400> SEQUENCE: 522
caauuuuucc cacucaguau u                                         21

<210> SEQ ID NO 523
<211> LENGTH: 19
<212> TYPE: RNA
<213> ORGANISM: Artificial
<220> FEATURE:
<223> OTHER INFORMATION: oligonucleotide

<400> SEQUENCE: 523
uugaaguucc uggagucuu                                            19

<210> SEQ ID NO 524
<211> LENGTH: 22
<212> TYPE: RNA
<213> ORGANISM: Artificial
<220> FEATURE:
<223> OTHER INFORMATION: oligonucleotide

<400> SEQUENCE: 524
uccucaggag gcagcucuaa au                                        22

<210> SEQ ID NO 525
<211> LENGTH: 16
<212> TYPE: RNA
<213> ORGANISM: Artificial
<220> FEATURE:
<223> OTHER INFORMATION: oligonucleotide

<400> SEQUENCE: 525
uggcucucuc ccaggg                                               16

<210> SEQ ID NO 526
<211> LENGTH: 27
<212> TYPE: RNA
<213> ORGANISM: Artificial
<220> FEATURE:
<223> OTHER INFORMATION: oligonucleotide

<400> SEQUENCE: 526
gagauggcuc ucucccaggg acccugg                                   27

<210> SEQ ID NO 527
<211> LENGTH: 17
<212> TYPE: RNA
<213> ORGANISM: Artificial
<220> FEATURE:
<223> OTHER INFORMATION: oligonucleotide

<400> SEQUENCE: 527
gggcacuuug uuuggcg                                              17

<210> SEQ ID NO 528
```

```
<211> LENGTH: 19
<212> TYPE: RNA
<213> ORGANISM: Artificial
<220> FEATURE:
<223> OTHER INFORMATION: oligonucleotide

<400> SEQUENCE: 528
ggucccagca aguuguuug                                                    19

<210> SEQ ID NO 529
<211> LENGTH: 25
<212> TYPE: RNA
<213> ORGANISM: Artificial
<220> FEATURE:
<223> OTHER INFORMATION: oligonucleotide

<400> SEQUENCE: 529
ugggaugguc ccagcaaguu guuug                                             25

<210> SEQ ID NO 530
<211> LENGTH: 21
<212> TYPE: RNA
<213> ORGANISM: Artificial
<220> FEATURE:
<223> OTHER INFORMATION: oligonucleotide

<400> SEQUENCE: 530
guagagcucu gucauuuugg g                                                 21

<210> SEQ ID NO 531
<211> LENGTH: 25
<212> TYPE: RNA
<213> ORGANISM: Artificial
<220> FEATURE:
<223> OTHER INFORMATION: oligonucleotide

<400> SEQUENCE: 531
gcucaagaga uccacugcaa aaaac                                             25

<210> SEQ ID NO 532
<211> LENGTH: 26
<212> TYPE: RNA
<213> ORGANISM: Artificial
<220> FEATURE:
<223> OTHER INFORMATION: oligonucleotide

<400> SEQUENCE: 532
gccauacgua cguaucauaa acauuc                                            26

<210> SEQ ID NO 533
<211> LENGTH: 25
<212> TYPE: RNA
<213> ORGANISM: Artificial
<220> FEATURE:
<223> OTHER INFORMATION: oligonucleotide

<400> SEQUENCE: 533
ucugcaggau auccaugggc ugguc                                             25

<210> SEQ ID NO 534
<211> LENGTH: 27
<212> TYPE: RNA
<213> ORGANISM: Artificial
<220> FEATURE:
<223> OTHER INFORMATION: oligonucleotide
```

```
<400> SEQUENCE: 534
gauccucccu guucgucccc uauuaug                                              27

<210> SEQ ID NO 535
<211> LENGTH: 24
<212> TYPE: RNA
<213> ORGANISM: Artificial
<220> FEATURE:
<223> OTHER INFORMATION: oligonucleotide

<400> SEQUENCE: 535
ugcuuuagac uccuguaccu gaua                                                 24

<210> SEQ ID NO 536
<211> LENGTH: 18
<212> TYPE: RNA
<213> ORGANISM: Artificial
<220> FEATURE:
<223> OTHER INFORMATION: oligonucleotide

<400> SEQUENCE: 536
ggcggccuuu guguugac                                                        18

<210> SEQ ID NO 537
<211> LENGTH: 25
<212> TYPE: RNA
<213> ORGANISM: Artificial
<220> FEATURE:
<223> OTHER INFORMATION: oligonucleotide

<400> SEQUENCE: 537
ggacaggccu uuauguucgu gcugc                                                25

<210> SEQ ID NO 538
<211> LENGTH: 19
<212> TYPE: RNA
<213> ORGANISM: Artificial
<220> FEATURE:
<223> OTHER INFORMATION: oligonucleotide

<400> SEQUENCE: 538
ccuuuauguu cgugcugcu                                                       19

<210> SEQ ID NO 539
<211> LENGTH: 20
<212> TYPE: RNA
<213> ORGANISM: Artificial
<220> FEATURE:
<223> OTHER INFORMATION: oligonucleotide

<400> SEQUENCE: 539
ucaaggaaga uggcauuucu                                                      20

<210> SEQ ID NO 540
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (5)..(5)
<223> OTHER INFORMATION: I
<220> FEATURE:
<221> NAME/KEY: misc_feature
<222> LOCATION: (5)..(5)
```

<223> OTHER INFORMATION: n is a, c, g, or u

<400> SEQUENCE: 540
ucaangaaga uggcauuucu                                           20

<210> SEQ ID NO 541
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (6)..(6)
<223> OTHER INFORMATION: I
<220> FEATURE:
<221> NAME/KEY: misc_feature
<222> LOCATION: (6)..(6)
<223> OTHER INFORMATION: n is a, c, g, or u

<400> SEQUENCE: 541
ucaagnaaga uggcauuucu                                           20

<210> SEQ ID NO 542
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(9)
<223> OTHER INFORMATION: n is a, c, g, or u

<400> SEQUENCE: 542
ucaaggaana uggcauuucu                                           20

<210> SEQ ID NO 543
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (12)..(12)
<223> OTHER INFORMATION: I
<220> FEATURE:
<221> NAME/KEY: misc_feature
<222> LOCATION: (12)..(12)
<223> OTHER INFORMATION: n is a, c, g, or u

<400> SEQUENCE: 543
ucaaggaaga ungcauuucu                                           20

<210> SEQ ID NO 544
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (13)..(13)
<223> OTHER INFORMATION: I
<220> FEATURE:
<221> NAME/KEY: misc_feature

```
<222> LOCATION: (13)..(13)
<223> OTHER INFORMATION: n is a, c, g, or u

<400> SEQUENCE: 544
ucaaggaaga ugncauuucu                                        20

<210> SEQ ID NO 545
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(1)
<223> OTHER INFORMATION: n is a, c, g, or u

<400> SEQUENCE: 545
ncaaggaaga uggcauuucu                                        20

<210> SEQ ID NO 546
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (11)..(11)
<223> OTHER INFORMATION: I
<220> FEATURE:
<221> NAME/KEY: misc_feature
<222> LOCATION: (11)..(11)
<223> OTHER INFORMATION: n is a, c, g, or u

<400> SEQUENCE: 546
ucaaggaaga nggcauuucu                                        20

<210> SEQ ID NO 547
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (16)..(16)
<223> OTHER INFORMATION: I
<220> FEATURE:
<221> NAME/KEY: misc_feature
<222> LOCATION: (16)..(16)
<223> OTHER INFORMATION: n is a, c, g, or u

<400> SEQUENCE: 547
ucaaggaaga uggcanuucu                                        20

<210> SEQ ID NO 548
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (17)..(17)
<223> OTHER INFORMATION: I
<220> FEATURE:
```

```
<221> NAME/KEY: misc_feature
<222> LOCATION: (17)..(17)
<223> OTHER INFORMATION: n is a, c, g, or u

<400> SEQUENCE: 548
ucaaggaaga uggcaunucu                                              20

<210> SEQ ID NO 549
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (18)..(18)
<223> OTHER INFORMATION: I
<220> FEATURE:
<221> NAME/KEY: misc_feature
<222> LOCATION: (18)..(18)
<223> OTHER INFORMATION: n is a, c, g, or u

<400> SEQUENCE: 549
ucaaggaaga uggcauuncu                                              20

<210> SEQ ID NO 550
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (20)..(20)
<223> OTHER INFORMATION: I
<220> FEATURE:
<221> NAME/KEY: misc_feature
<222> LOCATION: (20)..(20)
<223> OTHER INFORMATION: n is a, c, g, or u

<400> SEQUENCE: 550
ucaaggaaga uggcauuucn                                              20

<210> SEQ ID NO 551
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(3)
<223> OTHER INFORMATION: n is a, c, g, or u

<400> SEQUENCE: 551
ucnaggaaga uggcauuucu                                              20

<210> SEQ ID NO 552
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (4)..(4)
<223> OTHER INFORMATION: I
```

```
<220> FEATURE:
<221> NAME/KEY: misc_feature
<222> LOCATION: (4)..(4)
<223> OTHER INFORMATION: n is a, c, g, or u

<400> SEQUENCE: 552
ucanggaaga uggcauuucu                                               20

<210> SEQ ID NO 553
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (7)..(7)
<223> OTHER INFORMATION: I
<220> FEATURE:
<221> NAME/KEY: misc_feature
<222> LOCATION: (7)..(7)
<223> OTHER INFORMATION: n is a, c, g, or u

<400> SEQUENCE: 553
ucaaggnaga uggcauuucu                                               20

<210> SEQ ID NO 554
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (8)..(8)
<223> OTHER INFORMATION: I
<220> FEATURE:
<221> NAME/KEY: misc_feature
<222> LOCATION: (8)..(8)
<223> OTHER INFORMATION: n is a, c, g, or u

<400> SEQUENCE: 554 ucaaggganga uggcauuucu                                              20

<210> SEQ ID NO 555
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (10)..(10)
<223> OTHER INFORMATION: I
<220> FEATURE:
<221> NAME/KEY: misc_feature
<222> LOCATION: (10)..(10)
<223> OTHER INFORMATION: n is a, c, g, or u

<400> SEQUENCE: 555
ucaaggaagn uggcauuucu                                               20

<210> SEQ ID NO 556
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (15)..(15)
```

```
<223> OTHER INFORMATION: I
<220> FEATURE:
<221> NAME/KEY: misc_feature
<222> LOCATION: (15)..(15)
<223> OTHER INFORMATION: n is a, c, g, or u

<400> SEQUENCE: 556
ucaaggaaga uggcnuuucu                                              20

<210> SEQ ID NO 557
<211> LENGTH: 25
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (7)..(7)
<223> OTHER INFORMATION: I
<220> FEATURE:
<221> NAME/KEY: misc_feature
<222> LOCATION: (7)..(7)
<223> OTHER INFORMATION: n is a, c, g, or u

<400> SEQUENCE: 557
uuugccncug cccaaugcca uccug                                        25

<210> SEQ ID NO 558
<211> LENGTH: 25
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (10)..(10)
<223> OTHER INFORMATION: I
<220> FEATURE:
<221> NAME/KEY: misc_feature
<222> LOCATION: (10)..(10)
<223> OTHER INFORMATION: n is a, c, g, or u

<400> SEQUENCE: 558
uuugccgcun cccaaugcca uccug                                        25

<210> SEQ ID NO 559
<211> LENGTH: 25
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (17)..(17)
<223> OTHER INFORMATION: I
<220> FEATURE:
<221> NAME/KEY: misc_feature
<222> LOCATION: (17)..(17)
<223> OTHER INFORMATION: n is a, c, g, or u

<400> SEQUENCE: 559
uuugccgcug cccaauncca uccug                                        25

<210> SEQ ID NO 560
<211> LENGTH: 25
<212> TYPE: RNA
<213> ORGANISM: Artificial
<220> FEATURE:
<223> OTHER INFORMATION: oligonucleotide
<220> FEATURE:
<221> NAME/KEY: modified_base
```

```
<222> LOCATION: (4)..(4)
<223> OTHER INFORMATION: I
<220> FEATURE:
<221> NAME/KEY: misc_feature
<222> LOCATION: (4)..(4)
<223> OTHER INFORMATION: n is a, c, g, or u

<400> SEQUENCE: 560
uuunccgcug cccaaugcca uccug                                               25

<210> SEQ ID NO 561
<211> LENGTH: 25
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (25)..(25)
<223> OTHER INFORMATION: I
<220> FEATURE:
<221> NAME/KEY: misc_feature
<222> LOCATION: (25)..(25)
<223> OTHER INFORMATION: n is a, c, g, or u

<400> SEQUENCE: 561
uuugccgcug cccaaugcca uccun                                               25

<210> SEQ ID NO 562
<211> LENGTH: 25
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (1)..(1)
<223> OTHER INFORMATION: I
<220> FEATURE:
<221> NAME/KEY: misc_feature
<222> LOCATION: (1)..(1)
<223> OTHER INFORMATION: n is a, c, g, or u

<400> SEQUENCE: 562
nuugccgcug cccaaugcca uccug                                               25

<210> SEQ ID NO 563
<211> LENGTH: 25
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (2)..(2)
<223> OTHER INFORMATION: I
<220> FEATURE:
<221> NAME/KEY: misc_feature
<222> LOCATION: (2)..(2)
<223> OTHER INFORMATION: n is a, c, g, or u

<400> SEQUENCE: 563
unugccgcug cccaaugcca uccug                                               25

<210> SEQ ID NO 564
<211> LENGTH: 25
<212> TYPE: RNA
<213> ORGANISM: Artificial
<220> FEATURE:
<223> OTHER INFORMATION: oligonucleotide
<220> FEATURE:
```

```
<221> NAME/KEY: modified_base
<222> LOCATION: (3)..(3)
<223> OTHER INFORMATION: I
<220> FEATURE:
<221> NAME/KEY: misc_feature
<222> LOCATION: (3)..(3)
<223> OTHER INFORMATION: n is a, c, g, or u

<400> SEQUENCE: 564
uungccgcug cccaaugcca uccug                                              25

<210> SEQ ID NO 565
<211> LENGTH: 25
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (9)..(9)
<223> OTHER INFORMATION: I
<220> FEATURE:
<221> NAME/KEY: misc_feature
<222> LOCATION: (9)..(9)
<223> OTHER INFORMATION: n is a, c, g, or u

<400> SEQUENCE: 565
uuugccgcng cccaaugcca uccug                                              25

<210> SEQ ID NO 566
<211> LENGTH: 25
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (15)..(15)
<223> OTHER INFORMATION: I
<220> FEATURE:
<221> NAME/KEY: misc_feature
<222> LOCATION: (15)..(15)
<223> OTHER INFORMATION: n is a, c, g, or u

<400> SEQUENCE: 566
uuugccgcug cccanugcca uccug                                              25

<210> SEQ ID NO 567
<211> LENGTH: 25
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (20)..(20)
<223> OTHER INFORMATION: I
<220> FEATURE:
<221> NAME/KEY: misc_feature
<222> LOCATION: (20)..(20)
<223> OTHER INFORMATION: n is a, c, g, or u

<400> SEQUENCE: 567
uuugccgcug cccaaugccn uccug                                              25

<210> SEQ ID NO 568
<211> LENGTH: 25
<212> TYPE: RNA
<213> ORGANISM: Artificial
<220> FEATURE:
<223> OTHER INFORMATION: oligonucleotide
```

```
<220> FEATURE:
<221> NAME/KEY: modified_base
<222> LOCATION: (4)..(4)
<223> OTHER INFORMATION: I
<220> FEATURE:
<221> NAME/KEY: misc_feature
<222> LOCATION: (4)..(4)
<223> OTHER INFORMATION: n is a, c, g, or u
<220> FEATURE:
<221> NAME/KEY: modified_base
<222> LOCATION: (7)..(7)
<223> OTHER INFORMATION: I
<220> FEATURE:
<221> NAME/KEY: misc_feature
<222> LOCATION: (7)..(7)
<223> OTHER INFORMATION: n is a, c, g, or u

<400> SEQUENCE: 568
uuunccncug cccaaugcca uccug                                              25

<210> SEQ ID NO 569
<211> LENGTH: 25
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (16)..(16)
<223> OTHER INFORMATION: I
<220> FEATURE:
<221> NAME/KEY: misc_feature
<222> LOCATION: (16)..(16)
<223> OTHER INFORMATION: n is a, c, g, or u

<400> SEQUENCE: 569
uuugccgcug cccaangcca uccug                                              25

<210> SEQ ID NO 570
<211> LENGTH: 25
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (21)..(21)
<223> OTHER INFORMATION: I
<220> FEATURE:
<221> NAME/KEY: misc_feature
<222> LOCATION: (21)..(21)
<223> OTHER INFORMATION: n is a, c, g, or u

<400> SEQUENCE: 570
uuugccgcug cccaaugcca nccug                                              25

<210> SEQ ID NO 571
<211> LENGTH: 25
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (24)..(24)
<223> OTHER INFORMATION: I
<220> FEATURE:
<221> NAME/KEY: misc_feature
<222> LOCATION: (24)..(24)
<223> OTHER INFORMATION: n is a, c, g, or u
```

```
<400> SEQUENCE: 571
uuugccgcug cccaaugcca uccng                                                    25

<210> SEQ ID NO 572
<211> LENGTH: 25
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (14)..(14)
<223> OTHER INFORMATION: I
<220> FEATURE:
<221> NAME/KEY: misc_feature
<222> LOCATION: (14)..(14)
<223> OTHER INFORMATION: n is a, c, g, or u

<400> SEQUENCE: 572
uuugccgcug cccnaugcca uccug                                                    25

<210> SEQ ID NO 573
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (10)..(10)
<223> OTHER INFORMATION: I
<220> FEATURE:
<221> NAME/KEY: misc_feature
<222> LOCATION: (10)..(10)
<223> OTHER INFORMATION: n is a, c, g, or u

<400> SEQUENCE: 573
ucagcuucun uuagccacug                                                          20

<210> SEQ ID NO 574
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (14)..(14)
<223> OTHER INFORMATION: I
<220> FEATURE:
<221> NAME/KEY: misc_feature
<222> LOCATION: (14)..(14)
<223> OTHER INFORMATION: n is a, c, g, or u

<400> SEQUENCE: 574
ucagcuucug uuanccacug                                                          20

<210> SEQ ID NO 575
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (4)..(4)
<223> OTHER INFORMATION: I
<220> FEATURE:
<221> NAME/KEY: misc_feature
<222> LOCATION: (4)..(4)
```

```
<223> OTHER INFORMATION: n is a, c, g, or u

<400> SEQUENCE: 575
ucancuucug uuagccacug                                               20

<210> SEQ ID NO 576
<211> LENGTH: 20
<212> TYPE: RNA
<213> ORGANISM: Artificial
<220> FEATURE:
<223> OTHER INFORMATION: oligonucleotide
<220> FEATURE:
<221> NAME/KEY: modified_base
<222> LOCATION: (20)..(20)
<223> OTHER INFORMATION: I
<220> FEATURE:
<221> NAME/KEY: misc_feature
<222> LOCATION: (20)..(20)
<223> OTHER INFORMATION: n is a, c, g, or u

<400> SEQUENCE: 576
ucagcuucug uuagccacun                                               20

<210> SEQ ID NO 577
<211> LENGTH: 153
<212> TYPE: PRT
<213> ORGANISM: Homo sapiens

<400> SEQUENCE: 577

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser His Leu
            20                  25                  30

Phe Tyr Leu Ala Leu Cys Leu Leu Thr Phe Thr Ser Ser Ala Thr Ala
        35                  40                  45

Gly Pro Glu Thr Leu Cys Gly Ala Glu Leu Val Asp Ala Leu Gln Phe
    50                  55                  60

Val Cys Gly Asp Arg Gly Phe Tyr Phe Asn Lys Pro Thr Gly Tyr Gly
65                  70                  75                  80

Ser Ser Ser Arg Arg Ala Pro Gln Thr Gly Ile Val Asp Glu Cys Cys
                85                  90                  95

Phe Arg Ser Cys Asp Leu Arg Arg Leu Glu Met Tyr Cys Ala Pro Leu
            100                 105                 110

Lys Pro Ala Lys Ser Ala Arg Ser Val Arg Ala Gln Arg His Thr Asp
        115                 120                 125

Met Pro Lys Thr Gln Lys Glu Val His Leu Lys Asn Ala Ser Arg Gly
    130                 135                 140

Ser Ala Gly Asn Lys Asn Tyr Arg Met
145                 150
```

OLIGONUCLEOTIDE COMPRISING AN INOSINE FOR TREATING DMD

RELATED APPLICATIONS

This application is a continuation of U.S. application Ser. No. 16/694,980, filed Nov. 25, 2019, which is a continuation of U.S. application Ser. No. 15/468,239, filed Mar. 24, 2017, now U.S. Pat. No. 10,533,171, which is a continuation of U.S. application Ser. No. 15/168,662, filed May 31, 2016, which is a continuation of U.S. application Ser. No. 14/678,517, filed Apr. 3, 2015, which is a continuation of U.S. application Ser. No. 13/266,110, filed Oct. 24, 2011, which is a 371 of PCT International Application No. PCT/NL2010/050230, filed Apr. 26, 2010, which claims priority to European application No. 09158731.1, filed Apr. 24, 2009 and U.S. provisional application No. 61/172,506, filed Apr. 24, 2009, the entire contents of each of which are incorporated herein by reference in their entirety.

SEQUENCE LISTING

The attached Sequence Listing, titled "0105_09_US1CN5_SL.txt", created on May 4, 2021 and 140 KB in size, is herein incorporated by reference in its entirety.

FIELD OF THE INVENTION

The invention relates to the fields of molecular biology and medicine.

BACKGROUND OF THE INVENTION

A muscle disorder is a disease that usually has a significant impact on the life of an individual. A muscle disorder can have either a genetic cause or a non-genetic cause. An important group of muscle diseases with a genetic cause are Becker Muscular Dystrophy (BMD) and Duchenne Muscular Dystrophy (DMD). These disorders are caused by defects in a gene for a muscle protein.

Becker Muscular Dystrophy and Duchenne Muscular Dystrophy are genetic muscular dystrophies with a relatively high incidence. In both Duchenne and Becker muscular dystrophy the muscle protein dystrophin is affected. In Duchenne dystrophin is absent, whereas in Becker some dystrophin is present but its production is most often not sufficient and/or the dystrophin present is abnormally formed. Both diseases are associated with recessive X-linked inheritance. DMD results from a frameshift mutation in the DMD gene. The frameshift in the DMD gene's transcript (mRNA) results in the production of a truncated non-functional dystrophin protein, resulting in progressive muscle wasting and weakness. BMD occurs as a mutation does not cause a frame-shift in the DMD transcript (mRNA). As in BMD some partly to largely functional dystrophin is present in contrast to DMD where dystrophin is absent, BMD has generally less severe symptoms then DMD. The onset of DMD is earlier than BMD. DMD usually manifests itself in early childhood, BMD in the teens or in early adulthood. The progression of BMD is slower and less predictable than DMD. Patients with BMD can survive into mid to late adulthood. Patients with DMD rarely survive beyond their thirties.

Dystrophin plays an important structural role in the muscle fiber, connecting the extracellular matrix and the cytoskeleton. The N-terminal region binds actin, whereas the C-terminal end is part of the dystrophin glycoprotein complex (DGC), which spans the sarcolemma. In the absence of dystrophin, mechanical stress leads to sarcolemmal ruptures, causing an uncontrolled influx of calcium into the muscle fiber interior, thereby triggering calcium-activated proteases and fiber necrosis.

For most genetic muscular dystrophies no clinically applicable and effective therapies are currently available. Exon skipping techniques are nowadays explored in order to combat genetic muscular dystrophies. Promising results have recently been reported by us and others on a genetic therapy aimed at restoring the reading frame of the dystrophin pre-mRNA in cells from the mdx mouse, the GRMD dog (reference 59) and DMD patients[1-11]. By the targeted skipping of a specific exon, a DMD phenotype (lacking dystrophin) is converted into a milder BMD phenotype (partly to largely functional dystrophin). The skipping of an exon is preferably induced by the binding of antisense oligoribonucleotides (AONs) targeting either one or both of the splice sites, or exon-internal sequences. Since an exon will only be included in the mRNA when both the splice sites are recognised by the spliceosome complex, splice sites have been considered obvious targets for AONs. More preferably, one or more AONs are used which are specific for at least part of one or more exonic sequences involved in correct splicing of the exon. Using exon-internal AONs specific for an exon 46 sequence, we were previously able to modulate the splicing pattern in cultured myotubes from two different DMD patients with an exon 45 deletion[11]. Following AON treatment, exon 46 was skipped, which resulted in a restored reading frame and the induction of dystrophin synthesis in at least 75% of the cells. We have recently shown that exon skipping can also efficiently be induced in human control and patient muscle cells for 39 different DMD exons using exon-internal AONs[1, 2, 11-15].

Hence, exon skipping techniques applied on the dystrophin gene result in the generation of at least partially functional—albeit shorter—dystrophin protein in DMD patients. Since DMD is caused by a dysfunctional dystrophin protein, it would be expected that the symptoms of DMD are sufficiently alleviated once a DMD patient has been provided with functional dystrophin protein. However, the present invention provides the insight that, even though exon skipping techniques are capable of inducing dystrophin synthesis, the oligonucleotide used for exon skipping technique can be improved any further by incorporating an inosine and/or a nucleotide containing a base able to form a wobble base pair in said oligonucleotide.

DESCRIPTION OF THE INVENTION

Oligonucleotide

In a first aspect, there is provided an oligonucleotide comprising an inosine and/or a nucleotide containing a base able to form a wobble base pair or a functional equivalent thereof, wherein the oligonucleotide, or a functional equivalent thereof, comprises a sequence which is complementary to at least part of a dystrophin pre-mRNA exon or at least part of a non-exon region of a dystrophin pre-mRNA said part being a contiguous stretch comprising at least 8 nucleotides.

The use of an inosine and/or a nucleotide containing a base able to form a wobble base pair in an oligonucleotide of the invention is very attractive as explained below. Inosine for example is a known modified base which can pair with three bases: uracil, adenine, and cytosine. Inosine is a nucleoside that is formed when hypoxanthine is attached to a ribose ring (also known as a ribofuranose) via a β-N9-glycosidic bond. Inosine is commonly found in tRNAs and is essential for proper translation of the genetic code in wobble base pairs. A wobble base pair is a G-U and I-U/I-A/I-C pair fundamental in RNA secondary structure. Its thermodynamic stability is comparable to that of the Watson-Crick base pair. Wobble base pairs are critical for the proper translation of the genetic code. The genetic code makes up for disparities in the number of amino acids (20) for triplet codons (64), by using modified base pairs in the first base of the anti-codon. Similarly, when designing primers for polymerase chain reaction, inosine is useful in that it will indiscriminately pair with adenine, thymine, or cytosine. A first advantage of using such a base allows one to design a primer that spans a single nucleotide polymorphism (SNP), without worry that the polymorphism will disrupt the primer's annealing efficiency. Therefore in the invention, the use of such a base allows to design an oligonucleotide that may be used for an individual having a SNP within the dystrophin pre-mRNA stretch which is targeted by an oligonucleotide of the invention. A second advantage of using an inosine and/or a base able to form a wobble base pair in an oligonucleotide of the invention is when said oligonucleotide would normally contain a CpG if one would have designed it as being complementary to at least part of a dystrophin pre-mRNA exon or at least part of a non-exon region of a dystrophin pre-mRNA said part being a contiguous stretch comprising at least 8 nucleotides. The presence of a CpG in an oligonucleotide is usually associated with an increased immunogenicity of said oligonucleotide (reference 60). This increased immunogenicity is undesired since it may induce the breakdown of muscle fibers. Replacing one, two or more CpG by the corresponding inosine and/or a base able to form a wobble base pair in said oligonucleotide is expected to provide an oligonucleotide with a decreased and/or acceptable level of immunogenicity. Immunogenicity may be assessed in an animal model by assessing the presence of $CD4^+$ and/or $CD8^+$ cells and/or inflammatory mononucleocyte infiltration in muscle biopsy of said animal.

Immunogenicity may also be assessed in blood of an animal or of a human being treated with an oligonucleotide of the invention by detecting the presence of a neutralizing antibody and/or an antibody recognizing said oligonucleotide using a standard immunoassay known to the skilled person.

An increase in immunogenicity preferably corresponds to a detectable increase of at least one of these cell types by comparison to the amount of each cell type in a corresponding muscle biopsy of an animal before treatment or treated with a corresponding oligonucleotide having at least one inosine and/or a base able to form a wobble base pair. Alternatively, an increase in immunogenicity may be assessed by detecting the presence or an increasing amount of a neutralizing antibody or an antibody recognizing said oligonucleotide using a standard immunoassay.

A decrease in immunogenicity preferably corresponds to a detectable decrease of at least one of these cell types by comparison to the amount of corresponding cell type in a corresponding muscle biopsy of an animal before treatment or treated with a corresponding oligonucleotide having no inosine and/or a base able to form a wobble base pair. Alternatively a decrease in immunogenicity may be assessed by the absence of or a decreasing amount of said compound and/or neutralizing antibodies using a standard immunoassay.

A third advantage of using an inosine and/or a base able to form a wobble base pair in an oligonucleotide of the invention is to avoid or decrease a potential multimerisation or aggregation of oligonucleotides. It is for example known that an oligonucleotide comprising a G-quartet motif has the tendency to form a quadruplex, a multimer or aggregate formed by the Hoogsteen base-pairing of four single-stranded oligonucleotides (reference 61), which is of course not desired: as a result the efficiency of the oligonucleotide is expected to be decreased. Multimerisation or aggregation is preferably assessed by standard polyacrylamid non-denaturing gel electrophoresis techniques known to the skilled person. In a preferred embodiment, less than 20% or 15%, 10%, 7%, 5% or less of a total amount of an oligonucleotide of the invention has the capacity to multimerise or aggregate assessed using the assay mentioned above.

A fourth advantage of using an inosine and/or a base able to form a wobble base pair in an oligonucleotide of the invention is thus also to avoid quadruplex structures which have been associated with antithrombotic activity (reference 62) as well as with the binding to, and inhibition of, the macrophage scavenger receptor (reference 63).

A fifth advantage of using an inosine and/or a base able to form a wobble base pair in an oligonucleotide of the invention is to allow to design an oligonucleotide with improved RNA binding kinetics and/or thermodynamic properties. The RNA binding kinetics and/or thermodynamic properties are at least in part determined by the melting temperature of an oligonucleotide (Tm; calculated with the oligonucleotide properties calculator (http://www.unc.edu/~cail/biotool/oligo/index.html) for single stranded RNA using the basic Tm and the nearest neighbour model), and/or the free energy of the AON-target exon complex (using RNA structure version 4.5). If a Tm is too high, the oligonucleotide is expected to be less specific. An acceptable Tm and free energy depend on the sequence of the oligonucleotide. Therefore, it is difficult to give preferred ranges for each of these parameters. An acceptable Tm may be ranged between 35 and 65° C. and an acceptable free energy may be ranged between 15 and 45 kcal/mol.

The skilled person may therefore first choose an oligonucleotide as a potential therapeutic compound. In a second step, he may use the invention to further optimise said oligonucleotide by decreasing its immunogenicity and/or avoiding aggregation and/or quadruplex formation and/or by optimizing its Tm and/or free energy of the AON-target complex. He may try to introduce at least one inosine and/or a base able to form a wobble base pair in said oligonucleotide at a suitable position and assess how the immunogenicity and/or aggregation and/or quadruplex formation and/or Tm and/or free energy of the AON-target complex have been altered by the presence of said inosine and/or a base able to form a wobble base pair. If the alteration does not provide the desired alteration or decrease of immunogenicity and/or aggregation and/or quadruplex formation and/or its Tm and/or free energy of the AON-target complex he may choose to introduce a further inosine and/or a base able to form a wobble base pair in said oligonucleotide and/or to introduce a given inosine and/or a base able to form a wobble base pair at a distinct suitable position within said oligonucleotide.

An oligonucleotide comprising an inosine and/or a base able to form a wobble base pair may be defined as an oligonucleotide wherein at least one nucleotide has been substituted with an inosine and/or a base able to form a wobble base pair. The skilled person knows how to test whether a nucleotide contains a base able to form a wobble base pair. Since for example inosine can form a base pair with uracil, adenine, and/or cytosine, it means that at least one nucleotide able to form a base pair with uracil, adenine and/or cytosine has been substituted with inosine. However, in order to safeguard specificity, the inosine containing oligonucleotide preferably comprises the substitution of at least one, two, three, four nucleotide(s) able to form a base pair with uracil or adenine or cytosine as long as an acceptable level of a functional activity of said oligonucleotide is retained as defined later herein.

An oligonucleotide comprising an inosine and/or a base able to form a wobble base pair is preferably an olignucleotide, which is still able to exhibit an acceptable level of a functional activity of a corresponding oligonucleotide not comprising an inosine and/or a base able to form a wobble base pair. A functional activity of said oligonucleotide is preferably to provide an individual with a functional dystrophin protein anchor mRNA and/or at least in part decreasing the production of an aberrant dystrophin protein anchor mRNA. Each of these features are later defined herein. An acceptable level of such a functional activity is preferably at least 50%, 60%, 70%, 80%, 90%, 95% or 100% of the functional activity of the corresponding oligonucleotide which does not comprise an inosine and/or a base able to form a wobble base pair. Such functional activity may be as measured in a muscular tissue or in a muscular cell of an individual or in vitro in a cell by comparison to the functional activity of a corresponding oligonucleotides not comprising an inosine and/or a base able to form a wobble base pair. The assessment of the functionality may be carried out at the mRNA level, preferably using RT-PCR. The assessment of the functionality may be carried out at the protein level, preferably using western blot analysis or immunofluorescence analysis of cross-sections.

Within the context of the invention, an inosine and/or a base able to form a wobble base pair as present in an oligonucleotide is/are present in a part of said oligonucleotide which is complementary to at least part of a dystrophin pre-mRNA exon or at least part of a non-exon region of a dystrophin pre-mRNA said part being a contiguous stretch comprising at least 8 nucleotides. Therefore, in a preferred embodiment, an oligonucleotide comprising an inosine and/or a nucleotide containing a base able to form a wobble base pair or a functional equivalent thereof, wherein the oligonucleotide, or a functional equivalent thereof, comprises a sequence which is complementary to at least part of a dystrophin pre-mRNA exon or at least part of a non-exon region of a dystrophin pre-mRNA said part being a contiguous stretch comprising at least 8 nucleotides and wherein said inosine and/or a nucleotide containing a base able is/are present within the oligonucleotide sequence which is complementary to at least part of a dystrophin pre-mRNA as defined in previous sentence.

However, as later defined herein such inosine and/or a base able to form a wobble base pair may also be present in a linking moiety present in an oligonucleotide of the invention. Preferred linking moieties are later defined herein.

In a preferred embodiment, such oligonucleotide is preferably a medicament. More preferably, said medicament is for preventing or treating Duchenne Muscular Dystrophy or Becker Muscular Dystrophy in an individual or a patient. As defined herein a DMD pre-mRNA preferably means the pre-mRNA of a DMD gene of a DMD or BMD patient. A patient is preferably intended to mean a patient having DMD or BMD or a patient susceptible to develop DMD or BMD due to his or her genetic background. In the case of a DMD patient, an oligonucleotide used will preferably correct at least one of the DMD mutations as present in the DMD gene of said patient and therefore will preferably create a dystrophin that will look like a BMD dystrophin: said dystropin will preferably be a functional dystrophin as later defined herein.

In the case of a BMD patient, an oligonucleotide as used will preferably correct at least one of the BMD mutations as present in the DMD gene of said patient and therefore will preferably create a, or more of a, dystrophin, which will be more functional than the dystrophin which was originally present in said BMD patient. Even more preferably, said medicament provides an individual with a functional or more (of a) functional dystrophin protein and/or mRNA and/or at least in part decreases the production of an aberrant dystrophin protein and/or mRNA.

Preferably, a method of the invention by inducing and/or promoting skipping of at least one exon of the DMD pre-mRNA as identified herein in one or more cells, preferably muscle cells of a patient, provides said patient with an increased production of a more (of a) functional dystrophin protein and/or mRNA and/or decreases the production of an aberrant or less functional dystrophin protein and/or mRNA in said patient.

Providing a patient with a more functional dystrophin protein and/or mRNA and/or decreasing the production of an aberrant dystrophin protein and/or mRNA in said patient is typically applied in a DMD patient. Increasing the production of a more functional or functional dystrophin and/or mRNA is typically applied in a BMD patient.

Therefore a preferred method is a method, wherein a patient or one or more cells of said patient is provided with an increased production of a more functional or functional dystrophin protein and/or mRNA and/or wherein the production of an aberrant dystrophin protein and/or mRNA in said patient is decreased, wherein the level of said aberrant or more functional dystrophin protein and/or mRNA is assessed by comparison to the level of said dystrophin and/or mRNA in said patient at the onset of the method.

As defined herein, a functional dystrophin is preferably a wild type dystrophin corresponding to a protein having the amino acid sequence as identified in SEQ ID NO: 1. A functional dystrophin is preferably a dystrophin, which has an actin binding domain in its N terminal part (first 240 amino acids at the N terminus), a cystein-rich domain (amino acid 3361 till 3685) and a C terminal domain (last 325 amino acids at the C terminus) each of these domains being present in a wild type dystrophin as known to the skilled person. The amino acids indicated herein correspond to amino acids of the wild type dystrophin being represented by SEQ ID NO: 1. In another embodiment, a functional dystrophin is a dystrophin, which exhibits at least to some extent an activity of a wild type dystrophin. "At least to some extent" preferably means at least 30%, 40%, 50%, 60%, 70%, 80%, 90%, 95% or 100% of a corresponding activity of a wild type functional dystrophin. In this context, an activity of a wild type dystrophin is preferably binding to actin and to the dystrophin-associated glycoprotein complex (DGC)[56]. Binding of dystrophin to actin and to the DGC complex may be visualized by either co-immunoprecipitation using total protein extracts or immunofluorescence analysis of cross-sections, from a biopsy of a muscle suspected to be dystrophic, as known to the skilled person.

Individuals suffering from Duchenne muscular dystrophy typically have a mutation in the gene encoding dystrophin that prevents synthesis of the complete protein, i.e a premature stop prevents the synthesis of the C-terminus of the protein. In Becker muscular dystrophy the dystrophin gene also comprises a mutation compared to the wild type but the mutation does typically not include a premature stop and the C-terminus of the protein is typically synthesized. As a result a functional dystrophin protein is synthesized that has at least the same activity in kind as a wild type protein, although not necessarily the same amount of activity. In a preferred embodiment, a functional dystrophin protein means an in frame dystrophin gene. The genome of a BMD individual typically encodes a dystrophin protein comprising the N terminal part (first 240 amino acids at the N terminus), a cystein-rich domain (amino acid 3361 till 3685) and a C terminal domain (last 325 amino acids at the C terminus) but its central rod shaped domain may be shorter than the one of a wild type dystrophin[56]. Exon-skipping for the treatment of DMD is preferably but not exclusively directed to overcome a premature stop in the pre-mRNA by skipping an exon in the rod-domain shaped domain to correct the reading frame and allow synthesis of remainder of the dystrophin protein including the C-terminus, albeit that the protein is somewhat smaller as a result of a smaller rod domain. In a preferred embodiment, an individual having DMD and being treated using an oligonucleotide as defined herein will be provided a dystrophin, which exhibits at least to some extent an activity of a wild type dystrophin. More preferably, if said individual is a Duchenne patient or is suspected to be a Duchenne patient, a functional dystrophin is a dystrophin of an individual having BMD: preferably said dystrophin is able to interact with both actin and the DGC, but its central rod shaped domain may be shorter than the one of a wild type dystrophin (Aartsma-Rus et al (2006, ref 56). The central rod domain of wild type dystrophin comprises 24 spectrin-like repeats[56]. For example, a central rod shaped domain of a dystrophin as provided herein may comprise 5 to 23, 10 to 22 or 12 to 18 spectrin-like repeats as long as it can bind to actin and to DGC. Decreasing the production of an aberrant dystrophin in said patient or in a cell of said patient may be assessed at the mRNA level and preferably means that 99%, 90%, 80%, 70%, 60%, 50%, 40%, 30%, 20%, 10%, 5% or less of the initial amount of aberrant dystrophin mRNA, is still detectable by RT PCR. An aberrant dystrophin mRNA or protein is also referred to herein as a non-functional or less to non-functional or semi-functional dystrophin mRNA or protein. A non-functional pre-mRNA dystrophin is preferably leads to an out of frame dystrophin protein, which means that no dystrophin protein will be produced and/or detected. A non functional dystrophin protein is preferably a dystrophin protein which is not able to bind actin and/or members of the DGC protein complex. A non-functional dystrophin protein or dystrophin mRNA does typically not have, or does not encode a dystrophin protein with an intact C-terminus of the protein.

Increasing the production of a functional dystrophin in said patient or in a cell of said patient may be assessed at the mRNA level (by RT-PCR analysis) and preferably means that a detectable amount of a functional or in frame dystrophin mRNA is detectable by RT PCR. In another embodiment, 1%, 5%, 10%, 20%, 30%, 40%, 50%, 60%, 70%, 80%, 90% or more of the detectable dystrophin mRNA is a functional or in frame dystrophin mRNA.

Increasing the production of a functional dystrophin in said patient or in a cell of said patient may be assessed at the protein level (by immunofluorescence and western blot analyses) and preferably means that a detectable amount of a functional dystrophin protein is detectable by immunofluorescence or western blot analysis. In another embodiment, 1%, 5%, 10%, 20%, 30%, 40%, 50%, 60%, 70%, 80%, 90% or more of the detectable dystrophin protein is a functional dystrophin protein.

An increase or a decrease is preferably assessed in a muscular tissue or in a muscular cell of an individual or a patient by comparison to the amount present in said individual or patient before treatment with said molecule or composition of the invention. Alternatively, the comparison can be made with a muscular tissue or cell of said individual or patient, which has not yet been treated with said oligonucleotide or composition in case the treatment is local.

In a preferred method, one or more symptom(s) from a DMD or a BMD patient is/are alleviated and/or one or more characteristic(s) of a muscle cell or tissue from a DMD or a BMD patient is/are alleviated using a molecule or a composition of the invention. Such symptoms may be assessed on the patient self. Such characteristics may be assessed at the cellular, tissue level of a given patient. An alleviation of one or more characteristics may be assessed by any of the following assays on a myogenic cell or muscle cell from a patient: reduced calcium uptake by muscle cells, decreased collagen synthesis, altered morphology, altered lipid biosynthesis, decreased oxidative stress, and/or improved muscle fiber function, integrity, and/or survival. These parameters are usually assessed using immunofluorescence and/or histochemical analyses of cross sections of muscle biopsies.

Alleviating one or more symptom(s) of Duchenne Muscular Dystrophy or Becker Muscular Dystrophy in an individual using a molecule or a composition of the invention may be assessed by any of the following assays: prolongation of time to loss of walking, improvement of muscle strength, improvement of the ability to lift weight, improvement of the time taken to rise from the floor, improvement in the nine-meter walking time, improvement in the time taken for four-stairs climbing, improvement of the leg function grade, improvement of the pulmonary function, improvement of cardiac function, improvement of the quality of life. Each of these assays is known to the skilled person. As an example, the publication of Manzur at al (2008, ref 58) gives an extensive explanation of each of these assays. For each of these assays, as soon as a detectable improvement or prolongation of a parameter measured in an assay has been found, it will preferably mean that one or more symptoms of Duchenne Muscular Dystrophy or Becker Muscular Dystrophy has been alleviated in an individual using a molecule or composition of the invention. Detectable improvement or prolongation is preferably a statistically significant improvement or prolongation as described in Hodgetts et al (2006, ref 57). Alternatively, the alleviation of one or more symptom(s) of Duchenne Muscular Dystrophy or Becker Muscular Dystrophy may be assessed by measuring an improvement of a muscle fiber function, integrity and/or survival as later defined herein.

An oligonucleotide as used herein preferably comprises an antisense oligonucleotide or antisense oligoribonucleotide. In a preferred embodiment an exon skipping technique is applied. Exon skipping interferes with the natural splicing processes occurring within a eukaryotic cell. In higher eukaryotes the genetic information for proteins in the DNA of the cell is encoded in exons which are separated from each other by intronic sequences. These introns are in some cases very long. The transcription machinery of eukaryotes generates a pre-mRNA which contains both exons and introns, while the splicing machinery, often already during the production of the pre-mRNA, generates the actual coding region for the protein by splicing together the exons present in the pre-mRNA.

Exon-skipping results in mature mRNA that lacks at least one skipped exon. Thus, when said exon codes for amino acids, exon skipping leads to the expression of an altered product. Technology for exon-skipping is currently directed towards the use of antisense oligonucleotides (AONs). Much of this work is done in the mdx mouse model for Duchenne muscular dystrophy. The mdx mouse carries a nonsense mutation in exon 23. Despite the mdx mutation, which should preclude the synthesis of a functional dystrophin protein, rare, naturally occurring dystrophin positive fibers have been observed in mdx muscle tissue. These dystrophin-positive fibers are thought to have arisen from an apparently naturally occurring exon-skipping mechanism, either due to somatic mutations or through alternative splicing. AONs directed to, respectively, the 3' and/or 5' splice sites of introns 22 and 23 in dystrophin pre-mRNA, have been shown to interfere with factors normally involved in removal of intron 23 so that also exon 23 was removed from the mRNA[3, 5, 6, 89, 40].

By the targeted skipping of a specific exon, a DMD phenotype is converted into a milder BMD phenotype. The skipping of an exon is preferably induced by the binding of AONs targeting either one or both of the splice sites, or exon-internal sequences. An oligonucleotide directed toward an exon internal sequence typically exhibits no overlap with non-exon sequences. It preferably does not overlap with the splice sites at least not insofar, as these are present in the intron. An oligonucleotide directed toward an exon internal sequence preferably does not contain a sequence complementary to an adjacent intron. Further provided is thus an oligonucleotide according to the invention, wherein said oligonucleotide, or a functional equivalent thereof, is for inhibiting inclusion of an exon of a dystrophin pre-mRNA into mRNA produced from splicing of said pre-mRNA. An exon skipping technique is preferably applied such that the absence of an exon from mRNA produced from dystrophin pre-mRNA generates a coding region for a more functional—albeit shorter—dystrophin protein. In this context, inhibiting inclusion of an exon preferably means that the detection of the original, aberrant dystrophin mRNA and/or protein is decreased as earlier defined herein.

Since an exon of a dystrophin pre-mRNA will only be included into the resulting mRNA when both the splice sites are recognised by the spliceosome complex, splice sites have been obvious targets for AONs. One embodiment therefore provides an oligonucleotide, or a functional equivalent thereof, comprising a sequence which is complementary to a non-exon region of a dystrophin pre mRNA. In one embodiment an AON is used which is solely complementary to a non-exon region of a dystrophin pre mRNA. This is however not necessary: it is also possible to use an AON which comprises an intron-specific sequence as well as exon-specific sequence. Such AON comprises a sequence which is complementary to a non-exon region of a dystrophin pre mRNA, as well as a sequence which is complementary to an exon region of a dystrophin pre mRNA. Of course, an AON is not necessarily complementary to the entire sequence of a dystrophin exon or intron. AONs, which are complementary to a part of such exon or intron are preferred. An AON is preferably complementary to at least part of a dystrophin exon and/or intron, said part having at least 8, 10, 13, 15, 20 nucleotides.

Splicing of a dystrophin pre-mRNA occurs via two sequential transesterification reactions. First, the 2'OH of a specific branch-point nucleotide within the intron that is defined during spliceosome assembly performs a nucleophilic attack on the first nucleotide of the intron at the 5' splice site forming the lariat intermediate. Second, the 3'OH of the released 5' exon then performs a nucleophilic attack at the last nucleotide of the intron at the 3' splice site thus joining the exons and releasing the intron lariat. The branch point and splice sites of an intron are thus involved in a splicing event. Hence, an oligonucleotide comprising a sequence, which is complementary to such branch point and/or splice site is preferably used for exon skipping. Further provided is therefore an oligonucleotide, or a functional equivalent thereof, which comprises a sequence which is complementary to a splice site and/or branch point of a dystrophin pre mRNA.

Since splice sites contain consensus sequences, the use of an oligonucleotide or a functional equivalent thereof (herein also called an AON) comprising a sequence which is complementary of a splice site involves the risk of promiscuous hybridization. Hybridization of AONs to other splice sites than the sites of the exon to be skipped could easily interfere with the accuracy of the splicing process. To overcome these and other potential problems related to the use of AONs which are complementary to an intron sequence, one preferred embodiment provides an oligonucleotide, or a functional equivalent thereof, comprising a sequence which is complementary to a dystrophin pre-mRNA exon. Preferably, said AON is capable of specifically inhibiting an exon inclusion signal of at least one exon in said dystrophin pre-mRNA. Interfering with an exon inclusion signal (EIS) has the advantage that such elements are located within the exon. By providing an AON for the interior of the exon to be skipped, it is possible to interfere with the exon inclusion signal thereby effectively masking the exon from the splicing apparatus. The failure of the splicing apparatus to recognize the exon to be skipped thus leads to exclusion of the exon from the final mRNA. This embodiment does not interfere directly with the enzymatic process of the splicing machinery (the joining of the exons). It is thought that this allows the method to be more specific and/or reliable. It is thought that an EIS is a particular structure of an exon that allows splice acceptor and donor to assume a particular spatial conformation. In this concept, it is the particular spatial conformation that enables the splicing machinery to recognize the exon. However, the invention is certainly not limited to this model. In a preferred embodiment, use is made of an oligonucleotide, which is capable of binding to an exon and is capable of inhibiting an EIS. An AON may specifically contact said exon at any point and still be able to specifically inhibit said EIS.

Within the context of the invention, a functional equivalent of an oligonucleotide preferably means an oligonucleotide as defined herein wherein one or more nucleotides have been substituted and wherein an activity of said functional equivalent is retained to at least some extent. Preferably, an activity of said functional equivalent is providing a functional dystrophin protein. Said activity of said functional equivalent is therefore preferably assessed by quantifying the amount of a functional dystrophin protein or by quantifying the amount of a functional dystrophin mRNA. A functional dystrophin protein (or a functional dystrophin mRNA) is herein preferably defined as being a dystrophin protein (or a dystrophin protein encoded by said mRNA) able to bind actin and members of the DGC protein. The assessment of said activity of an oligonucleotide is preferably done by RT-PCR (m-RNA) or by immunofluorescence or Western blot analyses (protein). Said activity is preferably retained to at least some extent when it represents at least 50%, or at least 60%, or at least 70% or at least 80% or at least 90% or at least 95% or more of corresponding activity of said oligonucleotide the functional equivalent derives from. Such activity may be measured in a muscular tissue or in a muscular cell of an individual or in vitro in a cell by comparison to an activity of a corresponding oligonucleotide of said oligonucleotide the functional equivalent derives from. Throughout this application, when the word oligonucleotide is used it may be replaced by a functional equivalent thereof as defined herein.

Hence, an oligonucleotide, or a functional equivalent thereof, comprising or consisting of a sequence which is complementary to a dystrophin pre-mRNA exon provides good DMD therapeutic results. In one preferred embodiment an oligonucleotide, or a functional equivalent thereof, is used which comprises or consists of a sequence which is complementary to at least part of either dystrophin pre-mRNA exons 2 to 75 said part having or comprising at least 13 nucleotides. However, said part may also have at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides. A part of dystrophin pre-mRNA to which an oligonucleotide is complementary may also be called a contiguous stretch of dystrophin pre-mRNA.

Most preferably an AON is used which comprises or consists of a sequence which is complementary to at least part of dystrophin pre-mRNA exon 51, 45, 53, 44, 46, 52, 50, 43, 6, 7, 8, 55, 2, 11, 17, 19, 21, 57, 59, 62, 63, 65, 66, 69, and/or 75 said part having or comprising at least 13 nucleotides. However, said part may also have at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides. More preferred oligonucleotides are represented by a sequence that comprises or consists of each of the following sequences SEQ ID NO: 2 to SEQ ID NO:539 wherein at least one inosine and/or a base able to form a wobble base pair is present in said sequence. Preferably, an inosine has been introduced in one of these sequences to replace a guanosine, adenine, or a uracil. Accordingly, an even more preferred oligonucleotide as used herein is represented by a sequence that comprises or consists of SEQ ID NO:2 to SEQ ID NO:486 or SEQ ID NO:539, even more preferably SEQ ID NO:2 to NO 237 or SEQ ID NO:539, most preferably SEQ ID NO:76 wherein at least one inosine and/or a base able to form a wobble base pair is present in said sequence. Preferably, an inosine has been introduced in one of these sequences to replace a guanosine, adenine, or a uracil.

Accordingly, in another preferred embodiment, an oligonucleotide as used herein is represented by a sequence that comprises or consists of SEQ ID NO:540 to SEQ ID NO:576. More preferably, an oligonucleotide as used herein is represented by a sequence that comprises or consists of SEQ ID NO:557.

Said exons are listed in decreasing order of patient population applicability. Hence, the use of an AON comprising a sequence, which is complementary to at least part of dystrophin pre-mRNA exon 51 is suitable for use in a larger part of the DMD patient population as compared to an AON comprising a sequence which is complementary to dystrophin pre-mRNA exon 44, et cetera.

In a preferred embodiment, an oligonucleotide of the invention, which comprises a sequence that is complementary to part of dystrophin pre-mRNA is such that the complementary part is at least 50% of the length of the oligonucleotide of the invention, more preferably at least 60%, even more preferably at least 70%, even more preferably at least 80%, even more preferably at least 90% or even more preferably at least 95%, or even more preferably 98% or even more preferably at least 99%, or even more preferably 100%. In a most preferred embodiment, the oligonucleotide of the invention consists of a sequence that is complementary to part of dystrophin pre-mRNA as defined herein. As an example, an oligonucleotide may comprise a sequence that is complementary to part of dystrophin pre-mRNA as defined herein and additional flanking sequences. In a more preferred embodiment, the length of said complementary part of said oligonucleotide is of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides. Preferably, additional flanking sequences are used to modify the binding of a protein to the oligonucleotide, or to modify a thermodynamic property of the oligonucleotide, more preferably to modify target RNA binding affinity.

One preferred embodiment provides an oligonucleotide, or a functional equivalent thereof which comprises:

a sequence which is complementary to a region of a dystrophin pre-mRNA exon that is hybridized to another part of a dystrophin pre-mRNA exon (closed structure), and a sequence which is complementary to a region of a dystrophin pre-mRNA exon that is not hybridized in said dystrophin pre-mRNA (open structure).

For this embodiment, reference is made to WO 2004/083432, which is incorporated by reference in its entirety. RNA molecules exhibit strong secondary structures, mostly due to base pairing of complementary or partly complementary stretches within the same RNA. It has long since been thought that structures in the RNA play a role in the function of the RNA. Without being bound by theory, it is believed that the secondary structure of the RNA of an exon plays a role in structuring the splicing process. The structure of an exon is one parameter which is believed to direct its inclusion into the mRNA. However, other parameters may also play a role therein. Herein this signalling function is referred to as an exon inclusion signal. A complementary oligonucleotide of this embodiment is capable of interfering with the structure of the exon and thereby capable of interfering with the exon inclusion signal of the exon. It has been found that many complementary oligonucleotides indeed comprise this capacity, some more efficient than others. Oligonucleotides of this preferred embodiment, i.e. those with the said overlap directed towards open and closed structures in the native exon RNA, are a selection from all possible oligonucleotides. The selection encompasses oligonucleotides that can efficiently interfere with an exon inclusion signal. Without being bound by theory it is thought that the overlap with an open structure improves the invasion efficiency of the oligonucleotide and prevents the binding of splicing factors (i.e. increases the efficiency with which the oligonucleotide can enter the structure), whereas the overlap with the closed structure subsequently increases the efficiency of interfering with the secondary structure of the RNA of the exon, and thereby interfere with the exon inclusion signal. It is found that the length of the partial complementarity to both the closed and the open structure is not extremely restricted. We have observed high efficiencies with oligonucleotides with variable lengths of complementarity in either structure. The term complementarity is used herein to refer to a stretch of nucleic acids that can hybridise to another stretch of nucleic acids under physiological conditions. It is thus not absolutely required that all the bases in the region of complementarity are capable of pairing with bases in the opposing strand. For instance, when designing the oligonucleotide one may want to incorporate for instance a residue that does not base pair with the base on the complementary strand. Mismatches may, to some extent, be allowed, if under the circumstances in the cell, the stretch of nucleotides is sufficiently capable of hybridising to the complementary part. In this context, "sufficiently" preferably means that using a gel mobility shift assay as described in example 1 of EP 1 619 249, binding of an oligonucleotide is detectable. Optionally, said oligonucleotide may further be tested by transfection into muscle cells of patients. Skipping of the targeted exon may be assessed by RT-PCR (as described in EP 1 619 249). The complementary regions are preferably designed such that, when combined, they are specific for the exon in the pre-mRNA. Such specificity may be created with various lengths of complementary regions as this depends on the actual sequences in other (pre-)mRNA in the system. The risk that also one or more other pre-mRNA will be able to hybridise to the oligonucleotide decreases with increasing size of the oligonucleotide. It is clear that oligonucleotides comprising mismatches in the region of complementarity but that retain the capacity to hybridise to the targeted region(s) in the pre-mRNA, can be used in the present invention. However, preferably at least the complementary parts do not comprise such mismatches as these typically have a higher efficiency and a higher specificity, than oligonucleotides having such mismatches in one or more complementary regions. It is thought, that higher hybridisation strengths, (i.e. increasing number of interactions with the opposing strand) are favourable in increasing the efficiency of the process of interfering with the splicing machinery of the system. Preferably, the complementarity is between 90 and 100%. In general this allows for approximately 1 or 2 mismatch(es) in an oligonucleotide of around 20 nucleotides The secondary structure is best analysed in the context of the pre-mRNA wherein the exon resides. Such structure may be analysed in the actual RNA. However, it is currently possible to predict the secondary structure of an RNA molecule (at lowest energy costs) quite well using structure-modelling programs. A non-limiting example of a suitable program is RNA mfold version 3.1 server[41]. A person skilled in the art will be able to predict, with suitable reproducibility, a likely structure of the exon, given the nucleotide sequence. Best predictions are obtained when providing such modelling programs with both the exon and flanking intron sequences. It is typically not necessary to model the structure of the entire pre-mRNA.

The open and closed structure to which the oligonucleotide is directed, are preferably adjacent to one another. It is thought, that in this way the annealing of the oligonucleotide to the open structure induces opening of the closed structure whereupon annealing progresses into this closed structure. Through this action the previously closed structure assumes a different conformation. The different conformation results in the disruption of the exon inclusion signal. However, when potential (cryptic) splice acceptor and/or donor sequences are present within the targeted exon, occasionally a new exon inclusion signal is generated defining a different (neo) exon, i.e. with a different 5' end, a different 3' end, or both. This type of activity is within the scope of the present invention as the targeted exon is excluded from the mRNA. The presence of a new exon, containing part of the targeted exon, in the mRNA does not alter the fact that the targeted exon, as such, is excluded. The inclusion of a neo-exon can be seen as a side effect, which occurs only occasionally. There are two possibilities when exon skipping is used to restore (part of) an open reading frame of dystrophin that is disrupted as a result of a mutation. One is that the neo-exon is functional in the restoration of the reading frame, whereas in the other case the reading frame is not restored. When selecting oligonucleotides for restoring dystrophin reading frames by means of exon-skipping it is of course clear that under these conditions only those oligonucleotides are selected that indeed result in exon-skipping that restores the dystrophin open reading frame, with or without a neo-exon.

Further provided is an oligonucleotide, or a functional equivalent thereof, comprising a sequence that is complementary to a binding site for a serine-arginine (SR) protein in RNA of an exon of a dystrophin pre-mRNA. In WO 2006/112705 we have disclosed the presence of a correlation between the effectivity of an exon-internal antisense oligonucleotide (AON) in inducing exon skipping and the presence of a (for example by ESE finder) predicted SR binding site in the target pre-mRNA site of said AON. Therefore, in one embodiment an oligonucleotide is generated comprising determining a (putative) binding site for an SR (Ser-Arg) protein in RNA of a dystrophin exon and producing an oligonucleotide that is complementary to said RNA and that at least partly overlaps said (putative) binding site. The term "at least partly overlaps" is defined herein as to comprise an overlap of only a single nucleotide of an SR binding site as well as multiple nucleotides of said binding site as well as a complete overlap of said binding site. This embodiment preferably further comprises determining from a secondary structure of said RNA, a region that is hybridised to another part of said RNA (closed structure) and a region that is not hybridised in said structure (open structure), and subsequently generating an oligonucleotide that at least partly overlaps said (putative) binding site and that overlaps at least part of said closed structure and overlaps at least part of said open structure. In this way we increase the chance of obtaining an oligonucleotide that is capable of interfering with the exon inclusion from the pre-mRNA into mRNA. It is possible that a first selected SR-binding region does not have the requested open-closed structure in which case another (second) SR protein binding site is selected which is then subsequently tested for the presence of an open-closed structure. This process is continued until a sequence is identified which contains an SR protein binding site as well as a(n) (partly overlapping) open-closed structure. This sequence is then used to design an oligonucleotide which is complementary to said sequence.

Such a method, for generating an oligonucleotide, is also performed by reversing the described order, i.e. first generating an oligonucleotide comprising determining, from a secondary structure of RNA from a dystrophin exon, a region that assumes a structure that is hybridised to another part of said RNA (closed structure) and a region that is not hybridised in said structure (open structure), and subsequently generating an oligonucleotide, of which at least a part of said oligonucleotide is complementary to said closed structure and of which at least another part of said oligonucleotide is complementary to said open structure. This is then followed by determining whether an SR protein binding site at least overlaps with said open/closed structure. In this way the method of WO 2004/083432 is improved. In yet another embodiment the selections are performed simultaneously.

Without wishing to be bound by any theory it is currently thought that use of an oligonucleotide directed to an SR protein binding site results in (at least partly) impairing the binding of an SR protein to the binding site of an SR protein which results in disrupted or impaired splicing.

Preferably, an open/closed structure and an SR protein binding site partly overlap and even more preferred an open/closed structure completely overlaps an SR protein binding site or an SR protein binding site completely overlaps an open/closed structure. This allows for an improved disruption of exon inclusion.

Besides consensus splice sites sequences, many (if not all) exons contain splicing regulatory sequences such as exonic splicing enhancer (ESE) sequences to facilitate the recognition of genuine splice sites by the spliceosome[42, 43]. A subgroup of splicing factors, called the SR proteins, can bind to these ESEs and recruit other splicing factors, such as U1 and U2AF to (weakly defined) splice sites. The binding sites of the four most abundant SR proteins (SF2/ASF, SC35, SRp40 and SRp55) have been analyzed in detail and these results are implemented in ESE finder, a web source that predicts potential binding sites for these SR proteins[42, 43] There is a correlation between the effectiveness of an AON and the presence/absence of an SF2/ASF, SC35 and SRp40 binding site. In a preferred embodiment, the invention thus provides a combination as described above, wherein said SR protein is SF2/ASF or SC35 or SRp40.

In one embodiment an oligonucleotide, or a functional equivalent thereof is capable of specifically binding a regulatory RNA sequence which is required for the correct splicing of a dystrophin exon in a transcript. Several cis-acting RNA sequences are required for the correct splicing of exons in a transcript. In particular, supplementary elements such as intronic or exonic splicing enhancers (ISEs and ESEs) or silencers (ISSs and ESEs) are identified to regulate specific and efficient splicing of constitutive and alternative exons. Using sequence-specific antisense oligonucleotides (AONs) that bind to the elements, their regulatory function is disturbed so that the exon is skipped, as shown for DMD. Hence, in one preferred embodiment an oligonucleotide or functional equivalent thereof is used which is complementary to an intronic splicing enhancer (ISE), an exonic splicing enhancer (ESE), an intronic splicing silencer (ISS) and/or an exonic splicing silencer (ESS). As already described herein before, a dystrophin exon is in one preferred embodiment skipped by an agent capable of specifically inhibiting an exon inclusion signal of said exon, so that said exon is not recognized by the splicing machinery as a part that needs to be included in the mRNA. As a result, a mRNA without said exon is formed.

An AON used herein is preferably complementary to a consecutive part or a contiguous stretch of between 8 and 50 nucleotides of dystrophin exon RNA or dystrophin intron RNA. In one embodiment an AON used herein is complementary to a consecutive part or a contiguous stretch of between 14 and 50 nucleotides of a dystrophin exon RNA or dystrophin intron RNA. Preferably, said AON is complementary to a consecutive part or contiguous stretch of between 14 and 25 nucleotides of said exon RNA. More preferably, an AON is used which comprises a sequence which is complementary to a consecutive part or a contiguous stretch of between 20 and 25 nucleotides of a dystrophin exon RNA or a dystrophin intron RNA.

Different types of nucleic acid may be used to generate an oligonucleotide. Preferably, said oligonucleotide comprises RNA, as RNA/RNA hybrids are very stable. Since one of the aims of the exon skipping technique is to direct splicing in subjects it is preferred that the oligonucleotide RNA comprises a modification providing the RNA with an additional property, for instance resistance to endonucleases, exonucleases, and RNaseH, additional hybridisation strength, increased stability (for instance in a bodily fluid), increased or decreased flexibility, reduced toxicity, increased intracellular transport, tissue-specificity, etc. Preferably, said modification comprises a 2'-O-methyl-phosphorothioate oligoribonucleotide modification. Preferably, said modification comprises a 2'-O-methyl-phosphorothioate oligo deoxyribonucleotide modification. One embodiment thus provides an oligonucleotide is used which comprises RNA which contains a modification, preferably a 2'-O-methyl modified ribose (RNA) or deoxyribose (DNA) modification.

In one embodiment the invention provides a hybrid oligonucleotide comprising an oligonucleotide comprising a 2'-O-methyl-phosphorothioate oligo(deoxy)ribonucleotide modification and locked nucleic acid. This particular oligonucleotide comprises better sequence specificity compared to an equivalent consisting of locked nucleic acid, and comprises improved effectivity when compared with an oligonucleotide consisting of 2'-O-methyl-phosphorothioate oligo(deoxy)ribonucleotide modification.

With the advent of nucleic acid mimicking technology it has become possible to generate molecules that have a similar, preferably the same hybridisation characteristics in kind not necessarily in amount as nucleic acid itself. Such functional equivalents are of course also suitable for use in the invention. Preferred examples of functional equivalents of an oligonucleotide are peptide nucleic acid and/or locked nucleic acid. Most preferably, a morpholino phosphorodiamidate is used. Suitable but non-limiting examples of equivalents of oligonucleotides of the invention can be found in[44-50]. Hybrids between one or more of the equivalents among each other and/or together with nucleic acid are of course also suitable. In a preferred embodiment locked nucleic acid is used as a functional equivalent of an oligonucleotide, as locked nucleic acid displays a higher target affinity and reduced toxicity and therefore shows a higher efficiency of exon skipping.

In one embodiment an oligonucleotide, or a functional equivalent thereof, which is capable of inhibiting inclusion of a dystrophin exon into dystrophin mRNA is combined with at least one other oligonucleotide, or functional equivalent thereof, that is capable of inhibiting inclusion of another dystrophin exon into dystrophin mRNA. This way, inclusion of two or more exons of a dystrophin pre-mRNA in mRNA produced from this pre-mRNA is prevented. This embodiment is further referred to as double- or multi-exon skipping[2, 15]. In most cases double-exon skipping results in the exclusion of only the two targeted exons from the dystrophin pre-mRNA. However, in other cases it was found that the targeted exons and the entire region in between said exons in said pre-mRNA were not present in the produced mRNA even when other exons (intervening exons) were present in such region. This multi-exon skipping was notably so for the combination of oligonucleotides derived from the DMD gene, wherein one oligonucleotide for exon 45 and one oligonucleotide for exon 51 was added to a cell transcribing the DMD gene. Such a set-up resulted in mRNA being produced that did not contain exons 45 to 51. Apparently, the structure of the pre-mRNA in the presence of the mentioned oligonucleotides was such that the splicing machinery was stimulated to connect exons 44 and 52 to each other. Other preferred examples of multi-exon skipping are:

the use of an oligonucleotide targeting exon 17, and a second one exon 48 which may result in the skipping of said both exons or of the entire region between exon 17 and exon 48.

the use of an oligonucleotide targeting exon 17, and a second one exon 51 which may result in the skipping of said both exons or of the entire region between exon 17 and exon 51.

the use of an oligonucleotide targeting exon 42, and a second one exon 55 which may result in the skipping of said both exons or of the entire region between exon 42 and exon 55.

the use of an oligonucleotide targeting exon 43, and a second one exon 51 which may result in the skipping of said both exons or of the entire region between exon 43 and exon 51.

the use of an oligonucleotide targeting exon 43, and a second one exon 55 which may result in the skipping of said both exons or of the entire region between exon 43 and exon 55.

the use of an oligonucleotide targeting exon 45, and a second one exon 55 which may result in the skipping of said both exons or of the entire region between exon 45 and exon 55.

the use of an oligonucleotide targeting exon 45, and a second one exon 59 which may result in the skipping of said both exons or of the entire region between exon 45 and exon 59.

the use of an oligonucleotide targeting exon 48, and a second one exon 59 which may result in the skipping of said both exons or of the entire region between exon 48 and exon 59.

the use of an oligonucleotide targeting exon 50, and a second one exon 51 which may result in the skipping of said both exons.

the use of an oligonucleotide targeting exon 51, and a second one exon 52 which may result in the skipping of said both exons.

Further provided is therefore an oligonucleotide which comprises at least 8, preferably between 16 to 80, consecutive nucleotides that are complementary to a first exon of a dystrophin pre-mRNA and wherein a nucleotide sequence is used which comprises at least 8, preferably between 16 to 80, consecutive nucleotides that are complementary to a second exon of said dystrophin pre-mRNA. Said first and said second exon may be the same.

In one preferred embodiment said first and said second exon are separated in said dystrophin pre-mRNA by at least one exon to which said oligonucleotide is not complementary. Alternatively, said first and said second exon are adjacent.

It is possible to specifically promote the skipping of also the intervening exons by providing a linkage between the two complementary oligonucleotides. Hence, in one embodiment stretches of nucleotides complementary to at least two dystrophin exons are separated by a linking moiety. The at least two stretches of nucleotides are thus linked in this embodiment so as to form a single molecule. Further provided is therefore an oligonucleotide, or functional equivalent thereof which is complementary to at least two exons in a dystrophin pre-mRNA, said oligonucleotide or functional equivalent comprising at least two parts wherein a first part comprises an oligonucleotide having at least 8, preferably between 16 to 80, consecutive nucleotides that are complementary to a first of said at least two exons and wherein a second part comprises an oligonucleotide having at least 8, preferably between 16 to 80, consecutive nucleotides that are complementary to a second exon in said dystrophin pre-mRNA. The linkage may be through any means, but is preferably accomplished through a nucleotide linkage. In the latter case, the number of nucleotides that do not contain an overlap between one or the other complementary exon can be zero, but is preferably between 4 to 40 nucleotides. The linking moiety can be any type of moiety capable of linking oligonucleotides. Preferably, said linking moiety comprises at least 4 uracil nucleotides. Currently, many different compounds are available that mimic hybridisation characteristics of oligonucleotides. Such a compound, called herein a functional equivalent of an oligonucleotide, is also suitable for the present invention if such equivalent comprises similar hybridisation characteristics in kind not necessarily in amount. Suitable functional equivalents are mentioned earlier in this description. As mentioned, oligonucleotides of the invention do not have to consist of only oligonucleotides that contribute to hybridisation to the targeted exon. There may be additional material and/or nucleotides added.

The DMD gene is a large gene, with many different exons. Considering that the gene is located on the X-chromosome, it is mostly boys that are affected, although girls can also be affected by the disease, as they may receive a bad copy of the gene from both parents, or are suffering from a particularly biased inactivation of the functional allele due to a particularly biased X chromosome inactivation in their muscle cells. The protein is encoded by a plurality of exons (79) over a range of at least 2.4 Mb. Defects may occur in any part of the DMD gene. Skipping of a particular exon or particular exons can, very often, result in a restructured mRNA that encodes a shorter than normal but at least partially functional dystrophin protein. A practical problem in the development of a medicament based on exon-skipping technology is the plurality of mutations that may result in a deficiency in functional dystrophin protein in the cell. Despite the fact that already multiple different mutations can be corrected for by the skipping of a single exon, this plurality of mutations, requires the generation of a series of different pharmaceuticals as for different mutations different exons need to be skipped. An advantage of an oligonucleotide or of a composition comprising at least two distinct oligonucleotide as later defined herein capable of inducing skipping of two or more exons, is that more than one exon can be skipped with a single pharmaceutical. This property is not only practically very useful in that only a limited number of pharmaceuticals need to be generated for treating many different DMD or particular, severe BMD mutations. Another option now open to the person skilled in the art is to select particularly functional restructured dystrophin proteins and produce compounds capable of generating these preferred dystrophin proteins. Such preferred end results are further referred to as mild phenotype dystrophins.

Dose ranges of oligonucleotide according to the invention are preferably designed on the basis of rising dose studies in clinical trials (in vivo use) for which rigorous protocol requirements exist. A molecule or an oligonucleotide as defined herein may be used at a dose which is ranged between 0.1 and 20 mg/kg, preferably 0.5 and 10 mg/kg.

In a preferred embodiment, a concentration of an oligonucleotide as defined herein, which is ranged between 0.1 nM and 1 µM is used. Preferably, this range is for in vitro use in a cellular model such as muscular cells or muscular tissue. More preferably, the concentration used is ranged between 0.3 to 400 nM, even more preferably between 1 to 200 nM. If several oligonucleotides are used, this concentration or dose may refer to the total concentration or dose of oligonucleotides or the concentration or dose of each oligonucleotide added.

The ranges of concentration or dose of oligonucleotide(s) as given above are preferred concentrations or doses for in vitro or ex vivo uses. The skilled person will understand that depending on the oligonucleotide(s) used, the target cell to be treated, the gene target and its expression levels, the medium used and the transfection and incubation conditions, the concentration or dose of oligonucleotide(s) used may further vary and may need to be optimised any further.

An oligonucleotide as defined herein for use according to the invention may be suitable for administration to a cell, tissue and/or an organ in vivo of individuals affected by or at risk of developing DMD or BMD, and may be administered in vivo, ex vivo or in vitro. Said oligonucleotide may be directly or indirectly administrated to a cell, tissue and/or an organ in vivo of an individual affected by or at risk of developing DMD or BMD, and may be administered directly or indirectly in vivo, ex vivo or in vitro. As Duchenne and Becker muscular dystrophy have a pronounced phenotype in muscle cells, it is preferred that said cells are muscle cells, it is further preferred that said tissue is a muscular tissue and/or it is further preferred that said organ comprises or consists of a muscular tissue. A preferred organ is the heart. Preferably, said cells comprise a gene encoding a mutant dystrophin protein. Preferably, said cells are cells of an individual suffering from DMD or BMD.

An oligonucleotide of the invention may be indirectly administrated using suitable means known in the art. An oligonucleotide may for example be provided to an individual or a cell, tissue or organ of said indivival in the form of an expression vector wherein the expression vector encodes a transcript comprising said oligonucleotide. The expression vector is preferably introduced into a cell, tissue, organ or individual via a gene delivery vehicle. In a preferred embodiment, there is provided a viral-based expression vector comprising an expression cassette or a transcription cassette that drives expression or transcription of a molecule as identified herein. A preferred delivery vehicle is a viral vector such as an adeno-associated virus vector (AAV), or a retroviral vector such as a lentivirus vector[4, 51, 52] and the like. Also, plasmids, artificial chromosomes, plasmids suitable for targeted homologous recombination and integration in the human genome of cells may be suitably applied for delivery of an oligonucleotide as defined herein. Preferred for the current invention are those vectors wherein transcription is driven from PolIII promoters, and/or wherein transcripts are in the form fusions with U1 or U7 transcripts, which yield good results for delivering small transcripts. It is within the skill of the artisan to design suitable transcripts. Preferred are PolIII driven transcripts. Preferably, in the form of a fusion transcript with an U1 or U7 transcript[4, 51, 52]. Such fusions may be generated as described[53, 54]. The oligonucleotide may be delivered as is. However, the oligonucleotide may also be encoded by the viral vector. Typically, this is in the form of an RNA transcript that comprises the sequence of the oligonucleotide in a part of the transcript.

Improvements in means for providing an individual or a cell, tissue, organ of said individual with an oligonucleotide and/or an equivalent thereof, are anticipated considering the progress that has already thus far been achieved. Such future improvements may of course be incorporated to achieve the mentioned effect on restructuring of mRNA using a method of the invention. An oligonucleotide and/or an equivalent thereof can be delivered as is to an individual, a cell, tissue or organ of said individual. When administering an oligonucleotide and/or an equivalent thereof, it is preferred that an oligonucleotide and/or an equivalent thereof is dissolved in a solution that is compatible with the delivery method. For intravenous, subcutaneous, intramuscular, intrathecal and/or intraventricular administration it is preferred that the solution is a physiological salt solution. Particularly preferred in the invention is the use of an excipient that will aid in delivery of each of the constituents as defined herein to a cell and/or into a cell, preferably a muscle cell. Preferred are excipients capable of forming complexes, nanoparticles, micelles, vesicles and/or liposomes that deliver each constituent as defined herein, complexed or trapped in a vesicle or liposome through a cell membrane. Many of these excipients are known in the art. Suitable excipients comprise polyethylenimine (PEI), or similar cationic polymers, including polypropyleneimine or polyethylenimine copolymers (PECs) and derivatives, synthetic amphiphils (SAINT-18), Lipofectin™, DOTAP and/or viral capsid proteins that are capable of self assembly into particles that can deliver each constituent as defined herein to a cell, preferably a muscle cell. Such excipients have been shown to efficiently deliver an oligonucleotide such as antisense nucleic acids to a wide variety of cultured cells, including muscle cells. Their high transfection potential is combined with an excepted low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver each constituent as defined herein, preferably an oligonucleotide across cell membranes into cells.

In addition to these common nanoparticle materials, the cationic peptide protamine offers an alternative approach to formulate an oligonucleotide with colloids. This colloidal nanoparticle system can form so called proticles, which can be prepared by a simple self-assembly process to package and mediate intracellular release of an oligonucleotide. The skilled person may select and adapt any of the above or other commercially available alternative excipients and delivery systems to package and deliver an oligonucleotide for use in the current invention to deliver it for the treatment of Duchenne Muscular Dystrophy or Becker Muscular Dystrophy in humans.

In addition, an oligonucleotide could be covalently or non-covalently linked to a targeting ligand specifically designed to facilitate the uptake in to the cell, cytoplasm and/or its nucleus. Such ligand could comprise (i) a compound (including but not limited to peptide(-like) structures) recognising cell, tissue or organ specific elements facilitating cellular uptake and/or (ii) a chemical compound able to facilitate the uptake in to cells and/or the intracellular release of an oligonucleotide from vesicles, e.g. endosomes or lysosomes.

Therefore, in a preferred embodiment, an oligonucleotide is formulated in a composition or a medicament or a composition, which is provided with at least an excipient and/or a targeting ligand for delivery and/or a delivery device thereof to a cell and/or enhancing its intracellular delivery. Accordingly, the invention also encompasses a pharmaceutically acceptable composition comprising an oligonucleotide and further comprising at least one excipient and/or a targeting ligand for delivery and/or a delivery device of said oligonucleotide to a cell and/or enhancing its intracellular delivery. It is to be understood that if a composition comprises an additional constituent such as an adjunct compound as later defined herein, each constituent of the composition may not be formulated in one single combination or composition or preparation. Depending on their identity, the skilled person will know which type of formulation is the most appropriate for each constituent as defined herein. In a preferred embodiment, the invention provides a composition or a preparation which is in the form of a kit of parts comprising an oligonucleotide and a further adjunct compound as later defined herein.

A preferred oligonucleotide is for preventing or treating Duchenne Muscular Dystrophy (DMD) or Becker Muscular Dystrophy (BMD) in an individual. An individual, which may be treated using an oligonucleotide of the invention may already have been diagnosed as having a DMD or a BMD. Alternatively, an individual which may be treated using an oligonucleotide of the invention may not have yet been diagnosed as having a DMD or a BMD but may be an individual having an increased risk of developing a DMD or a BMD in the future given his or her genetic background. A preferred individual is a human being.

Composition

In a further aspect, there is provided a composition comprising an oligonucleotide as defined herein. Preferably, said composition comprises at least two distinct oligonucleotide as defined herein. More preferably, these two distinct oligonucleotides are designed to skip distinct two or more exons as earlier defined herein for multi-exon skipping.

In a preferred embodiment, said composition being preferably a pharmaceutical composition said pharmaceutical composition comprising a pharmaceutically acceptable carrier, adjuvant, diluent and/or excipient. Such a pharmaceutical composition may comprise any pharmaceutically acceptable carrier, filler, preservative, adjuvant, solubilizer, diluent and/or excipient is also provided. Such pharmaceutically acceptable carrier, filler, preservative, adjuvant, solubilizer, diluent and/or excipient may for instance be found in Remington: The Science and Practice of Pharmacy, 20th Edition. Baltimore, Md.: Lippincott Williams & Wilkins, 2000. Each feature of said composition has earlier been defined herein.

If several oligonucleotides are used, concentration or dose already defined herein may refer to the total concentration or dose of all oligonucleotides used or the concentration or dose of each oligonucleotide used or added. Therefore in one embodiment, there is provided a composition wherein each or the total amount of oligonucleotide used is dosed in an amount ranged between 0.5 mg/kg and 10 mg/kg.

A preferred composition additionally comprises:
  a) an adjunct compound for reducing inflammation, preferably for reducing muscle tissue inflammation, and/or
  b) an adjunct compound for improving muscle fiber function, integrity and/or survival and/or
  c) a compound exhibiting readthrough activity.

It has surprisingly been found that the skipping frequency of a dystrophin exon from a pre-MRNA comprising said exon, when using an oligonucleotide directed toward the exon or to one or both splice sites of said exon, is enhanced if cells expressing said pre-mRNA are also provided with an adjunct compound for reducing inflammation, preferably for reducing muscle tissue inflammation, and/or an adjunct compound for improving muscle fiber function, integrity and/or survival. The enhanced skipping frequency also increases the level of functional dystrophin protein produced in a muscle cell of a DMD or BMD individual.

According to the present invention, even when a dystrophin protein deficiency has been restored in a DMD patient by administering an oligonucleotide of the invention, the presence of tissue inflammation and damaged muscle cells still continues to contribute to the symptoms of DMD. Hence, even though the cause of DMD—i.e. a dysfunctional dystrophin protein—is alleviated, treatment of DMD is still further improved by additionally using an adjunct therapy according to the present invention. Furthermore, the present invention provides the insight that a reduction of inflammation does not result in significant reduction of AON uptake by muscle cells. This is surprising because, in general, inflammation enhances the trafficking of cells, blood and other compounds. As a result, AON uptake/delivery is also enhanced during inflammation. Hence, before the present invention it would be expected that an adjunct therapy counteracting inflammation involves the risk of negatively influencing AON therapy. This, however, appears not to be the case.

An adjunct compound for reducing inflammation comprises any therapy which is capable of at least in part reducing inflammation, preferably inflammation caused by damaged muscle cells. Said adjunct compound is most preferably capable of reducing muscle tissue inflammation. Inflammation is preferably assessed by detecting an increase in the number of infiltrating immune cells such as neutrophils and/or mast cells and/or dendritic cells and/or lymphocytes in muscle tissue suspected to be dystrophic. This assessment is preferably carried out in cross-sections of a biopsy[57] of muscle tissue suspected to be dystrophic after having specifically stained immune cells as identified above. The quantification is preferably carried out under the microscope. Reducing inflammation is therefore preferably assessed by detecting a decrease in the number of immune cells in a cross-section of muscle tissue suspected to be dystrophic. Detecting a decrease preferably means that the number of at least one sort of immune cells as identified above is decreased of at least 1%, 2%, 3%, 5%, 7%, 10%, 12%, 15%, 17%, 20%, 30%, 40%, 50%, 60%, 70%, 80%, 90% or more compared to the number of a corresponding immune cell in a same individual before treatment. Most preferably, no infiltrating immune cells are detected in cross-sections of said biopsy.

An adjunct compound for improving muscle fiber function, integrity and/or survival comprises any therapy, which is capable of measurably enhancing muscle fiber function, integrity and/or survival as compared to an otherwise similar situation wherein said adjunct compound is not present. The improvement of muscle fiber function, integrity and/or survival may be assessed using at least one of the following assays: a detectable decrease of creatine kinase in blood, a detectable decrease of necrosis of muscle fibers in a biopsy cross-section of a muscle suspected to be dystrophic, and/or a detectable increase of the homogeneity of the diameter of muscle fibers in a biopsy cross-section of a muscle suspected to be dystrophic. Each of these assays is known to the skilled person.

Creatine kinase may be detected in blood as described in 57. A detectable decrease in creatine kinase may mean a decrease of 5%, 10%, 20%, 30%, 40%, 50%, 60%, 70%, 80%, 90% or more compared to the concentration of creatine kinase in a same individual before treatment.

A detectable decrease of necrosis of muscle fibers is preferably assessed in a muscle biopsy, more preferably as described in 57 using biopsy cross-sections. A detectable decrease of necrosis may be a decrease of 5%, 10%, 20%, 30%, 40%, 50%, 60%, 70%, 80%, 90% or more of the area wherein necrosis has been identified using biopsy cross-sections. The decrease is measured by comparison to the necrosis as assessed in a same individual before treatment.

A detectable increase of the homogeneity of the diameter of a muscle fiber is preferably assessed in a muscle biopsy cross-section, more preferably as described in 57.

In one embodiment, an adjunct compound for increasing turnover of damaged muscle cells is used. An adjunct compound for increasing turnover of damaged muscle cells comprises any therapy, which is capable of at least in part inducing and/or increasing turnover of damaged muscle cells. Damaged muscle cells are muscle cells, which have significantly less clinically measurable functionality than a healthy, intact muscle cell. In the absence of dystrophin, mechanical stress leads to sarcolemmal ruptures, causing an uncontrolled influx of calcium into the muscle fiber interior, thereby triggering calcium-activated proteases and fiber necrosis, resulting in damaged muscle cells. Increasing turnover of damaged muscle cells means that damaged muscle cells are more quickly broken down and/or removed as compared to a situation wherein turnover of damaged muscle cells is not increased. Turnover of damaged muscle cells is preferably assessed in a muscle biopsy, more preferably as described in 57 using a cross-section of a biopsy. A detectable increase of turnover may be an increase of 5%, 10%, 20%, 30%, 40%, 50%, 60%, 70%, 80%, 90% or more of the area wherein turnover has been identified using a biopsy cross-section. The increase is measured by comparison to the turnover as assessed in a same individual before treatment.

Without wishing to be bound to theory, it is believed that increasing turnover of muscle cells is preferred because this reduces inflammatory responses.

According to the present invention, a composition of the invention further comprising an adjunct therapy for reducing inflammation, preferably for reducing muscle tissue inflammation in an individual, is particularly suitable for use as a medicament. Such composition is even better capable of alleviating one or more symptom(s) of Duchenne Muscular Dystrophy or Becker Muscular Dystrophy as compared to a combination not comprising said adjunct compound. This embodiment also enhances the skipping frequency of a dystrophin exon from a pre-mRNA comprising said exon, when using an oligonucleotide directed toward the exon or to one or both splice sites of said exon. The enhanced skipping frequency also increases the level of functional dystrophin protein produced in a muscle cell of a DMD or BMD individual.

Further provided is therefore a composition further comprising an adjunct compound for reducing inflammation, preferably for reducing muscle tissue inflammation in said individual, for use as a medicament, preferably for treating or preventing counteracting DMD. In one embodiment, said composition is used in order to alleviate one or more symptom(s) of a severe form of BMD wherein a very short dystrophin protein or altered or truncated dystrophin mRNA or protein is formed which is not sufficiently functional.

Preferred adjunct compound for reducing inflammation include a steroid, a TNFα inhibitor, a source of mIGF-1 and/or an antioxidant. However, any other compound able to reduce inflammation as defined herein is also encompassed within the present invention. Each of these compounds is later on extensively presented. Each of the compounds extensively presented may be used separately or in combination with each other and/or in combination with one or more of the adjunct compounds used for improving muscle fiber function, integrity and/or survival.

Furthermore, a composition comprising an adjunct therapy for improving muscle fiber function, integrity and/or survival in an individual is particularly suitable for use as a medicament, preferably for treating or preventing DMD. Such composition is even better capable of alleviating one or more symptom(s) of Duchenne Muscular Dystrophy as compared to a composition not comprising said adjunct compound.

Preferred adjunct compounds for improving muscle fiber function, integrity and/or survival include an ion channel inhibitor, a protease inhibitor, L-arginine and/or an angiotensin II type I receptor blocker. However, any other compound able to improving muscle fiber function, integrity and/or survival as defined herein is also encompassed within the present invention. Each of these compounds is later on extensively presented. Each of the compounds extensively presented may be used separately or in combination with each other and/or in combination with one or more of the adjunct compounds used for reducing inflammation.

In a particularly preferred embodiment, a composition further comprises a steroid. Such composition results in significant alleviation of DMD symptoms. This embodiment also enhances the skipping frequency of a dystrophin exon from a pre-mRNA comprising said exon, when using an oligonucleotide directed toward the exon or to one or both splice sites of said exon. The enhanced skipping frequency also increases the level of functional dystrophin protein produced in a muscle cell of a DMD or BMD individual.

In one embodiment, said composition is used in order to alleviate one or more symptom(s) of a severe form of BMD wherein a very short dystrophin protein is formed which is not sufficiently functional.

A steroid is a terpenoid lipid characterized by a carbon skeleton with four fused rings, generally arranged in a 6-6-6-5 fashion. Steroids vary by the functional groups attached to these rings and the oxidation state of the rings. Steroids include hormones and drugs, which are usually used to relieve swelling and inflammation, such as for instance prednisone, dexamethasone and vitamin D.

According to the present invention, supplemental effects of adjunct steroid therapy in DMD patients include reduction of tissue inflammation, suppression of cytotoxic cells, and improved calcium homeostasis. Most positive results are obtained in younger boys. Preferably, the steroid is a corticosteroid, more preferably, a glucocorticosteroid. Preferably, prednisone steroids such as prednisone, prednizolone or deflazacort are used in a combination according to the invention[21]. Dose ranges of steroid or of a glucocorticosteroid to be used in the therapeutic applications as described herein are designed on the basis of rising dose studies in clinical trials for which rigorous protocol requirements exist. The usual doses are 0.5-1.0 mg/kg/day, preferably 0.75 mg/kg/day for prednisone and prednisolone, and 0.4-1.4 mg/kg/day, preferably 0.9 mg/kg/day for deflazacort.

In one embodiment, a steroid is administered to said individual prior to administering a composition as earlier defined herein. In this embodiment, it is preferred that said steroid is administered at least one day, more preferred at least one week, more preferred at least two weeks, more preferred at least three weeks prior to administering said composition.

In another preferred embodiment, a combination further comprises a tumour necrosis factor-alpha (TNFα) inhibitor. Tumour necrosis factor-alpha (TNFα) is a pro-inflammatory cytokine that stimulates the inflammatory response. Pharmacological blockade of TNFα activity with the neutralising antibody infliximab (Remicade) is highly effective clinically at reducing symptoms of inflammatory diseases. In mdx mice, both infliximab and etanercept delay and reduce the necrosis of dystrophic muscle[21, 25], with additional physiological benefits on muscle strength, chloride channel function and reduced CK levels being demonstrated in chronically treated exercised adult mdx mice[26]. Such highly specific anti-inflammatory drugs designed for use in other clinical conditions, are attractive alternatives to the use of steroids for DMD. In one embodiment, the use of a TNFα inhibitor is limited to periods of intensive muscle growth in boys when muscle damage and deterioration are especially pronounced.

A composition further comprising a TNFα inhibitor for use as a medicament is also provided. In one embodiment, said composition is used in order to alleviate one or more symptom(s) of a severe form of BMD wherein a very short dystrophin protein is formed which is not sufficiently functional. A preferred TNFα inhibitor is a dimeric fusion protein consisting of the extracellular ligand-binding domain of the human p75 receptor of TNFα linked to the Fc portion of human IgG1. A more preferred TNFα inhibitor is ethanercept (Amgen, America)[26]. The usual doses of ethanercept is about 0.2 mg/kg, preferably about 0.5 mg/kg twice a week. The administration is preferably subcutaneous.

In another preferred embodiment, a composition of the invention further comprises a source of mIGF-1. As defined herein, a source of IGF-1 preferably encompasses mIGF-1 itself, a compound able of enhancing mIGF-1 expression and/or activity. Enhancing is herein synonymous with increasing. Expression of mIGF-1 is synonymous with amount of mIGF-1. mIGF-1 promotes regeneration of muscles through increase in satellite cell activity, and reduces inflammation and fibrosis[27]. Local injury of muscle results in increased mIGF-1 expression. In transgenic mice with extra IGF-1 genes, muscle hypertrophy and enlarged muscle fibers are observed[27]. Similarly, transgenic mdx mice show reduced muscle fiber degeneration[28]. Upregulation of the mIGF-1 gene and/or administration of extra amounts of mIGF-1 protein or a functional equivalent thereof (especially the mIGF-1 Ea isoform [as described in 27, human homolog IGF-1 isoform 4: SEQ ID NO: 577]) thus promotes the effect of other, preferably genetic, therapies for DMD, including antisense-induced exon skipping. The additional mIGF-1 levels in the above mentioned transgenic mice do not induce cardiac problems nor promote cancer, and have no pathological side effects. As stated before, the amount of mIGF-1 is for instance increased by enhancing expression of the mIGF-1 gene and/or by administration of mIGF-1 protein and/or a functional equivalent thereof (especially the mIGF-1 Ea isoform [as described in 27, human homolog IGF-1 isoform 4: SEQ ID NO: 577]). A composition of the invention further preferably comprises mIGF-1, a compound capable of enhancing mIGF-1 expression and/or an mIGF-1 activity, for use as a medicament is also provided. Said medicament is preferably for alleviating one or more symptom(s) of DMD. In one embodiment, such composition is used in order to alleviate one or more symptom(s) of a severe form of BMD wherein a very short dystrophin protein is formed which is not sufficiently functional.

Within the context of the invention, an increased amount or activity of mIGF-1 may be reached by increasing the gene expression level of an IGF-1 gene, by increasing the amount of a corresponding IGF-1 protein and/or by increasing an activity of an IGF1-protein. A preferred mIGF-1 protein has been earlier defined herein. An increase of an activity of said protein is herein understood to mean any detectable change in a biological activity exerted by said protein or in the steady state level of said protein as compared to said activity or steady-state in a individual who has not been treated. Increased amount or activity of mIGF-1 is preferably assessed by detection of increased expression of muscle hypertrophy biomarker GATA-2 (as described in 27).

Gene expression level is preferably assessed using classical molecular biology techniques such as (real time) PCR, arrays or Northern analysis. A steady state level of a protein is determined directly by quantifying the amount of a protein. Quantifying a protein amount may be carried out by any known technique such as Western blotting or immunoassay using an antibody raised against a protein. The skilled person will understand that alternatively or in combination with the quantification of a gene expression level and/or a corresponding protein, the quantification of a substrate of a corresponding protein or of any compound known to be associated with a function or activity of a corresponding protein or the quantification of said function or activity of a corresponding protein using a specific assay may be used to assess the alteration of an activity or steady state level of a protein.

In the invention, an activity or steady-state level of a said protein may be altered at the level of the protein itself, e.g. by providing a protein to a cell from an exogenous source.

Preferably, an increase or an up-regulation of the expression level of a said gene means an increase of at least 5% of the expression level of said gene using arrays. More preferably, an increase of the expression level of said gene means an increase of at least 10%, even more preferably at least 20%, at least 30%, at least 40%, at least 50%, at least 70%, at least 90%, at least 150% or more. In another preferred embodiment, an increase of the expression level of said protein means an increase of at least 5% of the expression level of said protein using Western blotting and/or using ELISA or a suitable assay. More preferably, an increase of the expression level of a protein means an increase of at least 10%, even more preferably at least 20%, at least 30%, at least 40%, at least 50%, at least 70%, at least 90%, at least 150% or more.

In another preferred embodiment, an increase of a polypeptide activity means an increase of at least 5% of a polypeptide activity using a suitable assay. More preferably, an increase of a polypeptide activity means an increase of at least 10%, even more preferably at least 20%, at least 30%, at least 40%, at least 50%, at least 70%, at least 90%, at least 150% or more. The increase is preferably assessed by comparison to corresponding activity in the individual before treatment.

A preferred way of providing a source of mIGF1 is to introduce a transgene encoding mIGF1, preferably an mIGF-1 Ea isoform (as described in 27, human homolog IGF-1 isoform 4: SEQ ID NO: 577), more preferably in an AAV vector as later defined herein. Such source of mIGF1 is specifically expressed in muscle tissue as described in mice in 27.

In another preferred embodiment, a composition further comprises an antioxidant. Oxidative stress is an important factor in the progression of DMD and promotes chronic inflammation and fibrosis[29]. The most prevalent products of oxidative stress, the peroxidized lipids, are increased by an average of 35% in Duchenne boys. Increased levels of the enzymes superoxide dismutase and catalase reduce the excessive amount of free radicals causing these effects. In fact, a dietary supplement Protandim® (LifeVantage) was clinically tested and found to increase levels of superoxide dismutase (up to 30%) and catalase (up to 54%), which indeed significantly inhibited the peroxidation of lipids in 29 healthy persons[30]. Such effective management of oxidative stress thus preserves muscle quality and so promotes the positive effect of DMD therapy. Idebenone is another potent antioxidant with a chemical structure derived from natural coenzyme Q10. It protects mitochondria where adenosine triphosphate, ATP, is generated by oxidative phosphorylation. The absence of dystrophin in DMD negatively affects this process in the heart, and probably also in skeletal muscle. Idebenone was recently applied in clinical trials in the US and Europe demonstrating efficacy on neurological aspects of Friedreich's Ataxia[31]. A phase-IIa double-blind, placebo-controlled randomized clinical trial with Idebenone has recently been started in Belgium, including 21 Duchenne boys at 8 to 16 years of age. The primary objective of this study is to determine the effect of Idebenone on heart muscle function. In addition, several further tests will be performed to detect the possible functional benefit on muscle strength in the patients. When effective, Idebenone is a preferred adjunct compound for use in a combination according to the present invention in order to enhance the therapeutic effect of DMD therapy, especially in the heart. A composition further comprising an antioxidant for use as a medicament is also provided. Said medicament is preferably for alleviating one or more symptom(s) of DMD. In one embodiment, said composition is used in order to alleviate one or more symptom(s) of a severe form of BMD wherein a very short dystrophin protein is formed which is not sufficiently functional. Depending on the identity of the antioxidant, the skilled person will know which quantities are preferably used. An antioxidant may include bacoside, silymarin, curcumin and/or a polyphenol. Preferably, a polyphenol is or comprises epigallocatechin-3-gallate (EGCG). Preferably, an antioxidant is a mixture of antioxidants as the dietary supplement Protandim® (LifeVantage). A daily capsule of 675 mg of Protandim® comprises 150 mg of *B. monniera* (45% bacosides), 225 mg of *S. marianum* (70-80% silymarin), 150 mg of *W. somnifera* powder, 75 mg green tea (98% polyphenols wherein 45% EGCG) and 75 mg turmeric (95% curcumin).

In another preferred embodiment, a composition further comprises an ion channel inhibitor. The presence of damaged muscle membranes in DMD disturbs the passage of calcium ions into the myofibers, and the consequently disrupted calcium homeostasis activates many enzymes, e.g. proteases, that cause additional damage and muscle necrosis. Ion channels that directly contribute to the pathological accumulation of calcium in dystrophic muscle are potential targets for adjunct compounds to treat DMD. There is evidence that some drugs, such as pentoxifylline, block exercise-sensitive calcium channels[32] and antibiotics that block stretch activated channels reduce myofibre necrosis in mdx mice and CK levels in DMD boys[33]. A composition further comprising an ion channel inhibitor for use as a medicament is also provided. Said medicament is preferably for alleviating one or more symptom(s) of DMD. In one embodiment, said composition is used in order to alleviate one or more symptom(s) of a severe form of BMD wherein a very short dystrophin protein is formed which is not sufficiently functional.

Preferably, an ion channel inhibitor of the class of xanthines is used. More preferably, said xanthines are derivatives of methylxanthines, and most preferably, said methylxanthine derivates are chosen from the group consisting of pentoxifylline, furafylline, lisofylline, propentofylline, pentifylline, theophylline, torbafylline, albifylline, enprofylline and derivatives thereof. Most preferred is the use of pentoxifylline. Ion channel inhibitors of the class of xanthines enhance the skipping frequency of a dystrophin exon from a pre-mRNA comprising said exon, when using an oligonucleotide directed toward the exon or to one or both splice sites of said exon. The enhanced skipping frequency also increases the level of functional dystrophin protein produced in a muscle cell of a DMD or BMD individual.

Depending on the identity of the ion channel inhibitor, the skilled person will know which quantities are preferably used. Suitable dosages of pentoxifylline are between 1 mg/kg/day to 100 mg/kg/day, preferred dosages are between 10 mg/kg/day to 50 mg/kg/day. Typical dosages used in humans are 20 mg/kg/day.

In one embodiment, an ion channel inhibitor is administered to said individual prior to administering a composition comprising an oligonucleotide. In this embodiment, it is preferred that said ion channel inhibitor is administered at least one day, more preferred at least one week, more preferred at least two weeks, more preferred at least three weeks prior to administering a composition comprising an oligonucleotide.

In another preferred embodiment, a composition further comprises a protease inhibitor. Calpains are calcium-activated proteases that are increased in dystrophic muscle and account for myofiber degeneration. Calpain inhibitors such as calpastatin, leupeptin[34], calpeptin, calpain inhibitor III, or PD150606 are therefore applied to reduce the degeneration process. A new compound, BN 82270 (Ipsen) that has dual action as both a calpain inhibitor and an antioxidant increased muscle strength, decreased serum CK and reduced fibrosis of the mdx diaphragm, indicating a therapeutic effect with this new compound[35]. Another compound of Leupeptin/Carnitine (Myodur) has recently been proposed for clinical trials in DMD patients.

MG132 is another proteasomal inhibitor that has shown to reduce muscle membrane damage, and to ameliorate the histopathological signs of muscular dystrophy[36]. MG-132 (CBZ-leucyl-leucyl-leucinal) is a cell-permeable, proteasomal inhibitor (Ki=4 nM), which inhibits NFkappaB activation by preventing IkappaB degradation (IC50=3 μM). In addition, it is a peptide aldehyde that inhibits ubiquitin-mediated proteolysis by binding to and inactivating 20S and 26S proteasomes. MG-132 has shown to inhibit the proteasomal degradation of dystrophin-associated proteins in the dystrophic mdx mouse model[36]. This compound is thus also suitable for use as an adjunct pharmacological compound for DMD. A composition further comprising a protease inhibitor for use as a medicament is also provided. Said medicament is preferably for alleviating one or more symptom(s) of DMD. In one embodiment, said combination is used in order to alleviate one or more symptom(s) of a severe form of BMD wherein a very short dystrophin protein is formed which is not sufficiently functional. Depending on the identity of the protease inhibitor, the skilled person will know which quantities are preferably used.

In another preferred embodiment, a composition further comprises L-arginine. Dystrophin-deficiency is associated with the loss of the DGC-complex at the fiber membranes, including neuronal nitric oxide synthase (nNOS). Expression of a nNOS transgene in mdx mice greatly reduced muscle membrane damage. Similarly, administration of L-arginine (the substrate for nitric oxide synthase) increased NO production and upregulated utrophin expression in mdx mice. Six weeks of L-arginine treatment improved muscle pathology and decreased serum CK in mdx mice[37]. The use of L-arginine as a further constituent in a composition of the invention has not been disclosed.

A composition further comprising L-arginine for use as a medicament is also provided. Said medicament is preferably for alleviating one or more symptom(s) of DMD. In one embodiment, said composition is used in order to alleviate one or more symptom(s) of a severe form of BMD wherein a very short dystrophin protein is formed which is not sufficiently functional.

In another preferred embodiment, a composition further comprises angiotensin II type 1 receptor blocker Losartan, which normalizes muscle architecture, repair and function, as shown in the dystrophin-deficient mdx mouse model[23]. A composition further comprising angiotensin II type 1 receptor blocker Losartan for use as a medicament is also provided. Said medicament is preferably for alleviating one or more symptom(s) of DMD. In one embodiment, said composition is used in order to alleviate one or more symptom(s) of a severe form of BMD wherein a very short dystrophin protein is formed which is not sufficiently functional. Depending on the identity of the angiotensin II type 1 receptor blocker, the skilled person will know which quantities are preferably used.

In another preferred embodiment, a composition further comprises an angiotensin-converting enzyme (ACE) inhibitor, preferably perindopril. ACE inhibitors are capable of lowering blood pressure. Early initiation of treatment with perindopril is associated with a lower mortality in DMD patients[22]. A composition further comprising an ACE inhibitor, preferably perindopril for use as a medicament is also provided. Said medicament is preferably for alleviating one or more symptom(s) of DMD. In one embodiment, said composition is used in order to alleviate one or more symptom(s) of a severe form of BMD wherein a very short dystrophin protein is formed which is not sufficiently functional. The usual doses of an ACE inhibitor, preferably perindopril are about 2 to 4 mg/day[22]. In a more preferred embodiment, an ACE inhibitor is combined with at least one of the previously identified adjunct compounds.

In another preferred embodiment, a composition further comprises a compound exhibiting a readthrough activity. A compound exhibiting a readthrough activity may be any compound, which is able to suppress a stop codon. For 20% of DMD patients, the mutation in the dystrophin gene is comprising a point mutation, of which 13% is a nonsense mutation. A compound exhibiting a readthrough activity or which is able to suppress a stop codon is a compound which is able to provide an increased amount of a functional dystrophin mRNA or protein and/or a decreased amount of an aberrant or truncated dystrophin mRNA or protein. Increased preferably means increased of at least 1%, 2%, 5%, 10%, 15%, 20%, 25%, 30%, 35%, 40%, 45%, 50%, 55%, 60%, 65%, 70%, 75%, 80%, 85%, 90%, 95%, 100% or more. Decreased preferably means decreased of at least 1%, 2%, 5%, 10%, 15%, 20%, 25%, 30%, 35%, 40%, 45%, 50%, 55%, 60%, 65%, 70%, 75%, 80%, 85%, 90%, 95%, 100% or more. An increase or a decrease of said protein is preferably assessed in a muscular tissue or in a muscular cell of an individual by comparison to the amount present in said individual before treatment with said compound exhibiting a readthrough activity. Alternatively, the comparison can be made with a muscular tissue or cell of said individual, which has not yet been treated with said compound in case the treatment is local. The assessment of an amount at the protein level is preferably carried out using western blot analysis.

Preferred compounds exhibiting a readthrough activity comprise or consist of aminoglycosides, including, but not limited to, geneticin (G418), paromomycin, gentamycin and/or 3-(5-(2-fluorophenyl)-1,2,4-oxadiazol-3-yl)benzoic acid), and derivatives thereof (references 64, 65). A more preferred compound exhibiting a readthrough activity comprises or consists of PTC124™, and/or a functional equivalent thereof. PTC124™ is a registered trademark of PTC Therapeutics, Inc. South Plainfield, N.J. 3-(5-(2-fluorophenyl)-1,2,4-oxadiazol-3-yl)benzoic acid) also known as PTC124™ (references 16, 17) belongs to a new class of small molecules that mimics at lower concentrations the readthrough activity of gentamicin (reference 55). A functional equivalent of 3-(5-(2-fluorophenyl)-1,2,4-oxadiazol-3-yl)benzoic acid) or of gentamicin is a compound which is able to exhibit a readthrough activity as earlier defined herein. Most preferably, a compound exhibiting a readthrough activity comprises or consists of gentamycin and/or 3-(5-(2-fluorophenyl)-1,2,4-oxadiazol-3-yl)benzoic acid) also known as PTC124™. A composition further comprising a compound exhibiting a readthrough activity, preferably comprising or consisting of gentamycin and/or 3-(5-(2-fluorophenyl)-1,2,4-oxadiazol-3-yl)benzoic acid) for use as a medicament is also provided. Said medicament is preferably for alleviating one or more symptom(s) of DMD. In one embodiment, said composition is used in order to alleviate one or more symptom(s) of a severe form of BMD wherein a very short dystrophin protein is formed which is not sufficiently functional. The usual doses of a compound exhibiting a readthrough activity, preferably 3-(5-(2-fluorophenyl)-1,2,4-oxadiazol-3-yl)benzoic acid) or of gentamicin are ranged between 3 mg/kg/day to 200 mg/kg/day, preferred dosages are between 10 mg/kg to 50 mg/kg per day or twice a day.

In a more preferred embodiment, a compound exhibiting a readthrough activity is combined with at least one of the previously identified adjunct compounds.

In another preferred embodiment, a composition further comprises a compound, which is capable of enhancing exon skipping and/or inhibiting spliceosome assembly and/or splicing. Small chemical compounds, such as for instance specific indole derivatives, have been shown to selectively inhibit spliceosome assembly and splicing[38], for instance by interfering with the binding of serine- and arginine-rich (SR) proteins to their cognate splicing enhancers (ISEs or ESEs) and/or by interfering with the binding of splicing repressors to silencer sequences (ESSs or ISSs). These compounds are therefore suitable for applying as adjunct compounds that enhance exon skipping. A composition further comprising a compound for enhancing exon skipping and/or inhibiting spliceosome assembly and/or splicing for use as a medicament is also provided. Said medicament is preferably for alleviating one or more symptom(s) of DMD. In one embodiment, said composition is used in order to alleviate one or more symptom(s) of a severe form of BMD wherein a very short dystrophin protein is formed which is not sufficiently functional. Depending on the identity of the compound, which is capable of enhancing exon skipping and/or inhibiting spliceosome assembly and/or splicing, the skilled person will know which quantities are preferably used. In a more preferred embodiment, a compound for enhancing exon skipping and/or inhibiting spliceosome assembly and/or splicing is combined with a ACE inhibitor and/or with any adjunct compounds as identified earlier herein.

The invention thus provides a composition further comprising an adjunct compound, wherein said adjunct compound comprises a steroid, an ACE inhibitor (preferably perindopril), angiotensin II type 1 receptor blocker Losartan, a tumour necrosis factor-alpha (TNFα) inhibitor, a source of mIGF-1, preferably mIGF-1, a compound for enhancing mIGF-1 expression, a compound for enhancing mIGF-1 activity, an antioxidant, an ion channel inhibitor, a protease inhibitor, L-arginine, a compound exhibiting a readthrough activity and/or inhibiting spliceosome assembly and/or splicing.

In one embodiment an individual is further provided with a functional dystrophin protein using a vector, preferably a viral vector, comprising a micro-mini-dystrophin gene. Most preferably, a recombinant adeno-associated viral (rAAV) vector is used. AAV is a single-stranded DNA parvovirus that is non-pathogenic and shows a helper-dependent life cycle. In contrast to other viruses (adenovirus, retrovirus, and herpes simplex virus), rAAV vectors have demonstrated to be very efficient in transducing mature skeletal muscle. Application of rAAV in classical DMD "gene addition" studies has been hindered by its restricted packaging limits (<5 kb). Therefore, rAAV is preferably applied for the efficient delivery of a much smaller micro- or mini-dystrophin gene. Administration of such micro- or mini-dystrophin gene results in the presence of an at least partially functional dystrophin protein. Reference is made to[18-20].

Each constituent of a composition can be administered to an individual in any order. In one embodiment, each constituent is administered simultaneously (meaning that each constituent is administered within 10 hours, preferably within one hour). This is however not necessary. In one embodiment at least one adjunct compound is administered to an individual in need thereof before administration of an oligonucleotide. Alternatively, an oligonucleotide is administered to an individual in need thereof before administration of at least one adjunct compound.

Use

In a further aspect, there is provided the use of a oligonucleotide or of a composition as defined herein for the manufacture of a medicament for preventing or treating Duchenne Muscular Dystrophy or Becker Muscular Dystrophy in an individual. Each feature of said use has earlier been defined herein.

A treatment in a use or in a method according to the invention is at least one week, at least one month, at least several months, at least one year, at least 2, 3, 4, 5, 6 years or more. Each molecule or oligonucleotide or equivalent thereof as defined herein for use according to the invention may be suitable for direct administration to a cell, tissue and/or an organ in vivo of individuals affected by or at risk of developing DMD or BMD, and may be administered directly in vivo, ex vivo or in vitro. The frequency of administration of an oligonucleotide, composition, compound or adjunct compound of the invention may depend on several parameters such as the age of the patient, the mutation of the patient, the number of molecules (i.e. dose), the formulation of said molecule. The frequency may be ranged between at least once in two weeks, or three weeks or four weeks or five weeks or a longer time period.

Method

In a further aspect, there is provided a method for alleviating one or more symptom(s) of Duchenne Muscular Dystrophy or Becker Muscular Dystrophy in an individual or alleviate one or more characteristic(s) of a myogenic or muscle cell of said individual, the method comprising administering to said individual an oligonucleotide or a composition as defined herein.

There is further provided a method for enhancing, inducing or promoting skipping of an exon from a dystrophin pre-mRNA in a cell expressing said pre-mRNA in an individual suffering from Duchenne Muscular Dystrophy or Becker Muscular Dystrophy, the method comprising administering to said individual an oligonucleotide or a composition as defined herein. Further provided is a method for increasing the production of a functional dystrophin protein and/or decreasing the production of an aberrant dystrophin protein in a cell, said cell comprising a pre-mRNA of a dystrophin gene encoding an aberrant dystrophin protein, the method comprising providing said cell with an oligonucleotide or composition of the invention and allowing translation of mRNA produced from splicing of said pre-mRNA. In one embodiment, said method is performed in vitro, for instance using a cell culture. Preferably, said method is in vivo.

In this context, increasing the production of a functional dystrophin protein has been earlier defined herein.

Unless otherwise indicated each embodiment as described herein may be combined with another embodiment as described herein.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a compound or adjunct compound as defined herein may comprise additional component(s) than the ones specifically identified, said additional component(s) not altering the unique characteristic of the invention.

In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "approximately" or "about" when used in association with a numerical value (approximately 10, about 10) preferably means that the value may be the given value of 10 more or less 1% of the value.

All patent and literature references cited in the present specification are hereby incorporated by reference in their entirety. Each embodiment as identified herein may be combined together unless otherwise indicated.

The invention is further explained in the following examples. These examples do not limit the scope of the invention, but merely serve to clarify the invention.

EXAMPLES

Example 1

Materials and Methods

AON design was based on (partly) overlapping open secondary structures of the target exon RNA as predicted by the m-fold program, on (partly) overlapping putative SR-protein binding sites as predicted by the ESE-finder software. AONs were synthesized by Prosensa Therapeutics B.V. (Leiden, Netherlands), and contain 2'-O-methyl RNA and full-length phosphorothioate (PS) backbones.

Tissue Culturing, Transfection and RT-PCR Analysis

Myotube cultures derived from a healthy individual ("human control") (examples 1, 3, and 4; exon 43, 50, 52 skipping) or a DMD patient carrying an exon 45 deletion (example 2; exon 46 skipping) were processed as described previously (Aartsma-Rus et al., Neuromuscul. Disord. 2002; 12: S71-77 and Hum Mol Genet 2003; 12(8): 907-14). For the screening of AONs, myotube cultures were transfected with 200 nM for each AON (PS220 and PS305). Transfection reagent UNIFectylin (Prosensa Therapeutics BV, Netherlands) was used, with 2 µl UNIFectylin per µg AON. Exon skipping efficiencies were determined by nested RT-PCR analysis using primers in the exons flanking the targeted exon 45. PCR fragments were isolated from agarose gels for sequence verification. For quantification, the PCR products were analyzed using the DNA 1000 LabChip Kit on the Agilent 2100 bioanalyzer (Agilent Technologies, USA).

Results

DMD Exon 45 Skipping.

Figure 1:
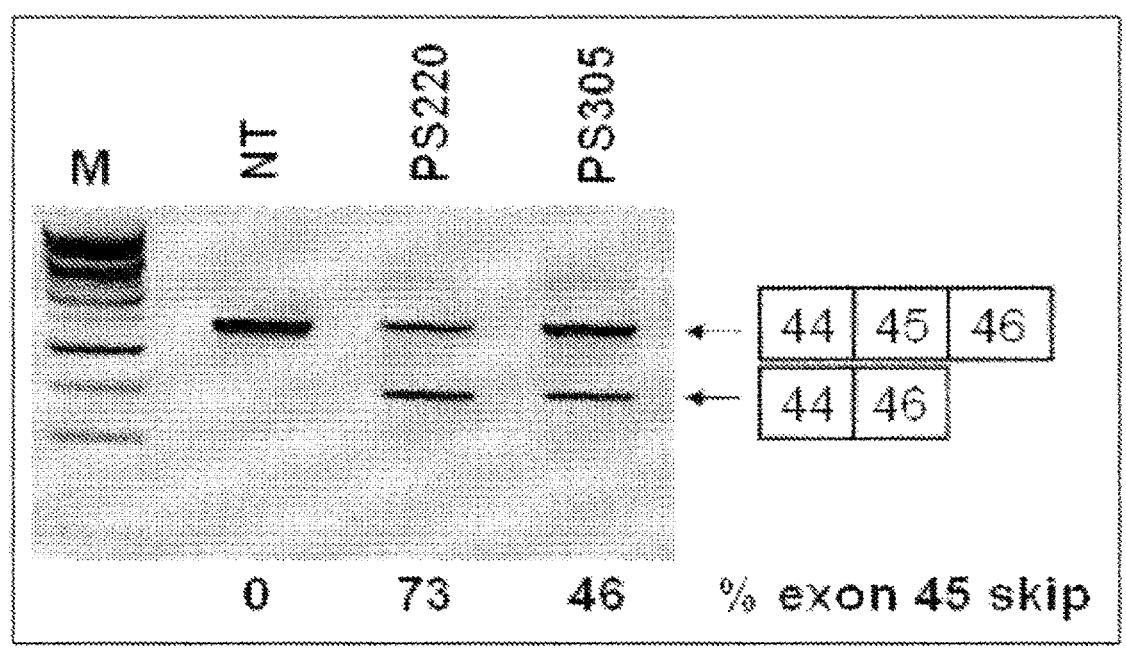
FIG. 1. In human control myotubes, PS220 and PS305 both targeting an identical sequence within exon 45, were directly compared for relative skipping efficiencies. PS220 reproducibly induced highest levels of exon 45 skipping (up to 73%), whereas with PS305 maximum exon 45 skipping levels of up to 46% were obtained. No exon 45 skipping was observed in non-treated cells. (M: DNA size marker; NT: non-treated cells)

Two AONs, PS220 (SEQ ID NO: 76; 5'-UUUGCCGCUGCCCAAUGCCAUCCUG-3') and PS305 (SEQ ID NO: 557; 5'-UUUGCCICUGCCCAAUGCCAUCCUG-3') both targeting an identical sequence within exon 45, were directly compared for relative skipping efficiencies in healthy control myotube cultures. Subsequent RT-PCR and sequence analysis of isolated RNA demonstrated that both AONs were indeed capable of inducing exon 45 skipping. PS220, consisting a GCCGC stretch, reproducibly induced highest levels of exon 45 skipping (up to 73%), as shown in FIG. 1. However, PS305, which is identical to PS220 but containing an inosine for a G substitution at position 4 within that stretch is also effective and leading to exon 45 skipping levels of up to 46%. No exon 45 skipping was observed in non-treated cells (NT).

Example 2

Materials and Methods

AON design was based on (partly) overlapping open secondary structures of the target exon 45 RNA as predicted by the m-fold program, on (partly) overlapping putative SR-protein binding sites as predicted by the ESE-finder software. AONs were synthesized by Prosensa Therapeutics B.V. (Leiden, Netherlands), and contain 2'-O-methyl RNA, full-length phosphorothioate (PS) backbones and one inosine for guanosine substitution.

Tissue Culturing, Transfection and RT-PCR Analysis

Myotube cultures derived from a healthy individual ("human control") were processed as described previously (Aartsma-Rus et al., Neuromuscul. Disord. 2002; 12: S71-77 and Hum Mol Genet 2003; 12(8): 907-14). For the screening of AONs, myotube cultures were transfected with 200 nM for each AON. Transfection reagent UNIFectylin (Prosensa Therapeutics BV, Netherlands) was used, with 2 µl UNIFectylin per µg AON. Exon skipping efficiencies were determined by nested RT-PCR analysis using primers in the exons flanking the targeted exon 45. PCR fragments were isolated from agarose gels for sequence verification. For quantification, the PCR products were analyzed using the DNA 1000 Lab Chip Kit on the Agilent 2100 bioanalyzer (Agilent Technologies, USA).

Results

DMD Exon 45 Skipping.

Figure 2:
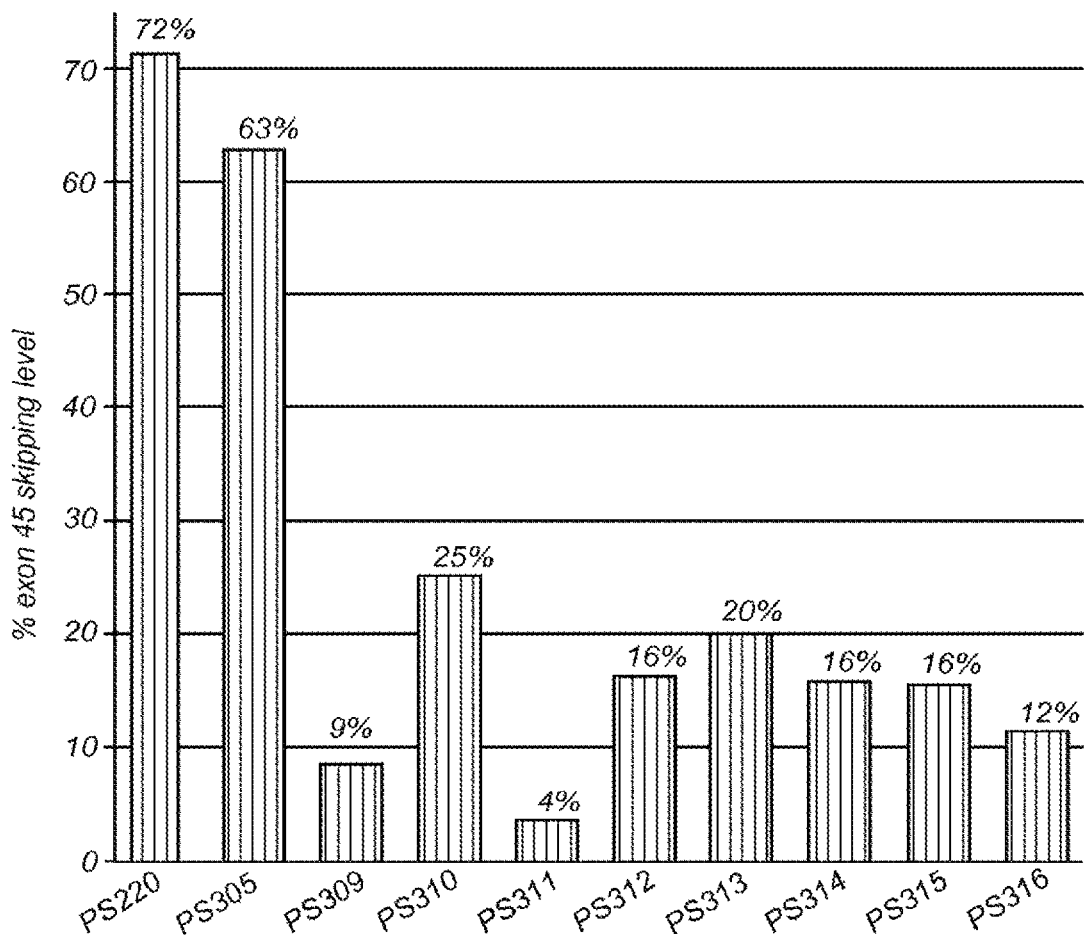
FIG. 2. Graph showing relative exon 45 skipping levels of inosine-containing AONs as assessed by RT-PCR analysis. In human control myotubes, a series of new AONs, all targeting exon 45 and containing one inosine for guanosine substitution were tested for relative exon 45 skipping efficiencies when compared with PS220 and PS305 (see FIG. 1). All new inosine-containing AONs were effective, albeit at variable levels (between 4% and 25%). PS220 induced highest levels of exon 45 skipping (up to 72%), whereas with PS305 maximum exon 45 skipping levels of up to 63% were obtained. No exon 45 skipping was observed in non-treated cells. (M: DNA size marker; NT: non-treated cells).

An additional series of AONs targeting exon 45 and containing one inosine-substitution were tested in healthy control myotube cultures for exon 45 skipping efficiencies, and directly compared to PS220 (without inosine; SEQ ID NO: 76)) and PS305 (identical sequence as PS220 but with inosine substitution; SEQ ID NO: 557). Subsequent RT-PCR and sequence analysis of isolated RNA demonstrated that all new AONs (PS309 to PS316) were capable of inducing exon 45 skipping between 4% (PS311) and 25% (PS310) as shown in FIG. 2. When compared to PS220 and PS305, PS220 induced highest levels of exon 45 skipping (up to 72%). Of the new inosine-containing AONs PS305 was most effective, showing exon 45 skipping levels of up to 63%. No exon 45 skipping was observed in non-treated cells (NT).

REFERENCES

1. Aartsma-Rus A, Janson A A, Kaman W E, et al. Therapeutic antisense-induced exon skipping in cultured muscle cells from six different DMD patients. Hum Mol Genet 2003; 12(8):907-14.
2. Aartsma-Rus A, Janson A A, Kaman W E, et al. Antisense-induced multi-exon skipping for Duchenne muscular dystrophy makes more sense. Am J Hum Genet 2004; 74(1): 83-92.
3. Alter J, Lou F, Rabinowitz A, et al. Systemic delivery of morpholino oligonucleotide restores dystrophin expression bodywide and improves dystrophic pathology. Nat Med 2006; 12(2):175-7.
4. Goyenvalle A, Vulin A, Fougerousse F, et al. Rescue of dystrophic muscle through U7 snRNA-mediated exon skipping. Science 2004; 306(5702):1796-9.
5. Lu Q L, Mann C J, Lou F, et al. Functional amounts of dystrophin produced by skipping the mutated exon in the mdx dystrophic mouse. Nat Med 2003; 6:6.
6. Lu Q L, Rabinowitz A, Chen Y C, et al. Systemic delivery of antisense oligoribonucleotide restores dystrophin expression in body-wide skeletal muscles. Proc Natl Acad Sci USA 2005; 102(1):198-203.
7. McClorey G, Fall A M, Moulton H M, et al. Induced dystrophin exon skipping in human muscle explants. Neuromuscul Disord 2006; 16(9-10):583-90.
8. McClorey G, Moulton H M, Iversen P L, et al. Antisense oligonucleotide-induced exon skipping restores dystrophin expression in vitro in a canine model of DMD. Gene Ther 2006; 13(19):1373-81.
9. Pramono Z A, Takeshima Y, Alimsardjono H, Ishii A, Takeda S, Matsuo M. Induction of exon skipping of the dystrophin transcript in lymphoblastoid cells by transfecting an antisense oligodeoxynucleotide complementary to an exon recognition sequence. Biochem Biophys Res Commun 1996; 226(2):445-9.
10. Takeshima Y, Yagi M, Wada H, et al. Intravenous infusion of an antisense oligonucleotide results in exon skipping in muscle dystrophin mRNA of Duchenne muscular dystrophy. Pediatr Res 2006; 59(5):690-4.
11. van Deutekom J C, Bremmer-Bout M, Janson A A, et al. Antisense-induced exon skipping restores dystrophin expression in DMD patient derived muscle cells. Hum Mol Genet 2001; 10(15):1547-54.
12. Aartsma-Rus A, Bremmer-Bout M, Janson A, den Dunnen J, van Ommen G, van Deutekom J. Targeted exon skipping as a potential gene correction therapy for Duchenne muscular dystrophy. Neuromuscul Disord 2002; 12 Suppl: S71-S77.
13. Aartsma-Rus A, De Winter C L, Janson A A, et al. Functional analysis of 114 exon-internal AONs for targeted DMD exon skipping: indication for steric hindrance of S R protein binding sites. Oligonucleotides 2005; 15(4):284-97.
14. Aartsma-Rus A, Janson A A, Heemskerk J A, C L de Winter, G J Van
Ommen, J C Van Deutekom. Therapeutic Modulation of DMD Splicing by Blocking Exonic Splicing Enhancer Sites with Antisense Oligonucleotides. Annals of the New York Academy of Sciences 2006; 1082:74-6.
15. Aartsma-Rus A, Kaman W E, Weij R, den Dunnen J T, van Ommen G J, van Deutekom J C. Exploring the frontiers of therapeutic exon skipping for Duchenne muscular dystrophy by double targeting within one or multiple exons. Mol Ther 2006; 14(3):401-7.
16. Welch E M, Barton E R, Zhuo J, et al. PTC124 targets genetic disorders caused by nonsense mutations. Nature 2007; 447(7140):87-91.
17. Hirawat S, Welch E M, Elfring G L, et al. Safety, tolerability, and pharmacokinetics of PTC124, a nonaminoglycoside nonsense mutation suppressor, following single- and multiple-dose administration to healthy male and female adult volunteers. Journal of clinical pharmacology 2007; 47(4):430-44.
18. Wang B, Li J, Xiao X. Adeno-associated virus vector carrying human minidystrophin genes effectively ameliorates muscular dystrophy in mdx mouse model. Proc Natl Acad Sci USA 2000; 97(25):13714-9.
19. Fabb S A, Wells D J, Serpente P, Dickson G. Adeno-associated virus vector gene transfer and sarcolemmal expression of a 144 kDa micro-dystrophin effectively restores the dystrophin-associated protein complex and inhibits myofibre degeneration in nude/mdx mice. Hum Mol Genet 2002; 11(7):733-41.
20. Wang Z, Kuhr C S, Allen J M, et al. Sustained AAV-mediated dystrophin expression in a canine model of Duchenne muscular dystrophy with a brief course of immunosuppression. Mol Ther 2007; 15(6):1160-6.
21. Manzur A Y, Kuntzer T, Pike M, Swan A. Glucocorticoid corticosteroids for Duchenne muscular dystrophy. Cochrane Database Syst Rev 2004; 2.
22. Duboc D, Meune C, Pierre B, et al. Perindopril preventive treatment on mortality in Duchenne muscular dystrophy: 10 years' follow-up. American heart journal 2007; 154(3):596-602.
23. Cohn R D, van Erp C, Habashi J P, et al. Angiotensin II type 1 receptor blockade attenuates TGF-beta-induced failure of muscle regeneration in multiple myopathic states. Nat Med 2007; 13(2):204-10.
24. Grounds M D, Torrisi J. Anti-TNFalpha (Remicade) therapy protects dystrophic skeletal muscle from necrosis. Faseb J 2004; 18(6):676-82.
25. Hodgetts S, Radley H, Davies M, Grounds M D. Reduced necrosis of dystrophic muscle by depletion of host neutrophils, or blocking TNFalpha function with Etanercept in mdx mice. Neuromuscul Disord 2006; 16(9-10):591-602.
26. Pierno S, Nico B, Burdi R, et al. Role of tumour necrosis factor alpha, but not of cyclo-oxygenase-2-derived eicosanoids, on functional and morphological indices of dystrophic progression in mdx mice: a pharmacological approach. Neuropathology and applied neurobiology 2007; 33(3):344-59.
27. Musaro A, McCullagh K, Paul A, et al. Localized Igf-1 transgene expression sustains hypertrophy and regeneration in senescent skeletal muscle. Nat Genet 2001; 27(2):195-200.
28. Barton E R, Morris L, Musaro A, Rosenthal N, Sweeney H L. Muscle-specific expression of insulin-like growth factor I counters muscle decline in mdx mice. J Cell Biol 2002; 157(1):137-48.
29. Disatnik M H, Dhawan J, Yu Y, et al. Evidence of oxidative stress in mdx mouse muscle: studies of the pre-necrotic state. J Neurol Sci 1998; 161(1):77-84.
30. Nelson S K, Bose S K, Grunwald G K, Myhill P, McCord J M. The induction of human superoxide dismutase and catalase in vivo: a fundamentally new approach to anti-oxidant therapy. Free radical biology & medicine 2006; 40(2):341-7.
31. Hart P E, Lodi R, Rajagopalan B, et al. Antioxidant treatment of patients with Friedreich ataxia: four-year follow-up. Archives of neurology 2005; 62(4):621-6.
32. Rolland J F, De Luca A, Burdi R, Andreetta F, Confalonieri P, Conte Camerino D. Overactivity of exercise-sensitive cation channels and their impaired modulation by IGF-1 in mdx native muscle fibers: beneficial effect of pentoxifylline. Neurobiol Dis 2006; 24(3):466-74.
33. Whitehead N P, Streamer M, Lusambili L I, Sachs F, Allen D G. Streptomycin reduces stretch-induced membrane permeability in muscles from mdx mice. Neuromuscul Disord 2006; 16(12):845-54.
34. Badalamente M A, Stracher A. Delay of muscle degeneration and necrosis in mdx mice by calpain inhibition. Muscle Nerve 2000; 23(1):106-11.
35. Burdi R, Didonna M P, Pignol B, et al. First evaluation of the potential effectiveness in muscular dystrophy of a novel chimeric compound, BN 82270, acting as calpain-inhibitor and anti-oxidant. Neuromuscul Disord 2006; 16(4):237-48.
36. Bonuccelli G, Sotgia F, Schubert W, et al. Proteasome inhibitor (MG-132) treatment of mdx mice rescues the expression and membrane localization of dystrophin and dystrophin-associated proteins. Am J Pathol 2003; 163 (4):1663-75.
37. Voisin V, Sebrie C, Matecki S, et al. L-arginine improves dystrophic phenotype in mdx mice. Neurobiol Dis 2005; 20(1):123-30.
38. Soret J, Bakkour N, Maire S, et al. Selective modification of alternative splicing by indole derivatives that target serine-arginine-rich protein splicing factors. Proc Natl Acad Sci USA 2005; 102(24):8764-9.
39. Mann C J, Honeyman K, McClorey G, Fletcher S, Wilton S D.
Improved antisense oligonucleotide induced exon skipping in the mdx mouse model of muscular dystrophy. J Gene Med 2002; 4(6):644-54.

40. Graham I R, Hill V J, Manoharan M, Inamati G B, Dickson G. Towards a therapeutic inhibition of dystrophin exon 23 splicing in mdx mouse muscle induced by antisense oligoribonucleotides (splicomers): target sequence optimisation using oligonucleotide arrays. J Gene Med 2004; 6(10):1149-58.
41. Mathews D H, Sabina J, Zuker M, Turner D H. Expanded sequence dependence of thermodynamic parameters improves prediction of RNA secondary structure. J Mol Biol 1999; 288(5):911-40.
42. Cartegni L, Chew S L, Krainer A R. Listening to silence and understanding nonsense: exonic mutations that affect splicing. Nat Rev Genet 2002; 3(4):285-98.
43. Cartegni L, Wang J, Zhu Z, Zhang M Q, Krainer A R. ESEfinder: A web resource to identify exonic splicing enhancers. Nucleic Acids Res 2003; 31(13):3568-71.
44. Braasch D A, Corey D R. Locked nucleic acid (LNA): fine-tuning the recognition of DNA and RNA. Chem Biol 2001; 8(1):1-7.
45. Braasch D A, Corey D R. Novel antisense and peptide nucleic acid strategies for controlling gene expression. Biochemistry 2002; 41(14):4503-10.
46. Elayadi A N, Corey D R. Application of PNA and LNA oligomers to chemotherapy. Curr Opin Investig Drugs 2001; 2(4):558-61.
47. Larsen H J, Bentin T, Nielsen P E. Antisense properties of peptide nucleic acid. Biochim Biophys Acta 1999; 1489(1):159-66.
48. Summerton J. Morpholino antisense oligomers: the case for an RNase H-independent structural type. Biochim Biophys Acta 1999; 1489(1):141-58.
49. Summerton J, Weller D. Morpholino antisense oligomers: design, preparation, and properties. Antisense Nucleic Acid Drug Dev 1997; 7(3):187-95.
50. Wahlestedt C, Salmi P, Good L, et al. Potent and nontoxic antisense oligonucleotides containing locked nucleic acids. Proc Natl Acad Sci USA 2000; 97(10): 5633-8.
51. De Angelis F G, Sthandier O, Berarducci B, et al. Chimeric snRNA molecules carrying antisense sequences against the splice junctions of exon 51 of the dystrophin pre-mRNA induce exon skipping and restoration of a dystrophin synthesis in Delta 48-50 DMD cells. Proc Natl Acad Sci USA 2002; 99(14):9456-61.
52. Denti M A, Rosa A, D'Antona G, et al. Chimeric adeno-associated virus/antisense U1 small nuclear RNA effectively rescues dystrophin synthesis and muscle function by local treatment of mdx mice. Hum Gene Ther 2006; 17(5):565-74.
53. Gorman L, Suter D, Emerick V, Schumperli D, Kole R. Stable alteration of pre-mRNA splicing patterns by modified U7 small nuclear RNAs. Proc Natl Acad Sci USA 1998; 95(9):4929-34.
54. Suter D, Tomasini R, Reber U, Gorman L, Kole R, Schumperli D. Double-target antisense U7 snRNAs promote efficient skipping of an aberrant exon in three human beta-thalassemic mutations. Hum Mol Genet 1999; 8(13): 2415-23.
55. Wagner K R, Hamed S, Hadley D W, et al. Gentamicin treatment of Duchenne and Becker muscular dystrophy due to nonsense mutations. Ann Neurol 2001; 49(6):706-11.
56. Aartsma-Rus A et al, (2006), Entries in the leiden Duchenne Muscular Dystrophy mutation database: an overview of mutation types and paradoxical cases that confirm the reading-frame rule, Muscle Nerve, 34: 135-144.
57. Hodgetts S., et al, (2006), Neuromuscular Disorders, 16: 591-602.
58. Manzur A Y et al, (2008), Glucocorticoid corticosteroids for Duchenne muscular dystrophy (review), Wiley publishers, The Cochrane collaboration.
59. Yokota T. et al., Mar. 13, 2009, e-publication: Efficacy of systemic morpholino exon-skipping in duchennes dystrophy dogs. Ann. Neurol. 2009
60. Dorn and Kippenberger, Curr Opin Mol Ther 2008 10(1) 10-20
61. Cheng and Van Dyke, Gene. 1997 Sep. 15; 197(1-2): 253-60
62. Macaya et al., Biochemistry. 1995 4; 34(13):4478-92.
63. Suzuki et al., Eur J Biochem. 1999, 260(3):855-6
64. Howard et al., Ann Neurol 2004 55(3): 422-6;
65 . . . Nudelman et al., 2006, Bioorg Med Chem Lett 16(24), 6310-5

```
Sequence listing
DMD gene amino acid sequence
SEQ ID NO 1:
MLWWEEVEDCYEREDVQKKTFTKWVNAQFSKFGKQHIENLFSDLQDGRRLLDLLEGL
TCQKLPKEKGSTRVHALNNVNKALRVLQNNNVDLVNIGSTDIVDGNHKLTLGLIWNIIL
HWQVKNVMKNIMAGLQQTNSEKILLSWVRQSTRNYPQVNVINFITSWSDGLALNALIH
SHRPDLFDWNSVVCQQSATQRLEHAFNIARYQLGIEKLLDPEDVDTTYPDKKSILMYIT
SLFQVLPQQVSIEAIQEVEMLPRPPKVTKEEHFQLHHQMHYSQQITVSLAQGYERTSSP
KPRFKSYAYTQAAYVTTSDPTRSPFPSQHLEAPEDKSFGSSLMESEVNLDRYQTALEEV
LSWLLSAEDTLQAQGEISNDVEVVKDQFHTHEGYMMDLTAHQGRVGNILQLGSKLIGT
GKLSEDEETEVQEQMNLLNSRWECLRVASMEKQSNLHRVLMDLQNQKLKELNDWLT
KTEERTRKMEEEPLGPDLEDLKRQVQQHKVLQEDLEQEQVRVNSLTHMVVVVDESSG
DHATAALEEQLKVLGDRWANICRWTEDRWVLLQDILLKWQRLTEEQCLFSAWLSEKE
DAVNKIHTTGFKDQNEMLSSLQKLAVLKADLEKKKQSMGKLYSLKQDLLSTLKNKSVT
QKTEAWLDNFARCWDNLVQKLEKSTAQISQAVTTTQPSLTQTTVMETVTTVTTREQILV
KHAQEELPPPPQKKRQITVDSEIRKRLDVDITELHSWITRSEAVLQSPEFAIFRKEGNF
SDLKEKVNAIEREKAEKFRKLQDASRSAQALVEQMVNEGVNADSIKQASEQLNSRWIE
FCQLLSERLNWLEYQNNIIAFYNQLQQLEQMTTTAENWLKIQPTTPSEPTAIKSQLKIC
KDEVNRLSGLQPQIERLKIQSIALKEKGQGPMFLDADFVAFTNHFKQVFSDVQAREKEL
QTIFDTLPPMRYQETMSAIRTWVQQSETKLSIPQLSVTDYEIMEQRLGELQALQSSLQE
QQSGLYYLSTTVKEMSKKAPSEISRKYQSEFEEIEGRWKKLSSQLVEHCQKLEEQMNK
LRKIQNHIQTLKKWMAEVDVFLKEEWPALGDSEILKKQLKQCRLLVSDIQTIQPSLNSV
NEGGQKIKNEAEPEFASRLETELKELNTQWDHMCQQVYARKEALKGGLEKTVSLQKD
LSEMHEWMTQAEEEYLERDFEYKTPDELQKAVEEMKRAKEEAQQKEAKVKLLTESV
NSVIAQAPPVAQEALKKELETLTTNYQWLCTRLNGKCKTLEEVWACWHELLSYLEKAN
KWLNEVEFKLKTTENIPGGAEEISEVLDSLENLMRHSEDNPNQIRILAQTLTDGGVMD
ELINEELETFNSRWRELHEEAVRRQKLLEQSIQSAQETEKSLHLIQESLTFIDKQLAAYI
ADKVDAAQMPQEAQKIQSDLTSHEISLEEMKKHNQGKEAAQRVLSQIDVAQKKLQDVS
```

-continued

```
MKFRLFQKPANFEQRLQESKMILDEVKMHLPALETKSVEQEVVQSQLNHCVNLYKSLS
EVKSEVEMVIKTGRQIVQKKQTENPKELDERVTALKLHYNELGAKVTERKQQLEKCLK
LSRKMRKEMNVLTEWLAATDMELTKRSAVEGMPSNLDSEVAWGKATQKEIEKQKVH
LKSITEVGEALKTVLGKKETLVEDKLSLLNSNWIAVTSRAEEWLNLLLEYQKHMETFD
QNVDHITKWIIQADTLLDESEKKKPQQKEDVLKRLKAELNDIRPKVDSTRDQAANLMA
NRGDHCRKLVE PQISELNHRFAAISHRIKTGKASIPLKELEQFNSDIQKLLEPLEAEIQQ
GVNLKEEDFNKDMNEDNEGTVKELLQRGDNLQQRITDERKREEIKIKQQLLQTKHNA
LKDLRSQRRKKALEISHQWYQYKRQADDLLKCLDDIEKKLASLPEPRDERKIKEIDREL
QKKKEELNAVRRQAEGLSEDGAAMAVEPTQIQLSKRWREIESKFAQFRRLNFAQIHTV
REETMMVMTEDMPLEISYVPSTYLTEITHVSQALLEVEQLLNAPDLCAKDFEDLFKQE
ESLKNIKDSLQQSSGRIDIIHSKKTAALQSATPVERVKLQEALSQLDFQWEKVNKMYKD
RQGRFDRSVEKWRRFHYDIKIFNQWLTEAEQFLRKTQIPENWEHAKYKWYLKELQDGI
CQRQTVVRTLNATGEEIIQQSSKTDASILQEKLGSLNLRWQEVCKQLSDRKKRLEEQKN
ILSEFQRDLNEFVLWLEEADNIASIPLEPGKEQQLKEKLEQVKLLVEELPLRQGILKQL
NETGGPVLVSAPISPEEQDKLENKLKQTNLQWIKVSRALPEKQGEIEAQIKDLGQLEKK
LEDLEEQLNHLLLWLSPIRNQLEIYNQPNQEGPFDVQETEIAVQAKQPDVEEILSKGQH
LYKEKPATQPVKRKLEDLSSEWKAVNRLLQELRAKQPDLAPGLTTIGASPTQTVTLVTQ
PVVTKETAISKLEMPSSLMLEVPALADFNRAWTELTDWLSLLDQVIKSQRVMVGDLEDI
NEMIIKQKATMQDLEQRRPQLEELITAAQNLKNKTSNQEARTIITDRIERIQNQWDEVQ
EHLQNRRQQLNEMLKDSTQWLEAKEEAEQVLGQARAKLESWKEGPYTVDAIQKKITE
TKQLAKDLRQWQTNVDVANDLALKLLRDYSADDTRKVHMITENINASWRSIHKRVSER
EAALEETHRLLQQFPLDLEKFLAWLTEAETTANVLQDATRKERLLEDSKGVKELMKQ
WQDLQGEIEAHTDVYHNLDENSQKILRSLEGSDDAVLLQRRLDNMNFKWSELRKKSL
NIRSHLEASSDQWKRLHLSLQELLVWLQLKDDELSRQAPIGGDFPAVQKQNDVHRAFK
RELKTKEPVIMSTLETVRIFLTEQPLEGLEKLYQEPRELPPEERAQNVTRLLRKQAEEV
NTEWEKLNLHSADWQRKIDETLERLQELQEATDELDLKLRQAEVIKGSWQPVGDLLID
SLQDHLEKVKALRGEIAPLKENVSHVNDLARQLTTLGIQLSPYNLSTLEDLNTRWKLLQ
VAVEDRVRQLHEAHRDFGPASQHFLSTSVQGPWERAISPNKVPYYINHETQTTCWDHP
KMTELYQSLADLNNVRFSAYRTAMKLRRLQKALCLDLLSLSAACDALDQHNLKQNDQ
PMDILQIINCLTTIYDRLEQEHNNLVNVPLCVDMCLNWLLNVYDTGRTGRIRVLSFKTG
IISLCKAHLEDKYRYLFKQVASSTGFCDQRRLGLLLHDSIQIPRQLGEVASFGGSNIEPSV
RSCFQFANNKPEIEAALFLDWMRLEPQSMVWLPVLHRVAAAETAKHQAKCNICKECPI
IGFRYRSLKHFNYDICQSCFFSGRVAKGHKMHYPMVEYCTPTTSGEDVRDFAKVLKNK
FRTKRYFAKHPRMGYLPVQTVLEGDNMETPVTLINFWPVDSAPASSPQLSHDDTHSRI
EHYASRLAEMENSNGSYLNDSISPNESIDDEHLLIQHYCQSLNQDSPLSQPRSPAQILIS
LESEERGELERILADLEEENRNLQAEYDRLKQQHEHKGLSPLPSPPEMMPTSPQSPRD
AELIAEAKLLRQHKGRLEARMQILEDHNKQLESQLHRLRQLLEQPQAEAKVNGTTVSS
PSTSLQRSDSSQPMLLRVVGSQTSDSMGEEDLLSPPQDTSTGLEEVMEQLNNSFPSSRG
RNTPGKPMREDTM
```

DMD Gene Exon 51

| | | | |
|---|---|---|---|
| SEQ ID NO 2 | GUACCUCCAACAUCAAGGAAGAUGG | SEQ ID NO 39 | GAGAUGGCAGUUUCCUUAGUAACCA |
| SEQ ID NO 3 | UACCUCCAACAUCAAGGAAGAUGGC | SEQ ID NO 40 | AGAUGGCAGUUUCCUUAGUAACCAC |
| SEQ ID NO 4 | ACCUCCAACAUCAAGGAAGAUGGCA | SEQ ID NO 41 | GAUGGCAGUUUCCUUAGUAACCACA |
| SEQ ID NO 5 | CCUCCAACAUCAAGGAAGAUGGCAU | SEQ ID NO 42 | AUGGCAGUUUCCUUAGUAACCACAG |
| SEQ ID NO 6 | CUCCAACAUCAAGGAAGAUGGCAUU | SEQ ID NO 43 | UGGCAGUUUCCUUAGUAACCACAGG |
| SEQ ID NO 7 | UCCAACAUCAAGGAAGAUGGCAUUU | SEQ ID NO 44 | GGCAGUUUCCUUAGUAACCACAGGU |
| SEQ ID NO 8 | CCAACAUCAAGGAAGAUGGCAUUUC | SEQ ID NO 45 | GCAGUUUCCUUAGUAACCACAGGUU |
| SEQ ID NO 9 | CAACAUCAAGGAAGAUGGCAUUUCU | SEQ ID NO 46 | CAGUUUCCUUAGUAACCACAGGUUG |
| SEQ ID NO 10 | AACAUCAAGGAAGAUGGCAUUUCUA | SEQ ID NO 47 | AGUUUCCUUAGUAACCACAGGUUGU |
| SEQ ID NO 11 | ACAUCAAGGAAGAUGGCAUUUCUAG | SEQ ID NO 48 | GUUUCCUUAGUAACCACAGGUUGUG |
| SEQ ID NO 12 | CAUCAAGGAAGAUGGCAUUUCUAGU | SEQ ID NO 49 | UUUCCUUAGUAACCACAGGUUGUGU |
| SEQ ID NO 13 | AUCAAGGAAGAUGGCAUUUCUAGUU | SEQ ID NO 50 | UUCCUUAGUAACCACAGGUUGUGUC |
| SEQ ID NO 14 | UCAAGGAAGAUGGCAUUUCUAGUUU | SEQ ID NO 51 | UCCUUAGUAACCACAGGUUGUGUCA |
| SEQ ID NO 15 | CAAGGAAGAUGGCAUUUCUAGUUUG | SEQ ID NO 52 | CCUUAGUAACCACAGGUUGUGUCAC |
| SEQ ID NO 16 | AAGGAAGAUGGCAUUUCUAGUUUGG | SEQ ID NO 53 | CUUAGUAACCACAGGUUGUGUCACC |
| SEQ ID NO 17 | AGGAAGAUGGCAUUUCUAGUUUGGA | SEQ ID NO 54 | UUAGUAACCACAGGUUGUGUCACCA |
| SEQ ID NO 18 | GGAAGAUGGCAUUUCUAGUUUGGAG | SEQ ID NO 55 | UAGUAACCACAGGUUGUGUCACCAG |
| SEQ ID NO 19 | GAAGAUGGCAUUUCUAGUUUGGAGA | SEQ ID NO 56 | AGUAACCACAGGUUGUGUCACCAGA |
| SEQ ID NO 20 | AAGAUGGCAUUUCUAGUUUGGAGAU | SEQ ID NO 57 | GUAACCACAGGUUGUGUCACCAGAG |
| SEQ ID NO 21 | AGAUGGCAUUUCUAGUUUGGAGAUG | SEQ ID NO 58 | UAACCACAGGUUGUGUCACCAGAGU |

-continued

| SEQ ID NO 22 | GAUGGCAUUUCUAGUUUGGAGAUGG | SEQ ID NO 59 | AACCACAGGUUGUGUCACCAGAGUA |
| --- | --- | --- | --- |
| SEQ ID NO 23 | AUGGCAUUUCUAGUUUGGAGAUGGC | SEQ ID NO 60 | ACCACAGGUUGUGUCACCAGAGUAA |
| SEQ ID NO 24 | UGGCAUUUCUAGUUUGGAGAUGGCA | SEQ ID NO 61 | CCACAGGUUGUGUCACCAGAGUAAC |
| SEQ ID NO 25 | GGCAUUUCUAGUUUGGAGAUGGCAG | SEQ ID NO 62 | CACAGGUUGUGUCACCAGAGUAACA |
| SEQ ID NO 26 | GCAUUUCUAGUUUGGAGAUGGCAGU | SEQ ID NO 63 | ACAGGUUGUGUCACCAGAGUAACAG |
| SEQ ID NO 27 | CAUUUCUAGUUUGGAGAUGGCAGUU | SEQ ID NO 64 | CAGGUUGUGUCACCAGAGUAACAGU |
| SEQ ID NO 28 | AUUUCUAGUUUGGAGAUGGCAGUUU | SEQ ID NO 65 | AGGUUGUGUCACCAGAGUAACAGUC |
| SEQ ID NO 29 | UUUCUAGUUUGGAGAUGGCAGUUUC | SEQ ID NO 66 | GGUUGUGUCACCAGAGUAACAGUCU |
| SEQ ID NO 30 | UUCUAGUUUGGAGAUGGCAGUUUCC | SEQ ID NO 67 | GUUGUGUCACCAGAGUAACAGUCUG |
| SEQ ID NO 31 | UCUAGUUUGGAGAUGGCAGUUUCCU | SEQ ID NO 68 | UUGUGUCACCAGAGUAACAGUCUGA |
| SEQ ID NO 32 | CUAGUUUGGAGAUGGCAGUUUCCUU | SEQ ID NO 69 | UGUGUCACCAGAGUAACAGUCUGAG |
| SEQ ID NO 33 | UAGUUUGGAGAUGGCAGUUUCCUUA | SEQ ID NO 70 | GUGUCACCAGAGUAACAGUCUGAGU |
| SEQ ID NO 34 | AGUUUGGAGAUGGCAGUUUCCUUAG | SEQ ID NO 71 | UGUCACCAGAGUAACAGUCUGAGUA |
| SEQ ID NO 35 | GUUUGGAGAUGGCAGUUUCCUUAGU | SEQ ID NO 72 | GUCACCAGAGUAACAGUCUGAGUAG |
| SEQ ID NO 36 | UUUGGAGAUGGCAGUUUCCUUAGUA | SEQ ID NO 73 | UCACCAGAGUAACAGUCUGAGUAGG |
| SEQ ID NO 37 | UUGGAGAUGGCAGUUUCCUUAGUAA | SEQ ID NO 74 | CACCAGAGUAACAGUCUGAGUAGGA |
| SEQ ID NO 38 | UGGAGAUGGCAGUUUCCUUAGUAAC | SEQ ID NO 75 | ACCAGAGUAACAGUCUGAGUAGGAG |
| SEQ ID NO 539 | UCAAGGAAGAUGGCAUUUCU | SEQ ID NO 548 | UCAAGGAAGAUGGCAUIUCU |
| SEQ ID NO 540 | UCAAIGAAGAUGGCAUUUCU | SEQ ID NO 549 | UCAAGGAAGAUGGCAUUICU |
| SEQ ID NO 541 | UCAAGIAAGAUGGCAUUUCU | SEQ ID NO 550 | UCAAGGAAGAUGGCAUUUCI |
| SEQ ID NO 542 | UCAAGGAAIAUGGCAUUUCU | SEQ ID NO 551 | UCIAGGAAGAUGGCAUUUCU |
| SEQ ID NO 543 | UCAAGGAAGAUIGCAUUUCU | SEQ ID NO 552 | UCAIGGAAGAUGGCAUUUCU |
| SEQ ID NO 544 | UCAAGGAAGAUGICAUUUCU | SEQ ID NO 553 | UCAAGGIAGAUGGCAUUUCU |
| SEQ ID NO 545 | ICAAGGAAGAUGGCAUUUCU | SEQ ID NO 554 | UCAAGGAIGAUGGCAUUUCU |
| SEQ ID NO 546 | UCAAGGAAGAIGGCAUUUCU | SEQ ID NO 555 | UCAAGGAAGIUGGCAUUUCU |
| SEQ ID NO 547 | UCAAGGAAGAUGGCAIUUCU | SEQ ID NO 556 | UCAAGGAAGAUGGCIUUUCU |

DMD Gene Exon 45

| SEQ ID NO 76 PS220 | UUUGCCGCUGCCCAAUGCCAUCCUG | SEQ ID NO 109 | GUUGCAUUCAAUGUUCUGACAACAG |
| --- | --- | --- | --- |
| SEQ ID NO 77 | AUUCAAUGUUCUGACAACAGUUUGC | SEQ ID NO 110 | UUGCAUUCAAUGUUCUGACAACAGU |
| SEQ ID NO 78 | CCAGUUGCAUUCAAUGUUCUGACAA | SEQ ID NO 111 | UGCAUUCAAUGUUCUGACAACAGUU |
| SEQ ID NO 79 | CAGUUGCAUUCAAUGUUCUGAC | SEQ ID NO 112 | GCAUUCAAUGUUCUGACAACAGUUU |
| SEQ ID NO 80 | AGUUGCAUUCAAUGUUCUGA | SEQ ID NO 113 | CAUUCAAUGUUCUGACAACAGUUUG |
| SEQ ID NO 81 | GAUUGCUGAAUUAUUUCUUCC | SEQ ID NO 114 | AUUCAAUGUUCUGACAACAGUUUGC |
| SEQ ID NO 82 | GAUUGCUGAAUUAUUUCUUCCCCAG | SEQ ID NO 115 | UCAAUGUUCUGACAACAGUUUGCCG |
| SEQ ID NO 83 | AUUGCUGAAUUAUUUCUUCCCCAGU | SEQ ID NO 116 | CAAUGUUCUGACAACAGUUUGCCGC |
| SEQ ID NO 84 | UUGCUGAAUUAUUUCUUCCCCAGUU | SEQ ID NO 117 | AAUGUUCUGACAACAGUUUGCCGCU |
| SEQ ID NO 85 | UGCUGAAUUAUUUCUUCCCCAGUUG | SEQ ID NO 118 | AUGUUCUGACAACAGUUUGCCGCUG |
| SEQ ID NO 86 | GCUGAAUUAUUUCUUCCCCAGUUGC | SEQ ID NO 119 | UGUUCUGACAACAGUUUGCCGCUGC |
| SEQ ID NO 87 | CUGAAUUAUUUCUUCCCCAGUUGCA | SEQ ID NO 120 | GUUCUGACAACAGUUUGCCGCUGCC |
| SEQ ID NO 88 | UGAAUUAUUUCUUCCCCAGUUGCAU | SEQ ID NO 121 | UUCUGACAACAGUUUGCCGCUGCCC |

-continued

| | | | |
|---|---|---|---|
| SEQ ID NO 89 | GAAUUAUUUCUUCCCCAGUUGCAUU | SEQ ID NO 122 | UCUGACAACAGUUUGCCGCUGCCCA |
| SEQ ID NO 90 | AAUUAUUUCUUCCCCAGUUGCAUUC | SEQ ID NO 123 | CUGACAACAGUUUGCCGCUGCCCAA |
| SEQ ID NO 91 | AUUAUUUCUUCCCCAGUUGCAUUCA | SEQ ID NO 124 | UGACAACAGUUUGCCGCUGCCCAAU |
| SEQ ID NO 92 | UUAUUUCUUCCCCAGUUGCAUUCAA | SEQ ID NO 125 | GACAACAGUUUGCCGCUGCCCAAUG |
| SEQ ID NO 93 | UAUUUCUUCCCCAGUUGCAUUCAAU | SEQ ID NO 126 | ACAACAGUUUGCCGCUGCCCAAUGC |
| SEQ ID NO 94 | AUUUCUUCCCCAGUUGCAUUCAAUG | SEQ ID NO 127 | CAACAGUUUGCCGCUGCCCAAUGCC |
| SEQ ID NO 95 | UUUCUUCCCCAGUUGCAUUCAAUGU | SEQ ID NO 128 | AACAGUUUGCCGCUGCCCAAUGCCA |
| SEQ ID NO 96 | UUCUUCCCCAGUUGCAUUCAAUGUU | SEQ ID NO 129 | ACAGUUUGCCGCUGCCCAAUGCCAU |
| SEQ ID NO 97 | UCUUCCCCAGUUGCAUUCAAUGUUC | SEQ ID NO 130 | CAGUUUGCCGCUGCCCAAUGCCAUC |
| SEQ ID NO 98 | CUUCCCCAGUUGCAUUCAAUGUUCU | SEQ ID NO 131 | AGUUUGCCGCUGCCCAAUGCCAUCC |
| SEQ ID NO 99 | UUCCCCAGUUGCAUUCAAUGUUCUG | SEQ ID NO 132 | GUUUGCCGCUGCCCAAUGCCAUCCU |
| SEQ ID NO 100 | UCCCCAGUUGCAUUCAAUGUUCUGA | SEQ ID NO 133 | UUUGCCGCUGCCCAAUGCCAUCCUG |
| SEQ ID NO 101 | CCCCAGUUGCAUUCAAUGUUCUGAC | SEQ ID NO 134 | UUGCCGCUGCCCAAUGCCAUCCUGG |
| SEQ ID NO 102 | CCCAGUUGCAUUCAAUGUUCUGACA | SEQ ID NO 135 | UGCCGCUGCCCAAUGCCAUCCUGGA |
| SEQ ID NO 103 | CCAGUUGCAUUCAAUGUUCUGACAA | SEQ ID NO 136 | GCCGCUGCCCAAUGCCAUCCUGGAG |
| SEQ ID NO 104 | CAGUUGCAUUCAAUGUUCUGACAAC | SEQ ID NO 137 | CCGCUGCCCAAUGCCAUCCUGGAGU |
| SEQ ID NO 105 | AGUUGCAUUCAAUGUUCUGACAACA | SEQ ID NO 138 | CGCUGCCCAAUGCCAUCCUGGAGUU |
| SEQ ID NO 106 | UCC UGU AGA AUA CUG GCA UC | SEQ ID NO 139 | UGUUUUUGAGGAUUGCUGAA |
| SEQ ID NO 107 | UGCAGACCUCCUGCCACCGCAGAUUCA | SEQ ID NO 140 | UGUUCUGACAACAGUUUGCCGCUGCCCAAUGCCAUCCUGG |
| SEQ ID NO 108 | UUGCAGACCUCCUGCCACCGCAGAUUCAGGCUUC | SEQ ID NO 557 PS305 | UUUGCCICUGCCCAAUGCCAUCCUG |
| SEQ ID NO 558 | UUUGCCGCUICCCAAUGCCAUCCUG | SEQ ID NO 566 | UUUGCCGCUGCCCAIUGCCAUCCUG |
| SEQ ID NO 559 | UUUGCCGCUGCCCAAUICCAUCCUG | SEQ ID NO 567 | UUUGCCGCUGCCCAAUGCCIUCCUG |
| SEQ ID NO 560 | UUUICCGCUGCCCAAUGCCAUCCUG | SEQ ID NO 568 | UUUICCICUGCCCAAUGCCAUCCUG |
| SEQ ID NO 561 | UUUGCCGCUGCCCAAUGCCAUCCUI | SEQ ID NO 569 | UUUGCCGCUGCCCAAIGCCAUCCUG |
| SEQ ID NO 562 | IUUGCCGCUGCCCAAUGCCAUCCUG | SEQ ID NO 570 | UUUGCCGCUGCCCAAUGCCAICCUG |
| SEQ ID NO 563 | UIUGCCGCUGCCCAAUGCCAUCCUG | SEQ ID NO 571 | UUUGCCGCUGCCCAAUGCCAUCCIG |
| SEQ ID NO 564 | UUIGCCGCUGCCCAAUGCCAUCCUG | SEQ ID NO 572 | UUUGCCGCUGCCCIAUGCCAUCCUG |
| SEQ ID NO 565 | UUUGCCGCIGCCCAAUGCCAUCCUG | | |

DMD Gene Exon 53

| | | | |
|---|---|---|---|
| SEQ ID NO 141 | CUCUGGCCUGUCCUAAGACCUGCUC | SEQ ID NO 165 | CAGCUUCUUCCUUAGCUUCCAGCCA |
| SEQ ID NO 142 | UCUGGCCUGUCCUAAGACCUGCUCA | SEQ ID NO 166 | AGCUUCUUCCUUAGCUUCCAGCCAU |
| SEQ ID NO 143 | CUGGCCUGUCCUAAGACCUGCUCAG | SEQ ID NO 167 | GCUUCUUCCUUAGCUUCCAGCCAUU |
| SEQ ID NO 144 | UGGCCUGUCCUAAGACCUGCUCAGC | SEQ ID NO 168 | CUUCUUCCUUAGCUUCCAGCCAUUG |
| SEQ ID NO 145 | GGCCUGUCCUAAGACCUGCUCAGCU | SEQ ID NO 169 | UUCUUCCUUAGCUUCCAGCCAUUGU |
| SEQ ID NO 146 | GCCUGUCCUAAGACCUGCUCAGCUU | SEQ ID NO 170 | UCUUCCUUAGCUUCCAGCCAUUGUG |
| SEQ ID NO 147 | CCUGUCCUAAGACCUGCUCAGCUUC | SEQ ID NO 171 | CUUCCUUAGCUUCCAGCCAUUGUGU |
| SEQ ID NO 148 | CUGUCCUAAGACCUGCUCAGCUUCU | SEQ ID NO 172 | UUCCUUAGCUUCCAGCCAUUGUGUU |
| SEQ ID NO 149 | UGUCCUAAGACCUGCUCAGCUUCUU | SEQ ID NO 173 | UCCUUAGCUUCCAGCCAUUGUGUUG |
| SEQ ID NO 150 | GUCCUAAGACCUGCUCAGCUUCUUC | SEQ ID NO 174 | CCUUAGCUUCCAGCCAUUGUGUUGA |
| SEQ ID NO 151 | UCCUAAGACCUGCUCAGCUUCUUCC | SEQ ID NO 175 | CUUAGCUUCCAGCCAUUGUGUUGAA |

| | | | |
|---|---|---|---|
| SEQ ID NO 152 | CCUAAGACCUGCUCAGCUUCUUCCU | SEQ ID NO 176 | UUAGCUUCCAGCCAUUGUGUUGAAU |
| SEQ ID NO 153 | CUAAGACCUGCUCAGCUUCUUCCUU | SEQ ID NO 177 | UAGCUUCCAGCCAUUGUGUUGAAUC |
| SEQ ID NO 154 | UAAGACCUGCUCAGCUUCUUCCUUA | SEQ ID NO 178 | AGCUUCCAGCCAUUGUGUUGAAUCC |
| SEQ ID NO 155 | AAGACCUGCUCAGCUUCUUCCUUAG | SEQ ID NO 179 | GCUUCCAGCCAUUGUGUUGAAUCCU |
| SEQ ID NO 156 | AGACCUGCUCAGCUUCUUCCUUAGC | SEQ ID NO 180 | CUUCCAGCCAUUGUGUUGAAUCCUU |
| SEQ ID NO 157 | GACCUGCUCAGCUUCUUCCUUAGCU | SEQ ID NO 181 | UUCCAGCCAUUGUGUUGAAUCCUUU |
| SEQ ID NO 158 | ACCUGCUCAGCUUCUUCCUUAGCUU | SEQ ID NO 182 | UCCAGCCAUUGUGUUGAAUCCUUUA |
| SEQ ID NO 159 | CCUGCUCAGCUUCUUCCUUAGCUUC | SEQ ID NO 183 | CCAGCCAUUGUGUUGAAUCCUUUAA |
| SEQ ID NO 160 | CUGCUCAGCUUCUUCCUUAGCUUCC | SEQ ID NO 184 | CAGCCAUUGUGUUGAAUCCUUUAAC |
| SEQ ID NO 161 | UGCUCAGCUUCUUCCUUAGCUUCCA | SEQ ID NO 185 | AGCCAUUGUGUUGAAUCCUUUAACA |
| SEQ ID NO 162 | GCUCAGCUUCUUCCUUAGCUUCCAG | SEQ ID NO 186 | GCCAUUGUGUUGAAUCCUUUAACAU |
| SEQ ID NO 163 | CUCAGCUUCUUCCUUAGCUUCCAGC | SEQ ID NO 187 | CCAUUGUGUUGAAUCCUUUAACAUU |
| SEQ ID NO 164 | UCAGCUUCUUCCUUAGCUUCCAGCC | SEQ ID NO 188 | CAUUGUGUUGAAUCCUUUAACAUUU |
| DMD Gene Exon 44 | | | |
| SEQ ID NO 189 | UCAGCUUCUGUUAGCCACUG | SEQ ID NO 214 | AGCUUCUGUUAGCCACUGAUUAAA |
| SEQ ID NO 190 | UUCAGCUUCUGUUAGCCACU | SEQ ID NO 215 | CAGCUUCUGUUAGCCACUGAUUAAA |
| SEQ ID NO 191 | UUCAGCUUCUGUUAGCCACUG | SEQ ID NO 216 | AGCUUCUGUUAGCCACUGAUUAAA |
| SEQ ID NO 192 | UCAGCUUCUGUUAGCCACUGA | SEQ ID NO 217 | AGCUUCUGUUAGCCACUGAU |
| SEQ ID NO 193 | UUCAGCUUCUGUUAGCCACUGA | SEQ ID NO 218 | GCUUCUGUUAGCCACUGAUU |
| SEQ ID NO 194 | UCAGCUUCUGUUAGCCACUGA | SEQ ID NO 219 | AGCUUCUGUUAGCCACUGAUU |
| SEQ ID NO 195 | UUCAGCUUCUGUUAGCCACUGA | SEQ ID NO 220 | GCUUCUGUUAGCCACUGAUUA |
| SEQ ID NO 196 | UCAGCUUCUGUUAGCCACUGAU | SEQ ID NO 221 | AGCUUCUGUUAGCCACUGAUUA |
| SEQ ID NO 197 | UUCAGCUUCUGUUAGCCACUGAU | SEQ ID NO 222 | GCUUCUGUUAGCCACUGAUUAA |
| SEQ ID NO 198 | UCAGCUUCUGUUAGCCACUGAUU | SEQ ID NO 223 | AGCUUCUGUUAGCCACUGAUUAA |
| SEQ ID NO 199 | UUCAGCUUCUGUUAGCCACUGAUU | SEQ ID NO 224 | GCUUCUGUUAGCCACUGAUUAAA |
| SEQ ID NO 200 | UCAGCUUCUGUUAGCCACUGAUUA | SEQ ID NO 225 | AGCUUCUGUUAGCCACUGAUUAAA |
| SEQ ID NO 201 | UUCAGCUUCUGUUAGCCACUGAUA | SEQ ID NO 226 | GCUUCUGUUAGCCACUGAUUAAA |
| SEQ ID NO 202 | UCAGCUUCUGUUAGCCACUGAUUAA | SEQ ID NO 227 | CCAUUUGUAUUUAGCAUGUUCCC |
| SEQ ID NO 203 | UUCAGCUUCUGUUAGCCACUGAUUAA | SEQ ID NO 228 | AGAUACCAUUUGUAUUUAGC |
| SEQ ID NO 204 | UCAGCUUCUGUUAGCCACUGAUUAA | SEQ ID NO 229 | GCCAUUUCUCAACAGAUCU |
| SEQ ID NO 205 | UUCAGCUUCUGUUAGCCACUGAUUAAA | SEQ ID NO 230 | GCCAUUUCUCAACAGAUCUGUCA |
| SEQ ID NO 206 | CAGCUUCUGUUAGCCACUG | SEQ ID NO 231 | AUUCUCAGGAAUUUGUGUCUUUC |
| SEQ ID NO 207 | CAGCUUCUGUUAGCCACUGAU | SEQ ID NO 232 | UCUCAGGAAUUUGUGUCUUUC |
| SEQ ID NO 208 | AGCUUCUGUUAGCCACUGAUU | SEQ ID NO 233 | GUUCAGCUUCUGUUAGCC |
| SEQ ID NO 209 | CAGCUUCUGUUAGCCACUGAUU | SEQ ID NO 234 | CUGAUUAAAUAUCUUUAUAU C |
| SEQ ID NO 210 | AGCUUCUGUUAGCCACUGAUUA | SEQ ID NO 235 | GCCGCCAUUUCUCAACAG |
| SEQ ID NO 211 | CAGCUUCUGUUAGCCACUGAUUA | SEQ ID NO 236 | GUAUUUAGCAUGUUCCCA |
| SEQ ID NO 212 | AGCUUCUGUUAGCCACUGAUUAA | SEQ ID NO 237 | CAGGAAUUUGUGUCUUUC |
| SEQ ID NO 213 | CAGCUUCUGUUAGCCACUGAUUAA | SEQ ID NO 575 | UCAICUUCUGUUAGCCACUG |
| SEQ ID NO 573 | UCAGCUUCUIUUAGCCACUG | SEQ ID NO 576 | UCAGCUUCUGUUAGCCACUI |

-continued

| SEQ ID NO 574 | UCAGCUUCUGUUAICCACUG | | |

DMD Gene Exon 46

| SEQ ID NO 238 | GCUUUUCUUUUAGUUGCUGCUCUUUU | SEQ ID NO 265 | CCAGGUUCAAGUGGGAUACUAGCAA |
| SEQ ID NO 239 | CUUUUCUUUUAGUUGCUGCUCUUUUU | SEQ ID NO 266 | CAGGUUCAAGUGGGAUACUAGCAAU |
| SEQ ID NO 240 | UUUUCUUUUAGUUGCUGCUCUUUUUC | SEQ ID NO 267 | AGGUUCAAGUGGGAUACUAGCAAUG |
| SEQ ID NO 241 | UUUCUUUUAGUUGCUGCUCUUUUCC | SEQ ID NO 268 | GGUUCAAGUGGGAUACUAGCAAUGU |
| SEQ ID NO 242 | UUCUUUUAGUUGCUGCUCUUUUCCA | SEQ ID NO 269 | GUUCAAGUGGGAUACUAGCAAUGUU |
| SEQ ID NO 243 | UCUUUUAGUUGCUGCUCUUUUCCAG | SEQ ID NO 270 | UUCAAGUGGGAUACUAGCAAUGUUA |
| SEQ ID NO 244 | CUUUUAGUUGCUGCUCUUUUCCAGG | SEQ ID NO 271 | UCAAGUGGGAUACUAGCAAUGUUAU |
| SEQ ID NO 245 | UUUUAGUUGCUGCUCUUUUCCAGGU | SEQ ID NO 272 | CAAGUGGGAUACUAGCAAUGUUAUC |
| SEQ ID NO 246 | UUUAGUUGCUGCUCUUUUCCAGGUU | SEQ ID NO 273 | AAGUGGGAUACUAGCAAUGUUAUCU |
| SEQ ID NO 247 | UUAGUUGCUGCUCUUUUCCAGGUUC | SEQ ID NO 274 | AGUGGGAUACUAGCAAUGUUAUCUG |
| SEQ ID NO 248 | UAGUUGCUGCUCUUUUCCAGGUUCA | SEQ ID NO 275 | GUGGGAUACUAGCAAUGUUAUCUGC |
| SEQ ID NO 249 | AGUUGCUGCUCUUUUCCAGGUUCAA | SEQ ID NO 276 | UGGGAUACUAGCAAUGUUAUCUGCU |
| SEQ ID NO 250 | GUUGCUGCUCUUUUCCAGGUUCAAG | SEQ ID NO 277 | GGGAUACUAGCAAUGUUAUCUGCUU |
| SEQ ID NO 251 | UUGCUGCUCUUUUCCAGGUUCAAGU | SEQ ID NO 278 | GGAUACUAGCAAUGUUAUCUGCUUC |
| SEQ ID NO 252 | UCCUGCUCUUUUCCAGGUUCAAGUG | SEQ ID NO 279 | GAUACUAGCAAUGUUAUCUGCUUCC |
| SEQ ID NO 253 | GCUGCUCUUUUCCAGGUUCAAGUGG | SEQ ID NO 280 | AUACUAGCAAUGUUAUCUGCUUCCU |
| SEQ ID NO 254 | CUGCUCUUUUCCAGGUUCAAGUGGG | SEQ ID NO 281 | UACUAGCAAUGUUAUCUGCUUCCUC |
| SEQ ID NO 255 | UGCUCUUUUCCAGGUUCAAGUGGGA | SEQ ID NO 282 | ACUAGCAAUGUUAUCUGCUUCCUCC |
| SEQ ID NO 256 | GCUCUUUUCCAGGUUCAAGUGGGAC | SEQ ID NO 283 | CUAGCAAUGUUAUCUGCUUCCUCCA |
| SEQ ID NO 257 | CUCUUUUCCAGGUUCAAGUGGGAUA | SEQ ID NO 284 | UAGCAAUGUUAUCUGCUUCCUCCAA |
| SEQ ID NO 258 | UCUUUUCCAGGUUCAAGUGGGAUAC | SEQ ID NO 285 | AGCAAUGUUAUCUGCUUCCUCCAAC |
| SEQ ID NO 259 | UCUUUUCCAGGUUCAAGUGG | SEQ ID NO 286 | GCAAUGUUAUCUGCUUCCUCCAACC |
| SEQ ID NO 260 | CUUUUCCAGGUUCAAGUGGGAUACU | SEQ ID NO 287 | CAAUGUUAUCUGCUUCCUCCAACCA |
| SEQ ID NO 261 | UUUUCCAGGUUCAAGUGGGAUACUA | SEQ ID NO 288 | AAUGUUAUCUGCUUCCUCCAACCAU |
| SEQ ID NO 262 | UUUCCAGGUUCAAGUGGGAUACUAG | SEQ ID NO 289 | AUGUUAUCUGCUUCCUCCAACCAUA |
| SEQ ID NO 263 | UUCCAGGUUCAAGUGGGAUACUAGC | SEQ ID NO 290 | UGUUAUCUGCUUCCUCCAACCAUAA |
| SEQ ID NO 264 | UCCAGGUUCAAGUGGGAUACUAGCA | | |

DMD Gene Exon 52

| SEQ ID NO 291 | AGCCUCUUGAUUGCUGGUCUUGUUU | SEQ ID NO 326 | UUGGGCAGCGGUAAUGAGUUCUUCC |
| SEQ ID NO 292 | GCCUCUUGAUUGCUGGUCUUGUUUU | SEQ ID NO 327 | UGGGCAGCGGUAAUGAGUUCUUCCA |
| SEQ ID NO 293 | CCUCUUGAUUGCUGGUCUUGUUUUU | SEQ ID NO 328 | GGGCAGCGGUAAUGAGUUCUUCCAA |
| SEQ ID NO 294 | CCUCUUGAUUGCUGGUCUUG | SEQ ID NO 329 | GGCAGCGGUAAUGAGUUCUUCCAAC |
| SEQ ID NO 295 | CUCUUGAUUGCUGGUCUUGUUUUUC | SEQ ID NO 330 | GCAGCGGUAAUGAGUUCUUCCAACU |
| SEQ ID NO 296 | UCUUGAUUGCUGGUCUUGUUUUUCA | SEQ ID NO 331 | CAGCGGUAAUGAGUUCUUCCAACUG |
| SEQ ID NO 297 | CUUGAUUGCUGGUCUUGUUUUUCAA | SEQ ID NO 332 | AGCGGUAAUGAGUUCUUCCAACUGG |
| SEQ ID NO 298 | UUGAUUGCUGGUCUUGUUUUUCAAA | SEQ ID NO 333 | GCGGUAAUGAGUUCUUCCAACUGGG |
| SEQ ID NO 299 | UGAUUGCUGGUCUUGUUUUUCAAAU | SEQ ID NO 334 | CGGUAAUGAGUUCUUCCAACUGGGG |
| SEQ ID NO 300 | GAUUGCUGGUCUUGUUUUUCAAAUU | SEQ ID NO 335 | GGUAAUGAGUUCUUCCAACUGGGGA |

| SEQ ID NO 301 | GAUUGCUGGUCUUGUUUUUC | SEQ ID NO 336 | GGUAAUGAGUUCUUCCAACUGG |
| --- | --- | --- | --- |
| SEQ ID NO 302 | AUUGCUGGUCUUGUUUUUCAAAUUU | SEQ ID NO 337 | GUAAUGAGUUCUUCCAACUGGGGAC |
| SEQ ID NO 303 | UUGCUGGUCUUGUUUUUCAAAUUUU | SEQ ID NO 338 | UAAUGAGUUCUUCCAACUGGGGACG |
| SEQ ID NO 304 | UGCUGGUCUUGUUUUUCAAAUUUUG | SEQ ID NO 339 | AAUGAGUUCUUCCAACUGGGGACGC |
| SEQ ID NO 305 | GCUGGUCUUGUUUUUCAAAUUUUGG | SEQ ID NO 340 | AUGAGUUCUUCCAACUGGGGACGCC |
| SEQ ID NO 306 | CUGGUCUUGUUUUUCAAAUUUUGGG | SEQ ID NO 341 | UGAGUUCUUCCAACUGGGGACGCCU |
| SEQ ID NO 307 | UGGUCUUGUUUUUCAAAUUUUGGGC | SEQ ID NO 342 | GAGUUCUUCCAACUGGGGACGCCUC |
| SEQ ID NO 308 | GGUCUUGUUUUUCAAAUUUUGGGCA | SEQ ID NO 343 | AGUUCUUCCAACUGGGGACGCCUCU |
| SEQ ID NO 309 | GUCUUGUUUUUCAAAUUUUGGGCAG | SEQ ID NO 344 | GUUCUUCCAACUGGGGACGCCUCUG |
| SEQ ID NO 310 | UCUUGUUUUUCAAAUUUUGGGCAGC | SEQ ID NO 345 | UUCUUCCAACUGGGGACGCCUCUGU |
| SEQ ID NO 311 | CUUGUUUUUCAAAUUUUGGGCAGCG | SEQ ID NO 346 | UCUUCCAACUGGGGACGCCUCUGUU |
| SEQ ID NO 312 | UUGUUUUUCAAAUUUUGGGCAGCGG | SEQ ID NO 347 | CUUCCAACUGGGGACGCCUCUGUUC |
| SEQ ID NO 313 | UGUUUUUCAAAUUUUGGGCAGCGGU | SEQ ID NO 348 | UUCCAACUGGGGACGCCUCUGUUCC |
| SEQ ID NO 314 | GUUUUUCAAAUUUUGGGCAGCGGUA | SEQ ID NO 349 | UCCAACUGGGGACGCCUCUGUUCCA |
| SEQ ID NO 315 | UUUUUCAAAUUUUGGGCAGCGGUAA | SEQ ID NO 350 | CCAACUGGGGACGCCUCUGUUCCAA |
| SEQ ID NO 316 | UUUUCAAAUUUUGGGCAGCGGUAAU | SEQ ID NO 351 | CAACUGGGGACGCCUCUGUUCCAAA |
| SEQ ID NO 317 | UUUCAAAUUUUGGGCAGCGGUAAUG | SEQ ID NO 352 | AACUGGGGACGCCUCUGUUCCAAAU |
| SEQ ID NO 318 | UUCAAAUUUUGGGCAGCGGUAAUGA | SEQ ID NO 353 | ACUGGGGACGCCUCUGUUCCAAAUC |
| SEQ ID NO 319 | UCAAAUUUUGGGCAGCGGUAAUGAG | SEQ ID NO 354 | CUGGGGACGCCUCUGUUCCAAAUCC |
| SEQ ID NO 320 | CAAAUUUUGGGCAGCGGUAAUGAGU | SEQ ID NO 355 | UGGGGACGCCUCUGUUCCAAAUCCU |
| SEQ ID NO 321 | AAAUUUUGGGCAGCGGUAAUGAGUU | SEQ ID NO 356 | GGGGACGCCUCUGUUCCAAAUCCUG |
| SEQ ID NO 322 | AAUUUUGGGCAGCGGUAAUGAGUUC | SEQ ID NO 357 | GGGACGCCUCUGUUCCAAAUCCUGC |
| SEQ ID NO 323 | AUUUUGGGCAGCGGUAAUGAGUUCU | SEQ ID NO 358 | GGACGCCUCUGUUCCAAAUCCUGCA |
| SEQ ID NO 324 | UUUUGGGCAGCGGUAAUGAGUUCUU | SEQ ID NO 359 | GACGCCUCUGUUCCAAAUCCUGCAU |
| SEQ ID NO 325 | UUUGGGCAGCGGUAAUGAGUUCUUC | | |

DMD Gene Exon 50

| SEQ ID NO 360 | CCAAUAGUGGUCAGUCCAGGAGCUA | SEQ ID NO 386 | CUAGGUCAGGCUGCUUUGCCCUCAG |
| --- | --- | --- | --- |
| SEQ ID NO 361 | CAAUAGUGGUCAGUCCAGGAGCUAG | SEQ ID NO 387 | UAGGUCAGGCUGCUUUGCCCUCAGC |
| SEQ ID NO 362 | AAUAGUGGUCAGUCCAGGAGCUAGG | SEQ ID NO 388 | AGGUCAGGCUGCUUUGCCCUCAGCU |
| SEQ ID NO 363 | AUAGUGGUCAGUCCAGGAGCUAGGU | SEQ ID NO 389 | GGUCAGGCUGCUUUGCCCUCAGCUC |
| SEQ ID NO 364 | AUAGUGGUCAGUCCAGGAGCU | SEQ ID NO 390 | GUCAGGCUGCUUUGCCCUCAGCUCU |
| SEQ ID NO 365 | UAGUGGUCAGUCCAGGAGCUAGGUC | SEQ ID NO 391 | UCAGGCUGCUUUGCCCUCAGCUCUU |
| SEQ ID NO 366 | AGUGGUCAGUCCAGGAGCUAGGUCA | SEQ ID NO 392 | CAGGCUGCUUUGCCCUCAGCUCUUG |
| SEQ ID NO 367 | GUGGUCAGUCCAGGAGCUAGGUCAG | SEQ ID NO 393 | AGGCUGCUUUGCCCUCAGCUCUUGA |
| SEQ ID NO 368 | UGGUCAGUCCAGGAGCUAGGUCAGG | SEQ ID NO 394 | GGCUGCUUUGCCCUCAGCUCUUGAA |
| SEQ ID NO 369 | GGUCAGUCCAGGAGCUAGGUCAGGC | SEQ ID NO 395 | GCUGCUUUGCCCUCAGCUCUUGAAG |
| SEQ ID NO 370 | GUCAGUCCAGGAGCUAGGUCAGGCU | SEQ ID NO 396 | CUGCUUUGCCCUCAGCUCUUGAAGU |
| SEQ ID NO 371 | UCAGUCCAGGAGCUAGGUCAGGCUG | SEQ ID NO 397 | UGCUUUGCCCUCAGCUCUUGAAGUA |
| SEQ ID NO 372 | CAGUCCAGGAGCUAGGUCAGGCUGC | SEQ ID NO 398 | GCUUUGCCCUCAGCUCUUGAAGUAA |
| SEQ ID NO 373 | AGUCCAGGAGCUAGGUCAGGCUGCU | SEQ ID NO 399 | CUUUGCCCUCAGCUCUUGAAGUAAA |

| SEQ ID NO 374 | GUCCAGGAGCUAGGUCAGGCUGCUU | SEQ ID NO 400 | UUUGCCCUCAGCUCUUGAAGUAAAC |
|---|---|---|---|
| SEQ ID NO 375 | UCCAGGAGCUAGGUCAGGCUGCUUU | SEQ ID NO 401 | UUGCCCUCAGCUCUUGAAGUAAACG |
| SEQ ID NO 376 | CCAGGAGCUAGGUCAGGCUGCUUUG | SEQ ID NO 402 | UGCCCUCAGCUCUUGAAGUAAACGG |
| SEQ ID NO 377 | CAGGAGCUAGGUCAGGCUGCUUUGC | SEQ ID NO 403 | GCCCUCAGCUCUUGAAGUAAACGGU |
| SEQ ID NO 378 | AGGAGCUAGGUCAGGCUGCUUUGCC | SEQ ID NO 404 | CCCUCAGCUCUUGAAGUAAACGGUU |
| SEQ ID NO 379 | GGAGCUAGGUCAGGCUGCUUUGCCC | SEQ ID NO 405 | CCUCAGCUCUUGAAGUAAAC |
| SEQ ID NO 380 | GAGCUAGGUCAGGCUGCUUUGCCCU | SEQ ID NO 406 | CCUCAGCUCUUGAAGUAAACG |
| SEQ ID NO 381 | AGCUAGGUCAGGCUGCUUUGCCCUC | SEQ ID NO 407 | CUCAGCUCUUGAAGUAAACG |
| SEQ ID NO 382 | GCUAGGUCAGGCUGCUUUGCCCUCA | SEQ ID NO 408 | CCUCAGCUCUUGAAGUAAACGGUUU |
| SEQ ID NO 383 | CUCAGCUCUUGAAGUAAACGGUUUA | SEQ ID NO 409 | UCAGCUCUUGAAGUAAACGGUUUAC |
| SEQ ID NO 384 | CAGCUCUUGAAGUAAACGGUUUACC | SEQ ID NO 410 | AGCUCUUGAAGUAAACGGUUUACCG |
| SEQ ID NO 385 | GCUCUUGAAGUAAACGGUUUACCGC | SEQ ID NO 411 | CUCUUGAAGUAAACGGUUUACCGCC |

DMD Gene Exon 43

| SEQ ID NO 412 | CCACAGGCGUUGCACUUUGCAAUGC | SEQ ID NO 443 | UCUUCUUGCUAUGAAUAAUGUCAAU |
|---|---|---|---|
| SEQ ID NO 413 | CACAGGCGUUGCACUUUGCAAUGCU | SEQ ID NO 444 | CUUCUUGCUAUGAAUAAUGUCAAUC |
| SEQ ID NO 414 | ACAGGCGUUGCACUUUGCAAUGCUG | SEQ ID NO 445 | UUCUUGCUAUGAAUAAUGUCAAUCC |
| SEQ ID NO 415 | CAGGCGUUGCACUUUGCAAUGCUGC | SEQ ID NO 446 | UCUUGCUAUGAAUAAUGUCAAUCCG |
| SEQ ID NO 416 | AGGCGUUGCACUUUGCAAUGCUGCU | SEQ ID NO 447 | CUUGCUAUGAAUAAUGUCAAUCCGA |
| SEQ ID NO 417 | GGCGUUGCACUUUGCAAUGCUGCUG | SEQ ID NO 448 | UUGCUAUGAAUAAUGUCAAUCCGAC |
| SEQ ID NO 418 | GCGUUGCACUUUGCAAUGCUGCUGU | SEQ ID NO 449 | UGCUAUGAAUAAUGUCAAUCCGACC |
| SEQ ID NO 419 | CGUUGCACUUUGCAAUGCUGCUGUC | SEQ ID NO 450 | GCUAUGAAUAAUGUCAAUCCGACCU |
| SEQ ID NO 420 | CGUUGCACUUUGCAAUGCUGCUG | SEQ ID NO 451 | CUAUGAAUAAUGUCAAUCCGACCUG |
| SEQ ID NO 421 | GUUGCACUUUGCAAUGCUGCUGUCU | SEQ ID NO 452 | UAUGAAUAAUGUCAAUCCGACCUGA |
| SEQ ID NO 422 | UUGCACUUUGCAAUGCUGCUGUCUU | SEQ ID NO 453 | AUGAAUAAUGUCAAUCCGACCUGAG |
| SEQ ID NO 423 | UGCACUUUGCAAUGCUGCUGUCUUC | SEQ ID NO 454 | UGAAUAAUGUCAAUCCGACCUGAGC |
| SEQ ID NO 424 | GCACUUUGCAAUGCUGCUGUCUUCU | SEQ ID NO 455 | GAAUAAUGUCAAUCCGACCUGAGCU |
| SEQ ID NO 425 | CACUUUGCAAUGCUGCUGUCUUCUU | SEQ ID NO 456 | AAUAAUGUCAAUCCGACCUGAGCUU |
| SEQ ID NO 426 | ACUUUGCAAUGCUGCUGUCUUCUUG | SEQ ID NO 457 | AUAAUGUCAAUCCGACCUGAGCUUU |
| SEQ ID NO 427 | CUUUGCAAUGCUGCUGUCUUCUUGC | SEQ ID NO 458 | UAAUGUCAAUCCGACCUGAGCUUUG |
| SEQ ID NO 428 | UUUGCAAUGCUGCUGUCUUCUUGCU | SEQ ID NO 459 | AAUGUCAAUCCGACCUGAGCUUUGU |
| SEQ ID NO 429 | UUGCAAUGCUGCUGUCUUCUUGCUA | SEQ ID NO 460 | AUGUCAAUCCGACCUGAGCUUUGUU |
| SEQ ID NO 430 | UGCAAUGCUGCUGUCUUCUUGCUAU | SEQ ID NO 461 | UGUCAAUCCGACCUGAGCUUUGUUG |
| SEQ ID NO 431 | GCAAUGCUGCUGUCUUCUUGCUAUG | SEQ ID NO 462 | GUCAAUCCGACCUGAGCUUUGUUGU |
| SEQ ID NO 432 | CAAUGCUGCUGUCUUCUUGCUAUGA | SEQ ID NO 463 | UCAAUCCGACCUGAGCUUUGUUGUA |
| SEQ ID NO 433 | AAUGCUGCUGUCUUCUUGCUAUGAA | SEQ ID NO 464 | CAAUCCGACCUGAGCUUUGUUGUAG |
| SEQ ID NO 434 | AUGCUGCUGUCUUCUUGCUAUGAAU | SEQ ID NO 465 | AAUCCGACCUGAGCUUUGUUGUAGA |
| SEQ ID NO 435 | UGCUGCUGUCUUCUUGCUAUGAAUA | SEQ ID NO 466 | AUCCGACCUGAGCUUUGUUGUAGAC |
| SEQ ID NO 436 | GCUGCUGUCUUCUUGCUAUGAAUAA | SEQ ID NO 467 | UCCGACCUGAGCUUUGUUGUAGACU |
| SEQ ID NO 437 | CUGCUGUCUUCUUGCUAUGAAUAAU | SEQ ID NO 468 | CCGACCUGAGCUUUGUUGUAGACUA |
| SEQ ID NO 438 | UGCUGUCUUCUUGCUAUGAAUAAUG | SEQ ID NO 469 | CGACCUGAGCUUUGUUGUAG |

-continued

| | | | |
|---|---|---|---|
| SEQ ID NO 439 | GCUGUCUUCUUGCUAUGAAUAAUGU | SEQ ID NO 470 | CGACCUGAGCUUUGUUGUAGACUAU |
| SEQ ID NO 440 | CUGUCUUCUUGCUAUGAAUAAUGUC | SEQ ID NO 471 | GACCUGAGCUUUGUUGUAGACUAUC |
| SEQ ID NO 441 | UGUCUUCUUGCUAUGAAUAAUGUCA | SEQ ID NO 472 | ACCUGAGCUUUGUUGUAGACUAUCA |
| SEQ ID NO 442 | GUCUUCUUGCUAUGAAUAAUGUCAA | SEQ ID NO 473 | CCUGAGCUUUGUUGUAGACUAUC |

DMD Gene Exon 6

| | | | |
|---|---|---|---|
| SEQ ID NO 474 | CAUUUUUGACCUACAUGUGG | SEQ ID NO 479 | AUUUUUGACCUACAUGGGAAA G |
| SEQ ID NO 475 | UUUGACCUACAUGUGGAAAG | SEQ ID NO 480 | UACGAGUUGAUUGUCGGACCCAG |
| SEQ ID NO 476 | UACAUUUUUGACCUACAUGUGGAAA G | SEQ ID NO 481 | GUGGUCUCCUUACCUAUGACUGUGG |
| SEQ ID NO 477 | GGUCUCCUUACCUAUGA | SEQ ID NO 482 | UGUCUCAGUAAUCUUCUUACCUAU |
| SEQ ID NO 478 | UCUUACCUAUGACUAUGGAUGAGA | | |

DMD Gene Exon 7

| | | | |
|---|---|---|---|
| SEQ ID NO 483 | UGCAUGUUCCAGUCGUUGUGUGG | SEQ ID NO 485 | AUUUACCAACCUUCAGGAUCGAGUA |
| SEQ ID NO 484 | CACUAUUCCAGUCAAAUAGGUCUGG | SEQ ID NO 486 | GGCCUAAAACACAUACACAUA |

DMD Gene Exon 8

| | | | |
|---|---|---|---|
| SEQ ID NO 487 | GAUAGGUGGUAUCAACAUCUGUAA | SEQ ID NO 490 | UGUUGUUGUUUAUGCUCAUU |
| SEQ ID NO 488 | GAUAGGUGGUAUCAACAUCUG | SEQ ID NO 491 | GUACAUUAAGAUGGACUUC |
| SEQ ID NO 489 | CUUCCUGGAUGGCUUGAAU | | |

DMD Gene Exon 55

| | | | |
|---|---|---|---|
| SEQ ID NO 492 | CUGUUGCAGUAAUCUAUGAG | SEQ ID NO 495 | UGCCAUUGUUUCAUCAGCUCUUU |
| SEQ ID NO 493 | UGCAGUAAUCUAUGAGUUUC | SEQ ID NO 496 | UCCUGUAGGACAUUGGCAGU |
| SEQ ID NO 494 | GAGUCUUCUAGGAGCCUU | SEQ ID NO 497 | CUUGGAGUCUUCUAGGAGCC |

DMD Gene Exon 2

| | | | |
|---|---|---|---|
| SEQ ID NO 498 | CCAUUUUGUGAAUGUUUUCUUUUG AACAUC | SEQ ID NO 500 | GAAAAUUGUGCAUUUACCCAUUUU |
| SEQ ID NO 499 | CCCAUUUUGUGAAUGUUUUCUUUU | SEQ ID NO 501 | UUGUGCAUUUACCCAUUUUGUG |

DMD Gene Exon 11

| | | | |
|---|---|---|---|
| SEQ ID NO 502 | CCCUGAGGCAUUCCCAUCUUGAAU | SEQ ID NO 504 | CUUGAAUUUAGGAGAUUCAUCUG |
| SEQ ID NO 503 | AGGACUUACUUGCUUUGUUU | SEQ ID NO 505 | CAUCUUCUGAUAAUUUCCUGUU |

DMD Gene Exon 17

| | | | |
|---|---|---|---|
| SEQ ID NO 506 | CCAUUACAGUUGUCUGUGUU | SEQ ID NO 508 | UAAUCUGCCUCUUCUUUUGG |
| SEQ ID NO 507 | UGACAGCCUGUGAAAUCUGUGAG | | |

DMD Gene Exon 19

| | | | |
|---|---|---|---|
| SEQ ID NO 509 | CAGCAGUAGUUGUCAUCUGC | SEQ ID NO 511 | GCCUGAGCUGAUCUGCUGGCAUCUUG CAGUU |
| SEQ ID NO 510 | GCCUGAGCUGAUCUGCUGGCAUCUU GC | SEQ ID NO 512 | UCUGCUGGCAUCUUGC |

DMD Gene Exon 21

| | | | |
|---|---|---|---|
| SEQ ID NO 513 | GCCGGUUGACUUCAUCCUGUGC | SEQ ID NO 516 | CUGCAUCCAGGAACAUGGGUCC |
| SEQ ID NO 514 | GUCUGCAUCCAGGAACAUGGGUC | SEQ ID NO 517 | GUUGAAGAUCUGAUAGCCGGUUGA |
| SEQ ID NO 515 | UACUUACUGUCUGUAGCUCUUUCU | | |

DMD Gene Exon 57

| | | | |
|---|---|---|---|
| SEQ ID NO 518 | UAGGUGCCUGCCGGCUU | SEQ ID NO 520 | CUGAACUGCUGGAAAGUCGCC |
| SEQ ID NO 519 | UUCAGCUGUAGCCACACC | SEQ ID NO 521 | CUGGCUUCCAAAUGGGACCUGAAAAA GAAC |

-continued

DMD Gene Exon 59
SEQ ID NO 522    CAAUUUUCCCACUCAGUAUU
SEQ ID NO 523    UUGAAGUUCCUGGAGUCUU
SEQ ID NO 524    UCCUCAGGAGGCAGCUCUAAAU DMD Gene Exon 62
SEQ ID NO 525    UGGCUCUCUCCCAGGG
SEQ ID NO 526    GAGAUGGCUCUCUCCCAGGGACCCUGG
SEQ ID NO 527    GGGCACUUUGUUUGGCG DMD Gene Exon 63
SEQ ID NO 528    GGUCCCAGCAAGUUGUUUG
SEQ ID NO 529    UGGGAUGGUCCCAGCAAGUUGUUUG
SEQ ID NO 530    GUAGAGCUCUGUCAUUUUGGG DMD Gene Exon 65
SEQ ID NO 531    GCUCAAGAGAUCCACUGCAAAAAAC
SEQ ID NO 532    GCCAUACGUACGUAUCAUAAACAUUC
SEQ ID NO 533    UCUGCAGGAUAUCCAUGGGCUGGUC DMD Gene Exon 66
SEQ ID NO 534    GAUCCUCCCUGUUCGUCCCCUAUUAUG DMD Gene Exon 69
SEQ ID NO 535    UGCUUUAGACUCCUGUACCUGAUA DMD Gene Exon 75
SEQ ID NO 536    GGCGGCCUUUGUGUUGAC
SEQ ID NO 537    GGACAGGCCUUUAUGUUCGUGCUGC
SEQ ID NO 538    CCUUUAUGUUCGUGCUGCU Human IGF-1 Isoform 4 amino acid sequence
SEQ ID NO 577:
MGKISSLPTQLFKCCFCDFLKVKMHTMSSSHLFYLALCLLTFTSSATAGPETLCGAELV
DALQFVCGDRGFYFNKPTGYGSSSRRAPQTGIVDECCFRSCDLRRLEMYCAPLKPAKSA
RSVRAQRHTDMPKTQKEVHLKNASRGSAGNKNYRM

---

What is claimed is:

1. An oligonucleotide consisting of the base sequence of any one of SEQ ID NO: 141, 142 or 144-188, wherein at least one guanosine base in the sequence is substituted with an inosine base, and wherein said oligonucleotide comprises a modification and induces skipping of exon 53 of human dystrophin pre-mRNA.

2. The oligonucleotide of claim 1, wherein one to four guanosine bases in the sequence are substituted with an inosine base.

3. The oligonucleotide of claim 1, wherein the modification is a base and/or sugar modification.

4. The oligonucleotide of claim 3, wherein the oligonucleotide is a 2'-O-methyl phosphorothioate oligonucleotide.

5. The oligonucleotide of claim 3, wherein the oligonucleotide is a peptide nucleic acid.

6. The oligonucleotide of claim 3, wherein the oligonucleotide is a phosphorodiamidate morpholino oligomer.

7. A pharmaceutical composition, comprising the oligonucleotide of claim 1 and a pharmaceutically acceptable carrier.

8. A method for inducing skipping of exon 53 of human dystrophin pre-mRNA in a human subject, comprising administering the oligonucleotide of claim 1 to the human subject in an amount and for a time which is effective to induce exon skipping.

9. A method for alleviating one or more symptom(s) of Duchenne Muscular Dystrophy or Becker Muscular Dystrophy in a human subject, comprising administering to the human subject the oligonucleotide of claim 1.

\* \* \* \* \*